US 12,247,073 B2

(12) United States Patent
Culp et al.

(10) Patent No.: US 12,247,073 B2
(45) Date of Patent: Mar. 11, 2025

(54) ANTI-CD33 ANTIBODIES AND METHODS OF USE THEREOF

(71) Applicant: Alector LLC, South San Francisco, CA (US)

(72) Inventors: Patricia Culp, Oakland, CA (US); Helen Lam, Union City, CA (US); Wei-Hsien Ho, Belmont, CA (US); Leonard G. Presta, Palo Alto, CA (US); Arnon Rosenthal, Woodside, CA (US)

(73) Assignee: ALECTOR LLC, South San Francisco, CA (US)

( * ) Notice: Subject to any disclaimer, the term of this patent is extended or adjusted under 35 U.S.C. 154(b) by 1046 days.

(21) Appl. No.: 17/272,083

(22) PCT Filed: Aug. 30, 2019

(86) PCT No.: PCT/US2019/048994
§ 371 (c)(1),
(2) Date: Feb. 26, 2021

(87) PCT Pub. No.: WO2020/047374
PCT Pub. Date: Mar. 5, 2020

(65) Prior Publication Data
US 2021/0317208 A1    Oct. 14, 2021

Related U.S. Application Data

(60) Provisional application No. 62/726,053, filed on Aug. 31, 2018.

(51) Int. Cl.
*C07K 16/28* (2006.01)

(52) U.S. Cl.
CPC ...... *C07K 16/2803* (2013.01); *C07K 2317/24* (2013.01); *C07K 2317/31* (2013.01); *C07K 2317/52* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,469,863 A | 9/1984 | Ts'o et al. |
| 4,657,760 A | 4/1987 | Kung et al. |
| 4,676,980 A | 6/1987 | Segal et al. |
| 4,816,567 A | 3/1989 | Cabilly et al. |
| 5,206,344 A | 4/1993 | Katre et al. |
| 5,225,212 A | 7/1993 | Martin et al. |
| 5,229,275 A | 7/1993 | Goroff et al. |
| 5,530,101 A | 6/1996 | Queen et al. |
| 5,536,821 A | 7/1996 | Agrawal et al. |
| 5,541,306 A | 7/1996 | Agrawal et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,573,905 A | 11/1996 | Lerner et al. |
| 5,585,089 A | 12/1996 | Queen et al. |
| 5,587,458 A | 12/1996 | King et al. |
| 5,591,669 A | 1/1997 | Krimpenfort et al. |
| 5,614,622 A | 3/1997 | Iyer et al. |
| 5,625,126 A | 4/1997 | Lonberg et al. |
| 5,633,425 A | 5/1997 | Lonberg et al. |
| 5,637,683 A | 6/1997 | Usher et al. |
| 5,637,684 A | 6/1997 | Cook et al. |
| 5,641,870 A | 6/1997 | Rinderknecht et al. |
| 5,648,237 A | 7/1997 | Carter et al. |
| 5,661,016 A | 8/1997 | Lonberg et al. |
| 5,693,761 A | 12/1997 | Queen et al. |
| 5,693,762 A | 12/1997 | Queen et al. |
| 5,700,922 A | 12/1997 | Cook |
| 5,717,083 A | 2/1998 | Cook et al. |
| 5,719,262 A | 2/1998 | Buchardt et al. |
| 5,730,982 A | 3/1998 | Scheinberg |
| 5,731,168 A | 3/1998 | Carter et al. |
| 5,739,277 A | 4/1998 | Presta et al. |
| 5,739,308 A | 4/1998 | Kandimalla et al. |
| 5,739,314 A | 4/1998 | Roy et al. |
| 5,750,373 A | 5/1998 | Garrard et al. |
| 5,766,886 A | 6/1998 | Studnicka et al. |
| 5,773,601 A | 6/1998 | Agrawal |

(Continued)

FOREIGN PATENT DOCUMENTS

| | | |
|---|---|---|
| CA | 2988982 A1 | 12/2016 |
| CN | 1078401 A | 11/1993 |

(Continued)

OTHER PUBLICATIONS

Nelson. Antibody Fragments. mAbs 2010; 2(1):77-83. (Year: 2010).*
Prins and Scheltens. Treating Alzheimer's disease with monoclonal antibodies: current status and outlook for the future. Alzheimer's Research & Therapy. 2013; (5)56:1-6. (Year: 2013).*
Frenzel et al. Expression of recombinant antibodies. Front Immunol, 2013 4:1-20 (Year: 2013).*
Sumner et al. Antibody Engineering for Optimized Immunotherapy in Alzheimer's Disease Disease Front Neurosci, 2018 12(254): 1-12. (Year: 2018).*
Bhattacherjee et al., (2019). "Repression of phagocytosis by human CD33 is not conserved with mouse CD33," Commun Biol., 2:450, 13 pages.

(Continued)

*Primary Examiner* — Daniel E Kolker
*Assistant Examiner* — Maureen Varina Driscoll
(74) *Attorney, Agent, or Firm* — MORRISON & FOERSTER LLP

(57) ABSTRACT

The present disclosure is generally directed to compositions that include antibodies, e.g., monoclonal, antibodies, antibody fragments, etc., that specifically bind a CD33 polypeptide, e.g., a mammalian CD33 or human CD33, and use of such compositions in preventing, reducing risk, or treating an individual in need thereof.

84 Claims, 13 Drawing Sheets
Specification includes a Sequence Listing.

(56) References Cited

U.S. PATENT DOCUMENTS

| | | |
|---|---|---|
| 5,789,199 A | 8/1998 | Joly et al. |
| 5,821,337 A | 10/1998 | Carter et al. |
| 5,840,523 A | 11/1998 | Simmons et al. |
| 5,869,046 A | 2/1999 | Presta et al. |
| 5,869,619 A | 2/1999 | Studnicka |
| 5,886,165 A | 3/1999 | Kandimalla et al. |
| 5,929,226 A | 7/1999 | Padmapriya et al. |
| 5,955,599 A | 9/1999 | Iyer et al. |
| 5,959,177 A | 9/1999 | Hein et al. |
| 5,962,674 A | 10/1999 | Iyer et al. |
| 5,977,296 A | 11/1999 | Nielsen et al. |
| 6,040,498 A | 3/2000 | Stomp et al. |
| 6,075,181 A | 6/2000 | Kucherlapati et al. |
| 6,117,992 A | 9/2000 | Iyer |
| 6,140,482 A | 10/2000 | Iyer et al. |
| 6,150,584 A | 11/2000 | Kucherlapati et al. |
| 6,248,516 B1 | 6/2001 | Winter et al. |
| 6,350,861 B1 | 2/2002 | Co et al. |
| 6,417,429 B1 | 7/2002 | Hein et al. |
| 6,420,548 B1 | 7/2002 | Vézina et al. |
| 6,455,308 B1 | 9/2002 | Freier |
| 6,982,321 B2 | 1/2006 | Winter |
| 7,041,870 B2 | 5/2006 | Tomizuka et al. |
| 7,087,409 B2 | 8/2006 | Barbas, III et al. |
| 7,125,978 B1 | 10/2006 | Vézina et al. |
| 7,189,826 B2 | 3/2007 | Rodman |
| 7,342,110 B2 | 3/2008 | Hoffee et al. |
| 7,420,041 B2 | 9/2008 | Young et al. |
| 7,527,791 B2 | 5/2009 | Adams et al. |
| 7,557,189 B2 | 7/2009 | Hoffee et al. |
| 7,566,772 B2 | 7/2009 | Green et al. |
| 8,119,787 B2 | 2/2012 | Hoffee et al. |
| 8,124,069 B2 | 2/2012 | Bae et al. |
| 8,337,855 B2 | 12/2012 | Hoffee et al. |
| 8,614,299 B2 | 12/2013 | Baurin et al. |
| 9,765,157 B2 | 9/2017 | Xiao et al. |
| 9,951,133 B2 | 4/2018 | Yu et al. |
| 10,711,062 B2 | 7/2020 | Culp et al. |
| 11,136,390 B2 | 10/2021 | Monroe et al. |
| 11,174,313 B2 | 11/2021 | Rosenthal et al. |
| 11,254,743 B2 | 2/2022 | Culp et al. |
| 2007/0061900 A1 | 3/2007 | Murphy et al. |
| 2007/0148167 A1 | 6/2007 | Strohl |
| 2007/0292936 A1 | 12/2007 | Barthelemy et al. |
| 2009/0002360 A1 | 1/2009 | Chen et al. |
| 2009/0181855 A1 | 7/2009 | Vasquez et al. |
| 2010/0056386 A1 | 3/2010 | Vasquez et al. |
| 2010/0280227 A1 | 11/2010 | Ambrose et al. |
| 2012/0082670 A1 | 4/2012 | Konopitzky et al. |
| 2013/0309223 A1 | 11/2013 | Sutherland et al. |
| 2016/0038566 A1 | 2/2016 | Tanzi et al. |
| 2019/0002560 A1 | 1/2019 | Monroe et al. |
| 2019/0040131 A1 | 2/2019 | Culp et al. |
| 2019/0085076 A1 | 3/2019 | Rosenthal et al. |
| 2021/0139581 A1 | 5/2021 | Culp et al. |
| 2022/0162309 A1 | 5/2022 | Culp et al. |
| 2022/0251190 A1 | 8/2022 | Monroe et al. |
| 2022/0281976 A1 | 9/2022 | Rosenthal et al. |
| 2023/0035072 A1 | 2/2023 | Robert et al. |

FOREIGN PATENT DOCUMENTS

| | | |
|---|---|---|
| CN | 1795009 A | 6/2006 |
| CN | 102952191 A | 3/2013 |
| CN | 103261227 A | 8/2013 |
| CN | 104936617 A | 9/2015 |
| CN | 107922480 A | 4/2018 |
| CN | 112912144 A | 6/2021 |
| EP | 308936 B1 | 7/1994 |
| EP | 404097 B1 | 9/1996 |
| EP | 546073 B1 | 9/1997 |
| IL | 235733 B | 7/2021 |
| JP | 2006505277 A | 2/2006 |
| JP | 2014500003 A | 1/2014 |
| JP | 2015520758 A | 7/2015 |
| JP | 2018518176 A | 7/2018 |
| JP | 7299160 B2 | 6/2023 |
| KR | 20050059332 A | 6/2005 |
| KR | 20150013321 A | 2/2015 |
| TW | 201408700 A | 3/2014 |
| WO | WO-1987004462 A1 | 7/1987 |
| WO | WO-1991000360 A1 | 1/1991 |
| WO | WO-1991009058 A1 | 6/1991 |
| WO | WO-1991010741 A1 | 7/1991 |
| WO | WO-1992000373 A1 | 1/1992 |
| WO | WO-1992020373 A1 | 11/1992 |
| WO | WO-1993001161 A1 | 1/1993 |
| WO | WO-1993008829 A1 | 5/1993 |
| WO | WO-1993011161 A1 | 6/1993 |
| WO | WO-1993016185 A2 | 8/1993 |
| WO | WO-1993020848 A1 | 10/1993 |
| WO | WO-1994004690 A1 | 3/1994 |
| WO | WO-1996027011 A1 | 9/1996 |
| WO | WO-1996033735 A1 | 10/1996 |
| WO | WO-1996034096 A1 | 10/1996 |
| WO | WO-1997011971 A1 | 4/1997 |
| WO | WO-1997017852 A1 | 5/1997 |
| WO | WO-1998024893 A2 | 6/1998 |
| WO | WO-1999032619 A1 | 7/1999 |
| WO | WO-1999058572 A1 | 11/1999 |
| WO | WO-2000044895 A1 | 8/2000 |
| WO | WO-2000056746 A2 | 9/2000 |
| WO | WO-2000075372 A1 | 12/2000 |
| WO | WO-2001014398 A1 | 3/2001 |
| WO | WO-2001029058 A1 | 4/2001 |
| WO | WO-2001036646 A1 | 5/2001 |
| WO | WO-2003024993 A2 | 3/2003 |
| WO | WO-2003093298 A2 | 11/2003 |
| WO | WO-2004042072 A2 | 5/2004 |
| WO | WO-2004043344 A2 | 5/2004 |
| WO | WO-2007014743 A2 | 2/2007 |
| WO | WO-2007106585 A1 | 9/2007 |
| WO | WO-2008058021 A2 | 5/2008 |
| WO | WO-2008079246 A2 | 7/2008 |
| WO | WO-2009036379 A2 | 3/2009 |
| WO | WO-2010105256 A1 | 9/2010 |
| WO | WO-2011036183 A2 | 3/2011 |
| WO | WO-2011038301 A2 | 3/2011 |
| WO | WO-2012009568 A2 | 1/2012 |
| WO | WO-2012045752 A1 | 4/2012 |
| WO | WO-2012074097 A1 | 6/2012 |
| WO | WO-2013173496 A2 | 11/2013 |
| WO | WO-2016052756 A1 * | 4/2016 | ............ C07K 16/28 |
| WO | WO-2016087651 A1 | 6/2016 |
| WO | WO-2016201388 A2 * | 12/2016 | ......... A61K 39/3955 |
| WO | WO-2016201389 A2 | 12/2016 |
| WO | WO-2019224711 A2 | 11/2019 |
| WO | WO-2020047452 A2 | 3/2020 |
| WO | WO-2021119400 A1 | 6/2021 |

OTHER PUBLICATIONS

Bostrom et al., (2009). "Improving antibody binding affinity and specificity for therapeutic development," Methods Mol Biol., 525:353-76.

Candia et al., (2017). "Assessment of Variability in the SOMAscan Assay," Sci Rep, 7:14248, 13 pages.

Caron et al., (1992). "Biological and Immunological Features of Humanized M195 (Anti-CD33) Monoclonal Antibodies," Cancer Research, 52(24):6761-7.

Declaration of Dr. Rudolph Emile Tanzi submitted before the European Patent Office for EP patent application No. 14773553.4, filed Mar. 27, 2014, dated Jun. 14, 2021, 8 pages.

Gonzales et al., (2005). "Minimizing the Immunogenicity of Antibodies for Clinical Application," Tumour Biol., 26(1):31-43.

Jiang et al., (2018). "Meta-analysis of the association between CD33 and Alzheimer's disease" Ann Transl Med., 6(10):169, 12 pages.

Kunik et al., (2012). "Structural consensus among antibodies defines the antigen binding site," PLoS Comput Biol., 8(2):e1002388, 12 pages.

(56) References Cited

OTHER PUBLICATIONS

Leoh et al., (2015). "Insights into the effector functions of human IgG3 in the context of an antibody targeting transferrin receptor 1," Molecular Immunology, 67:407-415, 22 pages.
Malik et al., (2015). "Genetics of CD33 in Alzheimer's disease and acute myeloid leukemia," Human Molecular Genetics, 24(12):3557-3570.
Mimoto et al., (2013). "Engineered antibody Fc variant with selectively enhanced FcγRIIb binding over both FcγRIIa$^{R131}$ and FcγγRIIa$^{H131}$," Protein Engineering Design and Selection, 26(10):589-598.
O'Bryant et al., (2010). "Validation of the New Interpretive Guidelines for the Clinical Dementia Rating Scale Sum of Boxes Score in the National Alzheimer's Coordinating Center Database," Arch Neurol, 67(6):746-49, 9 pages.
Ovacik et al., (2018). "Tutorial on Monoclonal Antibody Pharmacokinetics and Its Considerations in Early Development," Clin Transl Sci, 11(6):540-552.
Parekh et al., (2012). "Development and validation of an antibody-dependent cell-mediated cytotoxicity-reporter gene assay," MAbs, 4(3):310-318.
Schwartz et al., (2003). "Formalization of the MESF unit of fluorescence intensity," Cytometry Part B (Clinical Cytometry), 57B:1-6.
Sela-Culang et al., (2013). "The Structural Basis of Antibody-Antigen Recognition," Front Immunol, 4:302, 13 pages.
Wark et al., (2006). "Latest technologies for the enhancement of antibody affinity," Advanced Drug Delivery Reviews, 58(5-6):657-670.
Wu et al., (1999). "Humanization of a Murine Monoclonal Antibody by Simultaneous Optimization of Framework and CDR Residues," J. Mol. Biol., 294:151-162.
Yu et al., (2013). "Developing therapeutic antibodies for neurodegenerative disease," Neurotherapeutics, 10:459-472.
Zhang et al., (2014). "Progress in Antibody-Drug Conjugates Directed against CD33," Chinese Journal of Cell Biology, 36(1):106-114. English abstract only.
Zhao, (2019). "CD33 in Alzheimer's Disease—Biology, Pathogenesis, and Therapeutics: A Mini-Review," Gerontology, 65:323-331.
Chinese Search Report search date Feb. 24, 2023 for Chinese Application No. 201880027790.9, 5 pages. English translation.
Singaporean Search Report received for Singaporean Application No. 11202101552S date of completion Aug. 11, 2022, 2 pages.
Written Decision revoking European Patent EP2978446 mailed on Jun. 13, 2022, 14 pages.
Liang et al., (2008). "Application of the CD33 Monoclonal Antibody GO in the Treatment of Leukemia," National Medical Frontiers of China, 3(19):34-36. English abstract only.
Alegre et al., (1994). "A Non-Activating "Humanized" Anti-cd3 Monoclonal Antibody Retains Immunosuppressive Properties in Vivo," Transplantation, 57(11):1537-1543.
Almagro et al., (2008). "Humanization of Antibodies," Frontiers in Bio-Science, 13:1619-1633.
Al-Shawi et al., (2008). "Neurotoxic and Neurotrophic Roles of proNGF and the Receptor Sortilin in the Adult and Ageing Nervous System," European Journal of Neuroscience, 27:2103-2114.
Angal et al., (1993). "A Single Amino Acid Substitution Abolishes The Heterogeneity Of Chimeric Mouse/Human (IgG4) Antibody," Molecular Immunology, 30(1):105-108.
Anonymous, (2019). "EC50," Available online at: <en.wikipedia.org/wiki/EC50>, Sep. 16, 2019, 3 pages.
Applicant response to summons for European Patent Application No. 14773553.4 filed on Oct. 12, 2019, 10 pages.
Armour et al., (1999). "Recombinant Human IgG Molecules Lacking FcGamma Receptor I Binding and Monocyte Triggering Activities," Eur. J. Immunol. 29:2613-2624.
Armour et al., (2000). "Mutant IgG Lacking FcγRIII Binding and ADCC Activities,"The Haematology Journal, poster Session 1, Presented at the 5th Annual Meeting of the European Haematology Association, Birmingham, UK, 1(Suppl. 1):27, 2 pages.
Armour et al., (2003). "Differential Binding To Human Fcγriia and Fcγriib Receptors by Human IgG Wildtype and Mutant Antibodies," Molecular Immunology, 40:585-593.
Arnett et al., (Dec. 5, 2007; e-published on Oct. 26, 2007). "proNGF, Sortilin, and p75NTR: Potential Mediators of Injury-Induced Apoptosis in the Mouse Dorsal Root Ganglion," Brain Res., 1183:32-42.
Asquith et al., (2009). "Animal Models of Rheumatoid Arthritis," Eur. J. Immunol., 39:2040-2044.
Attrill et al., (Oct. 27, 2006; e-published on Aug. 8, 2006). "Siglec-7 Undergoes a Major Conformational Change When Complexed with the α(2,8)-Disialylganglioside GT1b," J. Biol. Chem., 281:32774-32783.
Baca et al., (1997). "Antibody Humanization Using Monovalent Phage Display," The Journal of Biological Chemistry, 272(16):10678-10684.
Balaian et al., (2001). "Direct Effect of Bispecific Anti-CD33 X Anti-CD64 Antibody on Proliferation and Signaling in Myeloid Cells," Leuk Res., 25(12):1115-1125.
Barbas III et al., (1994). "In Vitro Evolution of A Neutralizing Human Antibody To Human Immunodeficiency Virus Type 1 To Enhance Affinity And Broaden Strain Cross-Reactivity," Proc Nat. Acad. Sci. USA, 91:3809-3813.
Bartholomaeus et al., (2014). "Cell Contact-Dependent Priming and Fc Interaction with CD32+ Immune Cells Contribute to the TGN1412-Triggered Cytokine Response," The Journal of Immunology, 192:2091-2098.
Beattie et al., (2002). "ProNGF Induces p75-Mediated Death of Oligodendrocytes following Spinal Cord Injury," Neuron, 36(3):375-386.
Bertram et al., (2008). "Genome-wide Association Analysis Reveals Putative Alzheimer's Disease Susceptibility Loci in Addition to APOE," Am. J. Hum. Genet., 83(5):623-632.
Boerner et al., (1991). "Production Of Antigen-Specific Human Monoclonal Antibodies From In Vitro-Primed Human Splenocytes," Journal of Immunology, 147(1):86-95.
Bolt et al., (1993). "The Generation Of A Humanized, Non-Mitogenic Cd3 Monoclonal Antibody Which Retains In Vitro Immunosuppressive Properties," European Journal Immunol., 23:403-411.
Bradshaw et al., (Jul. 2013; e-published on May 23, 2013). "CD33 Alzheimer's Disease Locus: Altered Monocyte Function and Amyloid Biology," Nat. Neurosci., 16(7):848-850, fourteen pages.
Brehm et al., (2010). "Humanized Mouse Models to Study Human Diseases," Curr Opin Endocrinol Diabetes Obes., 17(2):120-125.
Brennan et al., (1985). "Preparation Of Bispecific Antibodies By Chemical Recombination Of Monoclonal Immunoglobulin G1 Fragments," Science, 229:81-83.
Brinkman-Van Der Linden et al., (2003). "CD33/Siglec-3 Binding Specificity, Expression Pattern, and Consequences of Gene Deletion in Mice," Mol. Cell Biol., 23(12):4199-4206.
Bross et al., (2001). "Approval Summary: Gemtuzumab Ozogamicin in Relapsed Acute Myeloid Leukemia," Clinical Cancer Researc,h 7:1490-1496.
Bruggemann et al., (1993). "Designer Mice: The Production of Human Antibody Repertoires in Transgenic Animals," Year in Immunol., 7:33-40.
Callige et al., (2005). "CSN5/Jab1 is Involved in Ligand-Dependent Degradation of Estrogen Receptor α by the Proteasome," Mol. Cell Biol., 25(11):4349-4358.
Cantoni et al., (2015). "Trem2 Regulates Microglial Cell Activation In Response To Demyelination In Vivo," Acta Neuropathol., 129(3):429-447, thirty three pages.
Cao et al., (2011). "Macrophage Polarization In The Maculae Of Age-Related Macular Degeneration: A Pilot Study," Pathology International, 61(9):528-535, fourteen pages.
Capel et al., (1994). "Heterogeneity of Human IgG Fc Receptors," Immunomethods, 4:25-34.
Carter et al., (1992). "High Level *Escherichia coli* Expression and Production of a Bivalent Humanized Antibody Fragment," Bio/technology, 10:163-167.
Carter et al., (1992). "Humanization of an Anti-p185HER2 Antibody for Human Cancer Therapy," Proc. Natl. Acad. Sci., USA 89:4285-4289.

(56) References Cited

OTHER PUBLICATIONS

Chan et al., (2010). "Therapeutic antibodies for autoimmunity and inflammation," Nat. Rev. Immunol., 10:301-316.
Chang et al., (2002). "Retinal Degeneration Mutants In The Mouse," Vision Research, 42:517-525.
Chen et al., (1999). "Selection and analysis of an optimized anti-VEGF antibody: crystal structure of an affinity-matured Fab in complex with antigen," J. Mol. Biol., 293:865-881.
Cheung, et al., (1990). "Epitope-specific antibody response to the surface antigen of duck hepatitis B virus in infected ducks," Virology, 176:546-552.
Chothia et al., (1987). "Canonical Structures for the Hypervariable Regions of Immunoglobulins," J. Mol. Biol,, 196:901-917.
Chu et al., (2008; e-pub. Aug. 8, 2008). "Inhibition of B cell Receptor-Mediated Activation of Primary Human B Cells by Coengagement of CD19 and FcγRIIb with Fc-Engineered Antibodies," Molecular Immunology, 45:3926-3933.
Clackson et al., (1991). "Making Antibody Fragments Using Phage Display Libraries," Nature, 352(15):624-628.
Cole et al., (1999). "HuM291, A Humanized Anti-Cd3 Antibody is Immunosuppressive to T Cells While Exhibiting Reduced Mitogenicity in Vitro," Transplantation, 68(4):563-571.
Compston et al., (2008). "Multiple Sclerosis," Lancet 372(9648):1502-1517.
Correale et al., (2013). "Bacterial Sensor Triggering Receptor Expressed on Myeloid Cells-2 Regulates the Mucosal Inflammatory Response," Gastroenterology, 144(2):346-356.
Crocker et al., (1999). "Molecular Analysis of Sialoside Binding to Sialoadhesin by NMR and Site-Directed Mutagenesis," Biochem, J. 341 (Pt. 2):355-361.
Crocker et al., (2007). "Siglecs and their Roles in the Immune System," Nat Rev Immunol., 7(4):255-266.
Crocker et al., (Apr. 2012; e-published on Feb. 21, 2012). "CD33-related Siglecs as Potential Modulators of Inflammatory Responses," Ann. NY Acad. Sci., 1253:102-111.
Crocker et al., (Jun. 1, 2001). "Siglecs, Sialic Acids and Innate Immunity," Trends Immunol., 22(6):337-342.
Cruts et al., (2008, e-pub. Mar. 6, 2008). "Loss of Progranulin Function in Frontotemporal Lobar Degeneration," Trends Genetics, 24(4):186-194.
Cunningham et al., (1989). "High-Resolution Epitope Mapping Of hGH-Receptor Interactions By Alanine-Scanning Mutagenesis," Science, 244:1081-1085.
Daeron, M., (1997). "FC Receptor Biology," Annu. Rev. Immunol., 15:203-234.
Dall' Acqua et al., (2006). "Properties of Human IgG1s Engineered for Enhanced Binding to the Neonatal Fc Receptor (FcRn)," The Journal Of Biological Chemistry, 281(33):23514-23524.
Daneman et al., (2010). "The Mouse Blood-Brain Barrier Transcriptome: A New Resource for Understanding the Development and Function of Brain Endothelial Cells," PloS One, 5(10):e13741, 16 pages.
Davis et al., (2007). "Abatacept Binds To The Fc Receptor Cd64 But Does Not Mediate Complement-Dependent Cytotoxicity Or Antibody-Dependent Cellular Cytotoxicity," The Journal of Rheumatology, 34(11):2204-2210.
De Haas et al., (1995). "Fcγ Receptors of Phagocytes," J. Lab. Clin. Med., 126(4):330-341.
Declaration of Dr. Anna Griciuc submitted before the USPTO Patent Trial and Appeal Board for U.S. Appl. No. 15/906,681, filed Feb. 27, 2018, dated Aug. 15, 2019, 7 pages.
Ducry et al., (Jan. 2010; e-published on Sep. 21, 2009). "Antibody-Drug Conjugates: Linking Cytotoxic Payloads to Monoclonal Antibodies," Bioconjugate Chemistry, 21(1):5-13.
Edwards et al., (2003). "The remarkable flexibility of the human antibody repertoire; isolation of over one thousand different antibodies to a single protein, BlyS," J. Mol. Biol., 334:103-118.
Eksioglu et al., (2014). "Novel Therapeutic Approach to Improve Hematopoiesis by Targeting Myeloid Derived Suppressor Cells with a Humanized Anti-CD33 Antibody," Blood 124(21):4597, located at <http://www.bloodjournal.org/content/124/21/4597>, last visited on Jan. 5, 2017, 3 pages.
El-Danaf et al., (2015). "Characteristic Patterns of Dendritic Remodeling in Early-Stage Glaucoma: Evidence from Genetically Identified Retinal Ganglion Cell Types," The Journal of Neuroscience, 35(6):2329-2343.
Estep et al., (2013). "High Throughput Solution-Based Measurement Of Antibody-Antigen Affinity And Epitope Binning," mAbs,. 5(2):270-278.
Estus et al., (2013). "Protective Allele Of Cd33 Gwas Snp Decreases Inclusion Of Exon Encoding Ligand Binding Domain; Are Cd33 Antagonists Ad Therapeutics?" 1 page. (Abstract Only).
Etemad et al., (2012). "A Novel In Vitro Human Microglia Model: Characterization of Human Monocyte-Derived Microglia," Journal of Neuroscience Methods, 209:79-89.
Fahnestock et al., (2001). "The Precursor Pro-Nerve Growth Factor Is the Predominant Form of Nerve Growth Factor in Brain and Is Increased in Alzheimer's Disease," Molecular and Cellular Neuroscience, 18:210-220.
Fan, Y. J., (2008). "Differential effects of Pro-BDNF on Sensory Neurons after Sciatic Nerve Transection in Neonatal Rats," European Journal of Neuroscience, 27:2380-2390.
Fasen et al., (Feb. 2008; e-published on Dec. 19, 2007). "Ligand Binding Induces Cbl-Dependent EphB1 Receptor Degradation Through the Lysosomal Pathway," Traffic, 9(2):251-266.
Feldhaus et al., (2004, e-pub. May 31, 2004). "Yeast Display of Antibody Fragments: A Discovery and Characterization Platform," Journal of Immunological Methods, 290:69-80.
Fellouse et al., (2004). "Synthetic Antibodies from a Four-Amino-Acid Code: A Dominant Role for Tyrosine in Antigen Recognition," PNAS, 101(34):12467-12472.
Ferlazzo et al., (2000). "Engagement Of CD33 Surface Molecules Prevents the Generation of Dendritic Cells From Both Monocytes and CD34+ Myeloid Precursors," Eur J Immunol., 30:827-833.
Fishwild et al., (1996). "High-Avidity Human Iggκ Monoclonal Antibodies from a Novel Strain of Minilocus Transgenic Mice," Nature Biotechnology, 14:845-851.
Gabathuler, R. (2010, e-pub. Aug. 5, 2009). "Approaches to Transport Therapeutic Drugs across the Blood-Brain Barrier to Treat Brain Diseases," Neurobiology of Disease, 37:48-57.
Gawish et al., (Apr. 2015; e.pub Dec. 4, 2014). "Triggering Receptor Expressed on Myeloid cells-2 Fine-Tunes Inflammatory Responses in Murine Gram-Negative Sepsis," The FASEB Journa,l 29(4):1247-1257.
Gerngross, T.U. (Nov. 2004, e-pub. Nov. 4, 2004). "Advances in the Production of Human Therapeutic Proteins in Yeasts and Filamentous Fungi," Nature Biotechnology, 22(11):1409-1414.
Graham et al., (1977). "Characteristics of a Human Cell Line Transformed by DNA from Human Adenovirus Type 5," Journal of General Virology, 36:59-72.
Griciuc et al., (May 22, 2013; e-published on Apr. 25, 2013). "Alzheimer's Disease Risk Gene CD33 Inhibits Microglial Uptake of Amyloid Beta," Neuron, 78(4):631-643.
Griffin et al., (1984). "A Monoclonal Antibody Reactive with Normal and Leukemic Human Myeloid Progenitor Cells," Leukemia Research, 8(4):521-534.
Griffiths et al., (1993). "Human Anti-Self Antibodies with High Specificity from Phage Display Libraries," The EMBO Journal, 12(2):725-734.
Grobe et al., (2002). "Role of Protein Kinase C in the Phosphorylation of CD33 (Siglec-3) and its Effect on Lectin Activity," Blood, 99(9):3188-3196.
Gruber et al., (1994). "Efficient Tumor Cell Lysis Mediated by a Bispecific Single Chain Antibody Expressed in *Escherichia Coli*," The Journal of Immunology, 152(11):5368-5374.
Gupta et al., (2003). "Activated Microglia in Human Retinitis Pigmentosa, Late-Onset Retinal Degeneration, and Age-Related Macular Degeneration," Experimental Eye Research, 76(4):463-471.

(56) References Cited

OTHER PUBLICATIONS

Hamann et al., (2002, e-pub. Dec. 19, 2001). "Gemtuzumab Ozogamicin, A Potent and Selective Anti-CD33 Antibody-Calicheamicin Conjugate for Treatment of Acute Myeloid Leukemia," Bioconjugate Chemistry, 13(1):47-58.
Hamers-Casterman et al., (1993). "Naturally Occurring Antibodies Devoid of Light Chains," Nature, 363:446-448.
Handgretinger et al., (1993). "Expression of an Early Myelopoietic Antigen (CD33) of a Subset of Human Umbilical Cord Blood-Derived Natural Killer Cells," Immunol Lett., 37(2-3):223-228.
Harrington et al., (2004). "Secreted proNGF is a Pathophysiological Death-Inducing Ligand After Adult CNS Injury," Proc. Natl. Acad. Sci USA 101(16):6226-6230.
Harris, W.J. (1995). "Therapeutic Monoclonals—Production of Humanized Monoclonal Antibodies for In Vivo Imaging and Therapy," Biochem. Soc. Transactions, 23(4):1035-1038.
Hawkins et al., (1992). "Selection of Phage Antibodies by Binding Affinity: Mimicking Affinity Maturation," Journal of Molecular Biology, 226:889-896.
Heider et al., (2012). "A Novel Fc-Engineered Antibody to CD33 with Enhanced ADCC Activity for Treatment of AML," Blood, 120(21):1363, located at <http://www.bloodjournal.org/content/120/21/1363>, last visited on Jan. 5, 2017, 5 pages.
Hernández-Caselles et al., (2006). "A Study of CD33 (SIGLEC-3) Antigen Expression and Function on Activated Human T and NK Cells: Two Isoforms of CD33 are Generated by Alternative Splicing," J Leukoc Biol., 79(1):46-58.
Hezareh et al., (2001). "Effector Function Activities of a Panel of Mutants of a Broadly Neutralizing Antibody against Human Immunodeficiency Virus Type 1," Journal of Virology, vol. 75(24):12161-12168.
Holliger et al., (1993). ""Diabodies": Small Bivalent and Bispecific Antibody Fragments," Proceedings of the National Academy of Sciences, 90:6444-6448.
Hollingworth et al., (May 2011; e-published on Apr. 3, 2011). "Common Variants in ABCA7, MS4A6A/MS4A4E, EPHA1, CD33 and CD2AP are Associated with Alzheimer's Disease," Nat. Genet., 43(5):429-435.
Hongo et al., (1995). "Development and Characterization of Murine Monoclonal Antibodies to the Latency-Associated Peptide of Transforming Growth Factor β1," Hybridoma, 14(3):253-260.
Hoogenboom et al., (1992). "By-Passing Immunisation. Human Antibodies from Synthetic Repertoires of Germline Hh Gene Segments Rearranged in Vitro," Journal of Molecular Biology, 227:381-388.
Hoyer et al., (2008). "CD33 Detection by Immunohistochemistry in Paraffin-Embedded Tissues: A New Antibody Shows Excellent Specificity and Sensitivity for Cells of Myelomonocytic Lineage," Am. J. Clin. Pathol., 129(2):316-323.
Hudson et al. (2003). "Engineered Antibodies," Nat. Med. 9(1):129-134.
Humphrey et al., (2006). "TREM2, a DAP12-Associated Receptor, Regulates Osteoclast Differentiation and Function," J Bone Miner Res., 21(2):237-245.
Hurle et al., (1994). "Protein Engineering Techniques for Antibody Humanization," Current Opinion in Biotechnology, 5:428-433.
Hutchins et al., (1995). "Improved Biodistribution, Tumor Targeting, and Reduced Immunogenicity in Mice with a Gamma 4 Variant of Campath-IH," Proc. Natl. Acad. Sci., 92:11980-11984.
Hutton et al., (1998). "Association of Missense and 5'-Splice-Site Mutations in Tau with the Inherited Dementia FTDP-17," Nature, 393:702-705.
Imai et al., (2006). "Comparing antibody and small-molecule therapies for cancer," Nat. Rev. Cancer, 6:714-727.
Ito et al., (2008). "NOD/Shi-scid IL2rγnull (NOG) Mice More Appropriate for Humanized Mouse Models," Curr Top Microbiol Immunol., 324:53-76.
Ito et al., (May 2012; e-published on Feb. 13, 2012). "Current Advances in Humanized Mouse Models," Cellular & Molecular Immunology, 9(3):208-214.

Jackson et al., (1995). "In Vitro Antibody Maturation. Improvement of a High Affinity, Neutralizing Antibody against IL-1 Beta," The Journal of Immunology, 157(7):3310-3319.
Jakobovits et al., (1993) "Germ-line Transmission and Expression of a Human-derived Yeast Artificial Chromosome," Nature, 362:255-258.
Jakobovits et al., (1993). "Analysis of Homozygous Mutant Chimeric Mice: Deletion of The Immunoglobulin Heavy-chain Joining Region Blocks B-Cell Development and Antibody Production," Proceedings of the National Academy of Sciences, 90:2551-2555.
Jandus et al., (Aug. 15, 2011; e-published on May 31, 2011). "Targeting Siglecs—A Novel Pharmacological Strategy For Immuno- and Glycotherapy," Biochem. Pharmacol., 82(4):323-332.
Jansen et al., (Nov. 2007, e-pub. Oct. 14, 2007). "Roles for the Pro-Neurotrophin Receptor Sortilin in Neuronal Development, Aging and Brain Injury," Nature Neuroscience, 10(11):1449-1457.
Jiang et al., (2014). "CD33 in Alzheimer's Disease," Mol. Neurobiol., 49:529-535.
Johnson et al., (1993). "Human antibody engineering: Current Opinion in Structural Biology," Current Opinion in Structural Biology, 3(4):564-571.
Jones et al., (1986). "Replacing the Complementarity-Determining Regions in a Human Antibody with Those from a Mouse," Nature, 321:522-525.
Jurcic, J.G., (Mar. 2012, e-pub. Nov. 23, 2011). "What Happened to Anti-CD33 Therapy for Acute Myeloid Leukemia?," Curr Hematol Malig Rep, 7(1):65-73.
Karch et al., (2012). "Expression of Novel Alzheimer's Disease Risk Genes in Control and Alzheimer's Disease Brains," PLOS One, 7(11):1-9.
Kelm et al., (1994). "Sialoadhesin, Myelin-Associated Glycoprotein and CD22 Define a New Family of Sialic Acid-Dependent Adhesion Molecules of the Immunoglobulin Superfamily," Current Biology, 4(11):965-972.
Keren-Shaul et al., (2017). "A Unique Microglia Type Associated with Restricting Development of Alzheimer's Disease," Cell, 169:1276-1290.
Kirkland et al., (1986). "Analysis of the fine specificity and cross-reactivity of monoclonal anti-lipid A antibodies," J. Immunol., 137:3614-3619.
Koga et al., (2004). "Costimulatory Signals Mediated by the ITAM Motif Cooperate with RANKL for Bone Homeostasis," Nature, 428:758-763.
Köhler et al., (1975). "Continuous Cultures of Fused Cells Secreting Antibody of Predefined Specificity," Nature, 256:495-497.
Kostelny et al., (1992). "Formation of a Bispecific Antibody by the Use of Leucine Zippers," The Journal of Immunology, 148(5):1547-1553.
Kozbor et al., (1984). "A Human Hybrid Myeloma for Production of Human Monoclonal Antibodies," The Journal of Immunology, 133(6):3001-3005.
Laird et al., (2010). "Progranulin is Neurotrophic in Vivo and Protects against a Mutant TDP-43 Induced Axonopathy," PLOS One, 5(10):e13368, 7 pages.
Lajaunias et al., (Jan. 2005; e-published on Dec. 16, 2004). "Constitutive Repressor Activity of CD33 on Human Monocytes Requires Sialic Acid Recognition and Phosphoinositide 3-Kinase-Mediated Intracellular Signaling," Eur J Immunol., 35(1):243-251.
Langer, R., (1990). "New Methods of Drug Delivery," Science 249(4976):1527-1533.
Lartigue, J.D. (2012). "Antibody-Drug Conjugates: Guided Missiles Deployed Against Cancerous Cells," OncologyLive, available online at <https://www.onclive.com/view/antibody-drug-conjugates-guided-missiles-deployed-against-cancerous-cells>, Obtained on Nov. 27, 2018, 4 pages.
Lavail et al., (2011). "Retinal Degeneration Rat Model Resource Availability of P23H and S334ter Mutant Rhodopsin Transgenic Rats and RCS Inbred and RCS Congenic Strains of Rats," University of California, 12 pages.
Lazar et al., (2006). "Engineered Antibody Fc variants with Enhanced Effector Function," PNAS, 103(11):4005-4010.

(56) References Cited

OTHER PUBLICATIONS

Lee et al., (2003). "Bivalent Antibody Phage Display Mimics Natural Immunoglobulin," Journal of Immunological Methods, 284(1-2):119-132.
Lee et al., (2004). "High-affinity Human Antibodies from Phage-displayed Synthetic Fab Libraries with a Single Framework Scaffold," Journal of Molecular Biology, 340:1073-1093.
Li et al., (2006). "Human Antibodies for Immunotherapy Development Generated via a Human B Cell Hybridoma Technology," PNAS, 103(10):3557-3562.
Li et al., (2006). "Optimization of Humanized IgGs in Glycoengineered Pichia Pastoris," Nature Biotechnology, 24(2):210-215.
Li et al., (Aug. 19, 2011). "Inhibitory Fcgamma Receptor Engagement Drives Adjuvant and Anti-Tumor Activities of Agonistic CD40 Antibodies," Science, 333(6045):1030-1034.
Lightle et al., (Mar. 24, 2010; e-published on Jan. 29, 2010). "Mutations Within a Human Lgg2 Antibody Form Distinct and Homogeneous Disulfide Isomers but do not Affect Fc Gamma Receptor or C1q Binding," Protein Science, 19:753-762.
Lipovsek et al., (2004, e-pub. May 31, 2004). "In-vitro protein evolution by ribosome display and mRNA display," Journal of Immunological Methods, 290:51-67.
Lloyd et al., (2009). "Modelling the human immune response: performance of a 1011 human antibody repertoire against a broad panel of therapeutically relevant antigens," Protein Eng. Design & Select, 22(3):159-168.
Lonberg et al., (1994). "Antigen-Specific Human Antibodies from Mice Comprising Four Distinct Genetic Modifications," Nature, 368:856-859.
Lonberg et al., (1995). "Human Antibodies from Transgenic Mice," International Reviews of Immunology., 13:65-93.
Lonberg. (2008). "Fully Human Antibodies From Transgenic Mouse and Phage Display Platforms," Curr. Opin. Immunol. 20(4):450-459.
Low et al., (2013). "Animal Models of Ulcerative Colitis and their Application in Drug Research," Drug Design, Development and Therapy, 7:1341-1357.
LüTje et al., (2014). "Anti-CEA Antibody Fragments Labeled with [18F]AlF for PET Imaging of CEA-Expressing Tumors," Bioconjugate Chemistry, 25(2):335-341.
Macauley et al., (Oct. 2014; e-published on Sep. 19, 2014). "Siglec Regulation of Immune Cell Function in Disease," Nature Reviews Immunology, 14(10):653-666, 29 pages.
Malik et al., (2013). "CD33 Alzheimer's Risk-Altering Polymorphism, CD33 Expression, and Exon 2 Splicing," J. Neurosci, 33(33):13320-13325.
Malik et al., (Nov. 1, 2015; e-published on Aug. 6, 2015). "VPS35 Pathogenic Mutations Confer no Dominant Toxicity but Partial Loss of Function in *Drosophila* and Genetically Interact With Parkin," Human Molecular Genetics, 24(21):6106-6117.
Marks et al., (1991). "By-passing immunization: Human antibodies from V-gene libraries displayed on phage," Journal of Molecular Biology, 222(3): 581-597.
Marks et al., (1992)."By-Passing Immunization: Building High Affinity Human Antibodies By Chain Shuffling," Bio/Technology, 10:779-782.
Martens et al., (2012). "Progranulin Deficiency Promotes Neuroinflammation and Neuron Loss Following Toxin-Induced Injury," The Journal of Clinical Investigation, 122(11):3955-3959.
Mather et al., (1982). "Culture of Testicular Cells in Hormone-Supplemented Serum-Free Medium," Annals of the New York Academy of Sciences, Testicular Cell Culture, 383:44-68.
Mather, J.P. (1980). "Establishment and Characterization of Two Distinct Mouse Testicular Epithelial Cell Lines," Biology of Reproduction, 23:243-252.
May et al., (1998). "Crystal Structure of the N-Terminal Domain of Sialoadhesin in Complex with 3' Sialyllactose at 1.85 A Resolution," Molecular Cell, 1(5):719-728.
Mccafferty et al., (1990). "Phage Antibodies: Filamentous Phage Displaying Antibody Variable Domains," Nature, 348:552-554.

Mcearchern et al., (Feb. 1, 2007, e-pub. Oct. 12, 2006). "Engineered Anti-CD70 Antibody with Multiple Effector Functions Exhibits in Vitro and in Vivo Antitumor Activities," Blood, 109(3):1185-1192.
Mcmillan et al., (Aug. 11, 2008; e-published on Jan. 17, 2008). "CD33-related Sialic-Acid-Binding Immunoglobulin-Like Lectins in Health and Disease," Carbohydrate Research, 343(12):2050-2056.
Milstein et al., (Oct. 6, 1983). "Hybrid Hybridomas and their use in Immunohistochemistry," Nature, 305:537-540.
Mizoguchi, A. (2012). "Animal Models of Inflammatory Bowel Disease," Progress in Molecular Biology and Translational Science, 105:263-320, fifty eight pages.
Moldenhauer et al., (1990). "Identity of HML-1 antigen on intestinal intraepithelial T cells and of B-ly7 antigen on hairy cell leukaemia," Scand. J. Immunol., 32:77-82.
Monsonego-Oran et al., (Sep. 25, 2002; e-published on Aug. 28, 2002). "FGF Receptors Ubiquitylation: Dependence on Tyrosine Kinase Activity and Role in Downregulation," FEBS Letters, 528(1-3):83-89.
Morel et al., (1988). "Monoclonal antibodies to bovine serum albumin: affinity and specificity determinations," Molec. Immunol., 25:7-15.
Morimoto et al., (1992). "Single-Step Purification of F(ab')2 Fragments of Mouse Monoclonal Antibodies (Immunoglobulins G1) by Hydrophobic Interaction High Performance Liquid Chromatography Using TSKgel Phenyl-5PW," Journal of Biochemical and Biophysical Methods, 24:107-117.
Morrison et al., (Nov. 1984). "Chimeric Human Antibody Molecules: Mouse Antigen-binding Domains with Human Constant Region Domains," Proc. Nat'l Acad. Sci, 81:6851-6855.
Morrison, S.L. (Apr. 28, 1994). "Success in Specification," Nature, 368:812-813.
Mortland et al., (Feb. 26, 2013). "Clinical Significance of CD33 Nonsynonymous SingleNucleotide Polymorphisms in Pediatric Patients with Acute Myeloid Leukemia Treated with Gemtuzumab-Ozogamicin-Containing Chemotherapy," Clin Cancer Res, pp. 1-8.
Munson et al., (1980). "Ligand: A Versatile Computerized Approach for Characterization of Ligand-binding Systems," Analytical Biochemistry, 107:220-239.
Naito et al., (2000). "Calicheamicin-Conjugated Humanized Anti-CD33 Monoclonal Antibody (gemtuzumab zogamicin, CMA-676) Shows Cytocidal effect on CD33-Positive Leukemia Cell Lines, But is Inactive on P-glycoprotein-Expressing sublines," Leukemia, 14:1436-1443.
Naj et al., (May 2011; e-published on Apr. 3, 2011). "Common Variants in MS4A4/MS4A6E, CD2uAP, CD33, and EPHA1 are Associated with Late-onset Alzheimer's Disease," Nat Genet., 43(5):436-441, 17 pages.
Nakamura et al., (2007)."Intracellular Sortilin Expression Pattern Regulates proNGF-Induced Naturally Occurring Cell Death during Development," Cell Death and Differentiation, 14:1552-1554.
NCBI Blast RID-WN0V0GA1114, Seq ID No. 1 vs. murine CD33, submitted Apr. 12, 2020, 3 pages.
Neary et al., (1998). "Frontotemporal Lobar Degeneration: A Consensus on Clinical Diagnostic Criteria," Neurology, 51:1546-1554.
Neuberger, M., (1996). "Generating high-avidity human Mabs in mice," Nature Biotechnology, 14:826, 1 page.
Neumann et al., (2007). "TDP-43 Proteinopathy in Frontotemporal Lobar Degeneration and Amyotrophic Lateral Sclerosis," Arch Neurol., 64(10):1388-1394.
Novack et al., (2008). "The Osteoclast: Friend or Foe?," Annu. Rev. Pathol. Mech. Dis., 3:457-484.
Nykjaer et al., (2004). "Sortilin is Essential for proNGF Induced Neuronal Cell Death," Nature, 427:843-848.
Nykjaer et al., (2005, e-pub. Jan. 26, 2005). "p75NTR—Live or Let Die," Current Opinion in Neurobiology, 15:49-57.
Oganesyan et al., (2008). "Structural characterization of a Human Fc Fragment Engineered for Lack of Effector Functions," Acta Crystallography, 64:700-704.
Ohgidani et al., (2014). "Direct induction of ramified microglia-like cells from human monocytes: Dynamic microglial dysfunction in Nasu-Hakola disease," Scientific Reports, 4(Article No. 4957):1-7.

(56) References Cited

OTHER PUBLICATIONS

O'reilly et al., (May 2009; e-published on Apr. 7, 2009). "Siglecs as Targets for Therapy in Immune Cell Mediated Disease," Trends Pharmacol. Sci., 30(5):240-248, 23 pages.
Otero et al., (2012; e-published on Feb. 6, 2012). "TREM2 and β-Catenin Regulate Bone Homeostasis by Controlling the Rate of Osteoclastogenesis," J Immunol, 188:2612-2621.
Park et al., (2015). "Triggering Receptor Expressed on Myeloid Cells 2 (TREM2) Promotes Adipogenesis and Diet-Induced Obesity," Diabetes, 64:117-127.
Paul et al., (2000). "Myeloid Specific Human CD33 is an Inhibitory Receptor With Differential ITIM Function in Recruiting the Phosphatases SHP-1 and SHP-2," Blood, 96(2):483-490.
Peiper et al., (1988). "Molecular Cloning, Expression, and Chromosomal Localization of a Human Gene Encoding the CD33 Myeloid Differentiation Antigen," Blood, 72(1):314-321.
Peng et al., (2010). "TREM2- and DAP12-Dependent Activation of PI3K Requires DAP10 and Is Inhibited by SHIP1," Science Signaling, 3(122):ra38, pp. 1-15.
Pennesi et al., (2012). "Animal Models of Age Related Macular Degeneration," Molecular Aspects of Medicine, 33(4):487-509, forty pages.
Pérez-Oliva et al., (Jun. 1, 2011; e-published on Jan. 28, 2011). "Epitope Mapping, Expression and Post-Translational Modifications of Two Isoforms Of CD33 (CD33M and CD33m) on Lymphoid and Myeloid Human Cells," Glycobiology, 21(6):757-770.
Peters, S.J. et al. (2012). "Engineering an Improved IgG4 Molecule with Reduced Disulfide Bond Heterogeneity and Increased Fab Domain Thermal Stability," The Journal of Biological Chemistry 287(29):24525-24533.
Pillai et al., (2012; Jan. 3, 2012). "Siglecs and Immune Regulation," Annu. Rev. Immunol., 30:357-392.
Plückthun, A., (1992). "Mono- and Bivalent Antibody Fragments Produced in *Escherichia coli*: Engineering, Folding and Antigen Binding," Immunological Reviews, 130:151-188.
Poduslo et al., (1994). "Macromolecular Permeability Across the Blood-Nerve and Blood-Brain Barriers," Proc. Natl. Acad. Sci. USA, 91:5705-5709.
Pollenz et al., (Dec. 1, 2006, e-pub. Aug. 25, 2006). "Ligand-Dependent and -Independent Degradation of the Human Aryl Hydrocarbon Receptor (hAHR) in Cell Culture Models," Chemico-Biological Interactions, 164(1-2):49-59.
Presta et al., (1993). "Humanization of an Antibody Directed Against IgE," The Journal of Immunology, 151(5):2623-2632.
Presta, L.G., (1992). "Antibody Engineering," Current Opinion in Structural Biology, 2:593-596.
Provenzano, M.J., (2008). "p75NTR and Sortilin Increase After Facial Nerve Injury," Laryngoscope, 118:87-93.
Raj et al., (May 15, 2014; e-published on Dec. 30, 2013). "CD33: Increased Inclusion of Exon 2 Implicates the Ig V-Set Domain in Alzheimer's Disease Susceptibility," Human Molecular Genetics, 23(10):2729-2736.
Ratnavalli et al., (2002). "The Prevalence of Frontotemporal Dementia," Neurology, 58(1 of 2):1615-1621.
Ravetch et al., (1991). "Fc Receptors," Annual Review Immunology, 9:457-492.
Reddy et al., (2000). "Elimination of Fc Receptor-Dependent Effector Functions of a Modified IgG4 Monoclonal Antibody to Human CD4," The Journal of Immunology, 164:1925-1933.
Ricart, A.D., (2011). "Antibody-Drug Conjugates of Calicheamicin Derivative: Gemtuzumab Ozogamicin and Inotuzumab Ozogamicin," Clin Cancer Res, 17(20):6417-6427.
Riechmann et al., (1988). "Reshaping Human Antibodies for Therapy," Nature, 332:323-327.
Roberts et al., (1997). "RNA-Peptide Fusions for the In Vitro Selection of Peptides and Proteins," Proc. Natl. Acad. Sci. USA, 94:12297-12302.
Rollins-Raval et al., (May 2012; e-published on Feb. 20, 2012). "The Value of Immunohistochemistry for CD14, CD123, CD33, Myeloperoxidase And CD68R in the Diagnosis of Acute and Chronic Myelomonocytic Leukaemias," Histopathology, 60(6):933-942.
Rosok et al., (1996). "Combinatorial Library Strategy for the Rapid Humanization of Anticarcinoma BR96 Fab," The Journal of Biological Chemistry, 271(37):22611-22618.
Sazinsky et al., (2008). "Aglycosylated Immunoglobulin G1 Variants Productively Engage Activating Fc Receptors," PNAS, 105(51):20167-20172.
Schabbauer et al., (2010). "Myeloid PTEN Promotes Inflammation but Impairs Bactericidal Activities During Murine Pneumococcal Pneumonia," The Journal of Immunology, 185(1):468-476.
Schaffitzel et al., (1999). "Ribosome Display: An In Vitro Method for Selection and Evolution of Antibodies from Libraries," Journal of Immunological Methods, 231:119-135.
Schier et al., (1996). "Identification of Functional and Structural Amino-Acid Residues by Parsimonious Mutagenesis," Gene, 169:147-155.
Schymick et al., (2007). "Progranulin Mutations and Amyotrophic Lateral Sclerosis or Amyotrophic Lateral Sclerosis-Frontotemporal Dementia Phenotypes," Journal of Neurology, Neurosurgery and Psychiatry, 78:754-756.
Seno et al., (2009). "Efficient Colonic Mucosal Wound Repair Requires Trem2 Signaling," PNAS, 106(1):256-261.
Shalaby et al., (1992). "Development of Humanized Bispecitic Antibodies Reactive with Cytotoxic Lymphocytes and Tumor Cells Overexpressing the HER2 Protooncogene," The Journal of Experimental Medicine, 175:217-225.
Sharif et al., (2014). "The Triggering Receptor Expressed on Myeloid Cells 2 Inhibits Complement Component 1 q Effector Mechanisms and Exerts Detrimental Effects during Pneumococcal Pneumonia," PLoS Pathogen, 10(6):e1004167, sixteen pages.
Sheriff et al., (1996). "Redefining the Minimal Antigen-binding Fragment," Nature Structural & Molecular Biology, 3(9):733-736.
Shields et al., (2001). "High Resolution Mapping of the Binding Site on Human IgG1 for FcγRI, FcγRII, FcγRIII, and FcRn and Design of IgG1 Variants with Improved Binding to the FcγR," The Journal Of Biological Chemistry, 276(9):6591-6604.
Sidhu et al., (2004). "Phage-displayed Antibody Libraries of Synthetic Heavy Chain Complementarity Determining Regions," Journal of Molecular Biology, 338(2):299-310.
Sieber et al., (2013). "Attenuated Inflammatory Response in Triggering Receptor Expressed on Myeloid Cells 2 (TREM2) Knock-Out Mice following Stroke," PLoS One, 8(1):e52982, 10 pages.
Simmons et al., (1988). "Isolation of a cDNA Encoding CD33, a Differentiation Antigen of Myeloid Progenitor Cells," J Immunol., 141(8):2797-2800.
Sims et al., (1993). "A Humanized CD18 Antibody Can Block Function Without Cell Destruction," The Journal of Immunology, 151(4):2296-2308.
Siolas et al., (2013). "Patient-Derived Tumor Xenografts: Transforming Clinical Samples into Mouse Models," Cancer Research, 73(17):5315-5319.
Skerra, A., (1993). "Bacterial Expression of Immunoglobulin Fragments," Current Opinion in Immunology, 5:256-262.
Sollid et al., (2008). "Animal Models of Inflammatory Bowel Disease at the Dawn of the New Genetics Era," PLoS Med, 5(9):1338-1342(e198).
Strohl, W.R., (2009; e-published on Nov. 4, 2009). "Optimization of Fc-mediated Effector Functions of Monoclonal Antibodies," Current Opinion in Biotechnology, 20:685-691.
Sun et al., (2013). "TREM-2 Promotes Host Resistance Against Pseudomonas aeruginosa Infection by Suppressing Corneal Inflammation via a PI3K/Akt Signaling Pathway," Investigative Ophthalmology & Visual Science, 54(5):3451-3462.
Suresh et al., (1986). "Bispecific Monoclonal Antibodies from Hybrid Hybridomas," Methods In Enzymology, 121:210-228.
Sutherland et al., (Sep.-Oct. 2009; e-published Sep. 15, 2009). "Anti-Leukemic Activity of Lintuzumab (SGN-33) in Preclinical Models of Acute Myeloid Leukemia," MABS, 1(5):481-490.

(56) References Cited

OTHER PUBLICATIONS

Takahashi et al., (2005). "Clearance of Apoptotic Neurons Without Inflammation by Microglial Triggering Receptor Expressed on Myeloid Cells-2," Journal of Experimental Medicine, 201(4):647-657.
Takahashi et al., (2007). "TREM2-Transduced Myeloid Precursors Mediate Nervous Tissue Debris Clearance and Facilitate Recovery in an Animal Model of Multiple Sclerosis," Plos Med, 4(4):e124, pp. 0675-0689.
Tanaka et al., (2013). "Exacerbated Inflammatory Responses Related To Activated Microglia After Traumatic Brain Injury In Progranulin-Deficient Mice," Neuroscience, 231:49-60.
Tavaré et al., (2014). "Engineered Antibody Fragments for Immuno-PET Imaging of Endogenous CD8+ T Cells in Vivo," PNAS, 111(3):1108-1113.
Taylor et al., (1999). "The Myeloid-specific Sialic Acid-binding Receptor, CD33, Associates with the Protein-tyrosine Phosphatases, SHP-1 and SHP-2," Journal of Biological Chemistry, 274(17):11505-11512.
Teng et al., (2005). "ProBDNF Induces Neuronal Apoptosis via Activation of a Receptor Complex of p75 NTR and Sortilin," The Journal of Neuroscience, 25(22):5455-5463.
Traunecker et al., (1991). "Bispecific Single Chain Molecules (Janusins) Target Cytotoxic Lymphocytes on HIV Infected Cells," The EMBO Journal, 10(12):3655-3659.
Tutt et al., (1991). "Trispecific F(ab')3 Derivatives that Use Cooperative Signaling Via the TCR/CD3 Complex and CD2 to Activate and Redirect Resting Cytotoxic T Cells1," The Journal of Immunology, 147(1):60-69.
Ulyanova et al., (1999). "The Sialoadhesin CD33 is a Myeloid-Specific Inhibitory Receptor," Eur J Immunol., 29:3440-3449.
Urlaub et al., (1980). "Isolation of Chinese Hamster Cell Mutants Deficient in Dihydrofolate Reductase Activity," Proc. Natl. Acad. Sci., 77(7):4216-4220.
Vafa et al., (2014; e-published on Jul. 17, 2013). "An Engineered Fc Variant of an IgG Eliminates All Immune Effector Functions Via Structural Perturbations," Methods, 65:114-126.
Van Dijk et al., (2001). "Human Antibodies as Next Generation Therapeutics," Current Opinion in Chemical Biology, 5:368-374.
Varki et al., (Jan. 1, 2006; e-published on Jul. 13, 2005). "Siglecs—The Major Subfamily of I-Type Lectins," Glycobiology, 16(1):1R-27R.
Vasu et al. (Jun. 9, 2016, e-pub. Mar. 24, 2016). "Decitabine Enhances Anti-CD33 Monoclonal Antibody BI 836858-Mediated Natural Killer ADCC Against AML Blasts," Blood, 127(23):2879-2889.
Vaswani et al., (1998). "Humanized Antibodies as Potential Therapeutic Drugs," Annals of Allergy, Asthma & Immunology, 81:105-119.
Verhoeyen et al., (1988). "Reshaping Human Antibodies: Grafting an Antilysozyme Activity," Science, 239:1534-1536.
Vetrano et al., (2008). "Unique Role of Junctional Adhesion Molecule-A in Maintaining Mucosal Homeostasis in Inflammatory Bowel Disease," Gastroenterology, 135(1):173-184.
Vincent et al. (Dec. 2012, e-pub. Nov. 1, 2012). "Current Strategies in Antibody Engineering: Fc Engineering and pH-Dependent Antigen Binding, Bispecific Antibodies and Antibody Drug Conjugates," Biotechnol J., 7(12):1444-1450.
Vitale et al., (2001). "Surface Expression and Function of P75/AIRM-1 or CD33 in Acute Myeloid Leukemias: Engagement of CD33 Induces Apoptosis of Leukemic Cells," Proc Natl Acad Sci USA, 98(10):5764-5769.
Vollmers et al. (2005). "Death by Stress: Natural IgM-Induced Apoptosis," Methods Find. Exp. Clin. Pharmacol. 27(3):185-191.
Vollmers et al. (2005). "The "Early Birds": Natural IgM Antibodies and Immune Surveillance," Histol. Histopathol. 20(3):927-937.
Volosin et al., (2006). "Interaction of Survival and Death Signaling in Basal Forebrain Neurons: Roles of Neurotrophins and Proneurotrophins," The Journal of Neuroscience, 26(29):7756-7766.
Volosin et al., (2008). "Induction of Proneurotrophins and Activation of P75ntr-Mediated Apoptosis Via Neurotrophin Receptor-Interacting Factor in Hippocampal Neurons After Seizures," The Journal of Neuroscience, 28(39):9870-9879, 25 pages.
Von Gunten et al., (2008). "Basic and Clinical Immunology of Siglecs," Ann. NY Acad. Sci., 1143:61-82, 25 pages.
Walker et al., (Feb. 2015; e-published on Oct. 2, 2014). "Association of CD33 Polymorphism Rs3865444 With Alzheimer's Disease Pathology and CD33 Expression in Human Cerebral Cortex," Neurobiology of Aging, 36(2):571-582, 32 pages.
Wang et al., (Mar. 12, 2015; e-published on Feb. 26, 2015). "TREM2 Lipid Sensing Sustains the Microglial Response in an Alzheimer's Disease Model," Cell, 160(6):1061-1071.
Waterhouse et al., (1993). "Combinatorial Infection and In Vivo Recombination: A Strategy for Making Large Phage Antibody Repertoires," Nucleic Acids Research, 21(9):2265-2266.
Wei et al., (2007). "Enhanced Protein Expressions of Sortilin and p75NTR in Retina of Rat Following Elevated Intraocular Pressure-Induced Retinal Ischemia," Neuroscience Letters, 429(2-3):169-174.
White et al., (2015). "Conformation of the Human Immunoglobulin G2 Hinge Imparts Superagonistic Properties to Immunostimulatory Anticancer Antibodies," Cancer Cell, 27:138-148.
White et al., (Aug. 15, 2011, e-pub. Jul. 8, 2011). "Interaction with FcgammaRIIB is Critical for the Agonistic Activity of Anti-CD40 Monoclonal Antibody," J Immunol., 187(4):1754-1763.
Wiehr et al., (2014). "Pharmacokinetics and PET Imaging Properties of Two Recombinant Anti-PSMA Antibody Fragments in Comparison to their Parental Antibody," The Prostate, 74(7):743-755.
Wilkinson et al., (2013). "Monovalent IgG4 Molecules: Immunoglobulin Fc Mutations that Result in a Monomeric Structure," mAbs, 5(3):406-417.
Wilson et al., (2011). "An Fcγ Receptor-Dependent Mechanism Drives Antibody-Mediated Target-Receptor Signaling in Cancer Cells," Cancer Cell, 19:101-113.
Winter et al. (1994). "Making Antibodies by Phage Display Technology," Annu. Rev. Immunol. 12:433-455.
Xu et al., (2000). "Diversity in the CDR3 Region of VH Is Sufficient for Most Antibody Specificities," Immunity, 13:37-45.
Xu et al., (2000). "In Vitro Characterization of Five Humanized OKT3 Effector Function Variant Antibodies," Cellular Immunology, 200(1):16-26.
Xu et al., (2013). "Addressing Polyspecificity of Antibodies Selected from an in Vitro Yeast presentation system: a FACS-based, High-throughput Selection and Analytical Tool," Protein Engineering, Design & Selection, 26(10):663-670.
Yano et al., (2009)."Proneurotrophin-3 Is a Neuronal Apoptotic Ligand: Evidence for Retrograde-Directed Cell Killing," The Journal of Neuroscience, 29(47):14790-14802.
Yelton et al., (1995). "Affinity maturation of the BR96 anti-carcinoma antibody by codon- based mutagenesis," The Journal of Immunology, 155:1994-2004.
Yin et al., (2009). "Exaggerated Inflammation, Impaired Host Defense, and Neuropathology in Progranulin-Deficient Mice," J. Exp. Med., 207(1):117-128.
Zapata et al., (1995). "Engineering Linear F(ab')2 Fragments for Efficient Production in *Escherichia coli* And Enhanced Antiproliferative Activity," Protein Engineering Designs and Selections, 8(10):1057-1062.
Zhou et al., (2014). "Humanized NOD-SCID IL2rg-/- Mice as a Preclinical Model For Cancer Research and its Potential Use For Individualized Cancer Therapies," Cancer Letters, 344(1):13-19.
Zhu et al., (Sep. 15, 2014, e-pub. Jul. 31, 2014). "CSF1/CSF1 R Blockade Reprograms Tumor-Infiltrating Macrophages and Improves Response to T Cell Checkpoint Immunotherapy in Pancreatic Cancer Models," Cancer Research, 74(18):5057-5069.
Chinese Search Report search date Nov. 17, 2020 for Chinese Application No. 201680047246.1 filed on Jun. 11, 2016, 5 pages.
International Preliminary Report on Patentability mailed on Dec. 21, 2017 for International Application No. PCT/US2016/037108, filed on Jun. 11, 2016, 11 pages.

(56) References Cited

OTHER PUBLICATIONS

International Preliminary Report on Patentability mailed on Dec. 21, 2017 for International Application No. PCT/US2016/037109, filed on Jun. 11, 2016, 15 pages.
International Preliminary Report on Patentability mailed on Feb. 13, 2020 for International Application No. PCT/US2018/045056, filed on Aug. 2, 2018, 9 pages.
International Preliminary Report on Patentability mailed on Mar. 11, 2021 for International Application No. PCT/US2019/048994, filed on Aug. 30, 2019, 8 pages.
International Search Report and Written Opinion mailed on Dec. 6, 2016 for International Application No. PCT/US2016/037108, filed on Jun. 11, 2016, 16 pages.
International Search Report and Written Opinion mailed on Dec. 6, 2016 for PCT Application No. PCT/US2016/037109 filed on Jun. 11, 2016, 20 pages.
International Search Report and Written Opinion mailed on Nov. 13, 2018 for PCT Application No. PCT/US2018/045056 filed on Aug. 2, 2018, 16 pages.
International Search Report and Written Opinion mailed on Nov. 13, 2019 for PCT Application No. PCT/US2019/048994 filed on Aug. 30, 2019, 15 pages.
International Search Report and Written Opinion mailed on Oct. 25, 2013 for PCT Application No. PCT/US2013/041209 filed on May 15, 2013, 9 pages.

\* cited by examiner

SEQUENCE LISTING

<160> NUMBER OF SEQ ID NOS: 122

<210> SEQ ID NO 1
<211> LENGTH: 364
<212> TYPE: PRT
<213> ORGANISM: Homo sapiens

<400> SEQUENCE: 1

```
Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285
```

```
Ala Ala Arg Thr Ala Val Gly Arg Asn Asp Thr His Pro Thr Thr Gly
        290                 295                 300

Ser Ala Ser Pro Lys His Gln Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
                340                 345                 350

Asp Thr Ser Thr Glu Tyr Ser Glu Val Arg Thr Gln
                355                 360

<210> SEQ ID NO 2
<211> LENGTH: 379
<212> TYPE: PRT
<213> ORGANISM: Macaca fascicularis

<400> SEQUENCE: 2

Met Asp Gly Glu His Leu Lys Gly Arg Asn Gln Gly Ala Gln Glu Thr
1               5                   10                  15

Ser Ala Ser Asp Met Pro Leu Leu Leu Pro Leu Leu Trp Ala Gly
                20                  25                  30

Ala Leu Ala Met Asp Pro Arg Val Arg Leu Glu Val Gln Glu Ser Val
                35                  40                  45

Thr Val Gln Glu Gly Leu Cys Val Leu Val Pro Cys Thr Phe Phe His
        50                  55                  60

Pro Val Pro Tyr His Thr Arg Asn Ser Pro Val His Gly Tyr Trp Phe
65                  70                  75                  80

Arg Glu Gly Ala Ile Val Ser Leu Asp Ser Pro Val Ala Thr Asn Lys
                85                  90                  95

Leu Asp Gln Glu Val Gln Glu Thr Gln Gly Arg Phe Arg Leu Leu
                100                 105                 110

Gly Asp Pro Ser Arg Asn Asn Cys Ser Leu Ser Ile Val Asp Ala Arg
                115                 120                 125

Arg Arg Asp Asn Gly Ser Tyr Phe Phe Arg Met Glu Lys Gly Ser Thr
130                 135                 140

Lys Tyr Ser Tyr Lys Ser Thr Gln Leu Ser Val His Val Thr Asp Leu
145                 150                 155                 160

Thr His Arg Pro Gln Ile Leu Ile Pro Gly Ala Leu Asp Pro Asp His
                165                 170                 175

Ser Lys Asn Leu Thr Cys Ser Val Pro Trp Ala Cys Glu Gln Gly Thr
                180                 185                 190

Pro Pro Ile Phe Ser Trp Met Ser Ala Ala Pro Thr Ser Leu Gly Leu
                195                 200                 205

Arg Thr Thr His Ser Ser Val Leu Ile Ile Thr Pro Arg Pro Gln Asp
        210                 215                 220

His Gly Thr Asn Leu Thr Cys Gln Val Lys Phe Pro Gly Ala Gly Val
225                 230                 235                 240

Thr Thr Glu Arg Thr Ile Gln Leu Asn Val Ser Tyr Ala Ser Gln Asn
                245                 250                 255

Pro Arg Thr Asp Ile Phe Leu Gly Asp Gly Ser Gly Lys Gln Gly Val
                260                 265                 270

Val Gln Gly Ala Ile Gly Gly Ala Gly Val Thr Val Leu Leu Ala Leu
                275                 280                 285

Cys Leu Cys Leu Ile Phe Phe Thr Val Lys Thr His Arg Arg Lys Ala
```

```
                290                 295                 300

Ala Arg Thr Ala Val Gly Arg Ile Asp Thr His Pro Ala Thr Gly Pro
305                 310                 315                 320

Thr Ser Ser Lys His Gln Lys Lys Ser Lys Leu His Gly Ala Thr Glu
                325                 330                 335

Thr Ser Gly Cys Ser Gly Thr Thr Leu Thr Val Glu Met Asp Glu Glu
                340                 345                 350

Leu His Tyr Ala Ser Leu Asn Phe His Gly Met Asn Pro Ser Glu Asp
                355                 360                 365

Thr Ser Thr Glu Tyr Ser Glu Val Arg Thr Gln
                370                 375

<210> SEQ ID NO 3
<211> LENGTH: 120
<212> TYPE: PRT
<213> ORGANISM: Mus musculus

<400> SEQUENCE: 3

Glu Val Lys Leu Glu Glu Ser Gly Gly Gly Leu Val Gln Pro Gly Gly
1               5                   10                  15

Ser Met Lys Leu Ser Cys Val Gly Ser Gly Phe Thr Phe Ser Asn Tyr
                20                  25                  30

Cys Met Asn Trp Val Arg Gln Ser Pro Glu Lys Gly Leu Glu Trp Val
            35                  40                  45

Ala Glu Ile Arg Leu Lys Ser Asn Asn Tyr Val Thr Asn Tyr Val Glu
        50                  55                  60

Ser Val Lys Gly Arg Phe Thr Ile Ser Arg Asp Ser Lys Ser Arg
65                  70                  75                  80

Val Tyr Leu Gln Met Asn Asn Leu Arg Gly Glu Asp Thr Gly Phe Tyr
                85                  90                  95

Tyr Cys Thr Arg Asp Gly Tyr Tyr Val Pro Phe Ala Tyr Trp Gly Gln
                100                 105                 110

Gly Thr Leu Val Thr Val Ser Ala
            115                 120

<210> SEQ ID NO 4
<211> LENGTH: 115
<212> TYPE: PRT
<213> ORGANISM: Mus musculus

<400> SEQUENCE: 4

Gln Leu Val Leu Thr Gln Ser Ser Ser Ala Ser Phe Ser Leu Gly Ala
1               5                   10                  15

Ser Ala Lys Leu Thr Cys Thr Leu Ser Ser Gln His Ser Thr Tyr Thr
                20                  25                  30

Ile Glu Trp Tyr Gln Gln Pro Leu Lys Pro Pro Lys Tyr Val Met
            35                  40                  45

Glu Leu Lys Lys Asp Gly Ser His Ser Thr Gly Asp Gly Ile Pro Asp
        50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asp
                85                  90                  95

Thr Ile Lys Glu Gln Phe Val Tyr Val Phe Gly Gly Gly Thr Lys Val
                100                 105                 110

Thr Val Leu
```

```
<210> SEQ ID NO 5
<211> LENGTH: 30
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Pro Gly Gly
1               5                   10                  15
Ser Leu Arg Leu Ser Cys Ala Gly Ser Gly Phe Thr Phe Ser
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15
Ser Leu Arg Leu Ser Cys Ala Ala Ser Gly Ser Thr Phe Ser
            20                  25                  30

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct

<400> SEQUENCE: 8

Asn Tyr Cys Met Asn
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Glu Tyr Ala Met Asn
1               5

<210> SEQ ID NO 10
<211> LENGTH: 5
```

```
<212> TYPE: PRT
<213> ORGANISM: Artificial Sequence
<220> FEATURE:
<223> OTHER INFORMATION: Synthetic Construct

<400> SEQUENCE: 10

Asn Tyr Gly Met Asn
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Construct

<400> SEQUENCE: 11

Asn Tyr Phe Met Asn
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Asn Tyr Ala Met Asn
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

<400> SEQUENCE: 13

Asn Tyr Ser Met Asn
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Asn Tyr Leu Met Asn
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct

<400> SEQUENCE: 15

Asn Tyr Tyr Met Asn
1               5

<210> SEQ ID NO 16
<211> LENGTH: 5
<212> TYPE: PRT
```

```
<213> ORGANISM: Artificial Sequence
<220> FEATURE:
<223> OTHER INFORMATION: Synthetic Construct

<400> SEQUENCE: 16

Asn Tyr His Met Asn
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Asn Tyr Arg Met Asn
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Construct

<400> SEQUENCE: 18

Asn Tyr Pro Met Asn
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Asn Tyr Gln Met Asn
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Construct

<400> SEQUENCE: 20

Asn Tyr Thr Met Asn
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Construct

<400> SEQUENCE: 21

Asn Tyr Val Met Asn
1               5

<210> SEQ ID NO 22
<211> LENGTH: 5
<212> TYPE: PRT
<213> ORGANISM: Artificial Sequence
```

```
<220> FEATURE:
<223> OTHER INFORMATION: Synthetic Construct

<400> SEQUENCE: 22

Asn Tyr Asn Met Asn
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Construct

<400> SEQUENCE: 23

Asn Tyr Glu Met Asn
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Construct

<400> SEQUENCE: 24

Asn Tyr Ile Met Asn
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Construct

<400> SEQUENCE: 25

Asp Tyr Thr Met Asn
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct

<400> SEQUENCE: 26

Asp Tyr Ser Met Asn
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27

Ala Tyr Ser Met Asn
1               5

<210> SEQ ID NO 28
<211> LENGTH: 5
<212> TYPE: PRT
<213> ORGANISM: Artificial Sequence
<220> FEATURE:
```

-continued

```
<223> OTHER INFORMATION: Synthetic Construct

<400> SEQUENCE: 28

Asn Tyr Trp Met Asn
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Glu Tyr Asp Met Leu
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Construct

<400> SEQUENCE: 30

Glu Tyr Ala Met Leu
1               5

<210> SEQ ID NO 31
<211> LENGTH: 14
<212> TYPE: PRT
<213> ORGANISM: Artificial Sequence
<220> FEATURE:
<223> OTHER INFORMATION: Synthetic Construct

<400> SEQUENCE: 31

Trp Val Arg Gln Ala Pro Gly Lys Gly Leu Glu Trp Val Gly
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic Construct

<400> SEQUENCE: 32

Trp Val Arg Gln Ala Pro Gly Lys Gly Leu Glu Trp Val Ala
1               5                   10

<210> SEQ ID NO 33
<211> LENGTH: 19
<212> TYPE: PRT
<213> ORGANISM: Artificial Sequence
<220> FEATURE:
<223> OTHER INFORMATION: Synthetic Construct

<400> SEQUENCE: 33

Glu Ile Arg Leu Lys Ser Asn Asn Tyr Val Thr Asn Tyr Ala Ala Ser
1               5                   10                  15

Val Lys Gly

<210> SEQ ID NO 34
<211> LENGTH: 32
<212> TYPE: PRT
<213> ORGANISM: Artificial Sequence
```

```
<220> FEATURE:
<223> OTHER INFORMATION: Synthetic Construct

<400> SEQUENCE: 34

Arg Phe Thr Ile Ser Arg Asp Asp Ser Lys Asn Ser Leu Tyr Leu Gln
1               5                   10                  15

Met Asn Ser Leu Lys Thr Glu Asp Thr Ala Val Tyr Tyr Cys Ala Arg
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: Synthetic Construct

<400> SEQUENCE: 35

Arg Phe Thr Ile Ser Arg Asp Asp Ser Lys Asn Ser Val Tyr Leu Gln
1               5                   10                  15

Met Asn Ser Leu Lys Thr Glu Asp Thr Gly Val Tyr Tyr Cys Thr Arg
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: Synthetic Construct

<400> SEQUENCE: 36

Arg Phe Thr Ile Ser Arg Asp Asp Ser Lys Asn Ser Leu Tyr Leu Gln
1               5                   10                  15

Met Asn Ser Leu Lys Thr Glu Asp Thr Ala Val Tyr Tyr Cys Thr Arg
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: Synthetic Construct

<400> SEQUENCE: 37

Arg Phe Thr Ile Ser Arg Asp Asp Thr Lys Asn Ser Val Tyr Leu Gln
1               5                   10                  15

Met Asn Ser Leu Lys Thr Glu Asp Thr Gly Val Tyr Tyr Cys Thr Arg
            20                  25                  30

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Asp Gly Tyr Tyr Val Pro Phe Ala Tyr
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 39

Ala Gly Tyr Tyr Val Pro Phe Ala Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Construct

<400> SEQUENCE: 40

Ala Gly Tyr Tyr Val Pro Phe Thr Tyr
1               5

<210> SEQ ID NO 41
<211> LENGTH: 11
<212> TYPE: PRT
<213> ORGANISM: Artificial Sequence
<220> FEATURE:
<223> OTHER INFORMATION: Synthetic Construct

<400> SEQUENCE: 41

Trp Gly Gln Gly Thr Leu Val Thr Val Ser Ser
1               5                   10

<210> SEQ ID NO 42
<211> LENGTH: 22
<212> TYPE: PRT
<213> ORGANISM: Artificial Sequence
<220> FEATURE:
<223> OTHER INFORMATION: Synthetic Construct

<400> SEQUENCE: 42

Gln Leu Val Leu Thr Gln Ser Pro Ser Ala Ser Ala Ser Leu Gly Ala
1               5                   10                  15

Ser Val Lys Leu Thr Cys
            20

<210> SEQ ID NO 43
<211> LENGTH: 22
<212> TYPE: PRT
<213> ORGANISM: Artificial Sequence
<220> FEATURE:
<223> OTHER INFORMATION: Synthetic Construct

<400> SEQUENCE: 43

Gln Leu Val Leu Thr Gln Ser Pro Ser Ala Ser Ala Ser Leu Gly Ala
1               5                   10                  15

Ser Ala Lys Leu Thr Cys
            20

<210> SEQ ID NO 44
<211> LENGTH: 22
<212> TYPE: PRT
<213> ORGANISM: Artificial Sequence
<220> FEATURE:
<223> OTHER INFORMATION: Synthetic Construct

<400> SEQUENCE: 44

Gln Pro Val Leu Thr Gln Ser Pro Ser Ala Ser Ala Ser Leu Gly Ala
1               5                   10                  15

Ser Val Lys Leu Thr Cys
            20
```

```
<210> SEQ ID NO 45
<211> LENGTH: 22
<212> TYPE: PRT
<213> ORGANISM: Artificial Sequence
<220> FEATURE:
<223> OTHER INFORMATION: Synthetic Construct

<400> SEQUENCE: 45

Gln Leu Met Leu Thr Gln Ser Pro Ser Ala Ser Ala Ser Leu Gly Ala
1               5                   10                  15

Ser Val Lys Leu Thr Cys
            20

<210> SEQ ID NO 46
<211> LENGTH: 22
<212> TYPE: PRT
<213> ORGANISM: Artificial Sequence
<220> FEATURE:
<223> OTHER INFORMATION: Synthetic Construct

<400> SEQUENCE: 46

Gln Pro Met Leu Thr Gln Ser Pro Ser Ala Ser Ala Ser Leu Gly Ala
1               5                   10                  15

Ser Val Lys Leu Thr Cys
            20

<210> SEQ ID NO 47
<211> LENGTH: 12
<212> TYPE: PRT
<213> ORGANISM: Artificial Sequence
<220> FEATURE:
<223> OTHER INFORMATION: Synthetic Construct

<400> SEQUENCE: 47

Thr Leu Ser Ser Gln His Ser Thr Tyr Thr Ile Glu
1               5                   10

<210> SEQ ID NO 48
<211> LENGTH: 15
<212> TYPE: PRT
<213> ORGANISM: Artificial Sequence
<220> FEATURE:
<223> OTHER INFORMATION: Synthetic Construct

<400> SEQUENCE: 48

Trp His Gln Gln Gln Pro Glu Lys Gly Pro Arg Tyr Leu Met Lys
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic Construct

<400> SEQUENCE: 49

Trp Tyr Gln Gln Gln Pro Glu Lys Gly Pro Arg Tyr Leu Met Glu
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic Construct
```

<400> SEQUENCE: 50

Trp Tyr Gln Gln Gln Pro Glu Lys Gly Pro Arg Tyr Val Met Glu
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic Construct

<400> SEQUENCE: 51

Trp Tyr Gln Gln Gln Pro Gly Lys Gly Pro Arg Tyr Leu Met Glu
1               5                   10                  15

<210> SEQ ID NO 52
<211> LENGTH: 11
<212> TYPE: PRT
<213> ORGANISM: Artificial Sequence
<220> FEATURE:
<223> OTHER INFORMATION: Synthetic Construct

<400> SEQUENCE: 52

Leu Lys Lys Asp Gly Ser His Ser Thr Gly Asp
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic Construct

<400> SEQUENCE: 53

Leu Lys Lys Glu Gly Ser His Ser Thr Gly Asp
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic Construct

<400> SEQUENCE: 54

Leu Lys Lys Lys Gly Ser His Ser Thr Gly Asp
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic Construct

<400> SEQUENCE: 55

Leu Lys Lys Gly Gly Ser His Ser Thr Gly Asp
1               5                   10

<210> SEQ ID NO 56
<211> LENGTH: 32
<212> TYPE: PRT
<213> ORGANISM: Artificial Sequence
<220> FEATURE:
<223> OTHER INFORMATION: Synthetic Construct

```
<400> SEQUENCE: 56

Gly Ile Pro Asp Arg Phe Ser Gly Ser Ser Gly Ala Glu Arg Tyr
1               5                   10                  15

Leu Thr Ile Ser Ser Leu Gln Ser Glu Asp Glu Ala Asp Tyr Tyr Cys
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Synthetic Construct

<400> SEQUENCE: 57

Gly Ile Pro Asp Arg Phe Ser Gly Ser Ser Gly Ala Glu Arg Tyr
1               5                   10                  15

Leu Thr Ile Ser Ser Ile Gln Ser Glu Asp Glu Ala Asp Tyr Ile Cys
            20                  25                  30

<210> SEQ ID NO 58
<211> LENGTH: 13
<212> TYPE: PRT
<213> ORGANISM: Artificial Sequence
<220> FEATURE:
<223> OTHER INFORMATION: Synthetic Construct

<400> SEQUENCE: 58

Gly Val Gly Asp Thr Ile Lys Glu Gln Phe Val Tyr Val
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic Construct

<400> SEQUENCE: 59

Gly Val Gly Val Thr Ile Lys Glu Gln Phe Val Tyr Val
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Synthetic Construct

<400> SEQUENCE: 60

Gly Val Gly His Thr Ile Lys Glu Gln Phe Val Tyr Glu
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Synthetic Construct

<400> SEQUENCE: 61

Gly Val Gly His Thr Ile Lys Glu Gln Phe Val Tyr Val
1               5                   10

<210> SEQ ID NO 62
<211> LENGTH: 13
```

```
<212> TYPE: PRT
<213> ORGANISM: Artificial Sequence
<220> FEATURE:
<223> OTHER INFORMATION: Synthetic Construct

<400> SEQUENCE: 62

Gly Val Gly Leu Thr Ile Lys Glu Gln Phe Val Tyr Val
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic Construct

<400> SEQUENCE: 63

Phe Gly Gly Gly Thr Lys Leu Thr Val Leu
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic Construct

<400> SEQUENCE: 64

Phe Gly Gly Gly Thr Lys Val Thr Val Leu
1               5                   10

<210> SEQ ID NO 65
<211> LENGTH: 120
<212> TYPE: PRT
<213> ORGANISM: Artificial Sequence
<220> FEATURE:
<223> OTHER INFORMATION: Synthetic Construct

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Cys Met Asn Trp Val Arg Gln Ala Pro Gly Lys Gly Leu Glu Trp Val
        35                  40                  45

Gly Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Gly Tyr Tyr Val Pro Phe Ala Tyr Trp Gly Gln
            100                 105                 110

Gly Thr Leu Val Thr Val Ser Ser
        115                 120

<210> SEQ ID NO 66
<211> LENGTH: 120
<212> TYPE: PRT
<213> ORGANISM: Artificial Sequence
<220> FEATURE:
<223> OTHER INFORMATION: Synthetic Construct

<400> SEQUENCE: 66
```

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
                20                  25                  30

Cys Met Asn Trp Val Arg Gln Ala Pro Gly Lys Gly Leu Glu Trp Val
            35                  40                  45

Ala Glu Ile Arg Leu Lys Ser Asn Asn Tyr Val Thr Asn Tyr Ala Ala
        50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Asp Gly Tyr Tyr Val Pro Phe Ala Tyr Trp Gly Gln
            100                 105                 110

Gly Thr Leu Val Thr Val Ser Ser
            115                 120

<210> SEQ ID NO 67
<211> LENGTH: 120
<212> TYPE: PRT
<213> ORGANISM: Artificial Sequence
<220> FEATURE:
<223> OTHER INFORMATION: Synthetic Construct

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
                20                  25                  30

Cys Met Asn Trp Val Arg Gln Ala Pro Gly Lys Gly Leu Glu Trp Val
            35                  40                  45

Ala Glu Ile Arg Leu Lys Ser Asn Asn Tyr Val Thr Asn Tyr Ala Ala
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Arg Asp Gly Tyr Tyr Val Pro Phe Ala Tyr Trp Gly Gln
            100                 105                 110

Gly Thr Leu Val Thr Val Ser Ser
            115                 120

<210> SEQ ID NO 68
<211> LENGTH: 120
<212> TYPE: PRT
<213> ORGANISM: Artificial Sequence
<220> FEATURE:
<223> OTHER INFORMATION: Synthetic Construct

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
                20                  25                  30

Cys Met Asn Trp Val Arg Gln Ala Pro Gly Lys Gly Leu Glu Trp Val
            35                  40                  45

Ala Glu Ile Arg Leu Lys Ser Asn Asn Tyr Val Thr Asn Tyr Ala Ala

```
                    50                  55                  60
Ser Val Lys Gly Arg Phe Thr Ile Ser Arg Asp Asp Ser Lys Asn Ser
 65                  70                  75                  80

Val Tyr Leu Gln Met Asn Ser Leu Lys Thr Glu Asp Thr Gly Val Tyr
                     85                  90                  95

Tyr Cys Thr Arg Ala Gly Tyr Tyr Val Pro Phe Ala Tyr Trp Gly Gln
                100                 105                 110

Gly Thr Leu Val Thr Val Ser Ser
            115                 120

<210> SEQ ID NO 69
<211> LENGTH: 120
<212> TYPE: PRT
<213> ORGANISM: Artificial Sequence
<220> FEATURE:
<223> OTHER INFORMATION: Synthetic Construct

<400> SEQUENCE: 69

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Glu Tyr
                 20                  25                  30

Ala Met Asn Trp Val Arg Gln Ala Pro Gly Lys Gly Leu Glu Trp Val
             35                  40                  45

Gly Glu Ile Arg Leu Lys Ser Asn Asn Tyr Val Thr Asn Tyr Ala Ala
         50                  55                  60

Ser Val Lys Gly Arg Phe Thr Ile Ser Arg Asp Asp Ser Lys Asn Ser
 65                  70                  75                  80

Val Tyr Leu Gln Met Asn Ser Leu Lys Thr Glu Asp Thr Gly Val Tyr
                     85                  90                  95

Tyr Cys Thr Arg Ala Gly Tyr Tyr Val Pro Phe Ala Tyr Trp Gly Gln
                100                 105                 110

Gly Thr Leu Val Thr Val Ser Ser
            115                 120

<210> SEQ ID NO 70
<211> LENGTH: 120
<212> TYPE: PRT
<213> ORGANISM: Artificial Sequence
<220> FEATURE:
<223> OTHER INFORMATION: Synthetic Construct

<400> SEQUENCE: 70

Glu Val Gln Leu Val Glu Ser Gly Gly Gly Leu Val Gln Pro Gly Gly
  1               5                  10                  15

Ser Leu Arg Leu Ser Cys Ala Gly Ser Gly Phe Thr Phe Ser Asn Tyr
                 20                  25                  30

Gly Met Asn Trp Val Arg Gln Ala Pro Gly Lys Gly Leu Glu Trp Val
             35                  40                  45

Ala Glu Ile Arg Leu Lys Ser Asn Asn Tyr Val Thr Asn Tyr Ala Ala
         50                  55                  60

Ser Val Lys Gly Arg Phe Thr Ile Ser Arg Asp Asp Ser Lys Asn Ser
 65                  70                  75                  80

Val Tyr Leu Gln Met Asn Ser Leu Lys Thr Glu Asp Thr Gly Val Tyr
                     85                  90                  95

Tyr Cys Thr Arg Ala Gly Tyr Tyr Val Pro Phe Ala Tyr Trp Gly Gln
                100                 105                 110
```

Gly Thr Leu Val Thr Val Ser Ser
        115                 120

<210> SEQ ID NO 71
<211> LENGTH: 120
<212> TYPE: PRT
<213> ORGANISM: Artificial Sequence
<220> FEATURE:
<223> OTHER INFORMATION: Synthetic Construct

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Phe Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
        115                 120

<210> SEQ ID NO 72
<211> LENGTH: 120
<212> TYPE: PRT
<213> ORGANISM: Artificial Sequence
<220> FEATURE:
<223> OTHER INFORMATION: Synthetic Construct

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
        115                 120

<210> SEQ ID NO 73
<211> LENGTH: 120
<212> TYPE: PRT
<213> ORGANISM: Artificial Sequence
<220> FEATURE:
<223> OTHER INFORMATION: Synthetic Construct

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Ser Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
            115                 120

<210> SEQ ID NO 74
<211> LENGTH: 120
<212> TYPE: PRT
<213> ORGANISM: Artificial Sequence
<220> FEATURE:
<223> OTHER INFORMATION: Synthetic Construct

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Leu Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
            115                 120

<210> SEQ ID NO 75
<211> LENGTH: 120
<212> TYPE: PRT
<213> ORGANISM: Artificial Sequence
<220> FEATURE:
<223> OTHER INFORMATION: Synthetic Construct

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Tyr Met Asn Trp Val Arg Gln Ala Pro Gly Lys Gly Leu Glu Trp Val
        35                  40                  45

-continued

```
Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
            115                 120

<210> SEQ ID NO 76
<211> LENGTH: 120
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

His Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
            115                 120

<210> SEQ ID NO 77
<211> LENGTH: 120
<212> TYPE: PRT
<213> ORGANISM: Artificial Sequence
<220> FEATURE:
<223> OTHER INFORMATION: Synthetic Construct

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Arg Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110
```

```
Gly Thr Leu Val Thr Val Ser Ser
        115                 120

<210> SEQ ID NO 78
<211> LENGTH: 120
<212> TYPE: PRT
<213> ORGANISM: Artificial Sequence
<220> FEATURE:
<223> OTHER INFORMATION: Synthetic Construct

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Pro Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
        115                 120

<210> SEQ ID NO 79
<211> LENGTH: 120
<212> TYPE: PRT
<213> ORGANISM: Artificial Sequence
<220> FEATURE:
<223> OTHER INFORMATION: Synthetic Construct

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gln Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
        115                 120

<210> SEQ ID NO 80
<211> LENGTH: 120
<212> TYPE: PRT
<213> ORGANISM: Artificial Sequence
<220> FEATURE:
<223> OTHER INFORMATION: Synthetic Construct
```

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Thr Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
            115                 120

<210> SEQ ID NO 81
<211> LENGTH: 120
<212> TYPE: PRT
<213> ORGANISM: Artificial Sequence
<220> FEATURE:
<223> OTHER INFORMATION: Synthetic Construct

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Val Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
            115                 120

<210> SEQ ID NO 82
<211> LENGTH: 120
<212> TYPE: PRT
<213> ORGANISM: Artificial Sequence
<220> FEATURE:
<223> OTHER INFORMATION: Synthetic Construct

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Asn Met Asn Trp Val Arg Gln Ala Pro Gly Lys Gly Leu Glu Trp Val
        35                  40                  45

```
Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                    85                  90                  95

Tyr Cys Thr Arg Ala Gly Tyr Tyr Val Pro Phe Ala Tyr Trp Gly Gln
                100                 105                 110

Gly Thr Leu Val Thr Val Ser Ser
            115                 120
```

<210> SEQ ID NO 83
<211> LENGTH: 120
<212> TYPE: PRT
<213> ORGANISM: Artificial Sequence
<220> FEATURE:
<223> OTHER INFORMATION: Synthetic Construct

<400> SEQUENCE: 83

```
Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Glu Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                    85                  90                  95

Tyr Cys Thr Arg Ala Gly Tyr Tyr Val Pro Phe Ala Tyr Trp Gly Gln
                100                 105                 110

Gly Thr Leu Val Thr Val Ser Ser
            115                 120
```

<210> SEQ ID NO 84
<211> LENGTH: 120
<212> TYPE: PRT
<213> ORGANISM: Artificial Sequence
<220> FEATURE:
<223> OTHER INFORMATION: Synthetic Construct

<400> SEQUENCE: 84

```
Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Ile Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                    85                  90                  95

Tyr Cys Thr Arg Ala Gly Tyr Tyr Val Pro Phe Ala Tyr Trp Gly Gln
```

```
                100                 105                 110

Gly Thr Leu Val Thr Val Ser Ser
        115                 120

<210> SEQ ID NO 85
<211> LENGTH: 120
<212> TYPE: PRT
<213> ORGANISM: Artificial Sequence
<220> FEATURE:
<223> OTHER INFORMATION: Synthetic Construct

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asp Tyr
            20                  25                  30

Thr Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
        115                 120

<210> SEQ ID NO 86
<211> LENGTH: 120
<212> TYPE: PRT
<213> ORGANISM: Artificial Sequence
<220> FEATURE:
<223> OTHER INFORMATION: Synthetic Construct

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asp Tyr
            20                  25                  30

Ser Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
        115                 120

<210> SEQ ID NO 87
<211> LENGTH: 120
<212> TYPE: PRT
<213> ORGANISM: Artificial Sequence
<220> FEATURE:
```

<223> OTHER INFORMATION: Synthetic Construct

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Ala Tyr
            20                  25                  30

Ser Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
            115                 120

<210> SEQ ID NO 88
<211> LENGTH: 120
<212> TYPE: PRT
<213> ORGANISM: Artificial Sequence
<220> FEATURE:
<223> OTHER INFORMATION: Synthetic Construct

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
            115                 120

<210> SEQ ID NO 89
<211> LENGTH: 120
<212> TYPE: PRT
<213> ORGANISM: Artificial Sequence
<220> FEATURE:
<223> OTHER INFORMATION: Synthetic Construct

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Ser Glu Tyr
            20                  25                  30

Asp Met Leu Trp Val Arg Gln Ala Pro Gly Lys Gly Leu Glu Trp Val 35                  40                  45
Gly Glu Ile Arg Leu Lys Ser Asn Asn Tyr Val Thr Asn Tyr Ala Ala
        50                  55                  60
Ser Val Lys Gly Arg Phe Thr Ile Ser Arg Asp Asp Ser Lys Asn Ser
65                  70                  75                  80
Val Tyr Leu Gln Met Asn Ser Leu Lys Thr Glu Asp Thr Gly Val Tyr
                85                  90                  95
Tyr Cys Thr Arg Ala Gly Tyr Tyr Val Pro Phe Ala Tyr Trp Gly Gln
            100                 105                 110
Gly Thr Leu Val Thr Val Ser Ser
        115                 120

<210> SEQ ID NO 90
<211> LENGTH: 120
<212> TYPE: PRT
<213> ORGANISM: Artificial Sequence
<220> FEATURE:
<223> OTHER INFORMATION: Synthetic Construct

<400> SEQUENCE: 90

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Glu Tyr
            20                  25                  30
Ala Met Leu Trp Val Arg Gln Ala Pro Gly Lys Gly Leu Glu Trp Val
        35                  40                  45
Gly Glu Ile Arg Leu Lys Ser Asn Asn Tyr Val Thr Asn Tyr Ala Ala
        50                  55                  60
Ser Val Lys Gly Arg Phe Thr Ile Ser Arg Asp Asp Ser Lys Asn Ser
65                  70                  75                  80
Val Tyr Leu Gln Met Asn Ser Leu Lys Thr Glu Asp Thr Gly Val Tyr
                85                  90                  95
Tyr Cys Thr Arg Ala Gly Tyr Tyr Val Pro Phe Thr Tyr Trp Gly Gln
            100                 105                 110
Gly Thr Leu Val Thr Val Ser Ser
        115                 120

<210> SEQ ID NO 91
<211> LENGTH: 120
<212> TYPE: PRT
<213> ORGANISM: Artificial Sequence
<220> FEATURE:
<223> OTHER INFORMATION: Synthetic Construct

<400> SEQUENCE: 91

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Glu Tyr
            20                  25                  30
Asp Met Leu Trp Val Arg Gln Ala Pro Gly Lys Gly Leu Glu Trp Val
        35                  40                  45
Gly Glu Ile Arg Leu Lys Ser Asn Asn Tyr Val Thr Asn Tyr Ala Ala
        50                  55                  60
Ser Val Lys Gly Arg Phe Thr Ile Ser Arg Asp Asp Thr Lys Asn Ser
65                  70                  75                  80
Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
        115                 120

<210> SEQ ID NO 92
<211> LENGTH: 120
<212> TYPE: PRT
<213> ORGANISM: Artificial Sequence
<220> FEATURE:
<223> OTHER INFORMATION: Synthetic Construct

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Asp Met Leu Trp Val Arg Gln Ala Pro Gly Lys Gly Leu Glu Trp Val
        35                  40                  45

Gly Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
        115                 120

<210> SEQ ID NO 93
<211> LENGTH: 120
<212> TYPE: PRT
<213> ORGANISM: Artificial Sequence
<220> FEATURE:
<223> OTHER INFORMATION: Synthetic Construct

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Ala Met Leu Trp Val Arg Gln Ala Pro Gly Lys Gly Leu Glu Trp Val
        35                  40                  45

Gly Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser
        115                 120

<210> SEQ ID NO 94
<211> LENGTH: 115
<212> TYPE: PRT
<213> ORGANISM: Artificial Sequence
<220> FEATURE:
<223> OTHER INFORMATION: Synthetic Construct

<400> SEQUENCE: 94

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp His Gln Gln Pro Glu Lys Gly Pro Arg Tyr Leu Met
            35                  40                  45

Lys Leu Lys Lys Asp Gly Ser His Ser Thr Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu
        115

<210> SEQ ID NO 95
<211> LENGTH: 115
<212> TYPE: PRT
<213> ORGANISM: Artificial Sequence
<220> FEATURE:
<223> OTHER INFORMATION: Synthetic Construct

<400> SEQUENCE: 95

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Arg Tyr Leu Met
            35                  40                  45

Glu Leu Lys Lys Asp Gly Ser His Ser Thr Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu
        115

<210> SEQ ID NO 96
<211> LENGTH: 115
<212> TYPE: PRT
<213> ORGANISM: Artificial Sequence
<220> FEATURE:
<223> OTHER INFORMATION: Synthetic Construct

<400> SEQUENCE: 96

Gln Leu Val Leu Thr Gln Ser Pro Ser Ala Ser Ala Ser Leu Gly Ala
1               5                   10                  15

Ser Ala Lys Leu Thr Cys Thr Leu Ser Ser Gln His Ser Thr Tyr Thr
            20                  25                  30

```
Ile Glu Trp Tyr Gln Gln Pro Glu Lys Gly Pro Arg Tyr Val Met
        35                  40                  45

Glu Leu Lys Lys Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Ile Gln Ser Glu Asp Glu Ala Asp Tyr Ile Cys Gly Val Gly Asp
                 85                  90                  95

Thr Ile Lys Glu Gln Phe Val Tyr Val Phe Gly Gly Gly Thr Lys Val
            100                 105                 110

Thr Val Leu
        115

<210> SEQ ID NO 97
<211> LENGTH: 115
<212> TYPE: PRT
<213> ORGANISM: Artificial Sequence
<220> FEATURE:
<223> OTHER INFORMATION: Synthetic Construct

<400> SEQUENCE: 97

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Arg Tyr Leu Met
        35                  40                  45

Glu Leu Lys Lys Glu Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Thr Ile Lys Glu Gln Phe Val Tyr Val Phe Gly Gly Gly Thr Lys Leu
            100                 105                 110

Thr Val Leu
        115

<210> SEQ ID NO 98
<211> LENGTH: 115
<212> TYPE: PRT
<213> ORGANISM: Artificial Sequence
<220> FEATURE:
<223> OTHER INFORMATION: Synthetic Construct

<400> SEQUENCE: 98

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Arg Tyr Leu Met
        35                  40                  45

Glu Leu Lys Lys Lys Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95
```

-continued

Thr Ile Lys Glu Gln Phe Val Tyr Val Phe Gly Gly Gly Thr Lys Leu
                100                 105                 110

Thr Val Leu
        115

<210> SEQ ID NO 99
<211> LENGTH: 115
<212> TYPE: PRT
<213> ORGANISM: Artificial Sequence
<220> FEATURE:
<223> OTHER INFORMATION: Synthetic Construct

<400> SEQUENCE: 99

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Arg Tyr Leu Met
        35                  40                  45

Glu Leu Lys Lys Gly Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
                100                 105                 110

Thr Val Leu
        115

<210> SEQ ID NO 100
<211> LENGTH: 115
<212> TYPE: PRT
<213> ORGANISM: Artificial Sequence
<220> FEATURE:
<223> OTHER INFORMATION: Synthetic Construct

<400> SEQUENCE: 100

Gln Pro Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Arg Tyr Leu Met
        35                  40                  45

Glu Leu Lys Lys Glu Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Val
                85                  90                  95

Thr Ile Lys Glu Gln Phe Val Tyr Val Phe Gly Gly Gly Thr Lys Leu
                100                 105                 110

Thr Val Leu
        115

<210> SEQ ID NO 101
<211> LENGTH: 115
<212> TYPE: PRT

<213> ORGANISM: Artificial Sequence
<220> FEATURE:
<223> OTHER INFORMATION: Synthetic Construct

<400> SEQUENCE: 101

```
Gln Leu Met Leu Thr Gln Ser Pro Ser Ala Ser Ala Ser Leu Gly Ala
1               5                   10                  15
Ser Val Lys Leu Thr Cys Thr Leu Ser Ser Gln His Ser Thr Tyr Thr
            20                  25                  30
Ile Glu Trp Tyr Gln Gln Pro Gly Lys Gly Pro Arg Tyr Leu Met
        35                  40                  45
Glu Leu Lys Lys Glu Gly Ser His Ser Thr Gly Asp Gly Ile Pro Asp
    50                  55                  60
Arg Phe Ser Gly Ser Ser Ser Gly Ala Glu Arg Tyr Leu Thr Ile Ser
65                  70                  75                  80
Ser Leu Gln Ser Glu Asp Glu Ala Asp Tyr Tyr Cys Gly Val Gly His
                85                  90                  95
Thr Ile Lys Glu Gln Phe Val Tyr Glu Phe Gly Gly Thr Lys Leu
            100                 105                 110
Thr Val Leu
        115
```

<210> SEQ ID NO 102
<211> LENGTH: 115
<212> TYPE: PRT
<213> ORGANISM: Artificial Sequence
<220> FEATURE:
<223> OTHER INFORMATION: Synthetic Construct

<400> SEQUENCE: 102

```
Gln Leu Met Leu Thr Gln Ser Pro Ser Ala Ser Ala Ser Leu Gly Ala
1               5                   10                  15
Ser Val Lys Leu Thr Cys Thr Leu Ser Ser Gln His Ser Thr Tyr Thr
            20                  25                  30
Ile Glu Trp Tyr Gln Gln Pro Gly Lys Gly Pro Arg Tyr Leu Met
        35                  40                  45
Glu Leu Lys Lys Glu Gly Ser His Ser Thr Gly Asp Gly Ile Pro Asp
    50                  55                  60
Arg Phe Ser Gly Ser Ser Ser Gly Ala Glu Arg Tyr Leu Thr Ile Ser
65                  70                  75                  80
Ser Leu Gln Ser Glu Asp Glu Ala Asp Tyr Tyr Cys Gly Val Gly His
                85                  90                  95
Thr Ile Lys Glu Gln Phe Val Tyr Val Phe Gly Gly Thr Lys Leu
            100                 105                 110
Thr Val Leu
        115
```

<210> SEQ ID NO 103
<211> LENGTH: 115
<212> TYPE: PRT
<213> ORGANISM: Artificial Sequence
<220> FEATURE:
<223> OTHER INFORMATION: Synthetic Construct

<400> SEQUENCE: 103

```
Gln Pro Met Leu Thr Gln Ser Pro Ser Ala Ser Ala Ser Leu Gly Ala
1               5                   10                  15
Ser Val Lys Leu Thr Cys Thr Leu Ser Ser Gln His Ser Thr Tyr Thr
            20                  25                  30
```

```
Ile Glu Trp Tyr Gln Gln Pro Gly Lys Gly Pro Arg Tyr Leu Met
        35                  40                  45

Glu Leu Lys Lys Glu Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Leu
                 85                  90                  95

Thr Ile Lys Glu Gln Phe Val Tyr Val Phe Gly Gly Gly Thr Lys Leu
             100                 105                 110

Thr Val Leu
        115

<210> SEQ ID NO 104
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 2, 3
<223> OTHER INFORMATION: Xaa = Any Amino Acid, and up to two can be
      present or absent
<220> FEATURE:
<221> NAME/KEY: VARIANT
<222> LOCATION: 5, 6
<223> OTHER INFORMATION: Xaa = Any Amino Acid
<220> FEATURE:
<221> NAME/KEY: VARIANT
<222> LOCATION: 7
<223> OTHER INFORMATION: Xaa = Leu or Ile
<220> FEATURE:
<221> NAME/KEY: VARIANT
<222> LOCATION: 8, 9, 10, 11, 12, 13, 14, 15
<223> OTHER INFORMATION: Xaa = Any Amino Acid, and up to two can be
      present or absent
<220> FEATURE:
<221> NAME/KEY: VARIANT
<222> LOCATION: 17, 18
<223> OTHER INFORMATION: Xaa = Any Amino Acid
<220> FEATURE:
<221> NAME/KEY: VARIANT
<222> LOCATION: 19
<223> OTHER INFORMATION: Xaa = Leu or Ile

<400> SEQUENCE: 104

Xaa Xaa Xaa Tyr Xaa Xaa Xaa Xaa Xaa Xaa Xaa Xaa Xaa Xaa Xaa Tyr
 1               5                  10                  15

Xaa Xaa Xaa

<210> SEQ ID NO 105
<211> LENGTH: 110
<212> TYPE: PRT
<213> ORGANISM: Artificial Sequence
<220> FEATURE:
<223> OTHER INFORMATION: Synthetic Construct

<400> SEQUENCE: 105

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro
                100                 105                 110

<210> SEQ ID NO 106
<211> LENGTH: 330
<212> TYPE: PRT
<213> ORGANISM: Homo sapiens

<400> SEQUENCE: 106

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

```
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 107
<211> LENGTH: 329
<212> TYPE: PRT
<213> ORGANISM: Homo sapiens

<400> SEQUENCE: 107

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 108
<211> LENGTH: 330
<212> TYPE: PRT
<213> ORGANISM: Homo sapiens

<400> SEQUENCE: 108

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 109
<211> LENGTH: 329
<212> TYPE: PRT
<213> ORGANISM: Homo sapiens

<400> SEQUENCE: 109

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Ser Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 110
<211> LENGTH: 330
<212> TYPE: PRT
<213> ORGANISM: Homo sapiens

<400> SEQUENCE: 110

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 111
<211> LENGTH: 329
<212> TYPE: PRT
<213> ORGANISM: Homo sapiens

<400> SEQUENCE: 111

Ala Ser Thr Lys Gly Pro Ser Val Phe Pro Leu Ala Pro Ser Ser Lys
1                5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

```
                        85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Ser Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 112
<211> LENGTH: 330
<212> TYPE: PRT
<213> ORGANISM: Homo sapiens

<400> SEQUENCE: 112

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
            115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 113
<211> LENGTH: 329
<212> TYPE: PRT
<213> ORGANISM: Homo sapiens

<400> SEQUENCE: 113

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Ser Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Gly Ala Leu His Asn His Tyr Thr
305                 310                 315                 320

Gln Lys Ser Leu Ser Leu Ser Pro Gly
                325

<210> SEQ ID NO 114
<211> LENGTH: 330
<212> TYPE: PRT
<213> ORGANISM: Homo sapiens

<400> SEQUENCE: 114

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Ser
        195                 200                 205

Lys Ala Phe Pro Ala Pro Ile Glu Lys Thr Ile Ser Lys Ala Lys Gly
    210                 215                 220
```

```
            210                 215                 220
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 115
<211> LENGTH: 329
<212> TYPE: PRT
<213> ORGANISM: Homo sapiens

<400> SEQUENCE: 115

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Ser
        195                 200                 205

Lys Ala Phe Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 116
<211> LENGTH: 330
<212> TYPE: PRT
<213> ORGANISM: Homo sapiens

<400> SEQUENCE: 116

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Phe Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 117
<211> LENGTH: 329
<212> TYPE: PRT
<213> ORGANISM: Homo sapiens

<400> SEQUENCE: 117

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Phe Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 118
<211> LENGTH: 326
<212> TYPE: PRT
<213> ORGANISM: Homo sapiens

<400> SEQUENCE: 118

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 119
<211> LENGTH: 325
<212> TYPE: PRT
<213> ORGANISM: Homo sapiens

<400> SEQUENCE: 119

Ala Ser Thr Lys Gly Pro Ser Val Phe Pro Leu Ala Pro Cys Ser Arg

```
                1               5                      10                      15
        Ser Thr Ser Glu Ser Thr Ala Ala Leu Gly Cys Leu Val Lys Asp Tyr
                        20                      25                      30

Phe Pro Glu Pro Val Thr Val Ser Trp Asn Ser Gly Ala Leu Thr Ser
                        35                      40                      45

Gly Val His Thr Phe Pro Ala Val Leu Gln Ser Ser Gly Leu Tyr Ser
                        50                      55                      60

Leu Ser Ser Val Val Thr Val Pro Ser Ser Asn Phe Gly Thr Gln Thr
        65                      70                      75                      80

Tyr Thr Cys Asn Val Asp His Lys Pro Ser Asn Thr Lys Val Asp Lys
                        85                      90                      95

Thr Val Glu Arg Lys Cys Cys Val Glu Cys Pro Pro Cys Pro Ala Pro
                        100                     105                     110

Pro Val Ala Gly Pro Ser Val Phe Leu Phe Pro Pro Lys Pro Lys Asp
                        115                     120                     125

Thr Leu Met Ile Ser Arg Thr Pro Glu Val Thr Cys Val Val Val Asp
                        130                     135                     140

Val Ser His Glu Asp Pro Glu Val Gln Phe Asn Trp Tyr Val Asp Gly
        145                     150                     155                     160

Val Glu Val His Asn Ala Lys Thr Lys Pro Arg Glu Glu Gln Phe Asn
                        165                     170                     175

Ser Thr Phe Arg Val Val Ser Val Leu Thr Val Val His Gln Asp Trp
                        180                     185                     190

Leu Asn Gly Lys Glu Tyr Lys Cys Lys Val Ser Asn Lys Gly Leu Pro
                        195                     200                     205

Ala Pro Ile Glu Lys Thr Ile Ser Lys Thr Lys Gly Gln Pro Arg Glu
                        210                     215                     220

Pro Gln Val Tyr Thr Leu Pro Pro Ser Arg Glu Glu Met Thr Lys Asn
        225                     230                     235                     240

Gln Val Ser Leu Thr Cys Leu Val Lys Gly Phe Tyr Pro Ser Asp Ile
                        245                     250                     255

Ala Val Glu Trp Glu Ser Asn Gly Gln Pro Glu Asn Asn Tyr Lys Thr
                        260                     265                     270

Thr Pro Pro Met Leu Asp Ser Asp Gly Ser Phe Phe Leu Tyr Ser Lys
                        275                     280                     285

Leu Thr Val Asp Lys Ser Arg Trp Gln Gln Gly Asn Val Phe Ser Cys
                        290                     295                     300

Ser Val Met His Glu Ala Leu His Asn His Tyr Thr Gln Lys Ser Leu
        305                     310                     315                     320

Ser Leu Ser Pro Gly
                        325

<210> SEQ ID NO 120
<211> LENGTH: 446
<212> TYPE: PRT
<213> ORGANISM: Artificial Sequence
<220> FEATURE:
<223> OTHER INFORMATION: Synthetic Construct

<400> SEQUENCE: 120

Glu Val Gln Leu Val Glu Ser Gly Gly Gly Leu Val Gln Pro Gly Gly
        1               5                      10                      15

Ser Leu Arg Leu Ser Cys Ala Gly Ser Gly Phe Thr Phe Ser Asn Tyr
                        20                      25                      30

Glu Met Asn Trp Val Arg Gln Ala Pro Gly Lys Gly Leu Glu Trp Val
```

```
                35                  40                  45
Ala Glu Ile Arg Leu Lys Ser Asn Asn Tyr Val Thr Asn Tyr Ala Ala
 50                  55                  60

Ser Val Lys Gly Arg Phe Thr Ile Ser Arg Asp Asp Ser Lys Asn Ser
 65                  70                  75                  80

Val Tyr Leu Gln Met Asn Ser Leu Lys Thr Glu Asp Thr Gly Val Tyr
                 85                  90                  95

Tyr Cys Thr Arg Ala Gly Tyr Tyr Val Pro Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 121
```

<211> LENGTH: 445
<212> TYPE: PRT
<213> ORGANISM: Artificial Sequence
<220> FEATURE:
<223> OTHER INFORMATION: Synthetic Construct

<400> SEQUENCE: 121

```
Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Glu Met Asn Trp Val Arg Gln Ala Pro Gly Lys Gly Leu Glu Trp Val
        35                  40                  45

Ala Glu Ile Arg Leu Lys Ser Asn Asn Tyr Val Thr Asn Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Arg Ala Gly Tyr Tyr Val Pro Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

```
Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 122
<211> LENGTH: 221
<212> TYPE: PRT
<213> ORGANISM: Artificial Sequence
<220> FEATURE:
<223> OTHER INFORMATION: Synthetic Construct

<400> SEQUENCE: 122

Gln Leu Met Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
                20                  25                  30

Ile Glu Trp Tyr Gln Gln Pro Gly Lys Gly Pro Arg Tyr Leu Met
            35                  40                  45

Glu Leu Lys Lys Glu Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly His
                85                  90                  95

Thr Ile Lys Glu Gln Phe Val Tyr Val Phe Gly Gly Gly Thr Lys Leu
            100                 105                 110

Thr Val Leu Gly Gln Pro Lys Ala Ala Pro Ser Val Thr Leu Phe Pro
            115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
            210                 215                 220
```

ANTI-CD33 ANTIBODIES AND METHODS OF USE THEREOF

CROSS REFERENCE TO RELATED APPLICATIONS

This application is a U.S. National Stage Application of PCT/US2019/048994, filed Aug. 30, 2019, which claims the benefit of U.S. Provisional Application Ser. No. 62/726,053, filed Aug. 31, 2018, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735022002800SEQLIST.TXT, date recorded: Feb. 25, 2021, size: 112 KB).

FIELD OF THE PRESENT DISCLOSURE

The present disclosure relates to anti-CD33 antibodies and therapeutic uses of such antibodies.

BACKGROUND OF THE PRESENT DISCLOSURE

Myeloid cell surface antigen CD33 precursor (CD33), also known as Siglec-3, is a type 1, immunoglobulin-like, transmembrane protein expressed on immune and hematopoietic cells, including immature and mature myeloid cells, dendritic cells, and microglial cells. (Crocker et al. (2007) Nat Rev Immunol. 7:255-266; McMillan and Crocker (2008) Carbohydr Res. 343:2050-2056; Von Gunten and Bochner (2008) Ann NY Acad Sci. 1143:61-82; Handgretinger et al. (1993) Immunol Lett. 37:223-228; and Hernández-Caselles et al. (2006) J Leukoc Biol. 79:46-58). CD33 contains an Ig-like C2-type (immunoglobulin-like) and an Ig-like V-type (immunoglobulin-like) extracellular domain, as well as two ITIM-like motifs in its cytoplasmic domain. Three alternatively spliced forms (isoforms) of CD33 have been identified, including a higher molecular weight variant, named CD33M and a smaller isoform CD33m that lacks the Ig-like V-type domain (the ligand-binding site), and the disulfide bond linking the V and C domains.

Genome-wide association studies (GWAS) performed on extended cohorts (e.g., thousands of individuals) have identified single nucleotide polymorphisms (SNPs) rs3865444$^{CC}$ (AKA rs3826656) and rs3865444$^{AA}$ in CD33 as genetic modulators of risk for late onset Alzheimer's disease (AD). In oncology, CD33 variants that lead to decreased expression of CD33 have been shown to be associated with improved survival rate from pediatric acute myeloid leukemia (AML). The 3-year overall survival rate from remission is 84%+/−8% for those carrying the variant rs35112940$^{GG}$, which is in strong linkage disequilibrium with the rs3865444$^{AA}$ variant, associated with lower full-length expression of CD33. The remission rate for the non-protective allele is 68%+/−15%. Carriers of the protective allele also have a lower relapse risk and superior disease-free survival. Likewise, patients homozygous for the minor variant allele (TT) of rs12459419, which is associated with over 46% lower expression of the fill-length CD33, are more likely to have favorable disease outcome than carriers of the variants CC and CT (52% vs. 31%) and have significantly lower diagnostic blast CD33 expression than other genotypes. This is the case even in patients undergoing treatment with anti-CD33 antibody and a toxic calicheamicin-gamma derivative (Mortland et al., (2013) Clin Cancer Res; 1-8). Carriers of the 2459419$^{TT}$ allele, as well as carriers of the rs12459419$^{CT}$ allele, which show over 25% reduction in expression of full-length CD33, also display reduced Alzheimer's disease risk (Malik M. et al. (2015) Human Molecular Genetics, 1-14). This suggests that reduced expression or functionality of CD33 may be beneficial in Alzheimer's disease and cancer.

Antibodies to CD33 have been described in, for example, U.S. Pat. Nos. 7,342,110, 7,557,189, 8,119,787, 8,337,855, 8,124,069, 5,730,982, WO20121074097, WO2004/043344, WO1993/020848, WO2012/045752, WO2007/014743, WO2003/093298, WO2011/036183, WO1991/009058, WO2008/058021, WO2011/038301, WO2016/201389, WO2016/201388, Hoyer et al (2008) Am J Clin Pathol, 129:316-323, Rollins-Ravel and Roth (2012) Histopathology 60:933-942, Perez-Olivia et al (2011) Glycobiol 21:757-770, Ferlasso et al (2000) Eur J Immunol 30:827-833, Vitale et al (2001) Proc Natl Acad Sci USA 98:5764-5769, Jandus et al (2011) Biochem Pharmacol 82:323-332, O'Reilly and Paulson (2009) Trends Pharmcol Sci 30:240-248, Jurcic (2012) Curr Hematol Malig Rep 7:65-73, and Ricart (2011) Clin Cancer Res 17:6417-6427.

Accordingly, there is a need for therapeutic anti-CD33 antibodies to treat diseases, disorders, and conditions associated with undesired CD33 activity.

All references cited herein, including patents, patent applications and publications, are hereby incorporated by reference in their entirety.

SUMMARY OF THE PRESENT DISCLOSURE

The present disclosure is generally directed to compositions that include antibodies, e.g., monoclonal, chimeric, humanized antibodies, antibody fragments, etc., that specifically bind human CD33, and to methods of using such compositions.

Certain aspects of the present disclosure are based, at least in part, on the identification of anti-CD33 antibodies with improved and/or enhanced functional characteristics. In some embodiments, anti-CD33 antibodies of the present disclosure comprise one or more improved and/or enhanced functional characteristics relative to a reference antibody (e.g., an anti-CD33 antibody comprising a heavy chain variable region comprising the amino acid sequence of SEQ ID NO: 3 and a light chain variable region comprising the amino acid sequence of SEQ ID NO: 4). In some embodiments, anti-CD33 antibodies of the present disclosure have an affinity for CD33 (e.g., human CD33) that is higher than that of a reference anti-CD33 antibody (e.g., an anti-CD33 antibody comprising a heavy chain variable region comprising the amino acid sequence of SEQ ID NO: 3 and a light chain variable region comprising the amino acid sequence of SEQ ID NO: 4). In some embodiments, anti-CD33 antibodies of the present disclosure bind to human cells, such as human primary dendritic cells, with a half-maximal effective concentration ($EC_{50}$) that is lower than that of a reference antibody (e.g., an anti-CD33 antibody comprising a heavy chain variable region comprising the amino acid sequence of SEQ ID NO: 3 and a light chain variable region comprising the amino acid sequence of SEQ ID NO: 4). In some embodiments, anti-CD33 antibodies of the present disclosure decrease cellular levels (e.g., decrease or reduce cell surface levels) of CD33 with a half-maximal effective concentration (EC$_{50}$) that is lower than that of a reference antibody (e.g., an anti-CD33 antibody comprising a heavy chain variable region comprising the sequence of SEQ ID NO: 3 and a light chain variable region comprising the sequence of SEQ ID NO: 4).

Accordingly, in one aspect, the present disclosure relates to an antibody that binds to a CD33 protein, wherein the antibody comprises a heavy chain variable region and a light chain variable region, wherein the heavy chain variable region comprises: an HVR-H1 comprising an amino acid sequence selected from SEQ ID NOs:8-30, an HVR-H2 comprising the amino acid sequence of SEQ ID NO:33, an HVR-H3 comprising an amino acid sequence selected from SEQ ID NOs:39-40, an HVR-L1 comprising the amino acid sequence of SEQ ID NO:47, an HVR-L2 comprising an amino acid sequence selected from SEQ ID NOs:53-55, and an HVR-L3 comprising an amino acid sequence selected from SEQ ID NOs: 58-62.

In another aspect, the present disclosure relates to an antibody that binds to a CD33 protein, wherein the antibody comprises a heavy chain variable region and a light chain variable region, wherein the heavy chain variable region comprises the HVR-H1, HVR-H2, and HVR-H3 of antibody 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, or 6C7H54.

In another aspect, the present disclosure relates to an antibody that binds to a CD33 protein, wherein the antibody comprises a heavy chain variable region and a light chain variable region, wherein the light chain variable region comprises the HVR-L1, HVR-L2, and HVR-L3 of antibody 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, or 6C7H54.

In another aspect, the present disclosure relates to an antibody that binds to a CD33 protein, wherein the antibody comprises a heavy chain variable region and a light chain variable region, wherein the heavy chain variable region comprises the HVR-H1, HVR-H2, and HVR-H3 of antibody 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, or 6C7H54; and the light chain variable region comprises the HVR-L1, HVR-L2, and HVR-L3 of antibody 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, or 6C7H54.

In another aspect, the present disclosure relates to an antibody that binds to a CD33 protein, wherein the antibody comprises the heavy chain variable region of antibody 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, or 6C7H54; and the antibody comprises the light chain variable region of antibody 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, or 6C7H54.

In another aspect, the present disclosure relates to an antibody that binds to a CD33 protein, wherein the antibody comprises a heavy chain variable region comprising an amino acid sequence selected from SEQ ID NOs:68-93; and/or a light chain variable region comprising an amino acid sequence selected from SEQ ID NOs:97-103.

In another aspect, the present disclosure relates to an antibody that binds to a CD33 protein, wherein the antibody comprises the heavy chain variable region of antibody 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, or 6C7H54; and the antibody comprises the light chain variable region of antibody 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, or 6C7H54.

In another aspect, the present disclosure relates to an isolated antibody that binds to CD33, wherein the antibody comprises a heavy chain variable region and a light chain variable region, wherein the heavy chain variable region comprises: an HVR-H1 comprising the amino acid sequence of SEQ ID NO: 23, an HVR-H2 comprising the amino acid sequence of SEQ ID NO:33, an HVR-H3 comprising the amino acid sequence of SEQ ID NO: 39; and wherein the light chain variable region comprises: an HVR-L1 comprising the amino acid sequence of SEQ ID NO:47, an HVR-L2 comprising the amino acid sequence of SEQ ID NO: 53, and an HVR-L3 comprising the amino acid sequence of SEQ ID NO: 61.

In another aspect, the present disclosure relates to an isolated antibody that binds to CD33, wherein the antibody comprises a heavy chain variable region comprising the amino acid sequence of SEQ ID NO: 83 and a light chain variable region comprising the amino acid sequence of SEQ ID NO: 102.

In another aspect, the present disclosure relates to an isolated antibody that binds to CD33, wherein the antibody comprises:

(a) a heavy chain comprising the amino acid sequence of SEQ ID. NO: 120 and a light chain comprising the amino acid sequence of SEQ ID NO: 122; or (b) a heavy chain comprising the amino acid sequence of SEQ ID. NO: 121 and a light chain comprising the amino acid sequence of SEQ ID NO: 122

In some embodiments that may be combined with any of the preceding embodiments, the heavy chain variable region comprises one, two, three, or four framework regions selected from VH FR1, VH FR2, VH FR3, and VH FR4, wherein: VH FR1 comprises a sequence selected from the group consisting of SEQ ID NOs:5-6; VH FR2 comprises a sequence selected from the group consisting of SEQ ID NOs:31-32; VH FR3 comprises a sequence selected from the group consisting of SEQ ID NOs:34-36; and VH FR4 comprises the sequence of SEQ ID NO:41; and the light chain variable region comprises one, two, three, or four framework regions selected from VL FR1, VL FR2, VL FR3, and VL FR4, wherein: VL FR1 comprises a sequence selected from the group consisting of SEQ ID NOs:42-46; VL FR2 comprises a sequence selected from the group consisting of SEQ ID NOs:48-51; VL FR3 comprises a sequence selected from the group consisting of SEQ ID NOs:56-57; and VL FR4 comprises a sequence selected form the group consisting of SEQ ID NOs:63-64.

In some embodiments that may be combined with any of the preceding embodiments, the antibody is of the IgG class the IgM class, or the IgA class. In some embodiments, the antibody is of the IgG class and has an IgG1, IgG2, IgG3, or IgG4 isotype. In some embodiments, the antibody has an IgG4 isotype, and wherein the antibody comprises an S228P amino acid substitution at residue position 228, an F234A amino acid substitution at residue position 234, and an L235A amino acid substitution at residue position 235, wherein the numbering of the residue position is according to EU numbering. In some embodiments, the antibody comprises one or more amino acid substitutions in the Fc region at a residue position selected from the group consisting of: C127S, L234A, L234F, L235A, L235E, S267E, K322A, L328F, A330S, P331S, E345R, E430G, S440Y, and any combination thereof, wherein the numbering of the residues is according to EU numbering. In some embodiments, the Fc region comprises an amino acid substitution at position E430G, wherein the numbering of the residue position is according to EU numbering; the Fc region comprises an amino acid substitution at positions L234A, L235A, and P331A, wherein the numbering of the residue position is according to EU numbering; the Fc region comprises an amino acid substitution at positions L234A, L235A, P331A, and E430G, wherein the numbering of the residue position is according to EU numbering; the Fc region comprises an amino acid substitution at positions K322A and E430G, wherein the numbering of the residue position is according to EU numbering; the Fc region comprises an amino acid substitution at positions P331S and E430G, wherein the numbering of the residue position is according to EU numbering; the Fc region comprises an amino acid substitution at positions A330S, P331S, and E430G, wherein the numbering of the residue position is according to EU numbering; the Fc region comprises an amino acid substitution at positions K322A, A330S, and P331S, wherein the numbering of the residue position is according to EU numbering; the Fc region comprises an amino acid substitution at positions K322A, P331S, and E430G, wherein the numbering of the residue position is according to EU numbering; the Fc region comprises an amino acid substitution at position E430G, wherein the numbering of the residue position is according to EU numbering; the Fc region comprises an amino acid substitution at positions A330S, P331S, and E430G, wherein the numbering of the residue position is according to EU numbering; the Fc region comprises an amino acid substitution at positions S267E and L328F, wherein the numbering of the residue position is according to EU numbering; the Fc region comprises an amino acid substitution at position C127S, wherein the numbering of the residue position is according to EU numbering; or the Fc region comprises an amino acid substitution at positions E345R, E430G, and S440Y, wherein the numbering of the residue position is according to EU numbering.

In some embodiments that may be combined with any of the preceding embodiments, the CD33 protein is a mammalian protein or a human protein. In some embodiments, the CD33 protein is a wildtype protein. In some embodiments, the CD33 protein is a naturally occurring variant. In some embodiments that may be combined with any of the preceding embodiments, the CD33 protein is expressed on one or more cells selected from the group consisting of human dendritic cells, human macrophages, human monocytes, human osteoclasts, human neutrophils, human T cells, human T helper cell, human cytotoxic T cells, human granulocytes, and human microglia.

In some embodiments that may be combined with any of the preceding embodiments, the antibody binds specifically to a human CD33 protein. In some embodiments, the antibody binds to a human CD33 protein and does not cross-react with a CD33 ortholog or homolog from another species. In some embodiments that may be combined with any of the preceding embodiments, the antibody is an antibody fragment that binds to an epitope comprising amino acid residues on human CD33 or a mammalian CD33 protein. In some embodiments that may be combined with any of the preceding embodiments, the antibody is an antibody fragment that binds to one or more human proteins selected from the group consisting of human CD33, a naturally occurring variant of human CD33, and a disease variant of human CD33. In some embodiments, the antibody fragment is cross-linked to a second antibody fragment that binds to one or more human proteins selected from the group consisting of human CD33, a naturally occurring variant of human CD33, and a disease variant of human CD33. In some embodiments, the fragment is an Fab, Fab', Fab'-SH, F(ab')2, Fv, or scFv fragment.

In some embodiments that may be combined with any of the preceding embodiments, the antibody is a humanized antibody, a bispecific antibody, a monoclonal antibody, a multivalent antibody, a conjugated antibody, or a chimeric antibody. In some embodiments, the antibody is a monoclonal antibody. In some embodiments, the antibody is a bispecific antibody recognizing a first antigen and a second antigen. In some embodiments, the first antigen is CD33 and the second antigen is: an antigen facilitating transport across the blood-brain-barrier; an antigen facilitating transport across the blood brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; a disease-causing agent selected from the group consisting of disease-causing peptides or proteins and disease-causing nucleic acids, wherein the disease-causing peptides or proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG(RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the disease-causing nucleic acids are antisense GGCCCC (G2C4) repeat-expansion RNA; ligands and/or proteins expressed on immune cells, wherein the ligands and/or proteins selected from the group consisting of CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR, LAG3, DR5, CD39, CD70, CD73, TREM1, TREM2, Siglec-5, Siglec-7, Siglec-9, Siglec-11, SirpA, CD47, CSF1-receptor, and phosphatidylserine; and a protein, lipid, polysaccharide, or glycolipid expressed on one or more tumor cells.

In some embodiments that may be combined with any of the preceding embodiments, the antibody is used in combination with one or more antibodies that specifically bind a disease-causing agent selected from the group consisting of disease-causing peptides, disease-causing proteins, amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and any combination thereof; or with one or more antibodies that bind an immunomodulatory protein selected from the group consisting of: CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR3, DR5, CD39, CD70, CD73, LAG3, TREM1, TREM2, Siglec-5, Siglec-7, Siglec-9, Siglec-11, SirpA, CD47, CSF1-receptor, phosphatidylserine, disease-causing nucleic acids, antisense GGCCCC (G2C4) repeat-expansion RNA, and any combination thereof.

In some embodiments that may be combined with any of the preceding embodiments, the antibody has a dissociation constant ($K_D$) for human CD33 that is at least 1.8-fold lower than an anti-CD33 antibody comprising a heavy chain variable region comprising the amino acid sequence of SEQ ID NO: 3 and a light chain variable region comprising the amino acid sequence of SEQ ID NO: 4, wherein the $K_D$ is determined by BioLayer Interferometry.

In some embodiments that may be combined with any of the preceding embodiments, the antibody has a dissociation constant ($K_D$) for human CD33 that ranges from about 2 nM to about 200 pM, or less than about 200 pM, and wherein the $K_D$ is determined by BioLayer Interferometry.

In some embodiments that may be combined with any of the preceding embodiments, the antibody reduces cell surface levels of CD33. In some embodiments, the CD33 is expressed on the surface of human dendritic cells. In some embodiments, the antibody reduces cell surface levels of CD33 in vitro. In some embodiments, the antibody reduces cell surface levels of CD33 in vitro with a half maximal effective concentration ($EC_{50}$) that is less than 40 pM, as measured by flow cytometry.

In some embodiments that may be combined with any of the preceding embodiments, the antibody increases expression of one or more disease-associated microglia (DAM) markers. In some embodiments, the one or more DAM markers is ApoE3, Tyrobp, B2m, Trem2, Cst7, Cts1, Lp1, Cd9, Ax1, Csf1, Ccl6, Itgax, Clec7a, Lilrb4, Timp2, or any combination thereof.

In some embodiments that may be combined with any of the preceding embodiments, the antibody competes with one or more antibodies selected from the group consisting of 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof for binding to human CD33.

In some embodiments that may be combined with any of the preceding embodiments, the antibody binds essentially the same or overlapping CD33 epitope as an antibody selected from the group consisting of 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54.

In some embodiments that may be combined with any of the preceding embodiments, the antibody has an Fc region comprising the amino acid sequence of SEQ ID NO: 118.

In some embodiments that may be combined with any of the preceding embodiments, anti-CD33 antibodies of the present disclosure comprise a heavy chain variable domain and a light chain variable domain, wherein (a) the HVR-H1 comprises the amino acid sequence of SEQ ID NO:8, the HVR-H2 comprises the amino acid sequence of SEQ ID NO:33, the HVR-H3 comprises the amino acid sequence of SEQ ID NO:38, the HVR-L1 comprises the amino acid sequence of SEQ ID NO:47, HVR-L2 comprises the amino acid sequence of SEQ ID NO:52, and the HVR-L3 comprises the amino acid sequence of SEQ ID NO:58; (b) the HVR-H1 comprises the amino acid sequence of SEQ ID NO:8, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (c) the HVR-H1 comprises the amino acid sequence of SEQ ID NO:9, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:54, and the HVR-L3 comprises the amino acid sequence of SEQ ID NO:58; (d) the HVR-H1 comprises the amino acid sequence of SEQ ID NO:9, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (e) the HVR-H1 comprises the amino acid sequence of SEQ ID NO:9, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:55, and the HVR-L3 comprises the amino acid sequence of SEQ ID NO:58; (f) the HVR-H1 comprises the amino acid sequence of SEQ ID NO:10, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (g) the HVR-H1 comprises the amino acid sequence of SEQ ID NO:11, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (h) the HVR-H1 comprises the amino acid sequence of SEQ ID NO:12, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (i) the HVR-H1 comprises the amino acid sequence of SEQ ID NO:13, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (j) the HVR-H1 comprises the amino acid sequence of SEQ ID NO:14, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (k) the HVR-H1 comprises the amino acid sequence of SEQ ID NO:15, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (l) the HVR-H1 comprises the amino acid sequence of SEQ ID NO:16, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (m) the HVR-H1 comprises the amino acid sequence of SEQ ID NO:17, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (n) the HVR-H1 comprises the amino acid sequence of SEQ ID NO:18, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (o) the HVR-H1 comprises the amino acid sequence of SEQ ID NO:19, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (p) the HVR-H1 comprises the amino acid sequence of SEQ ID NO:20, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (q) the HVR-H1 comprises the amino acid sequence of SEQ ID NO:21, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (r) the HVR-H1 comprises the amino acid sequence of SEQ ID NO:22, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (s) the HVR-H1 comprises the amino acid sequence of SEQ ID NO:23, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (t) the HVR-H1 comprises the amino acid sequence of SEQ ID NO:24, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (u) the HVR-H1 comprises the amino acid sequence of SEQ ID NO:25, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (v) the HVR-H1 comprises the amino acid sequence of SEQ ID NO:26, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (w) the HVR-H1 comprises the amino acid sequence of SEQ ID NO:27, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (x) the HVR-H1 comprises the amino acid sequence of SEQ ID NO:28, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (y) the HVR-H1 comprises the amino acid sequence of SEQ ID NO:29, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:59; (z) the HVR-H1 comprises the amino acid sequence of SEQ ID NO:29, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:60; (aa) the HVR-H1 comprises the amino acid sequence of SEQ ID NO:29, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:61; (bb) the HVR-H1 comprises the amino acid sequence of SEQ ID NO:29, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:62; (cc) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:40, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:59; (dd) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:40, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:60; (ee) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:40, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:61; (ff) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:40, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:62; (gg) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:60; (hh) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:62; (ii) the HVR-H1 comprises the amino acid sequence of SEQ ID NO:23, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:60; (jj) the HVR-H1 comprises the amino acid sequence of SEQ ID NO:23, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:62; (kk) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:59; (ll) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:61; (mm) the HVR-H1 comprises the amino acid sequence of SEQ ID NO:28, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:59; and (nn) the HVR-H1 comprises the amino acid sequence of SEQ ID NO:28, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:61.

In some embodiments that may be combined with any of the preceding embodiments, anti-CD33 antibodies of the present disclosure comprise a light chain variable region comprising an amino acid sequence selected from any of SEQ ID NOs:94-103; and/or a heavy chain variable domain comprising an amino acid sequence selected from any of SEQ ID NOs:65-93. In some embodiments, the light chain variable domain comprises the amino acid sequence of SEQ ID NO: 94; and the heavy chain variable domain comprises the amino acid sequence of SEQ ID NO: 65. In some embodiments, the light chain variable domain comprises the amino acid sequence of SEQ ID NO: 94; and the heavy chain variable domain comprises the amino acid sequence of SEQ ID NO: 66. In some embodiments, the light chain variable domain comprises the amino acid sequence of SEQ ID NO: 95; and the heavy chain variable domain comprises the amino acid sequence of SEQ ID NO: 65. In some embodiments, the light chain variable domain comprises the amino acid sequence of SEQ ID NO: 95; and the heavy chain variable domain comprises the amino acid sequence of SEQ ID NO: 67. In some embodiments, the light chain variable domain comprises the amino acid sequence of SEQ ID NO: 95; and the heavy chain variable domain comprises the amino acid sequence of SEQ ID NO: 66. In some embodiments, the light chain variable domain comprises the amino acid sequence of SEQ ID NO: %; and the heavy chain variable domain comprises the amino acid sequence of SEQ ID NO: 65. In some embodiments, the light chain variable domain comprises the amino acid sequence of SEQ ID NO: %; and the heavy chain variable domain comprises the amino acid sequence of SEQ ID NO: 67. In some embodiments, the light chain variable domain comprises the amino acid sequence of SEQ ID NO: 97; and the heavy chain variable domain comprises the amino acid sequence of SEQ ID NO: 68. In some embodiments, the light chain variable domain comprises the amino acid sequence of SEQ ID NO: 98; and the heavy chain variable domain comprises the amino acid sequence of SEQ ID NO: 69. In some embodiments, the light chain variable domain comprises the amino acid sequence of SEQ ID NO: 97; and the heavy chain variable domain comprises the amino acid sequence of SEQ ID NO: 69. In some embodiments, the light chain variable domain comprises the amino acid sequence of SEQ ID NO: 94; and the heavy chain variable domain comprises the amino acid sequence of SEQ ID NO: 65. In some embodiments, the light chain variable domain comprises the amino acid sequence of SEQ ID NO: 99; and the heavy chain variable domain comprises the amino acid sequence of SEQ ID NO: 69. In some embodiments, the light chain variable domain comprises the amino acid sequence of SEQ ID NO: 97; and the heavy chain variable domain comprises the amino acid sequence of SEQ ID NO: 70. In some embodiments, the light chain variable domain comprises the amino acid sequence of SEQ ID NO: 97; and the heavy chain variable domain comprises the amino acid sequence of SEQ ID NO: 71. In some embodiments, the light chain variable domain comprises the amino acid sequence of SEQ ID NO: 97; and the heavy chain variable domain comprises the amino acid sequence of SEQ ID NO: 72. In some embodiments, the light chain variable domain comprises the amino acid sequence of SEQ ID NO: 97; and the heavy chain variable domain comprises the amino acid sequence of SEQ ID NO: 73. In some embodiments, the light chain variable domain comprises the amino acid sequence of SEQ ID NO: 97; and the heavy chain variable domain comprises the amino acid sequence of SEQ ID NO: 74. In some embodiments, the light chain variable domain comprises the amino acid sequence of SEQ ID NO: 97; and the heavy chain variable domain comprises the amino acid sequence of SEQ ID NO: 75. In some embodiments, the light chain variable domain comprises the amino acid sequence of SEQ ID NO: 97; and the heavy chain variable domain comprises the amino acid sequence of SEQ ID NO: 76. In some embodiments, the light chain variable domain comprises the amino acid sequence of SEQ ID NO: 97; and the heavy chain variable domain comprises the amino acid sequence of SEQ ID NO: 77. In some embodiments, the light chain variable domain comprises the amino acid sequence of SEQ ID NO: 97; and the heavy chain variable domain comprises the amino acid sequence of SEQ ID NO: 78. In some embodiments, the light chain variable domain comprises the amino acid sequence of SEQ ID NO: 97; and the heavy chain variable domain comprises the amino acid sequence of SEQ ID NO: 79. In some embodiments, the light chain variable domain comprises the amino acid sequence of SEQ ID NO: 97; and the heavy chain variable domain comprises the amino acid sequence of SEQ ID NO: 80. In some embodiments, the light chain variable domain comprises the amino acid sequence of SEQ ID NO: 97; and the heavy chain variable domain comprises the amino acid sequence of SEQ ID NO: 81. In some embodiments, the light chain variable domain comprises the amino acid sequence of SEQ ID NO: 97; and the heavy chain variable domain comprises the amino acid sequence of SEQ ID NO: 82. In some embodiments, the light chain variable domain comprises the amino acid sequence of SEQ ID NO: 97; and the heavy chain variable domain comprises the amino acid sequence of SEQ ID NO: 83. In some embodiments, the light chain variable domain comprises the amino acid sequence of SEQ ID NO: 97; and the heavy chain variable domain comprises the amino acid sequence of SEQ ID NO: 84. In some embodiments, the light chain variable domain comprises the amino acid sequence of SEQ ID NO: 97; and the heavy chain variable domain comprises the amino acid sequence of SEQ ID NO: 85. In some embodiments, the light chain variable domain comprises the amino acid sequence of SEQ ID NO: 97; and the heavy chain variable domain comprises the amino acid sequence of SEQ ID NO: 86. In some embodiments, the light chain variable domain comprises the amino acid sequence of SEQ ID NO: 97; and the heavy chain variable domain comprises the amino acid sequence of SEQ ID NO: 87. In some embodiments, the light chain variable domain comprises the amino acid sequence of SEQ ID NO: 97; and the heavy chain variable domain comprises the amino acid sequence of SEQ ID NO: 88. In some embodiments, the light chain variable domain comprises the amino acid sequence of SEQ ID NO: 100; and the heavy chain variable domain comprises the amino acid sequence of SEQ ID NO: 89. In some embodiments, the light chain variable domain comprises the amino acid sequence of SEQ ID NO: 101; and the heavy chain variable domain comprises the amino acid sequence of SEQ ID NO: 89. In some embodiments, the light chain variable domain comprises the amino acid sequence of SEQ ID NO: 102; and the heavy chain variable domain comprises the amino acid sequence of SEQ ID NO: 89. In some embodiments, the light chain variable domain comprises the amino acid sequence of SEQ ID NO: 103; and the heavy chain variable domain comprises the amino acid sequence of SEQ ID NO: 89. In some embodiments, the light chain variable domain comprises the amino acid sequence of SEQ ID NO: 100; and the heavy chain variable domain comprises the amino acid sequence of SEQ ID NO: 90. In some embodiments, the light chain variable domain comprises the amino acid sequence of SEQ ID NO: 101; and the heavy chain variable domain comprises the amino acid sequence of SEQ ID NO: 90. In some embodiments, the light chain variable domain comprises the amino acid sequence of SEQ ID NO: 102; and the heavy chain variable domain comprises the amino acid sequence of SEQ ID NO: 90. In some embodiments, the light chain variable domain comprises the amino acid sequence of SEQ ID NO: 103; and the heavy chain variable domain comprises the amino acid sequence of SEQ ID NO: 90. In some embodiments, the light chain variable domain comprises the amino acid sequence of SEQ ID NO: 100; and the heavy chain variable domain comprises the amino acid sequence of SEQ ID NO: 91. In some embodiments, the light chain variable domain comprises the amino acid sequence of SEQ ID NO: 101; and the heavy chain variable domain comprises the amino acid sequence of SEQ ID NO: 91. In some embodiments, the light chain variable domain comprises the amino acid sequence of SEQ ID NO: 102; and the heavy chain variable domain comprises the amino acid sequence of SEQ ID NO: 91. In some embodiments, the light chain variable domain comprises the amino acid sequence of SEQ ID NO: 103; and the heavy chain variable domain comprises the amino acid sequence of SEQ ID NO: 91. In some embodiments, the light chain variable domain comprises the amino acid sequence of SEQ ID NO: 101; and the heavy chain variable domain comprises the amino acid sequence of SEQ ID NO: 92. In some embodiments, the light chain variable domain comprises the amino acid sequence of SEQ ID NO: 103; and the heavy chain variable domain comprises the amino acid sequence of SEQ ID NO: 92. In some embodiments, the light chain variable domain comprises the amino acid sequence of SEQ ID NO: 101; and the heavy chain variable domain comprises the amino acid sequence of SEQ ID NO:93. In some embodiments, the light chain variable domain comprises the amino acid sequence of SEQ ID NO: 103; and the heavy chain variable domain comprises the amino acid sequence of SEQ ID NO: 93. In some embodiments, the light chain variable domain comprises the amino acid sequence of SEQ ID NO: 101; and the heavy chain variable domain comprises the amino acid sequence of SEQ ID NO: 83. In some embodiments, the light chain variable domain comprises the amino acid sequence of SEQ ID NO: 103; and the heavy chain variable domain comprises the amino acid sequence of SEQ ID NO: 83. In some embodiments, the light chain variable domain comprises the amino acid sequence of SEQ ID NO: 100; and the heavy chain variable domain comprises the amino acid sequence of SEQ ID NO: 92. In some embodiments, the light chain variable domain comprises the amino acid sequence of SEQ ID NO: 102; and the heavy chain variable domain comprises the amino acid sequence of SEQ ID NO: 92. In some embodiments, the light chain variable domain comprises the amino acid sequence of SEQ ID NO: 100; and the heavy chain variable domain comprises the amino acid sequence of SEQ ID NO: 93. In some embodiments, the light chain variable domain comprises the amino acid sequence of SEQ ID NO: 102; and the heavy chain variable domain comprises the amino acid sequence of SEQ ID NO: 93. In some embodiments, the light chain variable domain comprises the amino acid sequence of SEQ ID NO: 100; and the heavy chain variable domain comprises the amino acid sequence of SEQ ID NO: 83. In some embodiments, the light chain variable domain comprises the amino acid sequence of SEQ ID NO: 102; and the heavy chain variable domain comprises the amino acid sequence of SEQ ID NO: 83.

In another aspect, the present disclosure relates to isolated nucleic acids comprising a nucleic acid sequence encoding any of the antibodies described herein.

In another aspect, the present disclosure relates to vectors comprising any of the nucleic acids described herein. In some embodiments, the vector is an expression vector and/or a display vector.

In another aspect, the present disclosure relates to isolated host cells comprising any of the nucleic acids or vectors described herein.

In another aspect, the present disclosure relates to a method of producing an antibody that binds to CD33 comprising culturing any of the host cells described herein so that the antibody is produced. In some embodiments, the method further comprises recovering the antibody produced by the cell.

In another aspect, the present disclosure relates to an antibody produced by any of the methods described herein.

In another aspect, the present disclosure relates to pharmaceutical compositions comprising any of the antibodies described herein and a pharmaceutically acceptable carrier. In some embodiments, the present disclosure relates to the use of any of the antibodies described herein for the preparation of a medicament.

In another aspect, the present disclosure relates to a method of preventing, reducing risk, or treating a disease, disorder, or injury selected from the group consisting of dementia, frontotemporal dementia, Alzheimer's disease, vascular dementia, mixed dementia, taupathy disease, infections, and cancer, comprising administering to an individual in need thereof a therapeutically effective amount of any of the antibodies described herein. In some embodiments, the disease, disorder, or injury is cancer. In some embodiments, the cancer is selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), and multiple myeloma. In some embodiments, the present disclosure relates to the use of any of the antibodies described herein for the preparation of a medicament useful for preventing, reducing risk, or treating a disease, disorder, or injury selected from the group consisting of dementia, frontotemporal dementia, Alzheimer's disease, vascular dementia, mixed dementia, taupathy disease, infections, and cancer. In some embodiments, the disease, disorder, or injury is cancer. In some embodiments, the cancer is selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), and multiple myeloma It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

DETAILED DESCRIPTION OF THE PRESENT DISCLOSURE

Figure 1:
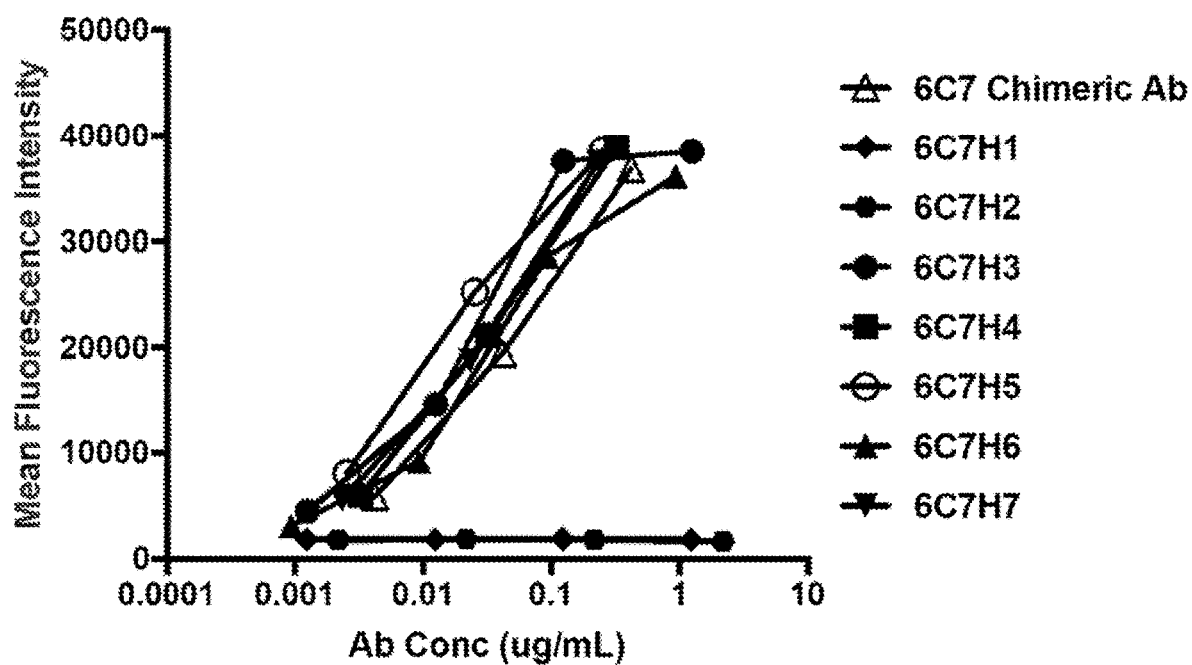
FIG. 1 sets forth data showing anti-CD33 antibodies of the present disclosure bind to primary human dendritic cells.

The present disclosure relates to anti-CD33 antibodies (e.g., monoclonal antibodies); methods of making and using such antibodies; pharmaceutical compositions comprising such antibodies; nucleic acids encoding such antibodies; and host cells comprising nucleic acids encoding such antibodies.

The techniques and procedures described or referenced herein are generally well understood and commonly employed using conventional methodology by those skilled in the art, such as, for example, the widely utilized methodologies such as those described in Sambrook et al. *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003); *Monoclonal Antibodies: A Practical Approach* (P. Shepherd and C. Dean, eds., Oxford University Press, 2000).

I. Definitions

The terms "CD33" or "CD33 polypepdde" are used interchangeably herein refer herein to any native CD33 from any vertebrate source, including mammals such as primates (e.g., humans and cynos) and rodents (e.g., mice and rats), unless otherwise indicated. In some embodiments, the term encompasses both wild-type sequences and naturally occurring variant sequences, e.g., splice variants or allelic variants. In some embodiments, the term encompasses "full-length," unprocessed CD33 as well as any form of CD33 that results from processing in the cell. In some embodiments, the CD33 is human CD33 isoform 1 (NCBI Reference Sequence: NP_001763.3). In some embodiments, the amino acid sequence of an exemplary human CD33 is SEQ ID NO: 1. The amino acid sequence of cyno CD33 is SEQ ID NO:2 (NCBI Reference Sequence: XP_005590138.1).

The terms "anti-CD33 antibody," an "antibody that binds to CD33," and "antibody that specifically binds CD33" refer to an antibody that is capable of binding CD33 with sufficient affinity such that the antibody is useful as a diagnostic and/or therapeutic agent in targeting CD33. In one embodiment, the extent of binding of an anti-CD33 antibody to an unrelated, non-CD33 polypeptide is less than about 10% of the binding of the antibody to CD33 as measured, e.g., by a radioimmunoassay (RIA). In certain embodiments, an antibody that binds to CD33 has a dissociation constant ($K_D$) of <1 µM, <100 nM, <10 nM, <1 nM, <0.1 nM, <0.01 nM, or <0.001 nM (e.g., $10^{-8}$ M or less, e.g. from $10^{-8}$ M to $10^{-13}$ M, e.g., from $10^{-4}$ M to $10^{-13}$ M). In certain embodiments, an anti-CD33 antibody binds to an epitope of CD33 that is conserved among CD33 from different species.

With regard to the binding of an antibody to a target molecule, the term "specific binding" or "specifically binds" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a $K_D$ for the target of about any of $10^{-4}$ M or lower, $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, $10^{-12}$ M or lower or a $K_D$ in the range of $10^{-4}$ M to $10^{-6}$ M or $10^{-6}$ M to $10^{-10}$ M or $10^{-7}$ M to $10^{-9}$M. As will be appreciated by the skilled artisan, affinity and $K_D$ values are inversely related. A high affinity for an antigen is measured by a low $K_D$ value. In one embodiment, the term "specific binding" refers to binding where a molecule binds to a particular polypeptide or epitope on a particular polypeptide without substantially binding to any other polypeptide or polypeptide epitope.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g., bispecific antibodies) including those formed from at least two intact antibodies, and antibody fragments so long as they exhibit the desired biological activity.

"Native antibodies" are usually heterotetrameric glycoproteins of about 150,000 Daltons, composed of two identical Light ("L") chains and two identical heavy ("H") chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

For the structure and properties of the different classes of antibodies, see, e.g., *Basic and Clinical Immunology*, 8th Ed., Daniel P. Stites, Abba I. Terr and Tristram G. Parslow (eds.), Appleton & Lange, Norwalk, Conn., 1994, page 71 and Chapter 6.

The light chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ"), and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three-dimensional configurations of different classes of immunoglobulins are well known and described generally in, for example, Abbas et al., Cellular and Molecular Immunology, $4^{th}$ ed. (W.B. Saunders Co., 2000).

The "variable region" or "variable domain" of an antibody, such as an anti-CD33 antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-CD33 antibodies of the present disclosure. The variable domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as a monoclonal anti-CD33 antibody of the present disclosure, obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, but not limited to one or more of the following methods, immunization methods of animals including, but not limited to rats, mice, rabbits, guinea pigs, hamsters and/or chickens with one or more of DNA(s), virus-like particles, polypetide(s), and/or cell(s), the hybridoma methods, B-cell cloning methods, recombinant DNA methods, and technologies for producing human or human-like antibodies in animals that have parts or all of the human immunoglobulin loci or genes encoding human immunoglobulin sequences.

The terms "full-length antibody," "intact antibody" or "whole antibody" are used interchangeably to refer to an antibody, such as an anti-CD33 antibody of the present disclosure, in its substantially intact form, as opposed to an antibody fragment. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" refers to a molecule other than an intact antibody that comprises a portion of an intact antibody that binds the antigen to which the intact antibody binds. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-CD33 antibodies of the present disclosure, produces two identical antigen-binding fragments, called "Fab" fragments, and a residual "Fc" fragment, a designation reflecting the ability to crystallize readily. The Fab fragment consists of an entire light chain along with the variable region domain of the heavy chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both heavy chains held together by disulfides. The effector functions of antibodies are determined by sequences in the Fc region, the region which is also recognized by Fc receptors (FcR) found on certain types of cells.

"Functional fragments" of antibodies, such as anti-CD33 antibodies of the present disclosure, comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the variable domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains.

As used herein, a "chimeric antibody" refers to an antibody (immunoglobulin), such as a chimeric anti-CD33 antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include PRI-MATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as humanized forms of anti-CD33 antibodies of the present disclosure, are chimeric antibodies comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one that possesses an amino-acid sequence corresponding to that of an antibody, such as an anti-CD33 antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries and yeast display libraries. Human antibodies can be prepared by administering the antigen to a transgenic animal that has been modified to produce such antibodies in response to antigenic challenge, but whose endogenous loci have been disabled, e.g., immunized xenomice as well as generated via a human B-cell hybridoma technology.

The term "hypervariable region," "HVR," or "HV," when used herein refers to the regions of an antibody-variable domain, such as that of an anti-CD33 antibody of the present disclosure, that are hypervariable in sequence and/or form structurally defined loops. Generally, antibodies comprise six HVRs; three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. Naturally occurring camelid antibodies consisting of a heavy chain only are functional and stable in the absence of light chain.

A number of HVR delineations are in use and are encompassed herein. In some embodiments, the HVRs may be Kabat complementarity-determining regions (CDRs) based on sequence variability and are the most commonly used (Kabat et al., supra). In some embodiments, the HVRs may be Chothia CDRs. Chothia refers instead to the location of the structural loops (Chothia and Lesk *J. Mol. Biol.* 196: 901-917 (1987)). In some embodiments, the HVRs may be AbM HVRs. The AbM HVRs represent a compromise between the Kabat CDRs and Chothia structural loops, and are used by Oxford Molecular's AbM antibody-modeling software. In some embodiments, the HVRs may be "contact" HVRs. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the $V_H$. The variable-domain residues are numbered according to Kabat et al., supra, for each of these extended-HVR definitions.

"Framework" or "FR" residues are those variable-domain residues other than the HVR residues as herein defined.

An "acceptor human framework" as used herein is a framework comprising the amino acid sequence of a $V_L$ or $V_H$ framework derived from a human immunoglobulin framework or a human consensus framework. An acceptor human framework "derived from" a human immunoglobulin framework or a human consensus framework may comprise the same amino acid sequence thereof, or it may comprise pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the $V_L$ human immunoglobulin framework sequence or human consensus framework sequence.

A "human consensus framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest*, 5th Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al., supra.

An "amino-acid modification" at a specified position, e.g., of an anti-CD33 antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an affinity matured anti-CD33 antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al. *Bio/Technology* 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155: 1994-2004 (1995); Jackson et al. *J. Immunol.* 154(7):3310-9 (1995); and Hawkins et al, *J. Mol. Biol.* 226:889-896 (1992).

"Fv" is the minimum antibody fragment which comprises a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains, which enables the sFv to form the desired structure for antigen binding.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80/6 homology with a native sequence Fc region and/or with an Fc region of a parent polypeptide, and most preferably at least about 90/6 homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. Other FcRs, including those to be identified in the future, are encompassed by the term "FcR" herein. FcRs can also increase the serum half-life of antibodies.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared.

The term "compete" when used in the context of antibodies (e.g., neutralizing antibodies) that compete for the same epitope means competition between antibody as determined by an assay in which the antibody being tested prevents or inhibits (e.g., reduces) specific binding of a reference molecule (e.g., a ligand, or a reference antibody) to a common antigen (e.g., CD33 or a fragment thereof). Numerous types of competitive binding assays can be used to determine if antibody competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antibody and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided herein. Usually, when a competing antibody is present in excess, it will inhibit (e.g., reduce) specific binding of a reference antibody to a common antigen by at least 20%, 30%, 40%, 50%, 60%, 70%, 80%, 85%, 90%, 95%, 97.5%, and/or near 100%.

As used herein, an "interaction" between a CD33 polypeptide and a second polypeptide encompasses, without limitation, protein-protein interaction, a physical interaction, a chemical interaction, binding, covalent binding, and ionic binding. As used herein, an antibody "inhibits interaction" between two polypeptides when the antibody disrupts, reduces, or completely eliminates an interaction between the two polypeptides. An antibody of the present disclosure, thereof, "inhibits interaction" between two polypeptides when the antibody thereof binds to one of the two polypeptides. In some embodiments, the interaction can be inhibited by at least about any of 20%, 30%, 40%, 50%, 60%, 70%, 80%, 85%, 90%, 95%, 97.5%, and/or near 100%.

The term "epitope" includes any determinant capable of being bound by an antibody. An epitope is a region of an antigen that is bound by an antibody that targets that antigen, and when the antigen is a polypeptide, includes specific amino acids that directly contact the antibody. Most often, epitopes reside on polypeptides, but in some instances, can reside on other kinds of molecules, such as nucleic acids. Epitope determinants can include chemically active surface groupings of molecules such as amino acids, sugar side chains, phosphoryl or sulfonyl groups, and can have specific three-dimensional structural characteristics, and/or specific charge characteristics. Generally, antibodies specific for a particular target antigen will preferentially recognize an epitope on the target antigen in a complex mixture of polypeptides and/or macromolecules.

An "agonist" antibody or an "activating" antibody is an antibody that induces (e.g., increases) one or more activities or functions of the antigen after the antibody binds the antigen.

An "antagonist" antibody or a "blocking" antibody or an "inhibitory" antibody is an antibody that reduces, inhibits, and/or eliminates (e.g., decreases) antigen binding to one or more ligand after the antibody binds the antigen, and/or that reduces, inhibits, and/or eliminates (e.g., decreases) one or more activities or functions of the antigen after the antibody binds the antigen. In some embodiments, antagonist antibodies, or blocking antibodies, or inhibitory antibodies substantially or completely inhibit antigen binding to one or more ligand and/or one or more activities or functions of the antigen.

An "isolated" antibody, such as an isolated anti-CD33 antibody of the present disclosure, is one that has been identified, separated and/or recovered from a component of its production environment (e.g., naturally or recombinantly). Preferably, the isolated antibody is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the antibody will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

An "isolated" nucleic acid molecule encoding an antibody, such as an anti-CD33 antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the present disclosure.

"Carriers" as used herein include pharmaceutically acceptable carriers, excipients, or stabilizers that are nontoxic to the cell or mammal being exposed thereto at the dosages and concentrations employed.

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration. In some embodiments, administration in conjunction is administration as a part of the same treatment regimen.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

Overview

The present disclosure relates, in part, to anti-CD33 antibodies that exhibit one or more improved and/or enhanced functional characteristics (e.g., relative to an anti-CD33 antibody having a heavy chain variable region comprising the sequence of SEQ ID NO:3 and a light chain variable region comprising the sequence of SEQ ID NO:4), including, for example, antibodies capable of decreasing cell surface levels of CD33 and/or binding CD33 with improved/enhanced kinetics; methods of making and using such antibodies; pharmaceutical compositions containing such antibodies; nucleic acids encoding such antibodies; and host cells containing nucleic acids encoding such antibodies.

In some embodiments, the anti-CD33 antibodies of the present disclosure have one or more activities that are due, at least in part, to the ability of the antibodies to inhibit the interaction between CD33 and one or more natural glycan ligands. In some embodiments, the anti-CD33 antibodies of the present disclosure may have one or more activities that are due, at least in part, to the ability of the antibodies to reduce cellular expression (e.g., cell surface expression) of CD33 by inducing degradation, down regulation, cleavage, receptor desensitization, and/or lysosomal targeting of CD33. In some embodiments, the anti-CD33 antibodies exhibit one or more of the following properties: a) have a dissociation constant ($K_D$) for human CD33 that is lower than that of an anti-CD33 antibody having a heavy chain variable region comprising the sequence of SEQ ID NO:3 and a light chain variable region comprising the sequence of SEQ ID NO:4; b) bind to human cells, such as primary human dendritic cells; c) decrease cell surface levels of CD33 (e.g., decrease cell surface levels of CD33 on primary human dendritic cells in vitro) with a half-maximal effective concentration ($EC_{50}$) that is lower than that of an anti-CD33 antibody having a heavy chain variable region comprising the sequence of SEQ ID NO:3 and a light chain variable region comprising the sequence of SEQ ID NO:4; d) have a dissociation constant ($K_D$) for human CD33 that may range from about 0.061 nM to about 0.40 nM, for example when the $K_D$ is determined by surface plasmon resonance or BioLayer Interferometry; and/or e. decrease cell surface levels of CD33 (e.g., decreases cell surface levels of CD33 on primary human dendritic cells in vitro) with a half-maximal effective concentration ($EC_{50}$) that may range from about 78 pM to about 40 pM, for example when the $EC_{50}$ is determined in vitro by flow cytometry. As disclosed herein half-maximal effective concentration ($EC_{50}$) refers to the concentration at which an anti-CD33 antibody of the present disclosure reduces cellular levels of CD33 on a cell or in a cell to half that of untreated cells, or the concentration at which the antibody achieves half-maximal binding to CD33 on a cell.

Advantageously, anti-CD33 antibodies of the present disclosure reduce cell surface expression (e.g., up to approximately 1.6-fold or up to 18-fold) of CD33 more potently (e.g., with a lower $EC_{50}$) as compared to a control anti-CD33 antibody (e.g., a control anti-CD33 antibody having a heavy chain variable region comprising the sequence of SEQ ID NO:3 and a light chain variable region comprising the sequence of SEQ ID NO:4) (See e.g., Example 3). Moreover, advantageously, anti-CD33 antibodies of the present disclosure have a higher affinity (e.g., up to approximately 7-fold higher affinity) for CD33 (e.g., a lower $K_D$ value as measured by surface plasmon resonance) as compared to a control anti-CD33 antibody (e.g., a control anti-CD33 antibody having a heavy chain variable region comprising the sequence of SEQ ID NO:3 and a light chain variable region comprising the sequence of SEQ ID NO:4. Surprisingly, higher affinity for CD33 does not necessarily correlate with an increase in ability or potency of reduction of cell surface expression of CD33.

Certain aspects of the present disclosure are based, at least in part, on the identification of anti-CD33 antibodies that exhibit one or more improved and/or enhanced functional characteristics (e.g., relative to an anti-CD33 antibody having a heavy chain variable region comprising the sequence of SEQ ID NO:3 and a light chain variable region comprising the sequence of SEQ ID NO:4), including, an improved/enhanced ability to decrease cell surface levels of CD33 on cells, resulting in the reduction, neutralization, prevention, or curbing of one or more CD33 activities, including, without limitation, reducing cell growth of monocytes, macrophages, T cells, dendritic cells and/or microglia; reducing T cell proliferation induced by dendritic cells, bone marrow-derived dendritic cells, monocytes, microglia, M1 microglia, activated M1 microglia, M2 microglia, macrophages, M1 macrophages, activated M1 macrophages, and/or M2 macrophages; decreasing survival of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing proliferation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting migration of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing one or more functions of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; reducing proliferation of monocytes, macrophages, T cells, dendritic cells, neutrophils, and/or microglia; reducing the overall functionality of monocytes, macrophages, T cells, dendritic cells, neutrophils, and/or microglia; inhibition of beneficial immune response to different types of cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, acute myeloid leukemia, pancreatic cancer, prostate cancer, ovarian cancer, fibrosarcoma, and thyroid cancer, inhibition of beneficial immune response to different types of neurological disorders selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, essential tremor, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, and multiple sclerosis; binding to CD33 ligand on tumor cells; binding to CD33 ligand on dendritic cells, bone marrow-derived dendritic cells, monocytes, microglia, T cells, neutrophils, and/or macrophages; inhibition of tumor cell killing by one or more of microglia, macrophages, dendritic cells, bone marrow-derived dendritic cells, neutrophils, T cells, T helper cells, or cytotoxic T cells; inhibition of anti-tumor cell proliferation activity of one or more of microglia, macrophages, dendritic cells, bone marrow-derived dendritic cells, neutrophils, T cells, T helper cells, or cytotoxic T cells; inhibition of anti-tumor cell metastasis activity of one or more of microglia, macrophages, dendritic cells, bone marrow-derived dendritic cells, neutrophils, T cells, T helper cells, or cytotoxic T cells; modulated expression of one or more inflammatory receptors, such as CD86, expressed on one or more of microglia, macrophages, dendritic cells, bone marrow-derived dendritic cells, neutrophils, T cells, T helper cells, or cytotoxic T cells; enhancing infiltration of one or more of immunosuppressor dendritic cells, immunosuppressor macrophages, myeloid derived suppressor cells, tumor-associated macrophages, immunosuppressor neutrophils, and regulatory T cells into tumors; increasing number of tumor-promoting myeloid/granulocytic immune-suppressive cells in a tumor, in peripheral blood, or other lymphoid organ; enhancing tumor-promoting activity of myeloid-derived suppressor cells; decreasing activation of tumor-specific T lymphocytes with tumor killing potential; decreasing infiltration of tumor-specific T lymphocytes with tumor killing potential; increasing tumor growth rate; increasing rate of tumor recurrence; decreasing efficacy of one or more immune-therapies that modulate anti-tumor T cell responses, optionally wherein the one or more immune-therapies are immune-therapies that target one or more proteins selected from CD40, OX40, ICOS, CD28, CD137/4-1BB, CD27, GITR, PD-L1, CTLA4, PD-L2, PD-1, B7-H3, B7-H4, HVEM, LIGHT, BTLA, VISTA, KIR, GAL9, TIM1, TIM3, TIM4, A2AR, LAG3, DR-5, CD39, CD70, TREM1, TREM2, Siglec-5, Siglec-7, Siglec-9, Siglec-11, SirpA, CD447, CSF-1 receptor, and any combination thereof, or of one or chemotherapy agents and/or more cancer vaccines.

In some embodiments, treatment of cancer with anti-CD33 antibodies as described herein may: (i) increasing the number of tumor infiltrating CD3$^+$ T cells; (ii) decreasing cellular levels of CD33 in non-tumorigenic CD14$^+$myeloid cells, optionally wherein the non-tumorigenic CD14$^+$ myeloid cells are tumor infiltrating cells or optionally wherein the non-tumorigenic CD14$^+$ myeloid cells are present in blood; (iii) reducing the number of non-tumorigenic CD14$^+$ myeloid cells, optionally wherein the non-tumorigenic CD14$^+$ myeloid cells are tumor infiltrating cells or optionally wherein the non-tumorigenic CD14$^+$ myeloid cells are present in blood; (iv) d reducing PD-L1, PD-L2, B7-H7, B7-H3, CD200R, CD163, and/or CD206 levels in one or more cells, optionally wherein the one or more cells are non-tumorigenic myeloid-derived suppressor cells (MDSC); (v) decreasing tumor growth rate of solid tumors; (vi) reducing tumor volume; (vii) increasing efficacy of one or more PD-1 inhibitors; (viii) increasing efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, OX40, TIM3, LAG3, or any combination thereof; (ix) increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof; (x) i increasing proliferation of T cells in the presence of non-tumorigenic myeloid-derived suppressor cells (MDSC); (xi) inhibiting differentiation, survival, and/or one or more functions of non-tumorigenic myeloid-derived suppressor cells (MDSC); and (xii) killing CD33-expressing immunosuppressor non-tumorigenic myeloid cells and/or non-tumorigenic CD14-expressing cells in solid tumors and associated blood vessels when conjugated to a chemical or radioactive toxin.

In some embodiments, myeloid cells of the present disclosure include, without limitation, CD45+CD14+ myeloid cells, CD14+ myeloid cells, and myeloid-derived suppressor cells (MDSC). In some embodiments, myeloid cells of the present disclosure are non-tumorigenic myeloid cells. Immunosuppressor cells are sometimes also referred to as myeloid-derived suppressor cells (MDSC). In humans, MDSCs can be defined by one of the following combination of markers: (1) CD14+ HLA-DRlow/−, (2) CD14+IL4Ra+, (3) CD14+ HLA-DR− IL4Ra+, (4) CD34+CD14+CD11b+ CD33+, (5) CD11b+CD14+CD33+, (6) CD33+ HLA-DR−, (7) Lin− HLA-DR−, (8) Lin− HLA-DR− CD33+, (9) Lin− HLA-DR− CD33+CD11b+, (10) Lin− CD33+CD11b+ CD15+, (11) Lin− HLA-DR− CD33+CD11b+CD14− CD15+, (12) CD11b+CD14− CD33+, (13) CD11b+CD14− HLA-DR− CD33+CD15+, (14) CD33+ HLA-DR− CD15+, (15) CD15+IL4Ra+, (16) CD11b+CD15+CD66b+, (17) CD15+ FSClow SSChigh, (18) CD15high CD33+, (19) CD11b+CD14− CD15+, (20) CD66b+ SSChigh, and (21) CD11b+CD15+(see also Solito S et al. Annals of the NY Academy of Sciences, 2014). In mice, MDSCs can be defined by the expression of the surface markers CD45+, CD11b+, Gr1+, and/or Il4Ra+. Additional exemplary immunosuppressive monocytic lineages are CD45+, CD11b+, Gr1low; and CD45+, CD11c+.

CD33 Proteins

In one aspect, the present disclosure provides antibodies, such as isolated (e.g., monoclonal) antibodies, that interact with or otherwise bind to a region, such as an epitope, within a CD33 protein of the present disclosure. In some embodiments, the antibodies interact with or otherwise bind to a region, such as an epitope, within a CD33 protein of the present disclosure with improved/enhanced kinetics (e.g., relative to an anti-CD33 antibody having a heavy chain variable region comprising the sequence of SEQ ID NO:3 and a light chain variable region comprising the sequence of SEQ ID NO:4). In some embodiments, the antibodies interact with or otherwise bind to a region, such as an epitope, within a CD33 protein on human cells, such as dendritic cells, with a half-maximal effective concentration ($EC_{50}$) that is lower than that of a control antibody (e.g., relative to an anti-CD33 antibody having a heavy chain variable region comprising the sequence of SEQ ID NO:3 and a light chain variable region comprising the sequence of SEQ ID NO:4). In some embodiments, anti-CD33 antibodies of the present disclosure bind to a CD33 protein and modulate one or more CD33 activities after binding to the CD33 protein, for example, an activity associated with CD33 expression on a cell. CD33 proteins of the present disclosure include, without limitation, a mammalian CD33 protein, human CD33 protein, mouse CD33 protein, and rat CD33 protein.

CD33 is variously referred to as a CD33 molecule, Siglec3, Siglec-3, CD33 antigen (Gp67), P67, Gp67, sialic acid-binding-Ig-like lectin 3, myeloid cell surface antigen CD33, or FU00391.

CD33 is an immunoglobulin-like receptor primarily expressed on myeloid lineage cells, including without limitation, macrophages, dendritic cells, osteoclasts, monocytes, and microglia. In some embodiments, CD33 forms a receptor-signaling complex with CD64. In some embodiments, CD33 signaling results in the downstream inhibition of PI3K or other intracellular signals. On myeloid cells, Toll-like receptor (TLR) signals are important for the inhibition of CD33 activities, e.g., in the context of an infection response. TLRs also play a key role in the pathological inflammatory response, e.g., TLRs expressed in macrophages and dendritic cells.

```
The amino acid sequence of human CD33 is set forth
below as SEQ ID NO: 1:
MPLLLLLPLLWAGALAMDPNFWLQVQESVTVQEGLCVLVPCTFFHPIPYY

DKNSPVHGYWFREGAIISRDSPVATNKLDQEVQEETQGRFRLLGDPSRNN

CSLSIVDARRRDNGSYFFRMERGSTKYSYKSPQLSVHVTDLTHRPKILIP

GTLEPGHSKNLTCSVSWACEQGTPPIFSWLSAAPTSLGPRTTHSSVLIIT

PRPQDHGTNLTCQVKFAGAGVTTERTIQLNVTYVPQNPTTGIFPGDGSGK

QETRAGVVHGAIGGAGVTALLALCLCLIFFIVKTHRRKAARTAVGRNDTH

PTTGSASPKHQKKSKLHGPTETSSCSGAAPTVEMDEELHYASLNFHGMNP

SKDTSTEYSEVRTQ

The amino acid sequence of cyno CD33 is set forth
below as SEQ ID NO: 2:
MDGEHLKGRNQGAQETSASDMPLLLLPLLWAGALAMDPRVRLEVQESVTV

QEGLCVLVPCTFFHPVPYHTRNSPVHGYWFREGAIVSLDSPVATNKLDQE

VQEETQGRFRLLGDPSRNNCSLSIVDARRRDNGSYFFRMEKGSTKYSYKS

TQLSVHVTDLTHRPQILIPGALDPDHSKNLTCSVPWACEQGTPPIFSWMS

AAPTSLGLRTTHSSVLIITPRPQDHGTNLTCQVKFPGAGVTTERTIQLNV

SYASQNPRTDIFLGDGSGKQGVVQGAIGGAGVTVLLALCLCLIFFTVKTH

RRKAARTAVGRIDTHPATGPTSSKHQKKSKLHGATETSGCSGTTLTVEMD

EELHYASLNFHGMNPSEDTSTEYSEVRTQ
```

In some embodiments, the CD33 is a preprotein that includes a signal sequence. In some embodiments, the CD33 is a mature protein. In some embodiments, the mature CD33 protein does not include a signal sequence. In some embodiments, the mature CD33 protein is expressed on a cell. In some embodiments, the mature CD33 protein is expressed on a cell, such as the surface of a cell, including, without limitation, human dendritic cells, human macrophages, human monocytes, human osteoclasts, human neutrophils, human T cells, human T helper cell, human cytotoxic T cells, human granulocytes, and human microglia. Anti-CD33 antibodies of the present disclosure may bind any of the CD33 proteins of the present disclosure expressed on any cell disclosed herein.

CD33 proteins of the present disclosure, such as human CD33, contain several domains, including without limitation, a signal sequence located at amino acid residues 1-17 of SEQ ID NO: 1, an extracellular immunoglobulin-like variable-type (IgV) domain located at amino acid residues 19-135 of SEQ ID NO: 1, an Ig-like C2-type domain located at amino acid residues 145-228 of SEQ ID NO: 1, a transmembrane domain located at amino acid residues 260-282 of SEQ ID NO: 1, an ITIM motif 1 located at amino acid residues 338-343 of SEQ ID NO: 1, and an ITIM motif 2 located at amino acid residues 356-361 of SEQ ID NO: 1. As one of skill in the art will appreciate, the beginning and ending residues of the domains of the present disclosure may vary depending upon the computer modeling program used or the method used for determining the domain.

Certain aspects of the present disclosure provide anti-CD33 antibodies that bind to a human CD33, or a homolog thereof, including without limitation a mammalian CD33 protein and CD33 orthologs from other species. In some embodiments, the anti-CD33 antibodies of the present disclosure bind to a human CD33, or homolog thereof, with improved/enhanced binding kinetics and/or improved activity, such as decreasing cellular levels of CD33 (e.g., relative to an anti-CD33 antibody having a heavy chain variable region comprising the sequence of SEQ ID NO:3 and a light chain variable region comprising the sequence of SEQ ID NO:4).

Accordingly, as used herein a "CD33" protein of the present disclosure includes, without limitation, a mammalian CD33 protein, human CD33 protein, primate CD33 protein, mouse CD33 protein, and rat CD33 protein. Additionally, anti-CD33 antibodies of the present disclosure may bind an epitope within a human CD33 protein, primate CD33. In some embodiments, anti-CD33 antibodies of the present disclosure may bind specifically to human CD33. In some embodiments, anti-CD33 antibodies of the present disclosure may bind to cyno CD33. In some embodiments, anti-CD33 antibodies of the present disclosure may bind to human CD33 and to cyno CD33.

In some embodiments, antibodies of the present disclosure may bind CD33 in a pH dependent manner. In some embodiments, antibodies of the present disclosure can bind to CD33 at a neutral pH and be internalized without dissociating from the CD33 protein. Alternatively, at an acidic pH, antibodies of the present disclosure may dissociate from CD33 once they are internalized and are then degraded by endosome/lysosome pathway. In certain embodiments, an anti-CD33 antibody binds CD33 at a pH that ranges from 5.5 to 8.0, from 5.5 to 7.5, from 5.5 to 7.0, from 5.5 to 6.5, from 5.5 to 6.0, from 6.0 to 8.0, from 6.5 to 8.0, from 7.0 to 8.0, from 7.5 to 8.0, from 6.0 to 7.5, from 6.0 to 7.0, from 6.5 to 7.5. In certain embodiments, an anti-CD33 antibody dissociates from CD33 at a pH of less than 6.0, less than 5.5, less than 5.0, less than 4.5, less than 4.0, less than 3.5, less than 3.0, less than 2.5, or less than 2.0.

In some embodiments, antibodies of the present disclosure, bind to a wild-type CD33 protein of the present disclosure, naturally occurring variants thereof, and/or disease variants thereof.

In some embodiments, antibodies of the present disclosure bind a variant of human CD33, wherein the variant contains a single nucleotide polymorphism (SNP) rs3865444C with a (C) nucleotide. In some embodiments, antibodies of the present disclosure that decrease cellular levels of CD33 and/or that bind or interact with CD33, bind to a variant of human CD33, wherein the variant contains a SNP rs3865444 with an (A) nucleotide. In some embodiments, anti-CD33 antibodies of the present disclosure bind a variant of human CD33, wherein the variant contains a SNP rs3865444$^{AC}$ or rs3865444$^{CC}$.

In some embodiments, antibodies of the present disclosure that decrease cellular levels of CD33 and/or that bind or interact with CD33, bind a variant of human CD33, wherein the variant contains a SNP rs35112940 with GG nucleotides, AA nucleotides, or AG nucleotides. In some embodiments, antibodies of the present disclosure that decrease cellular levels of CD33 and/or that bind or interact with CD33, bind a variant of human CD33, wherein the variant contains a SNP rs12459419 with CC, CT or TT genotypes. In certain embodiments, the subject has a homozygous or heterozygous for the coding SNPs, rs1803 with GG nucleotides, CG nucleotides, or CC nucleotides.

In some embodiments, antibodies of the present disclosure that decrease cellular levels of CD33 and/or that bind or interact with CD33, bind to a CD33 protein expressed on the surface of a cell including, without limitation, human dendritic cells, human macrophages, human monocytes, human osteoclasts, human neutrophils, human T cells, human T helper cell, human cytotoxic T cells, human granulocytes, and human microglia. In some embodiments, antibodies of the present disclosure that decrease cellular levels of CD33 and/or that bind or interact with CD33, bind to a CD33 protein expressed on the surface of a cell and modulate (e.g., induce or inhibit) at least one CD33 activity of the present disclosure after binding to the surface expressed CD33 protein. In some embodiments of the present disclosure, the anti-CD33 antibody binds specifically to a CD33 protein. In some embodiments of the present disclosure, the anti-CD33 antibody further binds to at least one additional Siglec protein. In some embodiments, the anti-CD33 antibody modulates one or more activities of the at least one additional Siglec protein or of a cell expressing the at least one additional Siglec protein.

CD33 Ligands

CD33 proteins of the present disclosure can interact with (e.g., bind to) one or more CD33 ligands.

Exemplary CD33 ligands include, without limitation, sialic acid, sialic acid-containing glycolipids, sialic acid-containing glycoproteins, alpha-2,6-linked sialic acid-containing glycolipids, alpha-2,6-linked sialic acid-containing glycoproteins, alpha-2,3-linked sialic acid-containing glycolipids, alpha-2,3-linked sialic acid-containing glycoproteins, alpha-1-acid glycoprotein (AGP), CD24 protein, gangliosides (e.g., glycolipids containing a ceramide linked to a sialylated glycan), secreted mucins, CD33 ligands expressed on red blood cells, CD33 ligands expressed on bacterial cells, CD33 ligands expressed on apoptotic cells, CD33 ligands expressed on tumor cells, CD33 ligands expressed on viruses, CD33 ligands expressed on dendritic cells, CD33 ligands expressed on nerve cells, CD33 ligands expressed on glial cells, CD33 ligands expressed on microglia, CD33 ligands expressed on astrocytes, CD33 ligands on beta amyloid plaques, CD33 ligands on Tau tangles, CD33 ligands on disease-causing proteins, CD33 ligands on disease-causing peptides, CD33 ligands expressed on macrophages, CD33 ligands expressed on natural killer cells, CD33 ligands expressed on T cells, CD33 ligands expressed on T helper cells, CD33 ligands expressed on cytotoxic T cells, CD33 ligands expressed on B cells, CD33 ligands expressed on tumor-imbedded immunosuppressor dendritic cells, CD33 ligands expressed on tumor-imbedded immunosuppressor macrophages, CD33 ligands expressed on myeloid-derived suppressor cells, and CD33 ligands expressed on regulatory T cells. In some embodiments, CD33 ligands of the present disclosure are gangliosides. Gangliosides generally share a common lacto-ceramide core and one or more sialic acid residues.

Further examples of suitable ganglioside ligands are listed in Table A. Generally, a ganglioside is a molecule composed of a glycosphingolipid with one or more sialic acids (e.g., n-acetyl-neuraminic acid, NANA) linked on the sugar chain.

TABLE A

Structures of exemplary ganglioside CD33 ligands

GM2-1 = aNeu5Ac(2-3)bDGalp(1-?)bDGalNAc(1-?)bDGalNAc(1-?)bDGlcp(1-1)Cer
GM3 = aNeu5Ac(2-3)bDGalp(1-4)bDGlcp(1-1)Cer
GM2, GM2a(?) = bDGalpNAc(1-4)[aNeu5Ac(2-3)]bDGalp(1-4)bDGlcp(1-1)Cer
GM2b(?) = aNeu5Ac(2-8)aNeu5Ac(2-3)bDGalp(1-4)bDGlcp(1-1)Cer
GM1, GM1a = bDGalp(1-3)bDGalNAc[aNeu5Ac(2-3)]bDGalp(1-4)bDGlcp(1-1)Cer
asialo-GM1, GA1 = bDGalp(1-3)bDGalpNAc(1-4)bDGalp(1-4)bDGlcp(1-1)Cer
asialo-GM2, GA2 = bDGalpNAc(1-4)bDGalp(1-4)bDGlcp(1-1)Cer
GM1b = aNeu5Ac(2-3)bDGalp(1-3)bDGalNAc(1-4)bDGalp(1-4)bDGlcp(1-1)Cer
GD3 = aNeu5Ac(2-8)aNeu5Ac(2-3)bDGalp(1-4)bDGlcp(1-1)Cer
GD2 = bDGalpNAc(1-4)[aNeu5Ac(2-8)aNeu5Ac(2-3)]bDGalp(1-4)bDGlcp(1-1)Cer
GD1a = aNeu5Ac(2-3)bDGalp(1-3)bDGalNAc(1-4)[aNeu5Ac(2-3)]bDGalp(1-4)bDGlcp(1-1)Cer
GD1alpha = aNeu5Ac(2-3)bDGalp(1-3)bDGalNAc(1-4)[aNeu5Ac(2-6)]bDGalp(1-4)bDGlcp(1-1)Cer
GD1b = bDGalp(1-3)bDGalNAc(1-4)[aNeu5Ac(2-8)aNeu5Ac(2-3)]bDGalp(1-4)bDGlcp(1-1)Cer
GT1a = aNeu5Ac(2-8)aNeu5Ac(2-3)bDGalp(1-3)bDGalNAc(1-4)[aNeu5Ac(2-3)]bDGalp(1-4)bDGlcp(1-1)Cer
GT1, GT1b = aNeu5Ac(2-3)bDGalp(1-3)bDGalNAc(1-4)[aNeu5Ac(2-8)aNeu5Ac(2-3)]bDGalp(1-4)bDGlcp(1-1)Cer
OAc-GT1b = aNeu5Ac(2-3)bDGalp(1-3)bDGalNAc(1-4)aXNeu5Ac9Ac(2-8)aNeu5Ac(2-3)]bDGalp(1-4)bDGlcp(1-1)Cer
GT1c = bDGalp(1-3)bDGalNAc(1-4)[aNeu5Ac(2-8)aNeu5Ac(2-3)]bDGalp(1-4)bDGlcp(1-1)Cer
GT3 = aNeu5Ac(2-8)aNeu5Ac(2-8)aNeu5Ac(2-3)bDGal(1-4)bDGlc(1-1)CerGQ1b = aNeu5Ac(2-8)aNeu5Ac(2-3)bDGalp(1-3)bDGalNAc(1-4)[aNeu5Ac(2-8)aNeu5Ac(2-3)]bDGalp(1-4)bDGlcp(1-1)Cer
GGal = aNeu5Ac(2-3)bDGalp(1-1)Cer
where:
aNeu5Ac = 5-acetyl-alpha-neuraminic acid
aNeu5Ac9Ac = 5,9-diacetyl-alpha-neuraminic acid
bDGalp = beta-D-galactopyranose
bDGalpNAc = N-acetyl-beta-D-galactopyranose
bDGlcp = beta-D-glucopyranose
Cer = ceramide (general N-acylated sphingoid)

Anti-CD33 Antibodies

Certain aspects of the present disclosure relate to anti-CD33 antibodies comprising one or more improved and/or enhanced functional characteristics. In some embodiments, anti-CD33 antibodies of the present disclosure comprise one or more improved and/or enhanced functional characteristics relative to a reference or control antibody (e.g., an anti-CD33 antibody comprising a heavy chain variable region comprising the amino acid sequence of SEQ ID NO: 3 and a light chain variable region comprising the amino acid sequence of SEQ ID NO: 4). In some embodiments, anti-CD33 antibodies of the present disclosure have an affinity for CD33 (e.g., human CD33) that is higher than that of a reference or control anti-CD33 antibody (e.g., an anti-CD33 antibody comprising a heavy chain variable region comprising the amino acid sequence of SEQ ID NO: 3 and a light chain variable region comprising the amino acid sequence of SEQ ID NO: 4). In some embodiments, anti-CD33 antibodies of the present disclosure bind to human cells, such as human primary dendritic cells, with a half-maximal effective concentration ($EC_{50}$) that is lower than that of a reference or control antibody (e.g., an anti-CD33 antibody comprising a heavy chain variable region comprising the amino acid sequence of SEQ ID NO: 3 and a light chain variable region comprising the amino acid sequence of SEQ ID NO: 4). In some embodiments, anti-CD33 antibodies of the present disclosure decrease cellular levels (e.g., decrease or reduce cell surface levels) of CD33 with a half-maximal effective concentration ($EC_{50}$) that is lower than that of a reference or control antibody (e.g., an anti-CD33 antibody comprising a heavy chain variable region comprising the sequence of SEQ ID NO: 3 and a light chain variable region comprising the sequence of SEQ ID NO: 4).

Cellular levels of CD33 may refer to, without limitation, cell surface levels of CD33, intracellular levels of CD33, and total levels of CD33. In some embodiments, a decrease in cellular levels of CD33 comprises decrease in cell surface levels of CD33. In some embodiments, anti-CD33 antibodies of the present disclosure that decrease cellular levels of CD33 (e.g., cell surface levels of CD33) have one or more of the following characteristics: (1) inhibits or reduces one or more CD33 activities; (2) the ability to inhibit or reduce binding of a CD33 to one or more of its ligands; (3) the ability to reduce CD33 expression in CD33-expressing cells; (4) the ability to interact, bind, or recognize a CD33 protein; (5) the ability to specifically interact with or bind to a CD33 protein; and (6) the ability to treat, ameliorate, or prevent any aspect of a disease or disorder described or contemplated herein.

Anti-CD33 antibodies of the present disclosure may have nanomolar or even picomolar affinities for the target antigen (e.g., human CD33). In certain embodiments, the dissociation constant ($K_D$) of the antibody is from about 0.001 to about 100 nM. In certain embodiments, the $K_D$ of the antibody is about 0.01 to about 10 nM. In certain embodiments, the $K_D$ of the antibody is about 0.23 to about 3.88 nM. In some embodiments, the $K_D$ of the antibody is less than about or equal to about 100 nM, 90 nM, 80 nM, 70 nM, 60 nM, 50 nM, 40 nM, 30 nM, 20 nM, 10 nM, 9.5 nM, 9 nM, 8.5 nM, 8 nM, 7.5 nM, 7 nM, 6.5 nM, 6 nM, 5.5 nM, 5 nM, 4.5 nM, 4 nM, 3.5 nM, 3 nM, 2.5 nM, 2 nM, 1.5 nM, 1 nM, 0.9 nM, 0.8 nM, 0.7 nM, 0.6 nM, 0.5 nM, 0.4 nM, 0.3 nM, 0.2 nM, 0.1 nM, 0.05 nM, 0.01 nM, or 0.005 nM. In some embodiments, the $K_D$ of the antibody is less than about 0.40 nM. In some embodiments, the $K_D$ of the antibody is less than about 0.30 nM. In some embodiments, the $K_D$ of the antibody is less than about 0.20 nM. In some embodiments, the $K_D$ is less than about 0.10 nM. In some embodiments, the $K_D$ of the antibody is about 0.061 nM. In some embodiments, the $K_D$ of the antibody is greater than about or equal to about 0.001 nM, 0.005 nM, 0.01 nM, 0.05 nM, 0.1 nM, 0.2 nM, 0.3 nM, 0.4 nM, 0.5 nM, 0.6 nM, 0.7 nM, 0.8 nM, 0.9 nM, 1 nM, 1.5 nM, 2 nM, 2.5 nM, 3 nM 3.5 nM, 4 nM, 4.5 nM, 5 nM, 5.5 nM, 6 nM, 6.5 nM, 7 nM, 7.5 nM, 8 nM, 8.5 nM, 9 nM, 9.5 nM, 10 nM. 20 nM, 30 nM, 40 nM, 50 nM, 60 nM, 70 nM, 80 nM, or 90 nM. That is, the $K_D$ of the antibody can be any of a range of affinities having an upper limit of about 100 nM, 90 nM, 80 nM, 70 nM, 60 nM, 50 nM, 40 nM, 30 nM, 20 nM, 10 nM, 9.5 nM, 9 nM, 8.5 nM, 8 nM, 7.5 nM, 7 nM, 6.5 nM, 6 nM, 5.5 nM, 5 nM, 4.5 nM, 4 nM, 3.5 nM, 3 nM, 2.5 nM, 2 nM, 1.5 nM, 1 nM, 0.9 nM, 0.8 nM, 0.7 nM, 0.6 nM, 0.5 nM, 0.4 nM, 0.3 nM, 0.2 nM, 0.1 nM, 0.05 nM, 0.01 nM, or 0.005 nM, and an independently selected lower limit of about 0.001 nM, 0.005 nM, 0.01 nM, 0.05 nM, 0.1 nM, 0.2 nM, 0.3 nM, 0.4 nM, 0.5 nM, 0.6 nM, 0.7 nM, 0.8 nM, 0.9 nM, 1 nM, 1.5 nM, 2 nM, 2.5 nM, 3 nM 3.5 nM, 4 nM, 4.5 nM, 5 nM, 5.5 nM, 6 nM, 6.5 nM, 7 nM, 7.5 nM, 8 nM, 8.5 nM, 9 nM, 9.5 nM, 10 nM. 20 nM, 30 nM, 40 nM, 50 nM, 60 nM, 70 nM, 80 nM, or 90 nM, wherein the lower limit is less than the upper limit. In some embodiments, the $K_D$ of the antibody is any of about 10 nM, about 9 nM, about 8 nM, about 7 nM, about 6 nM, about 5 nM, about 4 nM, about 3 nM, about 2 nM, about 1 nM, about 900 pM, about 800 pM, about 700 pM, about 600 pM, about 500 pM, about 400 pM, about 300 pM, about 200 pM, or about 100 pM. Various methods of measuring antibody affinity are known in the art, including, for example, using surface plasmon resonance or BioLayer Interferometry (See e.g., Example 3 below). In some embodiments, the $K_D$ for CD33 is determined at a temperature of approximately 25° C. In some embodiments, the $K_D$ for CD33 is determined at a temperature of approximately 4° C. In some embodiments, the $K_D$ is determined using a monovalent antibody (e.g., a Fab) or a full-length antibody in a monovalent form. In some embodiments, the $K_D$ is determined using a bivalent antibody and monomeric recombinant CD33 protein.

In some embodiments, anti-CD33 antibodies of the present disclosure have a lower dissociation constant ($K_D$) for CD33 than a reference anti-CD33 antibody (e.g., an anti-CD33 antibody comprising a heavy chain variable region comprising the amino acid sequence of SEQ ID NO: 3 and a light chain variable region comprising the amino acid sequence of SEQ ID NO: 4). In some embodiments, anti-CD33 antibodies of the present disclosure have a $K_D$ for a target (e.g., human CD33) that is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% lower than the $K_D$ of a reference anti-CD33 antibody for the target (e.g., an anti-CD33 antibody comprising a heavy chain variable region comprising the amino acid sequence of SEQ ID NO: 3 and a light chain variable region comprising the amino acid sequence of SEQ ID NO: 4). In some embodiments, anti-CD33 antibodies of the present disclosure have a $K_D$ for a target (e.g., human CD33) that is at least about 1-fold, at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 12.5-fold, at least about 15-fold, at least about 17.5-fold, at least about 20-fold, at least about 22.5-fold, at least about 25-fold, at least about 27.5-fold, at least about 30-fold, at least about 50-fold, or at least about 100-fold lower than the $K_D$ of a reference anti-CD33 antibody for the target (e.g., an anti-CD33 antibody comprising a heavy chain variable region comprising the amino acid sequence of SEQ ID NO: 3 and a light chain variable region comprising the amino acid sequence of SEQ ID NO: 4). In some embodiments, anti-CD33 antibodies of the present disclosure have a $K_D$ for human CD33 that is at least 7-fold greater than an anti-CD33 antibody having a heavy chain variable region comprising the amino acid sequence of SEQ ID NO: 3 and a light chain variable region comprising the amino acid sequence of SEQ ID NO: 4. In some embodiments, anti-CD33 antibodies of the present disclosure have a $K_D$ for human CD33 that is at least 1.8-fold greater than an anti-CD33 antibody having a heavy chain variable region comprising the amino acid sequence of SEQ ID NO: 3 and a light chain variable region comprising the amino acid sequence of SEQ ID NO: 4. In some embodiments, the affinity is measured by surface plasmon resonance. In some embodiments, the affinity is measured at a temperature of approximately 25° C. In some embodiments, the affinity is measured at a temperature of approximately 4° C. In some embodiments, the affinity is measured using the experimental approach as described in Examples below.

Anti-CD33 antibodies of the present disclosure may decrease cellular levels (e.g., cell surface levels) of CD33 with a half-maximal effective concentration ($EC_{50}$) (e.g., when measured in vitro using primary human dendritic cells) in the picomolar range. In certain embodiments, the $EC_{50}$ of the antibody is about 0.1 to about 500 pM. In certain embodiments, the $EC_{50}$ of the antibody is about 1 to about 250 pM. In certain embodiments, the $EC_{50}$ of the antibody is about 27 pM to about 40 pM. In certain embodiments, the $EC_{50}$ of the antibody is about 78 pM to about 40 pM. In some embodiments, the $EC_{50}$ of the antibody is less than about or equal to about 500 pM, 400 pM, 300 pM, 250 pM, 225 pM, 200 pM, 175 pM, 150 pM, 125 pM, 100 pM, 75 pM, 50 pM, 25 pM, 10 pM, 1 pM, or 0.5 pM. In some embodiments, the $EC_{50}$ of the antibody is less than about 74.3 pM. In some embodiments, the $EC_{50}$ of the antibody is greater than about or equal to about 0.1 pM, 0.5 pM, 1 pM, 10 pM, 25 pM, 50 pM, 75 pM, 100 pM, 125 pM, 150 pM, 175 pM, 200 pM, 225 pM, 250 pM, 300 pM, or 400 pM. That is, the $EC_{50}$ of the antibody can be any of a range having an upper limit of about 500 pM, 400 pM, 300 pM, 250 pM, 225 pM, 200 pM, 175 pM, 150 pM, 125 pM, 100 pM, 75 pM, 50 pM, 25 pM, 10 pM, 1 pM, or 0.5 pM, and an independently selected lower limit of about 0.1 pM, 0.5 pM, 1 pM, 10 pM, 25 pM, 50 pM, 75 pM, 100 pM, 125 pM, 150 pM, 175 pM, 200 pM, 225 pM, 250 pM, 300 pM, or 400 pM, wherein the lower limit is less than the upper limit. In some embodiments, the $EC_{50}$ of the antibody is any of about 1 pM, 2 pM, 3 pM, 4 pM, 5 pM, 6 pM, 7 pM, 8 pM, 9 pM, 10 pM, 15 pM, 20 pM, 25 pM, 30 pM, 35 pM, 40 pM, 45 pM, 50 pM, 55 pM, 60 pM, 65 pM, 70 pM, 75 pM, 80 pM, 85 pM, 90 pM, 95 pM, 100 pM, 105 pM, 110 pM, 115 pM, 120 pM, 125 pM, 130 pM, 135 pM, 140 pM, 145 pM, 150 pM, 155 pM, 160 pM, 165 pM, 170 pM, 175 pM, 180 pM, 185 pM, 190 pM, 195 pM, or 200 pM. Various methods of measuring antibody $EC_{50}$ values are known in the art, including, for example, by flow cytometry (See e.g., Example 3 below). In some embodiments, the $EC_{50}$ is measured in vitro using primary human dendritic cells. In some embodiments, the $EC_{50}$ is measured in vitro using primary human monocytes. In some embodiments, the $EC_{50}$ is measured in vitro using primary human macrophages. In some embodiments, the $EC_{50}$ is measured in vitro using cultured cells transfected with human CD33. In some embodiments, the $EC_{50}$ is measured at a temperature of approximately 4° C. In some embodiments, the $EC_{50}$ is measured at a temperature of approximately 25° C. In some embodiments, the $EC_{50}$ is measured at a temperature of approximately 35° C. In some embodiments, the $EC_{50}$ is measured at a temperature of approximately 37° C. In some embodiments, the $EC_{50}$ is determined using a monovalent antibody (e.g., a Fab) or a full-length antibody in a monovalent form. In some embodiments, the $EC_{50}$ is determined using antibodies containing constant regions that demonstrate enhanced Fc receptor binding. In some embodiments, the $EC_{50}$ is determined using antibodies containing constant regions that demonstrate reduced Fc receptor binding.

In some embodiments, anti-CD33 antibodies of the present disclosure decrease cellular levels (e.g., decrease or reduce cell surface levels) of CD33 with a lower $EC_{50}$ (e.g., as measured in vitro using primary human dendritic cells) than a reference anti-CD33 antibody (e.g., an anti-CD33 antibody comprising a heavy chain variable region comprising the amino acid sequence of SEQ ID NO: 3 and a light chain variable region comprising the amino acid sequence of SEQ ID NO: 4). In some embodiments, anti-CD33 antibodies of the present disclosure decrease cellular levels (e.g., decrease or reduce cell surface levels) of CD33 with an $EC_{50}$ that is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% lower than the $EC_{50}$ of a reference anti-CD33 antibody (e.g., an anti-CD33 antibody comprising a heavy chain variable region comprising the amino acid sequence of SEQ ID NO: 3 and a light chain variable region comprising the amino acid sequence of SEQ ID NO: 4). In some embodiments, anti-CD33 antibodies of the present disclosure decrease cellular levels (e.g., decrease or reduce cell surface levels) of CD33 with an $EC_{50}$ that is at least about 1-fold, at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 12.5-fold, at least about 15-fold, at least about 17.5-fold, at least about 20-fold, at least about 22.5-fold, at least about 25-fold, at least about 27.5-fold, at least about 30-fold, at least about 50-fold, or at least about 100-fold lower than the ECs of a reference anti-CD33 antibody (e.g., an anti-CD33 antibody comprising a heavy chain variable region comprising the amino acid sequence of SEQ ID NO: 3 and a light chain variable region comprising the amino acid sequence of SEQ ID NO: 4). In some embodiments, anti-CD33 antibodies of the present disclosure have an $EC_{50}$ that is at least 1.2-fold to 1.6-fold or 1.1-fold to 1.6-fold lower than an anti-CD33 antibody having a heavy chain variable region comprising the amino acid sequence of SEQ ID NO: 3 and a light chain variable region comprising the amino acid sequence of SEQ ID NO: 4. In some embodiments, the $EC_{50}$ is measured in vitro using primary human dendritic cells. In some embodiments, the $EC_{50}$ is measured in vitro using primary human monocytes. In some embodiments, the $EC_{50}$ is measured in vitro using primary human macrophages. In some embodiments, the EC$_{50}$ is measured in vitro using cultured cells transfected with human CD33. In some embodiments, the EC$_{50}$ is measured by flow cytometry. In some embodiments, the EC$_{50}$ is measured at a temperature of approximately 25° C. In some embodiments, the EC$_{50}$ is measured at a temperature of approximately 35° C. In some embodiments, the EC$_{50}$ is measured at a temperature of approximately 37° C. In some embodiments, the EC$_{50}$ is determined using antibodies containing constant regions that demonstrate enhanced Fc receptor binding. In some embodiments, the EC$_{50}$ is determined using antibodies containing constant regions that demonstrate reduced Fc receptor binding. In some embodiments, the EC$_{50}$ is measured using the experimental approach as described in the Example 3 below.

Any in vitro cell-based assays or suitable in vivo model described herein or known in the art may be used to measure inhibition of interaction (e.g., binding) between CD33 and one or more CD33 ligands. In some embodiments, anti-CD33 antibodies of the present disclosure inhibit interaction (e.g., binding) between CD33 and one or more CD33 ligands by at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more at saturating antibody concentrations utilizing any in vitro assay or cell-based culture assay described herein or known in the art.

In some embodiments, anti-CD33 antibodies of the present disclosure inhibit cell surface clustering of CD33. In some embodiments, anti-CD33 antibodies of the present disclosure inhibit one or more activities of a CD33 protein, including, without limitation, counteracting one or more of phosphorylation of Tyr-340 and Tyr-358 by a Src family tyrosine kinase, such as LCK and FYN; recruitment of and binding to the tyrosine-specific protein phosphatases SHP1 and SHP2; recruitment of and binding to PLC-gamma1, which acts as a guanine nucleotide exchange factor for Dynamini-1; recruitment of and binding to SH2-domain containing protein (e.g., Crkl); recruitment of and binding to the spleen tyrosine kinase Syk; recruitment of and binding to SH3-SH2-SH3 growth factor receptor-bound protein 2 (Grb2); recruitment of and binding to multiple SH2-containing proteins; phosphorylation of Ser-307 and Ser-342 by protein kinase C; modulated expression of one or more anti-inflammatory cytokines, IL-4, IL-10, IL-13, IL-35, IL-16, TGF-beta, IL-1Ra, G-CSF, and soluble receptors for TNF, IFN-beta1a, IFN-beta1b, or IL-6 in monocytes, macrophages, T cells, dendritic cells neutrophils, and/or microglia; decreasing intracellular calcium mobilization; modulated expression of one or more pro-inflammatory cytokines IFN-α4, IFN-b, IL-1β, TNF-α, IL-6, IL-8, CRP, IL-20 family members, LIF, IFN-gamma, OSM, CNTF, GM-CSF, IL-li, IL-12, IL-17, IL-18, IL-23, CXCL10, IL-33, CRP, IL-33, MCP-1, and MIP-1-beta in monocytes, macrophages, T cells, dendritic cells, neutrophils, and/or microglia; modulated expression of one or more proteins selected from C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, PYCARD, CD14, CD16, HLA-DR, and CCR2; inhibition of extracellular signal-regulated kinase (ERK) phosphorylation; decreasing tyrosine phosphorylation on multiple cellular proteins; modulated expression of C—C chemokine receptor 7 (CCR7); inhibition of microglial cell chemotaxis toward CCL19 and CCL21 expressing cells; activation of phosphoinositide 3-kinase; reducing cell growth of monocytes, macrophages, T cells, dendritic cells and/or microglia; reducing T cell proliferation induced by dendritic cells, bone marrow-derived dendritic cells, monocytes, microglia, M1 microglia, activated M1 microglia, M2 microglia, macrophages, M1 macrophages, activated M1 macrophages, and/or M2 macrophages; inhibition of osteoclast production, decreased rate of osteoclastogenesis, or both; decreasing survival of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing proliferation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting migration of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing one or more functions of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting maturation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; increasing cell death and apoptosis of monocytes, macrophages, T cells, dendritic cells, neutrophils, and/or microglia; reducing phagocytic activity of monocytes, macrophages, T cells, dendritic cells, neutrophils, and/or microglia; reducing proliferation of monocytes, macrophages, T cells, dendritic cells, neutrophils, and/or microglia; reducing the overall functionality of monocytes, macrophages, T cells, dendritic cells, neutrophils, and/or microglia, phosphorylation of an ITAM containing receptor, phosphorylation of a signaling molecules that mediates ITAM signaling; reducing the activation of pattern recognition receptors; reducing the activation of Toll-like receptors; reducing the activation of damage-associated of clearance of cellular and protein debris; interaction between CD33 and one or more of its ligands; interaction between CD33 and a co-receptor such as CD64; reducing one or more types of clearance selected from apoptotic neuron clearance, nerve tissue debris clearance, dysfunctional synapse clearance, non-nerve tissue debris clearance, bacteria or other foreign body clearance, disease-causing protein clearance, and tumor cell clearance; inhibition of phagocytosis of one or more of apoptotic neurons, nerve tissue debris, non-nerve tissue debris, bacteria, other foreign bodies, disease-causing proteins, disease-causing peptides, disease-causing nucleic acid, disease-causing lipids, or tumor cells; inhibition of clearance of a disease-causing nucleic acid, such as the disease-causing nucleic acid is antisense GGCCCC (G2C4) repeat-expansion RNA; activation of clearance of, a disease-causing protein selected from amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; inhibition of beneficial immune response to different types of cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, acute myeloid leukemia, pancreatic cancer, prostate cancer, ovarian cancer, fibrosarcoma, and thyroid cancer; inhibition of beneficial immune response to different types of neurological disorders selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, essential tremor, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, -traumatic brain injury, age related macular degeneration, glaucoma, retinitis pigmentosa, retinal degeneration, and multiple sclerosis; inhibition of beneficial immune response-to different types of inflammatory and infectious disorders selected from lupus, acute and chronic colitis, wound healing, Crohn's disease, inflammatory bowel disease, ulcerative colitis, obesity, malaria, respiratory tract infection, sepsis, eye infection, systemic infection, lupus, arthritis, low bone density, osteoporosis, osteogenesis, osteopetrotic disease, and Paget's disease of bone; binding to CD33 ligand on tumor cells; binding to CD33 ligand on dendritic cells, bone marrow-derived dendritic cells, monocytes, microglia, T cells, neutrophils, and/or macrophages; inhibition of tumor cell killing by one or more of microglia, macrophages, dendritic cells, bone marrow-derived dendritic cells, neutrophils, T cells, T helper cells, or cytotoxic T cells; inhibition of anti-tumor cell proliferation activity of one or more of microglia, macrophages, dendritic cells, bone marrow-derived dendritic cells, neutrophils, T cells, T helper cells, or cytotoxic T cells; inhibition of anti-tumor cell metastasis activity of one or more of microglia, macrophages, dendritic cells, bone marrow-derived dendritic cells, neutrophils, T cells, T helper cells, or cytotoxic T cells; promotion of immunosuppressor dendritic cells, immunosuppressor macrophages, myeloid-derived suppressor cells, tumor-associated macrophages, or regulatory T cells; inhibition of one or more ITAM motif containing receptors, such as TREM1, TREM2, FcgR, DAP10, and DAP12; inhibition of one or more receptors containing the motif D/Ex0-2YxxL/IX6-8YxxL/I (SEQ ID NO: 104); inhibition of signaling by one or more pattern recognition receptors (PRRs), such as receptors that identify pathogen-associated molecular patterns (PAMPs), and receptors that identify damage-associated molecular patterns (DAMPs); inhibition of signaling by one or more Toll-like receptors; inhibition of the JAK-STAT signaling pathway; inhibition of nuclear factor kappa-light-chain-enhancer of activated B cells (NFκB); inhibition of PLCγ/PKC/calcium mobilization; inhibition of PI3K/Akt, Ras/MAPK signaling; reduced expression of one or more inflammatory receptors, such as CD86, expressed on one or more of microglia, macrophages, dendritic cells, bone marrow-derived dendritic cells, neutrophils, T cells, T helper cells, or cytotoxic T cells; increasing expression of one or more CD33-dependent genes; normalization of disrupted CD33-dependent gene expression; and decreasing expression of one or more ITAM-dependent genes, such as NFAT transcription factors.

In some embodiments, anti-CD33 antibodies of the present disclosure exhibit one or more activities of a CD33 protein, including, without limitation, increasing the number of tumor infiltrating $CD3^+$ T cells; decreasing cellular levels of CD33 in $CD14^+$ myeloid cells, such as tumor infiltrating $CD14^+$ myeloid cells and $CD14^+$ myeloid cells present in blood; reducing the number of $CD14^+$ myeloid cells, such as tumor infiltrating $CD14^+$ myeloid cells and $CD14^+$ myeloid cells present in blood; reducing PD-L1, PD-L2, B7-H7, B7-H3, CD200R, CD163, and/or CD206 levels in one or more cells, such as myeloid-derived suppressor cells (MDSC); decreasing tumor growth rate of solid tumors; reducing tumor volume; increasing efficacy of one or more PD-1 inhibitors; increasing efficacy of one or more checkpoint inhibitor therapies and/or immune-modulating therapies, such as checkpoint inhibitor therapies and/or immune-modulating therapies that target one or more of CTL4, the adenosine pathway, PD-L1, PD-L2, OX40, TIM3, LAG3, or any combination thereof; increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), oxaliplatin (Elotaxin®), leucovorin, temazolamide (Temodar®), and any combination thereof; increasing proliferation of T cells in the presence of myeloid-derived suppressor cells (MDSC); inhibiting differentiation, survival, and/or one or more functions of myeloid-derived suppressor cells (MDSC); and killing CD33-expressing immunosuppressor non-tumorigenic myeloid cells and/or non-tumorigenic CD14-expressing cells in solid tumors and associated blood vessels when conjugated to a chemical or radioactive toxin.

In some embodiments, the anti-CD33 antibodies inhibit interaction (e.g., binding) between a CD33 protein of the present disclosure and one or more CD33 ligands including, without limitation, CD33 ligands expressed on red blood cells, CD33 ligands expressed on bacterial cells, CD33 ligands expressed on apoptotic cells, CD33 ligands expressed on tumor cells, CD33 ligands expressed on viruses, CD33 ligands expressed on dendritic cells, CD33 ligands expressed on nerve cells, CD33 ligands expressed on glial cells, CD33 ligands expressed on microglia, CD33 ligands expressed on astrocytes, CD33 ligands on beta amyloid plaques, CD33 ligands on Tau tangles, CD33 ligands on disease-causing proteins, CD33 ligands on disease-causing peptides, CD33 ligands expressed on macrophages, CD33 ligands expressed on natural killer cells, CD33 ligands expressed on T cells, CD33 ligands expressed on T helper cells, CD33 ligands expressed on cytotoxic T cells, CD33 ligands expressed on B cells, CD33 ligands expressed on tumor-imbedded immunosuppressor dendritic cells, CD33 ligands expressed on tumor-imbedded immunosuppressor macrophages, CD33 ligands expressed on myeloid-derived suppressor cells, CD33 ligands expressed on regulatory T cells, secreted mucins, sialic acid, sialic acid-containing glycolipids, sialic acid-containing glycoproteins, alpha-2,6-linked sialic acid-containing glycolipids, alpha-2,6-linked sialic acid-containing glycoproteins, alpha-2,3-linked sialic acid-containing glycolipids, alpha-2,3-linked sialic acid-containing glycoproteins, alpha-1-acid glycoprotein (AGP), CD24 protein, and gangliosides.

In some embodiments, anti-CD33 antibodies of the present disclosure bind to a CD33 protein of the present disclosure expressed on the surface of cell and the naked antibodies inhibit interaction (e.g., binding) between the CD33 protein and one or more CD33 ligands. In some embodiments, anti-CD33 antibodies of the present disclosure that bind to a CD33 protein of the present inhibit interaction (e.g., binding) between the CD33 protein and one or more CD33 ligands by reducing the effective levels of CD33 that is available to interact with these proteins either on the cell surface or inside the cell. In some embodiments, anti-CD33 antibodies of the present disclosure that bind to a CD33 protein of the present inhibit interaction (e.g., binding) between the CD33 protein and one or more CD33 ligands by inducing degradation of CD33.

As used herein, levels of CD33 may refer to expression levels of the gene encoding CD33; to expression levels of one or more transcripts encoding CD33; to expression levels of CD33 protein; and/or to the amount of CD33 protein present within cells and/or on the cell surface. Any methods known in the art for measuring levels of gene expression, transcription, translation, and/or protein abundance or localization may be used to determine the levels of CD33.

Additionally, anti-CD33 antibodies of the present disclosure can be used to prevent, reduce risk of, or treat dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and/or *Haemophilus* influenza. In some embodiments, anti-CD33 antibodies of the present disclosure can be used for inducing or promoting the survival, maturation, functionality, migration, or proliferation of one or more immune cells in an individual in need thereof; or for decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, and/or chronic myeloid leukemia (CML) cell in an individual in need thereof. In some embodiments, anti-CD33 antibodies of the present disclosure are monoclonal antibodies.

In some embodiments, an isolated anti-CD33 antibody of the present disclosure decreases cellular levels of CD33 (e.g., cell surface levels, intracellular levels, and/or total levels). In some embodiments, an isolated anti-CD33 antibody of the present disclosure induces downregulation of CD33. In some embodiments, an isolated anti-CD33 antibody of the present disclosure induces cleavage of CD33. In some embodiments, an isolated anti-CD33 antibody of the present disclosure induces internalization of CD33. In some embodiments, an isolated anti-CD33 antibody of the present disclosure induces shedding of CD33. In some embodiments, an isolated anti-CD33 antibody of the present disclosure induces degradation of CD33. In some embodiments, an isolated anti-CD33 antibody of the present disclosure induces desensitization of CD33. In some embodiments, an isolated anti-CD33 antibody of the present disclosure acts as a ligand mimetic to transiently activate CD33. In some embodiments, an isolated anti-CD33 antibody of the present disclosure acts as a ligand mimetic and transiently activates CD33 before inducing a decrease in cellular levels of CD33 and/or inhibition of interaction (e.g., binding) between CD33 and one or more CD33 ligands. In some embodiments, an isolated anti-CD33 antibody of the present disclosure acts as a ligand mimetic and transiently activates CD33 before inducing degradation of CD33. In some embodiments, an isolated anti-CD33 antibody of the present disclosure acts as a ligand mimetic and transiently activates CD33 before inducing cleavage of CD33. In some embodiments, an isolated anti-CD33 antibody of the present disclosure acts as a ligand mimetic and transiently activates CD33 before inducing internalization of CD33. In some embodiments, an isolated anti-CD33 antibody of the present disclosure acts as a ligand mimetic and transiently activates CD33 before inducing shedding of CD33. In some embodiments, an isolated anti-CD33 antibody of the present disclosure acts as a ligand mimetic and transiently activates CD33 before inducing downregulation of CD33 expression. In some embodiments, an isolated anti-CD33 antibody of the present disclosure acts as a ligand mimetic and transiently activates CD33 before inducing desensitization of CD33.

In some embodiments, an isolated anti-CD33 antibody of the present disclosure is a human antibody, a humanized antibody, a bispecific antibody, a monoclonal antibody, a multivalent antibody, or a chimeric antibody. Exemplary descriptions of such antibodies are found throughout the present disclosure.

In some embodiments, anti-CD33 antibodies of the present disclosure bind to a human CD33, or a homolog thereof, including without limitation, a mammalian CD33 protein. In some embodiments, anti-CD33 antibodies of the present disclosure specifically bind to human CD33. In some embodiments, anti-CD33 antibodies of the present disclosure bind to human CD33 and are not cross-reactive with CD33 orthologs or homologs from other species. In some embodiments, anti-CD33 antibodies of the present disclosure bind human CD33 but do not bind cyno CD33. In some embodiments, anti-CD33 antibodies of the present disclosure bind both human CD33 and cyno CD33.

In some embodiments, anti-CD33 antibodies of the present disclosure bind to a CD33 protein of the present disclosure expressed on the surface of a cell and modulate (e.g., induce or inhibit) one or more CD33 activities of the present disclosure after binding to the surface-expressed CD33 protein. In some embodiments, anti-CD33 antibodies of the present disclosure are inert antibodies.

Anti-CD33 Antibody Binding Regions

In some embodiments, anti-CD33 antibodies of the present disclosure may bind a conformational epitope. In some embodiments, anti-CD33 antibodies of the present disclosure may bind a discontinuous CD33 epitope. In some embodiments, the discontinuous CD33 epitope comprises two or more peptides, three or more peptides, four or more peptides, five or more peptides, six or more peptides, seven or more peptides, eight or more peptides, nine or more peptides, or 10 or more peptides. In some embodiments, anti-CD33 antibodies of the present disclosure may bind a CD33 epitope comprising one or more peptides. As disclosed herein, CD33 epitopes may comprise one or more peptides comprising five or more, six or more, seven or more, eight or more, nine or more, 10 or more, 11 or more, 12 or more, 13 or more 14 or more, 15 or more, 16 or more, 17 or more, 18 or more, 19 or more, or 20 or more amino acid residues of the amino acid sequence of SEQ ID NO: 1, or five or more, six or more, seven or more, eight or more, nine or more, 10 or more, 11 or more, 12 or more, 13 or more 14 or more, 15 or more, 16 or more, 17 or more, 18 or more, 19 or more, or 20 or more amino acid residues on a mammalian CD33 protein corresponding to the amino acid sequence of SEQ ID NO: 1.

In some embodiments, anti-CD33 antibodies of the present disclosure bind to an epitope of human CD33 that is the same as or overlaps with the CD33 epitope bound by an anti-CD33 antibody comprising a heavy chain variable region comprising the amino acid sequence of SEQ ID NO: 3 and a light chain variable region comprising the amino acid sequence of SEQ ID NO: 4. In some embodiments, anti-CD33 antibodies of the present disclosure bind essentially the same CD33 epitope bound by an anti-CD33 antibody comprising a heavy chain variable region comprising the amino acid sequence of SEQ ID NO: 3 and a light chain variable region comprising the amino acid sequence of SEQ ID NO: 4.

In some embodiments, anti-CD33 antibodies of the present disclosure competitively inhibit binding of an anti-CD33 antibody comprising a heavy chain variable region comprising the amino acid sequence of SEQ ID NO: 3 and a light chain variable region comprising the amino acid sequence of SEQ ID NO: 4. In some embodiments, anti-CD33 antibodies of the present disclosure compete with an anti-CD33 antibody comprising a heavy chain variable region comprising the amino acid sequence of SEQ ID NO: 3 and a light chain variable region comprising the amino acid sequence of SEQ ID NO: 4 for binding to CD33 (e.g. human CD33).

In some embodiments, anti-CD33 antibodies of the present disclosure competitively inhibit binding of at least one antibody selected from any of the antibodies listed in Tables 7, 8, 9, 10, 11, and 12. In some embodiments, anti-CD33 antibodies of the present disclosure competitively inhibit binding of at least one antibody selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof. In some embodiments, an anti-CD33 antibody of the present disclosure competes with one or more antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof, for binding to CD33 when the anti-CD33 antibody reduces the binding of one or more antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof to CD33 by an amount the ranges from about 50% to 100%, as compared to binding to CD33 in the absence of the anti-CD33 antibody. In some embodiments, an anti-CD33 antibody of the present disclosure competes with one or more antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof for binding to CD33 when the anti-CD33 antibody reduces the binding of one or more antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof to CD33 by at least 50%, at least 55%, by at least 60%, at least 65%, at least 70%, at least 75%, at least 80%, at least 85%, at least 90%, at least 95%, or 100%, as compared to binding to CD33 in the absence of the anti-CD33 antibody. In some embodiments, an anti-CD33 antibody of the present disclosure that reduces the binding of one or more antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof to CD33 by 100% indicates that the anti-CD33 antibody essential completely blocks the binding of one or more antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof to CD33. In some embodiments, the anti-CD33 antibody and the one or more antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof are present in an amount that corresponds to a 10:1 ratio, 9:1 ratio, 8:1 ratio, 7:1 ratio, 6:1 ratio, 5:1 ratio, 4:1 ratio, 3:1 ratio, 2:1 ratio, 1:1 ratio, 0.75:1 ratio, 0.5:1 ratio, 0.25:1 ratio, 0.1:1 ratio, 0.075:1 ratio, 0.050:1 ratio, 0.025:1 ratio, 0.01:1 ratio, 0.0075: ratio, 0.0050:1 ratio, 0.0025:1 ratio, 0.001: ratio, 0.00075:1 ratio, 0.00050:1 ratio, 0.00025:1 ratio, 0.0001: ratio, 1:10 ratio, 1:9 ratio, 1:8 ratio, 1:7 ratio, 1:6 ratio, 1:5 ratio, 1:4 ratio, 1:3 ratio, 1:2 ratio, 1:0.75 ratio, 1:0.5 ratio, 1:0.25 ratio, 1:0.1 ratio, 1:0.075 ratio, 1:0.050 ratio, 1:0.025 ratio, 1:0.01 ratio, 1:0.0075 ratio, 1:0.0050 ratio, 1:0.0025 ratio, 1:0.001 ratio, 1:0.00075 ratio, 1:0.00050 ratio, 1:0.00025 ratio, or 1:0.0001 ratio of anti-CD33 antibody to one or more antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof. In some embodiments, the anti-CD33 antibody is present in excess by an amount that ranges from about 1.5-fold to 100-fold, or greater than 100-fold compared to the amount of the one or more antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof. In some embodiments, the anti-CD33 antibody is present in an amount that is about a 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold excess compared to the amount of the one or more antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof.

In some embodiments, anti-CD33 antibodies of the present disclosure bind to an epitope of human CD33 that is the same as or overlaps with the CD33 epitope bound by at least one antibody selected from any of the antibodies listed in Tables 7, 8, 9, 10, 11 and 12. In some embodiments, anti-CD33 antibodies of the present disclosure bind to an epitope of human CD33 that is the same as or overlaps with the CD33 epitope bound by at least one antibody selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54.

In some embodiments, anti-CD33 antibodies of the present disclosure bind essentially the same CD33 epitope bound by at least one antibody selected from any of the antibodies listed in Tables 7, 8, 9, 10, 11 and 12. In some embodiments, anti-CD33 antibodies of the present disclosure bind essentially the same CD33 epitope bound by at least one antibody selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54. Detailed exemplary methods for mapping an epitope to which an antibody binds are provided in Morris (1996) "Epitope Mapping Protocols," in Methods in Molecular Biology vol. 66 (Humana Press, Totowa, N.J.).

In some embodiments, anti-CD33 antibodies of the present disclosure compete with one or more antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof for binding to CD33 (e.g., human CD33).

Any suitable competition assay or CD33 binding assay known in the art, such as BIAcore analysis, ELISA assays, or flow cytometry, may be utilized to determine whether an anti-CD33 antibody competes with one or more antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof for binding to CD33. In an exemplary competition assay, immobilized CD33 or cells expressing CD33 on the cell surface are incubated in a solution comprising a first labeled antibody that binds to CD33 (e.g., human or non-human primate) and a second unlabeled antibody that is being tested for its ability to compete with the first antibody for binding to CD33. The second antibody may be present in a hybridoma supernatant. As a control, immobilized CD33 or cells expressing CD33 is incubated in a solution comprising the first labeled antibody but not the second unlabeled antibody. After incubation under conditions permissive for binding of the first antibody to CD33, excess unbound antibody is removed, and the amount of label associated with immobilized CD33 or cells expressing CD33 is measured. If the amount of label associated with immobilized CD33 or cells expressing CD33 is substantially reduced in the test sample relative to the control sample, then that indicates that the second antibody is competing with the first antibody for binding to CD33. See, Harlow and Lane (1988) *Antibodies: A Laboratory Manual* ch. 14 (Cold Spring Harbor Laboratory, Cold Spring Harbor, N.Y.).

Anti-CD33 Antibody Light Chain and Heavy Chain Variable Regions

In some embodiments, anti-CD33 antibodies of the present disclosure comprise a heavy chain variable region comprising one or more (e.g., one or more, two or more, or all three) HVRs selected from HVR-H1, HVR-H2, and HVR-H3 (as shown in Table 7). In some embodiments, the heavy chain variable region comprises an HVR-H1, an HVR-H2, and an HVR-H3 (as shown in Table 7). In some embodiments, anti-CD33 antibodies of the present disclosure comprise a light chain variable region comprising one or more (e.g., one or more, two or more, or all three) HVRs selected from HVR-L1, HVR-L2, and HVR-L3 (as shown in Table 8). In some embodiments, the heavy chain variable region comprises an HVR-L1, an HVR-L2, and an HVR-L3 (as shown in Table 8).

In some embodiments, anti-CD33 antibodies of the present disclosure comprise (a) a light chain variable region comprising at least one, two, or three HVRs selected from HVR-L1, HVR-L2, and HVR-L3 of any one of the antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, 6C7H54, and any combination thereof; and/or (b) a heavy chain variable region comprising at least one, two, or three HVRs selected from HVR-H1, HVR-H2, and HVR-H3 of any one of the antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, 6C7H54, and any combination thereof. In some embodiments, anti-CD33 antibodies of the present disclosure comprise at least one, two, three, four, five, or six HVRs selected from (i) HVR-L1 comprising the amino acid sequence from an antibody selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54; (ii) HVR-L2 comprising the amino acid sequence from an antibody selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54; (iii) HVR-L3 comprising the amino acid sequence from an antibody selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54; (iv) HVR-H1 comprising the amino acid sequence from an antibody selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54; (v) HVR-H2 comprising the amino acid sequence from an antibody selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54; and (vi) HVR-H3 comprising the amino acid sequence from an antibody selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54. In some embodiments, the HVR-L1, HVR-L2, HVR-L3, HVR-H1, HVR-H2, and HVR-H3 comprise EU or Kabat CDR, Chothia CDR, or Contact CDR sequences from an antibody selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54, and any combination thereof.

In some embodiments, anti-CD33 antibodies of the present disclosure comprise a light chain variable domain and a heavy chain variable domain, wherein the light chain variable domain comprises one or more of: (a) an HVR-L1 comprising the amino acid sequence of SEQ ID NO: 47; (b) an HVR-L2 comprising an amino acid sequence selected from SEQ ID NOs: 52-55; and (c) an HVR-L3 comprising an amino acid sequence selected from SEQ ID NOs: 58-62; and/or wherein the heavy chain variable domain comprises one or more of: (a) an HVR-H1 comprising an amino acid sequence selected from SEQ ID NOs: 8-30; (b) an HVR-H2 comprising the amino acid sequence of SEQ ID NO: 33; and (c) an HVR-H3 comprising an amino acid sequence selected from SEQ ID NOs: 38-40.

In some embodiments, anti-CD33 antibodies of the present disclosure comprise a heavy chain variable domain and a light chain variable domain, wherein (a) the HVR-H1 comprises the amino acid sequence of SEQ ID NO:8, the HVR-H2 comprises the amino acid sequence of SEQ ID NO:33, the HVR-H3 comprises the amino acid sequence of SEQ ID NO:38, the HVR-L1 comprises the amino acid sequence of SEQ ID NO:47, HVR-L2 comprises the amino acid sequence of SEQ ID NO:52, and the HVR-L3 comprises the amino acid sequence of SEQ ID NO:58; (b) the HVR-H1 comprises the amino acid sequence of SEQ ID NO:8, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (c) the HVR-H1 comprises the amino acid sequence of SEQ ID NO:9, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:54, and the HVR-L3 comprises the amino acid sequence of SEQ ID NO:58; (d) the HVR-H1 comprises the amino acid sequence of SEQ ID NO:9, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (e) the HVR-H1 comprises the amino acid sequence of SEQ ID NO:9, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:55, and the HVR-L3 comprises the amino acid sequence of SEQ ID NO:58; (f) the HVR-H1 comprises the amino acid sequence of SEQ ID NO:10, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (g) the HVR-H1 comprises the amino acid sequence of SEQ ID NO:11, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (h) the HVR-H1 comprises the amino acid sequence of SEQ ID NO:12, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (i) the HVR-H1 comprises the amino acid sequence of SEQ ID NO:13, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; ( ) the HVR-H1 comprises the amino acid sequence of SEQ ID NO:14, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (k) the HVR-H1 comprises the amino acid sequence of SEQ ID NO:15, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (l) the HVR-H1 comprises the amino acid sequence of SEQ ID NO:16, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (m) the HVR-H1 comprises the amino acid sequence of SEQ ID NO:17, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (n) the HVR-H1 comprises the amino acid sequence of SEQ ID NO:18, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (o) the HVR-H1 comprises the amino acid sequence of SEQ ID NO:19, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (p) the HVR-H1 comprises the amino acid sequence of SEQ ID NO:20, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (q) the HVR-H1 comprises the amino acid sequence of SEQ ID NO:21, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (r) the HVR-H1 comprises the amino acid sequence of SEQ ID NO:22, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (s) the HVR-H1 comprises the amino acid sequence of SEQ ID NO:23, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (t) the HVR-H1 comprises the amino acid sequence of SEQ ID NO:24, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (u) the HVR-H1 comprises the amino acid sequence of SEQ ID NO:25, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (v) the HVR-H1 comprises the amino acid sequence of SEQ ID NO:26, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (w) the HVR-H1 comprises the amino acid sequence of SEQ ID NO:27, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (x) the HVR-H1 comprises the amino acid sequence of SEQ ID NO:28, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:58; (y) the HVR-H1 comprises the amino acid sequence of SEQ ID NO:29, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:59; (z) the HVR-H1 comprises the amino acid sequence of SEQ ID NO:29, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:60; (aa) the HVR-H1 comprises the amino acid sequence of SEQ ID NO:29, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:61; (bb) the HVR-H1 comprises the amino acid sequence of SEQ ID NO:29, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:62; (cc) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:40, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:59; (dd) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:40, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:60; (ee) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:40, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:61; (f) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:40, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:62; (gg) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:60; (hh) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:62; (ii) the HVR-H1 comprises the amino acid sequence of SEQ ID NO:23, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:60; (jj) the HVR-H1 comprises the amino acid sequence of SEQ ID NO:23, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:62; (kk) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:59; (ll) the HVR-H1 comprises the amino acid sequence of SEQ ID NO:30, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:61; (mm) the HVR-H1 comprises the amino acid sequence of SEQ ID NO:28, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:59; and (nn) the HVR-H1 comprises the amino acid sequence of SEQ ID NO:28, the HVR-H2 comprises the amino acid sequence of SEQ ID NO:33, the HVR-H3 comprises the amino acid sequence of SEQ ID NO:39, the HVR-L1 comprises the amino acid sequence of SEQ ID NO:47, the HVR-L2 comprises the amino acid sequence of SEQ ID NO:53, and the HVR-L3 comprises the amino acid sequence of SEQ ID NO:61.

In some embodiments, anti-CD33 antibodies of the present disclosure comprise a light chain variable region of any one of the antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54; and/or a heavy chain variable region of any one of the antibodies selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54. In some embodiments, anti-CD33 antibodies of the present disclosure comprise a light chain variable region of any one of the antibodies listed in Table 11, or selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54; and/or a heavy chain variable region of any one of the antibodies listed in Table 12, or selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54.

In some embodiments, anti-CD33 antibodies of the present disclosure comprise a light chain variable region comprising an amino acid sequence selected from any of SEQ ID NOs:94-103; and/or a heavy chain variable domain comprising an amino acid sequence selected from any of SEQ ID NOs:65-93. In some embodiments, the light chain variable domain comprises the amino acid sequence of SEQ ID NO: 94; and the heavy chain variable domain comprises the amino acid sequence of SEQ ID NO: 65. In some embodiments, the light chain variable domain comprises the amino acid sequence of SEQ ID NO: 94; and the heavy chain variable domain comprises the amino acid sequence of SEQ ID NO: 66. In some embodiments, the light chain variable domain comprises the amino acid sequence of SEQ ID NO: 95; and the heavy chain variable domain comprises the amino acid sequence of SEQ ID NO: 65. In some embodiments, the light chain variable domain comprises the amino acid sequence of SEQ ID NO: 95; and the heavy chain variable domain comprises the amino acid sequence of SEQ ID NO: 67. In some embodiments, the light chain variable domain comprises the amino acid sequence of SEQ ID NO: 95; and the heavy chain variable domain comprises the amino acid sequence of SEQ ID NO: 66. In some embodiments, the light chain variable domain comprises the amino acid sequence of SEQ ID NO: 96; and the heavy chain variable domain comprises the amino acid sequence of SEQ ID NO: 65. In some embodiments, the light chain variable domain comprises the amino acid sequence of SEQ ID NO: 96; and the heavy chain variable domain comprises the amino acid sequence of SEQ ID NO: 67. In some embodiments, the light chain variable domain comprises the amino acid sequence of SEQ ID NO: 97; and the heavy chain variable domain comprises the amino acid sequence of SEQ ID NO: 68. In some embodiments, the light chain variable domain comprises the amino acid sequence of SEQ ID NO: 98; and the heavy chain variable domain comprises the amino acid sequence of SEQ ID NO: 69. In some embodiments, the light chain variable domain comprises the amino acid sequence of SEQ ID NO: 97; and the heavy chain variable domain comprises the amino acid sequence of SEQ ID NO: 69. In some embodiments, the light chain variable domain comprises the amino acid sequence of SEQ ID NO: 94; and the heavy chain variable domain comprises the amino acid sequence of SEQ ID NO: 65. In some embodiments, the light chain variable domain comprises the amino acid sequence of SEQ ID NO: 99; and the heavy chain variable domain comprises the amino acid sequence of SEQ ID NO: 69. In some embodiments, the light chain variable domain comprises the amino acid sequence of SEQ ID NO: 97; and the heavy chain variable domain comprises the amino acid sequence of SEQ ID NO: 70. In some embodiments, the light chain variable domain comprises the amino acid sequence of SEQ ID NO: 97; and the heavy chain variable domain comprises the amino acid sequence of SEQ ID NO: 71. In some embodiments, the light chain variable domain comprises the amino acid sequence of SEQ ID NO: 97; and the heavy chain variable domain comprises the amino acid sequence of SEQ ID NO: 72. In some embodiments, the light chain variable domain comprises the amino acid sequence of SEQ ID NO: 97; and the heavy chain variable domain comprises the amino acid sequence of SEQ ID NO: 73. In some embodiments, the light chain variable domain comprises the amino acid sequence of SEQ ID NO: 97; and the heavy chain variable domain comprises the amino acid sequence of SEQ ID NO: 74. In some embodiments, the light chain variable domain comprises the amino acid sequence of SEQ ID NO: 97; and the heavy chain variable domain comprises the amino acid sequence of SEQ ID NO: 75. In some embodiments, the light chain variable domain comprises the amino acid sequence of SEQ ID NO: 97; and the heavy chain variable domain comprises the amino acid sequence of SEQ ID NO: 76. In some embodiments, the light chain variable domain comprises the amino acid sequence of SEQ ID NO: 97; and the heavy chain variable domain comprises the amino acid sequence of SEQ ID NO: 77. In some embodiments, the light chain variable domain comprises the amino acid sequence of SEQ ID NO: 97; and the heavy chain variable domain comprises the amino acid sequence of SEQ ID NO: 78. In some embodiments, the light chain variable domain comprises the amino acid sequence of SEQ ID NO: 97; and the heavy chain variable domain comprises the amino acid sequence of SEQ ID NO: 79. In some embodiments, the light chain variable domain comprises the amino acid sequence of SEQ ID NO: 97; and the heavy chain variable domain comprises the amino acid sequence of SEQ ID NO: 80. In some embodiments, the light chain variable domain comprises the amino acid sequence of SEQ ID NO: 97; and the heavy chain variable domain comprises the amino acid sequence of SEQ ID NO: 81. In some embodiments, the light chain variable domain comprises the amino acid sequence of SEQ ID NO: 97; and the heavy chain variable domain comprises the amino acid sequence of SEQ ID NO: 82. In some embodiments, the light chain variable domain comprises the amino acid sequence of SEQ ID NO: 97; and the heavy chain variable domain comprises the amino acid sequence of SEQ ID NO: 83. In some embodiments, the light chain variable domain comprises the amino acid sequence of SEQ ID NO: 97; and the heavy chain variable domain comprises the amino acid sequence of SEQ ID NO: 84. In some embodiments, the light chain variable domain comprises the amino acid sequence of SEQ ID NO: 97; and the heavy chain variable domain comprises the amino acid sequence of SEQ ID NO: 85. In some embodiments, the light chain variable domain comprises the amino acid sequence of SEQ ID NO: 97; and the heavy chain variable domain comprises the amino acid sequence of SEQ ID NO: 86. In some embodiments, the light chain variable domain comprises the amino acid sequence of SEQ ID NO: 97; and the heavy chain variable domain comprises the amino acid sequence of SEQ ID NO: 87. In some embodiments, the light chain variable domain comprises the amino acid sequence of SEQ ID NO: 97; and the heavy chain variable domain comprises the amino acid sequence of SEQ ID NO: 88. In some embodiments, the light chain variable domain comprises the amino acid sequence of SEQ ID NO: 100; and the heavy chain variable domain comprises the amino acid sequence of SEQ ID NO: 89. In some embodiments, the light chain variable domain comprises the amino acid sequence of SEQ ID NO: 101; and the heavy chain variable domain comprises the amino acid sequence of SEQ ID NO: 89. In some embodiments, the light chain variable domain comprises the amino acid sequence of SEQ ID NO: 102; and the heavy chain variable domain comprises the amino acid sequence of SEQ ID NO: 89. In some embodiments, the light chain variable domain comprises the amino acid sequence of SEQ ID NO: 103; and the heavy chain variable domain comprises the amino acid sequence of SEQ ID NO: 89. In some embodiments, the light chain variable domain comprises the amino acid sequence of SEQ ID NO: 100; and the heavy chain variable domain comprises the amino acid sequence of SEQ ID NO: 90. In some embodiments, the light chain variable domain comprises the amino acid sequence of SEQ ID NO: 101; and the heavy chain variable domain comprises the amino acid sequence of SEQ ID NO: 90. In some embodiments, the light chain variable domain comprises the amino acid sequence of SEQ ID NO: 102; and the heavy chain variable domain comprises the amino acid sequence of SEQ ID NO: 90. In some embodiments, the light chain variable domain comprises the amino acid sequence of SEQ ID NO: 103; and the heavy chain variable domain comprises the amino acid sequence of SEQ ID NO: 90. In some embodiments, the light chain variable domain comprises the amino acid sequence of SEQ ID NO: 100; and the heavy chain variable domain comprises the amino acid sequence of SEQ ID NO: 91. In some embodiments, the light chain variable domain comprises the amino acid sequence of SEQ ID NO: 101; and the heavy chain variable domain comprises the amino acid sequence of SEQ ID NO: 91. In some embodiments, the light chain variable domain comprises the amino acid sequence of SEQ ID NO: 102; and the heavy chain variable domain comprises the amino acid sequence of SEQ ID NO: 91. In some embodiments, the light chain variable domain comprises the amino acid sequence of SEQ ID NO: 103; and the heavy chain variable domain comprises the amino acid sequence of SEQ ID NO: 91. In some embodiments, the light chain variable domain comprises the amino acid sequence of SEQ ID NO: 101; and the heavy chain variable domain comprises the amino acid sequence of SEQ ID NO: 92. In some embodiments, the light chain variable domain comprises the amino acid sequence of SEQ ID NO: 103; and the heavy chain variable domain comprises the amino acid sequence of SEQ ID NO: 92. In some embodiments, the light chain variable domain comprises the amino acid sequence of SEQ ID NO: 101; and the heavy chain variable domain comprises the amino acid sequence of SEQ ID NO:93. In some embodiments, the light chain variable domain comprises the amino acid sequence of SEQ ID NO: 103; and the heavy chain variable domain comprises the amino acid sequence of SEQ ID NO: 93. In some embodiments, the light chain variable domain comprises the amino acid sequence of SEQ ID NO: 101; and the heavy chain variable domain comprises the amino acid sequence of SEQ ID NO: 83. In some embodiments, the light chain variable domain comprises the amino acid sequence of SEQ ID NO: 103; and the heavy chain variable domain comprises the amino acid sequence of SEQ ID NO: 83. In some embodiments, the light chain variable domain comprises the amino acid sequence of SEQ ID NO: 100; and the heavy chain variable domain comprises the amino acid sequence of SEQ ID NO: 92. In some embodiments, the light chain variable domain comprises the amino acid sequence of SEQ ID NO: 102; and the heavy chain variable domain comprises the amino acid sequence of SEQ ID NO: 92. In some embodiments, the light chain variable domain comprises the amino acid sequence of SEQ ID NO: 100; and the heavy chain variable domain comprises the amino acid sequence of SEQ ID NO: 93. In some embodiments, the light chain variable domain comprises the amino acid sequence of SEQ ID NO: 102; and the heavy chain variable domain comprises the amino acid sequence of SEQ ID NO: 93. In some embodiments, the light chain variable domain comprises the amino acid sequence of SEQ ID NO: 100; and the heavy chain variable domain comprises the amino acid sequence of SEQ ID NO: 83. In some embodiments, the light chain variable domain comprises the amino acid sequence of SEQ ID NO: 102; and the heavy chain variable domain comprises the amino acid sequence of SEQ ID NO: 83.

In some embodiments, an anti-CD33 antibody is provided, wherein the antibody comprises a $V_H$ as in any of the embodiments provided above, and a $V_L$ as in any of the embodiments provided above. In some embodiments, provided herein are anti-CD33 antibodies, wherein the antibody comprises a $V_H$ as in any of the embodiments provided above, and a $V_L$ as in any of the embodiments provided above. In one embodiment, an anti-CD33 antibody of the present disclosure comprises a $V_H$ sequence selected from SEQ ID NO: 65, 66, 67, 68, 69, 70, 71, 72, 73, 74, 75, 76, 77, 78, 79, 80, 81, 82, 83, 84, 85, 86, 87, 88, 89, 90, 91, 92, and 93; and $V_L$ sequence selected from SEQ ID NO: 94, 95, 96, 97, 98, 99, 100, 101, 102, and 103, including post-translational modifications of those sequences. In some embodiments, the anti-CD33 antibody comprises the $V_H$ sequence and $V_L$ sequence of an antibody selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54.

In some embodiments, provided herein are anti-CD33 antibodies, wherein the antibody comprises a $V_H$ as in any of the embodiments provided above, and a $V_L$ as in any of the embodiments provided above. In some embodiments, an anti-CD33 antibody of the present disclosure comprises a $V_H$ sequence selected from SEQ ID NO: 65, 66, 67, 68, 69, 70, 71, 72, 73, 74, 75, 76, 77, 78, 79, 80, 81, 82, 83, 84, 85, 86, 87, 88, 89, 90, 91, 92, and 93; and $V_L$ sequence selected from SEQ ID NO: 94, 95, 96, 97, 98, 99, 100, 101, 102, and 103, including post-translational modifications of those sequences. In some embodiments, the anti-CD33 antibody comprises the $V_H$ sequence and $V_L$ sequence of an antibody selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54.

In another aspect, an anti-CD33 antibody of the present disclosure comprises a heavy chain variable domain ($V_H$) sequence having at least 90%, 91%, 92%, 93%, 94%, 95%, 96%, 97%, 98%, 99/6, or 100% sequence identity to the amino acid sequence of SEQ ID NO: 65, 66, 67, 68, 69, 70, 71, 72, 73, 74, 75, 76, 77, 78, 79, 80, 81, 82, 83, 84, 85, 86, 87, 88, 89, 90, 91, 92, or 93. In certain embodiments, a $V_H$ sequence having at least 90%, 91%, 92%, 93%, 94%, 95%, 96%, 97%, 98%, or 99% identity to the amino acid sequence of SEQ ID NO: 65, 66, 67, 68, 69, 70, 71, 72, 73, 74, 75, 76, 77, 78, 79, 80, 81, 82, 83, 84, 85, 86, 87, 88, 89, 90, 91, 92, or 93 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted, and/or deleted in SEQ ID NO: 65, 66, 67, 68, 69, 70, 71, 72, 73, 74, 75, 76, 77, 78, 79, 80, 81, 82, 83, 84, 85, 86, 87, 88, 89, 90, 91, 92, or 93. In certain embodiments, a total of 1 to 5 amino acids have been substituted, inserted and/or deleted in SEQ ID NO: 65, 66, 67, 68, 69, 70, 71, 72, 73, 74, 75, 76, 77, 78, 79, 80, 81, 82, 83, 84, 85, 86, 87, 88, 89, 90, 91, 92, or 93. In certain embodiments, substitutions, insertions, or deletions occur in regions outside the HVRs (i.e., in the FRs). Optionally, the anti-CD33 antibody comprises the $V_H$ sequence of SEQ ID NO: 65, 66, 67, 68, 69, 70, 71, 72, 73, 74, 75, 76, 77, 78, 79, 80, 81, 82, 83, 84, 85, 86, 87, 88, 89, 90, 91, 92, or 93, including post-translational modifications of that sequence. In a particular embodiment, the $V_H$ comprises one, two or three HVRs selected from: (a) HVR-H1 comprising an amino acid sequence of an HVR-H1 shown in Table 7; (b) HVR-H2 comprising an amino acid sequence of an HVR-H1 shown in Table 7; (c) HVR-H3 comprising an amino acid sequence of an HVR-H3 shown in Table 7.

In another aspect, an anti-CD33 antibody of the present disclosure comprises a light chain variable domain ($V_L$) having at least 90%, 91%, 92%, 93%, 94%, 95%, %%, 97%, 98%, 99%, or 100% sequence identity to the amino acid sequence of SEQ ID NO: 94, 95, %, 97, 98, 99, 100, 101, 102, or 103. In certain embodiments, a $V_L$ sequence having at least 90%, 91%, 92%, 93%, 94%, 95%, %%, 97%, 98%, or 99% identity to the amino acid sequence of SEQ ID NO: 94, 95, 96, 97, 98, 99, 100, 101, 102, or 103 contains substitutions (e.g., conservative substitutions), insertions, or deletions relative to the reference sequence, but an anti-CD33 antibody comprising that sequence retains the ability to bind to CD33. In some embodiments, a total of 1 to 10 amino acids have been substituted, inserted and/or deleted in SEQ ID NO: 94, 95, 96, 97, 98, 99, 100, 101, 102, or 103. In certain embodiments, a total of 1 to 5 amino acids have been substituted, inserted and/or deleted in SEQ ID NO: 94, 95, 96, 97, 98, 99, 100, 101, 102, or 103. In certain embodiments, the substitutions, insertions, or deletions occur in regions outside the HVRs (i.e., in the FRs). Optionally, the anti-CD33 antibody comprises the $V_L$ sequence of SEQ ID NO: 94, 95, 96, 97, 98, 99, 100, 101, 102, or 103, including post-translational modifications of that sequence. In a particular embodiment, the $V_L$ comprises one, two or three HVRs selected from (a) HVR-L 1 comprising an amino acid sequence of an HVR-L1 shown in Table 8; (b) HVR-L2 comprising an amino acid sequence of an HVR-L2 shown in Table 8; and (c) HVR-L3 comprising an amino acid sequence of an HVR-L3 shown in Table 8.

In some embodiments, provided herein are anti-CD33 antibodies comprising (a) HVR-H1 comprising the amino acid sequence of SEQ ID NO:8; (b) HVR-H2 comprising the amino acid sequence of SEQ ID NO:33; (c) HVR-H3 comprising the amino acid sequence of SEQ ID NO:38; (d) HVR-L1 comprising the amino acid sequence of SEQ ID NO:47; (e) HVR-L2 comprising the amino acid sequence of SEQ ID NO:52; and (f) HVR-L3 comprising the amino acid sequence of SEQ ID NO:58. In some embodiments, the anti-CD33 antibody is anti-CD33 monoclonal antibody 6C7H1. In some embodiments, the anti-CD33 antibody is anti-CD33 monoclonal antibody 6C7H2. In some embodiments, the anti-CD33 antibody is anti-CD33 monoclonal antibody 6C7H3. In some embodiments, the anti-CD33 antibody is anti-CD33 monoclonal antibody 6C7H4. In some embodiments, the anti-CD33 antibody is anti-CD33 monoclonal antibody 6C7H5. In some embodiments, the anti-CD33 antibody is anti-CD33 monoclonal antibody 6C7H6. In some embodiments, the anti-CD33 antibody is anti-CD33 monoclonal antibody 6C7H7.

In some embodiments, provided herein are anti-CD33 antibodies comprising (a) HVR-H1 comprising the amino acid sequence of SEQ ID NO:8; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H8.

In some embodiments, provided herein are anti-CD33 antibodies comprising (a) HVR-H1 comprising the amino acid sequence of SEQ ID NO:9; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:54; (f) and HVR-L3 comprising the amino acid sequence of SEQ ID NO:58. In some embodiments, the anti-CD33 antibody is anti-CD33 monoclonal antibody 6C7H9.

In some embodiments, provided herein are anti-CD33 antibodies comprising (a) HVR-H1 comprising the amino acid sequence of SEQ ID NO:9; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H10.

In some embodiments, provided herein are anti-CD33 antibodies comprising (a) HVR-H1 comprising the amino acid sequence of SEQ ID NO:9; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:55; and (f) HVR-L3 comprising the amino acid sequence of SEQ ID NO:58. In some embodiments, the anti-CD33 antibody is anti-CD33 monoclonal antibody 6C7H11.

In some embodiments, provided herein are anti-CD33 antibodies comprising (a) HVR-H1 comprising the amino acid sequence of SEQ ID NO:10; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H12.

In some embodiments, provided herein are anti-CD33 antibodies comprising (a) HVR-H1 comprising the amino acid sequence of SEQ ID NO:11; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H13.

In some embodiments, provided herein are anti-CD33 antibodies comprising (a) HVR-H1 comprising the amino acid sequence of SEQ ID NO:12; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H14.

In some embodiments, provided herein are anti-CD33 antibodies comprising (a) HVR-H1 comprising the amino acid sequence of SEQ ID NO:13; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H15.

In some embodiments, provided herein are anti-CD33 antibodies comprising (a) HVR-H1 comprising the amino acid sequence of SEQ ID NO:14; (b) HVR-H2 comprising the amino acid sequence of SEQ ID NO:33; (c) HVR-H3 comprising the amino acid sequence of SEQ ID NO:39; (d) HVR-L1 comprises the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H16.

In some embodiments, provided herein are anti-CD33 antibodies comprising (a) HVR-H1 comprising the amino acid sequence of SEQ ID NO:15; (b) HVR-H2 comprising the amino acid sequence of SEQ ID NO:33; (c) HVR-H3 comprising the amino acid sequence of SEQ ID NO:39; (d) HVR-L1 comprises the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H17.

In some embodiments, provided herein are anti-CD33 antibodies comprising (a) HVR-H1 comprising the amino acid sequence of SEQ ID NO:16; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H18.

In some embodiments, provided herein are anti-CD33 antibodies comprising (a) HVR-H1 comprising the amino acid sequence of SEQ ID NO:17; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H19.

In some embodiments, provided herein are anti-CD33 antibodies comprising (a) HVR-H1 comprising the amino acid sequence of SEQ ID NO:18; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprises the amino acid sequence of SEQ ID NO:58. In some embodiments, the anti-CD33 antibody is anti-CD33 monoclonal antibody 6C7H20.

In some embodiments, provided herein are anti-CD33 antibodies comprising (a) HVR-H1 comprising the amino acid sequence of SEQ ID NO:19; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H21.

In some embodiments, provided herein are anti-CD33 antibodies comprising (a) HVR-H1 comprising the amino acid sequence of SEQ ID NO:20; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H22.

In some embodiments, provided herein are anti-CD33 antibodies comprising (a) HVR-H1 comprising the amino acid sequence of SEQ ID NO:21; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H23.

In some embodiments, provided herein are anti-CD33 antibodies comprising (a) HVR-H1 comprising the amino acid sequence of SEQ ID NO:22; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H24.

In some embodiments, provided herein are anti-CD33 antibodies comprising (a) HVR-H1 comprising the amino acid sequence of SEQ ID NO:23; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H25.

In some embodiments, provided herein are anti-CD33 antibodies comprising (a) HVR-H1 comprising the amino acid sequence of SEQ ID NO:24; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H26.

In some embodiments, provided herein are anti-CD33 antibodies comprising (a) HVR-H1 comprising the amino acid sequence of SEQ ID NO:25; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H27.

In some embodiments, provided herein are anti-CD33 antibodies comprising (a) HVR-H1 comprising the amino acid sequence of SEQ ID NO:26; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H28.

In some embodiments, provided herein are anti-CD33 antibodies comprising (a) HVR-H1 comprising the amino acid sequence of SEQ ID NO:27; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H29.

In some embodiments, provided herein are anti-CD33 antibodies comprising (a) HVR-H1 comprising the amino acid sequence of SEQ ID NO:28; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:58. In some embodiments, the anti-CD33 antibody is anti-CD33 monoclonal antibody 6C7H30.

In some embodiments, provided herein are anti-CD33 antibodies comprising (a) HVR-H1 comprising the amino acid sequence of SEQ ID NO:29; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprises the amino acid sequence of SEQ ID NO:59. In some embodiments, the anti-CD33 antibody is anti-CD33 monoclonal antibody 6C7H31. In some embodiments, the anti-CD33 antibody is anti-CD33 monoclonal antibody 6C7H39. In some embodiments, the anti-CD33 antibody is anti-CD33 monoclonal antibody 6C7H49.

In some embodiments, provided herein are anti-CD33 antibodies comprising (a) HVR-H1 comprising the amino acid sequence of SEQ ID NO:29; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:60. In some embodiments, the anti-CD33 antibody is anti-CD33 monoclonal antibody 6C7H32. In some embodiments, the anti-CD33 antibody is anti-CD33 monoclonal antibody 6C7H40. In some embodiments, the anti-CD33 antibody is anti-CD33 monoclonal antibody 6C7H43.

In some embodiments, provided herein are anti-CD33 antibodies comprising (a) HVR-H1 comprising the amino acid sequence of SEQ ID NO:29; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:61. In some embodiments, the anti-CD33 antibody is anti-CD33 monoclonal antibody 6C7H33. In some embodiments, the anti-CD33 antibody is anti-CD33 monoclonal antibody 6C7H41. In some embodiments, the anti-CD33 antibody is anti-CD33 monoclonal antibody 6C7H50.

In some embodiments, provided herein are anti-CD33 antibodies comprising (a) HVR-H1 comprising the amino acid sequence of SEQ ID NO:29; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:62. In some embodiments, the anti-CD33 antibody is anti-CD33 monoclonal antibody 6C7H34. In some embodiments, the anti-CD33 antibody is anti-CD33 monoclonal antibody 6C7H42. In some embodiments, the anti-CD33 antibody is anti-CD33 monoclonal antibody 6C7H44.

In some embodiments, provided herein are anti-CD33 antibodies comprising (a) HVR-H1 comprising the amino acid sequence of SEQ ID NO:30; (b) HVR-H2 comprising the amino acid sequence of SEQ ID NO:33; (c) HVR-H3 comprising the amino acid sequence of SEQ ID NO:40; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:59. In some embodiments, the anti-CD33 antibody is anti-CD33 monoclonal antibody 6C7H35.

In some embodiments, provided herein are anti-CD33 antibodies comprising (a) HVR-H1 comprising the amino acid sequence of SEQ ID NO:30; (b) HVR-H2 comprising the amino acid sequence of SEQ ID NO:33; (c) HVR-H3 comprising the amino acid sequence of SEQ ID NO:40; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:60. In some embodiments, the anti-CD33 antibody is anti-CD33 monoclonal antibody 6C7H36.

In some embodiments, provided herein are anti-CD33 antibodies comprising (a) HVR-H1 comprising the amino acid sequence of SEQ ID NO:30; (b) HVR-H2 comprising the amino acid sequence of SEQ ID NO:33; (c) HVR-H3 comprising the amino acid sequence of SEQ ID NO:40; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:61. In some embodiments, the anti-CD33 antibody is anti-CD33 monoclonal antibody 6C7H37.

In some embodiments, provided herein are anti-CD33 antibodies comprising (a) HVR-H1 comprising the amino acid sequence of SEQ ID NO:30; (b) HVR-H2 comprising the amino acid sequence of SEQ ID NO:33; (c) HVR-H3 comprising the amino acid sequence of SEQ ID NO:40; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:62. In some embodiments, the anti-CD33 antibody is anti-CD33 monoclonal antibody 6C7H38.

In some embodiments, provided herein are anti-CD33 antibodies comprising (a) HVR-H1 comprising the amino acid sequence of SEQ ID NO:30; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:60. In some embodiments, the anti-CD33 antibody is anti-CD33 monoclonal antibody 6C7H45.

In some embodiments, provided herein are anti-CD33 antibodies comprising (a) HVR-H1 comprising the amino acid sequence of SEQ ID NO:30; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:62. In some embodiments, the anti-CD33 antibody is anti-CD33 monoclonal antibody 6C7H46.

In some embodiments, provided herein are anti-CD33 antibodies comprising (a) HVR-H1 comprising the amino acid sequence of SEQ ID NO:23; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprises the amino acid sequence of SEQ ID NO:60. In some embodiments, the anti-CD33 antibody is anti-CD33 monoclonal antibody 6C7H47.

In some embodiments, provided herein are anti-CD33 antibodies comprising (a) HVR-H1 comprising the amino acid sequence of SEQ ID NO:23; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:62. In some embodiments, the anti-CD33 antibody is anti-CD33 monoclonal antibody 6C7H48.

In some embodiments, provided herein are anti-CD33 antibodies comprising (a) HVR-H1 comprising the amino acid sequence of SEQ ID NO:30; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:59. In some embodiments, the anti-CD33 antibody is anti-CD33 monoclonal antibody 6C7H51.

In some embodiments, provided herein are anti-CD33 antibodies comprising (a) HVR-H1 comprising the amino acid sequence of SEQ ID NO:30; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:61. In some embodiments, the anti-CD33 antibody is anti-CD33 monoclonal antibody 6C7H52.

In some embodiments, provided herein are anti-CD33 antibodies comprising (a) HVR-H1 comprising the amino acid sequence of SEQ ID NO:23; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:59. In some embodiments, the anti-CD33 antibody is anti-CD33 monoclonal antibody 6C7H53.

In some embodiments, provided herein are anti-CD33 antibodies comprising (a) HVR-H1 comprising the amino acid sequence of SEQ ID NO:23; (b) HVR-H2 comprising the amino acid sequence of SEQ ID NO:33; (c) HVR-H3 comprising the amino acid sequence of SEQ ID NO:39; (d) HVR-L1 comprising the amino acid sequence of SEQ ID NO:47; (e) HVR-L2 comprising the amino acid sequence of SEQ ID NO:53; and (f) HVR-L3 comprising the amino acid sequence of SEQ ID NO:61. In some embodiments, the anti-CD33 antibody is anti-CD33 monoclonal antibody 6C7H54.

Provided herein are anti-CD33 antibodies. Antibodies provided are useful, e.g., for the diagnosis or treatment of CD33-mediated and/or CD33-associated diseases, conditions, or disorders.

In some embodiments, the anti-CD33 antibody according to any of the above embodiments is a monoclonal antibody, including a humanized and/or human antibody. In some embodiments, the anti-CD33 antibody is an antibody fragment, e.g., a Fv, Fab, Fab', scFv, diabody, or F(ab')2 fragment. In some embodiments, the anti-CD33 antibody is a substantially full-length antibody, e.g., an IgG1 antibody, IgG2a antibody or other antibody class or isotype as defined herein.

In some embodiments, an anti-CD33 antibody according to any of the above embodiments may incorporate any of the features, singly or in combination, as described below:

Anti-CD33 Antibody Binding Affinity

In some embodiments of any of the antibodies provided herein, the antibody has a dissociation constant (Kd) of <1 µM, <100 nM, <10 nM, <1 nM, <0.1 nM, <0.01 nM, or <0.001 nM (e.g., $10^{-8}$ M or less, e.g., from $10^{-8}$ M to $10^{-13}$ M, e.g., from $10^{-9}$ M to $10^{-13}$ M). Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. In one embodiment, Kd is measured by a radiolabeled antigen binding assay (RIA). In some embodiment, an RIA is performed with the Fab version of an antibody of interest and its antigen, for example as described in Chen et al. *J. Mol. Biol.* 293:865-881 (1999)). In some embodiments, Kd is measured using a BIACORE surface plasmon resonance assay, for example, an assay using a BIACORE-2000 or a BIACORE-3000 (BIAcore, Inc., Piscataway, N.J.) is performed at 25° C. with immobilized antigen CM5 chips at µ10 response units (RU). In some embodiments, the $K_D$ is determined using a monovalent antibody (e.g., a Fab) or a full-length antibody. In some embodiments, the $K_D$ is determined using a full-length antibody in a monovalent form.

Antibody Fragments

In some embodiments of any of the antibodies provided herein, the antibody is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med* 9:129-134 (2003). For a review of scFv fragments, see, e.g., WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP404097; WO 1993/01161; Hudson et al. *Nat. Med* 9:129-134 (2003). Triabodies and tetrabodies are also described in Hudson et al. *Nat. Med.* 9:129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

Chimeric and Humanized Antibodies

In some embodiments of any of the antibodies provided herein, the antibody is a chimeric antibody. Certain chimeric antibodies are described, e.g., in U.S. Pat. No. 4,816,567. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments of any of the antibodies provided herein, the antibody is a humanized antibody. Typically, a non-human antibody is humanized to reduce immunogenicity to humans, while retaining the specificity and affinity of the parental non-human antibody. In certain embodiments, a humanized antibody is substantially non-immunogenic in humans. In certain embodiments, a humanized antibody has substantially the same affinity for a target as an antibody from another species from which the humanized antibody is derived. See, e.g., U.S. Pat. Nos. 5,530,101, 5,693,761; 5,693,762; and 5,585,089. In certain embodiments, amino acids of an antibody variable domain that can be modified without diminishing the native affinity of the antigen binding domain while reducing its immunogenicity are identified. See, e.g., U.S. Pat. Nos. 5,766,886 and 5,869,619. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. *Front. Biosci.* 13:161 9-1633 (2008), and are further described, e.g., in U.S. Pat. Nos. 5,821,337, 7,527,791, 6,982,321, and 7,087,409. Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Nal. Acad. Sci. USA* 89:4285 (1992); and Presta et al., *J. Immunol.* 151:2623 (1993)); human mature (somatically mutated) framework regions or human germline framework regions (see, e.g., Almagro and Fransson *Front. Biosci.* 13:1619-1633 (2008)); and framework regions derived from screening FR libraries (see, e.g., Baca et al. *J. Biol. Chem.* 272:10678-10684 (1997) and Rosok et al. *J. Biol. Chem.* 271:22611-22618 (1996)).

Human Antibodies

In some embodiments of any of the antibodies provided herein, the antibody is a human antibody. Human antibodies can be produced using various techniques known in the art. Human antibodies are described generally in van Dijk et al. *Curr. Opin. Pharmacol.* 5:368-74 (2001) and Lonberg *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human MAbs with the desired specificity can be produced and selected. Certain exemplary methods are described in U.S. Pat. No. 5,545,807, EP 546073, and EP 546073. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.* 133:3001 (1984) and Boerner et al. *J. Immunol.* 147:86 (1991)). Human antibodies generated via human B-cell hybridoma technology are also described in Li et al. *Proc. Natl. Acad Sci. USA,* 1 03:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers et al. *Histology and Histopathology* 20(3):927-937 (2005) and Vollmers et al. *Methods and Findings in Experimental and Clinical Pharmacology* 27(3): 185-91 (2005). Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

In some embodiments of any of the antibodies provided herein, the antibody is a human antibody isolated by in vitro methods and/or screening combinatorial libraries for antibodies with the desired activity or activities. Suitable examples include but are not limited to phage display (CAT, Morphosys, Dyax, Biosite/Medarex, Xoma, Symphogen, Alexion (formerly Proliferon), Affimed) ribosome display (CAT), yeast display (Adimab), and the like. In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.* 12: 433-455 (1994). For example, a variety of methods are known in the art for generating phage display libraries and screening such libraries for antibodies possessing the desired binding characteristics. See also Sidhu et al. *J. Mol. Biol.* 338(2): 299-310, 2004; Lee et al. *J. Mol. Biol.* 340(5): 1073-1093, 2004; Fellouse *Proc. Natl. Acad Sci. USA* 101(34):12467-12472 (2004); and Lee et al. *J. Immunol. Methods* 284(-2):1 19-132 (2004). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al. *EMBO J.* 12: 725-734 (1993). Finally, naive libraries can also be made synthetically by cloning unrearranged V-gene segments from stem cells, and using PCR primers comprising random sequence to encode the highly variable HVR3 regions and to accomplish rearrangement in vitro, as described by Hoogenboom et al. *J. Mol. Biol.*, 227: 381-388, 1992. Patent publications describing human antibody phage libraries include, for example: U.S. Pat. No. 5,750,373, and US Patent Publication Nos. 2007/0292936 and 2009/0002360. Antibodies isolated from human antibody libraries are considered human antibodies or human antibody fragments herein.

Constant Regions Including Fc Regions

In certain embodiments, the anti-CD33 antibody is an antagonist antibody. In certain embodiments, the anti-CD33 antibody is an agonist antibody or an inert antibody. In some embodiments, anti-CD33 antibodies of the present disclosure are of the IgG class the IgM class, or the IgA class. In some embodiments, anti-CD33 antibodies of the present disclosure are of the IgG class and have an IgG1, IgG2, IgG3, or IgG4 isotype. In some embodiments of any of the antibodies provided herein, the antibody comprises an Fc. In some embodiments, the Fc is a human IgG1, IgG2, IgG3, and/or IgG4 isotype. In some embodiments, the antibody is of the IgG class, the IgM class, or the IgA class.

In certain embodiments, the Fc region comprises the Fc variants listed in Table E, below. The Fc variant may be with or without the C-terminal lysine residue, as shown in Table E.

TABLE E

Human Fc variants

| Human Fc variant | Amino acid sequence | SEQ ID NO: |
|---|---|---|
| IgG1 - WT | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPELLGGPSVFLFPPKPKDTLMISRTPEVTCVVVDVS HEDPEVKFNWYVDGVEVHNAKTKPREEQYNSTYRV VSVLTVLHQDWLNGKEYKCKVSNKALPAPIEKTISK AKGQPREPQVYTLPPSRDELTKNQVSLTCLVKGFYPS DIAVEWESNGQPENNYKTTPPVLDSDGSFFLYSKLTV DKSRWQQGNVFSCSVMHEALHNHYTQKSLSLSPGK | 106 |
| IgG1 - WT without terminal lysine. | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPELLGGPSVFLFPPKPKDTLMISRTPEVTCVVVDVS HEDPEVKFNWYVDGVEVHNAKTKPREEQYNSTYRV VSVLTVLHQDWLNGKEYKCKVSNKALPAPIEKTISK AKGQPREPQVYTLPPSRDELTKNQVSLTCLVKGFYPS DIAVEWESNGQPENNYKTTPPVLDSDGSFFLYSKLTV DKSRWQQGNVFSCSVMHEALHNHYTQKSLSLSPG | 107 |
| IgG1 - LALAPS (L234A, L235A, and P331S) | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPEAAGGPSVFLFPPKPKDTLMISRTPEVTCVVVDVS HEDPEVKFNWYVDGVEVHNAKTKPREEQYNSTYRV VSVLTVLHQDWLNGKEYKCKVSNKALPASIEKTISK AKGQPREPQVYTLPPSRDELTKNQVSLTCLVKGFYPS DIAVEWESNGQPENNYKTTPPVLDSDGSFFLYSKLTV DKSRWQQGNVFSCSVMHEALHNHYTQKSLSLSPGK | 108 |
| IgG1 - LALAPS (L234A, L235A, and P331S) without terminal lysine. | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPEAAGGPSVFLFPPKPKDTLMISRTPEVTCVVVDVS HEDPEVKFNWYVDGVEVHNAKTKPREEQYNSTYRV VSVLTVLHQDWLNGKEYKCKVSNKALPASIEKTISK AKGQPREPQVYTLPPSRDELTKNQVSLTCLVKGFYPS DIAVEWESNGQPENNYKTTPPVLDSDGSFFLYSKLTV DKSRWQQGNVFSCSVMHEALHNHYTQKSLSLSPG | 109 |
| IgG1 - PS (P331S) | ASTKGPSVFPLAPSSKSTSGGTAALGCLVKDYFPEPVT VSWNSGALTSGVHTFPAVLQSSGLYSLSSVVTVPSSS | 110 |

TABLE E-continued

Human Fc variants

| Human Fc variant | Amino acid sequence | SEQ ID NO: |
|---|---|---|
| | LGTQTYICNVNHKPSNTKVDKKVEPKSCDKTHTCPPC<br>PAPELLGGPSVFLFPPKPKDTLMISRTPEVTCVVVDVS<br>HEDPEVKFNWYVDGVEVHNAKTKPREEQYNSTYRV<br>VSVLTVLHQDWLNGKEYKCKVSNKALPASIEKTISK<br>AKGQPREPQVYTLPPSRDELTKNQVSLTCLVKGFYPS<br>DIAVEWESNGQPENNYKTTPPVLDSDGSFFLYSKLTV<br>DKSRWQQGNVFSCSVMHEALHNHYTQKSLSLSPGK | |
| IgG1 - PS<br>(P331S)<br>without terminal<br>lysine. | ASTKGPSVFPLAPSSKSTSGGTAALGCLVKDYFPEPVT<br>VSWNSGALTSGVHTFPAVLQSSGLYSLSSVVTVPSSS<br>LGTQTYICNVNHKPSNTKVDKKVEPKSCDKTHTCPPC<br>PAPELLGGPSVFLFPPKPKDTLMISRTPEVTCVVVDVS<br>HEDPEVKFNWYVDGVEVHNAKTKPREEQYNSTYRV<br>VSVLTVLHQDWLNGKEYKCKVSNKALPASIEKTISK<br>AKGQPREPQVYTLPPSRDELTKNQVSLTCLVKGFYPS<br>DIAVEWESNGQPENNYKTTPPVLDSDGSFFLYSKLTV<br>DKSRWQQGNVFSCSVMHEALHNHYTQKSLSLSPG | 111 |
| IgG1 - PSEG<br>(P331S and<br>E430G) | ASTKGPSVFPLAPSSKSTSGGTAALGCLVKDYFPEPVT<br>VSWNSGALTSGVHTFPAVLQSSGLYSLSSVVTVPSSS<br>LGTQTYICNVNHKPSNTKVDKKVEPKSCDKTHTCPPC<br>PAPELLGGPSVFLFPPKPKDTLMISRTPEVTCVVVDVS<br>HEDPEVKFNWYVDGVEVHNAKTKPREEQYNSTYRV<br>VSVLTVLHQDWLNGKEYKCKVSNKALPASIEKTISK<br>AKGQPREPQVYTLPPSRDELTKNQVSLTCLVKGFYPS<br>DIAVEWESNGQPENNYKTTPPVLDSDGSFFLYSKLTV<br>DKSRWQQGNVFSCSVMHGALHNHYTQKSLSLSPGK | 112 |
| IgG1 - PSEG<br>(P331S and<br>E430G)<br>without terminal<br>lysine. | ASTKGPSVFPLAPSSKSTSGGTAALGCLVKDYFPEPVT<br>VSWNSGALTSGVHTFPAVLQSSGLYSLSSVVTVPSSS<br>LGTQTYICNVNHKPSNTKVDKKVEPKSCDKTHTCPPC<br>PAPELLGGPSVFLFPPKPKDTLMISRTPEVTCVVVDVS<br>HEDPEVKFNWYVDGVEVHNAKTKPREEQYNSTYRV<br>VSVLTVLHQDWLNGKEYKCKVSNKALPASIEKTISK<br>AKGQPREPQVYTLPPSRDELTKNQVSLTCLVKGFYPS<br>DIAVEWESNGQPENNYKTTPPVLDSDGSFFLYSKLTV<br>DKSRWQQGNVFSCSVMHGALHNHYTQKSLSLSPG | 113 |
| IgG1 - NSLF<br>(N325S and<br>L328F) | ASTKGPSVFPLAPSSKSTSGGTAALGCLVKDYFPEPVT<br>VSWNSGALTSGVHTFPAVLQSSGLYSLSSVVTVPSSS<br>LGTQTYICNVNHKPSNTKVDKKVEPKSCDKTHTCPPC<br>PAPELLGGPSVFLFPPKPKDTLMISRTPEVTCVVVDVS<br>HEDPEVKFNWYVDGVEVHNAKTKPREEQYNSTYRV<br>VSVLTVLHQDWLNGKEYKCKVSSKAFPAPIEKTISKA<br>KGQPREPQVYTLPPSRDELTKNQVSLTCLVKGFYPSD<br>IAVEWESNGQPENNYKTTPPVLDSDGSFFLYSKLTVD<br>KSRWQQGNVFSCSVMHEALHNHYTQKSLSLSPGK | 114 |
| IgG1 - NSLF<br>(N325S and<br>L328F)<br>without terminal<br>lysine. | ASTKGPSVFPLAPSSKSTSGGTAALGCLVKDYFPEPVT<br>VSWNSGALTSGVHTFPAVLQSSGLYSLSSVVTVPSSS<br>LGTQTYICNVNHKPSNTKVDKKVEPKSCDKTHTCPPC<br>PAPELLGGPSVFLFPPKPKDTLMISRTPEVTCVVVDVS<br>HEDPEVKFNWYVDGVEVHNAKTKPREEQYNSTYRV<br>VSVLTVLHQDWLNGKEYKCKVSSKAFPAPIEKTISKA<br>KGQPREPQVYTLPPSRDELTKNQVSLTCLVKGFYPSD<br>IAVEWESNGQPENNYKTTPPVLDSDGSFFLYSKLTVD<br>KSRWQQGNVFSCSVMHEALHNHYTQKSLSLSPG | 115 |
| IgG1 - SELF<br>(S267E and<br>L328F) | ASTKGPSVFPLAPSSKSTSGGTAALGCLVKDYFPEPVT<br>VSWNSGALTSGVHTFPAVLQSSGLYSLSSVVTVPSSS<br>LGTQTYICNVNHKPSNTKVDKKVEPKSCDKTHTCPPC<br>PAPELLGGPSVFLFPPKPKDTLMISRTPEVTCVVVDVE<br>HEDPEVKFNWYVDGVEVHNAKTKPREEQYNSTYRV<br>VSVLTVLHQDWLNGKEYKCKVSNKAFPAPIEKTISKA<br>KGQPREPQVYTLPPSRDELTKNQVSLTCLVKGFYPSD<br>IAVEWESNGQPENNYKTTPPVLDSDGSFFLYSKLTVD<br>KSRWQQGNVFSCSVMHEALHNHYTQKSLSLSPGK | 116 |
| IgG1 - SELF<br>(S267E and<br>L328F)<br>without terminal<br>lysine. | ASTKGPSVFPLAPSSKSTSGGTAALGCLVKDYFPEPVT<br>VSWNSGALTSGVHTFPAVLQSSGLYSLSSVVTVPSSS<br>LGTQTYICNVNHKPSNTKVDKKVEPKSCDKTHTCPPC<br>PAPELLGGPSVFLFPPKPKDTLMISRTPEVTCVVVDVE<br>HEDPEVKFNWYVDGVEVHNAKTKPREEQYNSTYRV<br>VSVLTVLHQDWLNGKEYKCKVSNKAFPAPIEKTISKA<br>KGQPREPQVYTLPPSRDELTKNQVSLTCLVKGFYPSD | 117 |

TABLE E-continued

Human Fc variants

| Human Fc variant | Amino acid sequence | SEQ ID NO: |
|---|---|---|
| | IAVEWESNGQPENNYKTTPPVLDSDGSFFLYSKLTVD KSRWQQGNVFSCSVMHEALHNHYTQKSLSLSPG | |
| IgG2 | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKCCVECPPCPA PPVAGPSVFLFPPKPKDTLMISRTPEVTCVVVDVSHED PEVQFNWYVDGVEVHNAKTKPREEQFNSTFRVVSVL TVVHQDWLNGKEYKCKVSNKGLPAPIEKTISKTKGQ PREPQVYTLPPSREEMTKNQVSLTCLVKGFYPSDIAV EWESNGQPENNYKTTPPMLDSDGSFFLYSKLTVDKS RWQQGNVFSCSVMHEALHNHYTQKSLSLSPGK | 118 |
| IgG2 without terminal lysine. | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKCCVECPPCPA PPVAGPSVFLFPPKPKDTLMISRTPEVTCVVVDVSHED PEVQFNWYVDGVEVHNAKTKPREEQFNSTFRVVSVL TVVHQDWLNGKEYKCKVSNKGLPAPIEKTISKTKGQ PREPQVYTLPPSREEMTKNQVSLTCLVKGFYPSDIAV EWESNGQPENNYKTTPPMLDSDGSFFLYSKLTVDKS RWQQGNVFSCSVMHEALHNHYTQKSLSLSPG | 119 |

Additional anti-CD33 antibodies, e.g., antibodies that specifically bind to a CD33 protein of the present disclosure, may be identified, screened, and/or characterized for their physical/chemical properties and/or biological activities by various assays known in the art.

Anti-CD33 Antibodies Capable of Binding Fc Gamma Receptors

In some embodiments, anti-CD33 antibodies of the present disclosure retain the ability to bind Fc gamma receptors. In some embodiments, such antibodies when they have the correct epitope specificity that is compatible with receptor activation may have features that enable them to cluster and transiently stimulate, for example, the CD33 receptor. In some embodiments, such antibodies may subsequently act as longer-term inhibitors of CD33 expression and/or one or more activities of a CD33 protein by inducing CD33 degradation, CD33 desensitization, CD33 cleavage, CD33 internalization, CD33 shedding, downregulation of CD33 expression, and/or lysosomal degradation of CD33.

In vivo, anti-CD33 antibodies of the present disclosure may cluster receptors and transiently activate CD33 by any one or more of multiple potential mechanisms. Some isotypes of human antibodies such as IgG2 have, due to their unique structure, an intrinsic ability to cluster receptors, or retain receptors in a clustered configuration, thereby transiently activating receptors such as CD33 without binding to an Fc receptor (e.g., White et al., (2015) Cancer Cell 27, 138-148).

In some embodiments, other antibodies may cluster receptors (e.g., CD33) by binding to Fcg receptors on adjacent cells. In some embodiments, binding of the constant IgG Fc region of the antibody to Fcg receptors may lead to aggregation of the antibodies, and the antibodies in turn may aggregate the receptors to which they bind through their variable region (Chu et al (2008) Mol Immunol, 45:3926-3933; and Wilson et al., (2011) Cancer Cell 19, 101-113). In some embodiments, binding to the inhibitory Fcg receptor FcgR (FcgRIIB) that does not elicit cytokine secretion, oxidative burst, increased phagocytosis, and enhanced antibody-dependent, cell-mediated cytotoxicity (ADCC) is a preferred way to cluster antibodies in vivo, since binding to FcgRIIB is not associated with adverse immune response effects.

There are other mechanisms by which anti-CD33 antibodies of the present disclosure can cluster receptors. For example, antibody fragments (e.g., Fab fragments) that are cross-linked together may be used to cluster receptors (e.g., CD33) in a manner similar to antibodies with Fc regions that bind Fcg receptors, as described above. In some embodiments, cross-linked antibody fragments (e.g., Fab fragments) may transiently function as agonist antibodies if they induce receptor clustering on the cell surface and bind an appropriate epitope on the target (e.g., CD33).

Therefore, in some embodiments, antibodies of the present disclosure that bind a CD33 protein may include antibodies that due to their epitope specificity bind CD33 and transiently activate one or more CD33 activities before they, for example, decrease cellular levels of CD33, inhibit one or more CD33 activities, and/or inhibit interaction (e.g., binding) between CD33 and one or more CD33 ligands. In some embodiments, such antibodies may bind to the ligand-binding site on CD33 and transiently mimic the action of a natural ligand, or stimulate the target antigen to transduce signal by binding to one or more domains that are not the ligand-binding sites. In some embodiments, such antibodies would not interfere with ligand binding. In some embodiments, regardless of whether antibodies bind or do not bind to the ligand-binding site on CD33, the antibodies may subsequently act as longer-term inhibitors of CD33 expression and/or one or more activities of a CD33 protein by inducing CD33 degradation, CD33 desensitization, CD33 cleavage, CD33 internalization, CD33 shedding, downregulation of CD33 expression, and/or lysosomal degradation of CD33.

In some embodiments, an anti-CD33 antibody of the present disclosure is an antibody that transiently induces one or more activities of a CD33 protein. In some embodiments, the antibody transiently induces the one or more activities after binding to a CD33 protein that is expressed in a cell. In some embodiments, the CD33 protein is expressed on a cell surface. In some embodiments, the one or more activities of a CD33 protein that are transiently induced by anti-CD33 antibodies of the present disclosure may include, without limitation, phosphorylation of Tyr-340 and Tyr-358 by a Src family tyrosine kinase, such as LCK and FYN; recruitment of and binding to the tyrosine-specific protein phosphatases SHP1 and SHP2; recruitment of and binding to PLC-gamma1, which acts as a guanine nucleotide exchange factor for Dynamini-1; recruitment of and binding to SH2-domain containing protein (e.g., Crkl); recruitment of and binding to the spleen tyrosine kinase Syk; recruitment of and binding to SH3-SH2-SH3 growth factor receptor-bound protein 2 (Grb2); recruitment of and binding to multiple SH2-containing proteins; phosphorylation of Ser-307 and Ser-342 by protein kinase C; modulated expression of one or more anti-inflammatory cytokines, IL-4, IL-10, IL-13, IL-35, IL-16, TGF-beta, IL-1Ra, G-CSF, and soluble receptors for TNF, IFN-beta1a, IFN-beta1b, or IL-6 in monocytes, macrophages, T cells, dendritic cells neutrophils, and/or microglia; decreasing intracellular calcium mobilization; modulated expression of one or more pro-inflammatory cytokines IFN-α4, IFN-b, IL-10, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, and MIP-1-beta in monocytes, macrophages, T cells, dendritic cells, neutrophils, and/or microglia; modulated expression of one or more proteins selected from C1qa, C1qB, C1qC, Cis, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, PYCARD, CD14, CD16, HLA-DR, and CCR2; inhibition of extracellular signal-regulated kinase (ERK) phosphorylation; decreasing tyrosine phosphorylation on multiple cellular proteins; modulated expression of C-C chemokine receptor 7 (CCR7); inhibition of microglial cell chemotaxis toward CCL 19 and CCL21 expressing cells; activation of phosphoinositide 3-kinase; reducing cell growth of monocytes, macrophages, T cells, dendritic cells and/or microglia; reducing T cell proliferation induced by dendritic cells, bone marrow-derived dendritic cells, monocytes, microglia, M1 microglia, activated M1 microglia, M2 microglia, macrophages, M1 macrophages, activated M1 macrophages, and/or M2 macrophages; inhibition of osteoclast production, decreased rate of osteoclastogenesis, or both; decreasing survival of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing proliferation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting migration of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing one or more functions of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting maturation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; increasing cell death and apoptosis of monocytes, macrophages, T cells, dendritic cells, neutrophils, and/or microglia; reducing phagocytic activity of monocytes, macrophages, T cells, dendritic cells, neutrophils, and/or microglia; reducing proliferation of monocytes, macrophages, T cells, dendritic cells, neutrophils, and/or microglia; reducing the overall functionality of monocytes, macrophages, T cells, dendritic cells, neutrophils, and/or microglia, phosphorylation of an ITAM containing receptor; phosphorylation of a signaling molecules that mediates ITAM signaling; reducing the activation of pattern recognition receptors; reducing the activation of Toll-like receptors; reducing the activation of damage-associated of clearance of cellular and protein debris; interaction between CD33 and one or more of its ligands; interaction between CD33 and a co-receptor such as CD64; reducing one or more types of clearance selected from apoptotic neuron clearance, dysfunctional synapse clearance, nerve tissue debris clearance, non-nerve tissue debris clearance, bacteria or other foreign body clearance, disease-causing protein clearance, and tumor cell clearance; inhibition of phagocytosis of one or more of apoptotic neurons, nerve tissue debris, non-nerve tissue debris, bacteria, other foreign bodies, disease-causing proteins, disease-causing peptides, disease-causing nucleic acid, disease-causing lipids, or tumor cells; inhibition of clearance of a disease-causing nucleic acid, such as the disease-causing nucleic acid is antisense GGCCCC (G2C4) repeat-expansion RNA; activation of clearance of, a disease-causing protein selected from amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; inhibition of beneficial immune response to different types of cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, acute myeloid leukemia, pancreatic cancer, prostate cancer, ovarian cancer, fibrosarcoma, and thyroid cancer; inhibition of beneficial immune response to different types of neurological disorders selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, essential tremor, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, -traumatic brain injury, age related macular degeneration, glaucoma, retinitis pigmentosa, retinal degeneration, and multiple sclerosis; inhibition of beneficial immune response-to different types of inflammatory and infectious disorders selected from lupus, acute and chronic colitis, wound healing, Crohn's disease, inflammatory bowel disease, ulcerative colitis, obesity, malaria, respiratory tract infection, sepsis, eye infection, systemic infection, lupus, arthritis, low bone density, osteoporosis, osteogenesis, osteopetrotic disease, and Paget's disease of bone; inhibition of phagocytosis of one or more of apoptotic neurons, nerve tissue debris, dysfunctional synapses, non-nerve tissue debris, bacteria, other foreign bodies, disease-causing proteins, disease-causing peptides, disease-causing nucleic acids, or tumor cells, where the disease-causing nucleic acids may be an antisense GGCCCC (G2C4) repeat-expansion RNA, the disease-causing proteins may include amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells may be from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer, binding to CD33 ligand on tumor cells; binding to CD33 ligand on dendritic cells, bone marrow-derived dendritic cells, monocytes, microglia, T cells, neutrophils, and/or macrophages; inhibition of tumor cell killing by one or more of microglia, macrophages, dendritic cells, bone marrow-derived dendritic cells, neutrophils, T cells, T helper cells, or cytotoxic T cells; inhibition of anti-tumor cell proliferation activity of one or more of microglia, macrophages, dendritic cells, bone marrow-derived dendritic cells, neutrophils, T cells, T helper cells, or cytotoxic T cells; inhibition of anti-tumor cell metastasis activity of one or more of microglia, macrophages, dendritic cells, bone marrow-derived dendritic cells, neutrophils, T cells, T helper cells, or cytotoxic T cells; promotion of immunosuppressor dendritic cells, immunosuppressor macrophages, myeloid-derived suppressor cells, tumor-associated macrophages, or regulatory T cells; inhibition of one or more ITAM motif containing receptors, such as TREM1, TREM2, FcgR, DAP10, and DAP12; inhibition of one or more receptors containing the motif D/Ex0-2YxxL/IX6-8YxxL/I (SEQ ID NO:104); inhibition of signaling by one or more pattern recognition receptors (PRRs), such as receptors that identify pathogen-associated molecular patterns (PAMPs), and receptors that identify damage-associated molecular patterns (DAMPs); inhibition of signaling by one or more Toll-like receptors; inhibition of the JAK-STAT signaling pathway; inhibition of nuclear factor kappa-light-chain-enhancer of activated B cells (NFκB); inhibition of PLCγ/PKC/calcium mobilization; inhibition of PI3K/Akt, Ras/MAPK signaling; modulated expression of one or more inflammatory receptors, such as CD86, expressed on one or more of microglia, macrophages, dendritic cells, bone marrow-derived dendritic cells, neutrophils, T cells, T helper cells, or cytotoxic T cells; increasing expression of one or more CD33-dependent genes; normalization of disrupted CD33-dependent gene expression; and decreasing expression of one or more ITAM-dependent genes, such as NFAT transcription factors. Anti-CD33 antibodies of the present disclosure may be tested for their ability to transiently induce one or more activities of a CD33 protein utilizing any suitable technique or assay known in the art and disclosed herein. Regardless of the activities that such antibodies transiently induce, such antibodies may subsequently act as longer-term inhibitors of CD33 expression and/or one or more activities of a CD33 protein by inducing CD33 degradation, CD33 desensitization, CD33 cleavage, CD33 internalization, CD33 shedding, downregulation of CD33 expression, and/or lysosomal degradation of CD33. In some embodiments, the CD33 antibody transiently induces one or more activities of a CD33 protein independently of binding to an Fc receptor.

Exemplary antibody Fc isotypes and modifications are provided in Table B below. In some embodiments, an anti-CD33 antibody of the present disclosure that is capable of binding an Fc gamma receptor has an Fc isotype listed in Table B below.

TABLE B

| Exemplary anti-CD33 antibody Fc isotypes that are capable of binding Fc gamma receptor | |
|---|---|
| Fc Isotype | Mutation (EU numbering scheme) |
| IgG1 | N297A |
| IgG1 | D265A and N297A |
| IgG1 | D270A |
| IgG1 | L234A and L235A |
|  | L234A and G237A |
|  | L234A and L235A and G237A |
| IgG1 | D270A, and/or P238D, and/or L328E, and/or E233D, and/or G237D and/or H268D, and/or P271G, and/or A330R |
| IgG1 | P238D and L328E and E233D and G237D and H268D and P271G and A330R |
| IgG1 | P238D and L328E and G237D and H268D and P271G and A330R |
| IgG1 | P238D and S267E and L328F and E233D and G237D and H268D and P271G and A330R |
| IgG1 | P238D and S267E and L328F and G237D and H268D and P271G and A330R |

TABLE B-continued

Exemplary anti-CD33 antibody Fc isotypes that
are capable of binding Fc gamma receptor

| Fc Isotype | Mutation (EU numbering scheme) |
|---|---|
| IgG2 | V234A and G237A |
| IgG4 | L235A and G237A and E318A |
| IgG4 | S228P and L236E |
| IgG2/4 hybrid | IgG2 aa 118 to 260 and IgG4 aa 261 to 447 H268Q and V309L; and A330S and P331S |
| IgG1 | C226S and C229S and E233P and L234V and L235A |
| IgG1 | L234F and L235E and P331S |
| IgG2 | C232S or C233S |
| IgG2 | A330S and P331S |
| IgG1 | S267E and L328F S267E alone |
| IgG2 | S267E and L328F |
| IgG4 | S267E and L328F |
| IgG2 | WT HC with Kappa (light chain) LC HC C127S with Kappa LC Kappa LC C214S Kappa LC C214S and HC C233S Kappa LC C214S and HC C232S Any of the above listed mutations together with P330S and P331S mutations F(ab')2 fragment of WT IgG1 and any of the above listed mutations |
| IgG1 | Substitute the Constant Heavy 1 (CH1) and hinge region of IgG1 With CH1 and hinge region of IGg2 ASTKGPSVFP LAPCSRSTSE STAALGCLVK DYFPEPVTVS WNSGALTSGV HTFPAVLQSS GLYSLSSVVT VPSSNFGTQT YTCNVDHKPS NTKVDKTVER KCCVECPPCP (SEQ ID NO: 105) With a Kappa LC |
| IgG1 | Any of the above listed mutations together with A330L/A330S and/ or L234F and/or L235E and/or P331S |
| IgG1, IgG2, or IgG4 | Any of the above listed mutations together with M252Y and/or S254T and/or T256E |
| Mouse IgG1, mouse IgG2a, mouse IgG2b | For mouse disease models |
| IgG4 | WT |
| IgG1 | Any of the above listed mutation together with E430G, E430S, E430F, E430T, E345K, E345Q, E345R, E345Y, S440Y, S440W and/or any combination thereof. |
| IgG2 | Any of the above listed mutation together with E430G, E430S, E430F, E430T, E345K, E345Q, E345R, E345Y, S440Y, S440W and/or any combination thereof. |

In addition to the isotypes described in Table B, and without wishing to be bound to theory, it is thought that antibodies with human IgG1 or IgG3 isotypes and mutants thereof (e.g. Strohl (2009) Current Opinion in Biotechnology 2009, 20:685-691) that bind the Fcg Receptors I, IIA, IIC, IIIA, IIIB in human and/or Fcg Receptors I, III and IV in mouse, may also act as transient agonist antibodies.

In some embodiments, the Fc gamma receptor-binding antibody is of the IgG class, the IgM class, or the IgA class. In some embodiments, the Fc gamma receptor-binding antibody has an IgG1, IgG2, IgG3, or IgG4 isotype. In some embodiments, the antibody comprises one or more (e.g., one or more, two or more, three or more, four or more, five or more, six or more, seven or more, eight or more, nine or more, 10 or more, 11 or more, 12 or more, or all thirteen) amino acid substitutions in the Fc region at a residue position selected from the group consisting of: C127S, L234A, L234F, L235A, L235E, S267E, K322A, L328F, A330S, P331S, E345R, E430G, S440Y in any combination (residue position according to EU numbering). In some embodiments, the Fc region comprises an amino acid substitution at position E430G. In some embodiments, the Fc region comprises an amino acid substitution at positions L234A, L235A, and P331A. In some embodiments, the Fc region comprises an amino acid substitution at positions L234A, L235A, P331A. In some embodiments, the Fc region comprises an amino acid substitution at positions K322A and E430G. In some embodiments, the Fc region comprises an amino acid substitution at positions P331S and E430G. In some embodiments, the Fc region comprises an amino acid substitution at positions A330S, P331S, and E430G. In some embodiments, the Fc region comprises an amino acid substitution at positions K322A, A330S, and P331S. In some embodiments, the Fc region comprises an amino acid substitution at positions K322A, P331S, and E430G. In some embodiments, the Fc region comprises an amino acid substitution at positions A330S, P331S, and E430G. In some embodiments, the Fc region comprises an amino acid substitution at positions S267E and L328F. In some embodiments, the Fc region comprises an amino acid substitution at position C127S. In some embodiments, the Fc region comprises an amino acid substitution at positions E345R, E430G and S440Y. In some embodiments, the Fc region comprises the amino acid substitution at position P331S. In some embodiments, the Fc region comprises an amino acid substitution at positions L234A, L235A, and P331S. In some embodiments, the Fc region comprises an amino acid substitution at positions S267E and L328F. In some embodiments, the numbering of the above amino acid substitutions is according to EU numbering.

In certain embodiments, the Fc gamma receptor-binding antibody has an IgG2 isotype. In some embodiments, the Fc gamma receptor-binding antibody contains a human IgG2 constant region. In some embodiments, the human IgG2 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from V234A (Alegre et al., (1994) *Transplantation* 57:1537-1543. 31; Xu et al., (2000) *Cell Immunol,* 200:16-26), G237A (Cole et al. (1999) *Transplantation,* 68:563-571), H268Q, V309L, A330S, P331S (US 2007/0148167; Armour et al. (1999) *Eur J Immunol* 29: 2613-2624; Armour et al. (2000) *The Haematolog Journal* 1(Suppl.1):27; Armour et al. (2000) *The Haematology Journal* 1(Suppl.1):27), C232S, and/or C233S (White et al. (2015) *Cancer Cell* 27, 138-148), S267E, L328F (Chu et al., (2008) *Mol Immunol,* 45:3926-3933), M252Y, S254T, and/or T256E, where the amino acid position is according to the EU numbering convention.

In some embodiments, the Fc gamma receptor-binding antibody has an IgG2 isotype with a heavy chain constant domain that contains a C127S amino acid substitution, where the amino acid position is according to the EU numbering convention (White et al., (2015) *Cancer Cell* 27, 138-148; Lightle et al., (2010) *PROTEIN SCIENCE* 19:753-762; and WO2008079246).

In some embodiments, the Fc gamma receptor-binding antibody has an IgG2 isotype with a Kappa light chain constant domain that contains a C214S amino acid substitution, where the amino acid position is according to the EU numbering convention (White et al., (2015) *Cancer Cell* 27, 138-148; Lightde et al., (2010) *PROTEIN SCIENCE* 19:753-762; and WO2008079246).

In certain embodiments, the Fc gamma receptor-binding antibody has an IgG1 isotype. In some embodiments, the Fc gamma receptor-binding antibody contains a mouse IgG1 constant region. In some embodiments, the Fc gamma receptor-binding antibody contains a human IgG1 constant region. In some embodiments, the human IgG1 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) R. *J. Biol. Chem.* 276, 6591-6604), D270A, L234A, L235A (Hutchins et al. (1995) *Proc Natl Acad Sci USA,* 92:11980-11984; Alegre et al., (1994) *Transplantation* 57:1537-1543. 31; Xu et al., (2000) *Cell Immunol,* 200:16-26), G237A (Alegre et al. (1994) *Transplantation* 57:1537-1543. 31; Xu et al. (2000) *Cell Immunol,* 200:16-26), P238D, L328E, E233D, G237D, H268D, P271G, A330R, C226S, C229S, E233P, L234V, L234F, L235E (McEarchern et al., (2007) *Blood,* 109:1185-1192), P331S (Sazinsky et al., (2008) *Proc Natl Acad Sci USA* 2008, 105:20167-20172), S267E, L328F, A330L, M252Y, S254T, T256E, N297Q, P238S, P238A, A327Q, A327G, P329A, K322A, and/or T394D, where the amino acid position is according to the EU numbering convention.

In some embodiments, the antibody includes an IgG2 isotype heavy chain constant domain 1(CH1) and hinge region (White et al., (2015) *Cancer Cell* 27, 138-148). In certain embodiments, the IgG2 isotype CH1 and hinge region contain the amino acid sequence of ASTKGPSVF-PLAPCSRSTSESTAALGCLVKDYF-PEPVTVSWNSGALTSGVHTFPAVLQSSGLY SLSSVVTVPSSNFGTQTYTCNVDHKPSNTKVDKTVE RKCCVECPPCP (SEQ ID NO: 105). In some embodiments, the antibody Fc region contains a S267E amino acid substitution, a L328F amino acid substitution, or both, and/or a N297A or N297Q amino acid substitution, where the amino acid position is according to the EU numbering convention.

In certain embodiments, the Fc gamma receptor-binding antibody has an IgG4 isotype. In some embodiments, the Fc gamma receptor-binding antibody contains a human IgG4 constant region. In some embodiments, the human IgG4 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from L235A, G237A, S228P, L236E (Reddy et al., (2000) *J Immunol,* 164:1925-1933), S267E, E318A, L328F, M252Y, S254T, and/or T256E, where the amino acid position is according to the EU numbering convention.

In certain embodiments, the Fc gamma receptor-binding antibody has a hybrid IgG2/4 isotype. In some embodiments, the Fc gamma receptor-binding antibody includes an amino acid sequence containing amino acids 118 to 260 according to EU numbering of human IgG2 and amino acids 261-447 according to EU numbering of human IgG4 (WO 1997/11971; WO 2007/106585).

In certain embodiments, the antibody contains a mouse IgG4 constant region (Bartholomaeus, et al. (2014). J. Immunol. 192, 2091-2098).

In some embodiments, the Fc region further contains one or more additional amino acid substitutions selected from the group consisting of A330L, L234F; L235E, or P331S according to EU and any combination thereof.

In certain embodiments, the antibody contains one or more amino acid substitutions in the Fc region at a residue position selected from C127S, L234A, L234F, L235A, L235E, S267E, K322A, L328F, A330S, P331S, E345R, E430G, S440Y, and any combination thereof, where the numbering of the residues is according to EU numbering. In some embodiments, the Fc region contains an amino acid substitution at positions E430G, L234A, L235A, and P331S, where the numbering of the residue position is according to EU numbering. In some embodiments, the Fc region contains an amino acid substitution at positions E430G and P331S, where the numbering of the residue position is according to EU numbering. In some embodiments, the Fc region contains an amino acid substitution at positions E430G and K322A, where the numbering of the residue position is according to EU numbering. In some embodiments, the Fc region contains an amino acid substitution at positions E430G, A330S, and P331S, where the numbering of the residue position is according to EU numbering. In some embodiments, the Fc region contains an amino acid substitution at positions E430G, K322A, A330S, and P331S, where the numbering of the residue position is according to EU numbering. In some embodiments, the Fc region contains an amino acid substitution at positions E430G, K322A, and A330S, where the numbering of the residue position is according to EU numbering. In some embodiments, the Fc region contains an amino acid substitution at positions E430G, K322A, and P331S, where the numbering of the residue position is according to EU numbering. In some embodiments, the Fc region contains an amino acid substitution at positions S267E and L328F, where the numbering of the residue position is according to EU numbering. In some embodiments, the Fc region contains an amino acid substitution at position C127S, where the numbering of the residue position is according to EU numbering. In some embodiments, the Fc region contains an amino acid substitution at positions E345R, E430G and S440Y, where the numbering of the residue position is according to EU numbering. In some embodiments, the Fc region comprises an amino acid substitution at positions L234A, L235A, and P331S, wherein the numbering of the residue position is according to EU numbering.

Inert Antibodies

Another class of anti-CD33 antibodies of the present disclosure includes inert antibodies. As used herein, "inert" antibodies refer to antibodies that specifically bind their target antigen (e.g., CD33) but do not modulate (e.g., decrease/inhibit or activate/induce) antigen function. For example, in the case of CD33, inert antibodies do not modulate cellular levels of CD33, do not modulate interaction (e.g., binding) between CD33 and one or more CD33 ligands, or do not modulate one or more activities of a CD33 protein. In some embodiments, antibodies that do not have the ability to cluster CD33 on the cell surface may be inert antibodies even if they have an epitope specificity that is compatible with receptor activation.

In some embodiments, antibodies that bind a CD33 protein may include antibodies that bind CD33 but, due to their epitope specificity, or characteristics, do not decrease cellular levels of CD33 and/or inhibit interaction (e.g., binding) between CD33 and one or more CD33 ligands. In some embodiments, such antibodies can be used as cargo to, for example, transport toxins (e.g., chemotherapeutics) into tumor cells. Therefore, in some embodiments, antibodies of the present disclosure are inert antibodies that bind CD33 but are incapable of decreasing cellular levels of CD33, inhibiting interaction (e.g., binding) between CD33 and one or more CD33 ligands, or inducing one or more activities of a CD33 protein.

Antibodies that either decrease or do not decrease cellular levels of CD33 on cells can be combined with an inert Fc region that displays reduced binding to one or more Fcg Receptor. Examples of such Fc regions and modifications are provided in Table C below. In some embodiments, the antibody with an inert Fc region has an Fc isotype listed in Table C below.

Inhibitory Anti-CD33 Antibodies

A third class of anti-CD33 antibodies of the present disclosure includes antibodies that block or otherwise inhibit one or more CD33 activities. In some embodiments, antibodies that bind a CD33 protein may include antibodies that reduce cellular levels of CD33 (e.g., cell surface levels of CD33), inhibit interaction (e.g., binding) between CD33 and/or one or more CD33 ligands, and inhibit one or more activities of a CD33 protein. Such antibodies inhibit one or more activities of a CD33 protein either by preventing interaction (e.g., binding) between CD33 and one or more CD33 ligands or by preventing signal transduction from the extracellular domain of CD33 into the cell cytoplasm in the presence of one or more CD33 ligands. Antibodies also can inhibit one or more activities of a CD33 protein by decreasing cell surface levels of CD33 by inducing CD33 degradation, CD33 desensitization, CD33 cleavage, CD33 internalization, CD33 shedding, downregulation of CD33 expression, and/or lysosomal degradation of CD33. In some embodiments, such anti-CD33 antibodies may not transiently activate CD33.

In some embodiments, anti-CD33 antibodies of the present disclosure may have the epitope specificity of a transient agonist anti-CD33 antibody of the present disclosure, but have an Fc domain that is not capable of binding Fcg receptors and thus is unable to, for example, transiently clustering and activating CD33.

In some embodiments, anti-CD33 antibodies of the present disclosure have, without limitation, one or more of the following activities: the ability to decrease binding of a CD33 protein to one or more CD33 ligands, such as sialic acid-containing glycolipid s or sialic acid-containing glycoproteins, the ability to decrease the binding of a suppressor of cytokine signaling (SOCS) protein (e.g., SOCS3 protein) to a CD33 protein, the ability to increase the proteasomal degradation of a CD33 protein, the ability to reduce functional expression of CD33 on the surface of circulating dendritic cells, macrophages, monocytes, T cells, and/or microglia, the ability to decrease phosphorylation of Tyr-340 and Tyr-358 by a Src family tyrosine kinase such as LCK and FYN, the ability to decrease recruitment of and binding to the tyrosine-specific protein phosphatases SHP1 and SHP2, the ability to decrease recruitment of and binding to PLC-g1, which acts as a guanine nucleotide, exchange factor for Dynamin-1, the ability to decrease recruitment of and binding to Crkl, the ability to decrease recruitment of and binding to the Spleen tyrosine kinase Syk, the ability to decrease recruitment of and binding to SH3-SH2-SH3 growth factor receptor-bound protein 2 (Grb2), the ability to decrease recruitment of and binding to multiple SH2 containing proteins, the ability to increase intracellular calcium mobilization, the ability to modulate production of pro-inflammatory cytokines IL-1β, IL-8, and TNF-α, the ability to decrease activation of phosphoinositide 3-kinase, the ability to increase the growth of monocytes, macrophages, dendritic cells, T cells, and/or microglia, the ability to increase the survival of monocytes, macrophages, dendritic cells, T cells, and/or microglia, the ability to increase tyrosine phosphorylation on multiple cellular proteins, the ability to increase phagocytic activity of monocytes, macrophages, dendritic cells and/or microglia, the ability to increase cell proliferation of monocytes, macrophages, dendritic cells, T cells, and/or microglia, the ability to increase phosphorylation of signaling molecules that mediates ITAM signaling, the ability to increase the function of pattern recognition receptors, the ability to increase the function of Toll-like receptors, the ability to increases the function of damage-associated molecular pattern (DAMP) receptors, the ability to modulate expression of C-C chemokine receptor 7 (CCR7), and the ability to increase of clearance of cellular and protein debris.

In some embodiments, anti-CD33 antibodies of the present disclosure have an Fc region that displays reduced binding to one or more Fcg Receptor. Examples of such Fc regions and modifications are provided in Table C below. In some embodiments, the antibody has an Fc isotype listed in Table C below.

Antibody Fc Isotypes with Reduced Binding to Fc Gamma Receptors

In some embodiments, anti-CD33 antibodies with reduced binding to Fc gamma receptors have an Fc isotype listed in Table C below.

TABLE C

Exemplary anti-CD33 antibody Fc isotypes with reduced binding to Fc gamma receptor

| Fc Isotype | Mutation (EU numbering scheme) |
|---|---|
| IgG1 | N297A or N297Q and/or D270A |
| IgG1 | D265A, D270A, and/or N297A |
| IgG1 | L234A and L235A |
| IgG2 | V234A and G237A |
| IgG4 | F235A and G237A and E318A |
| | E233P and/or F234V |
| | N297A or N297Q |
| IgG4 | S228P and L236E |
| | S241P |
| | S241P and L248E |
| | S228P and F234A and L235A |
| IgG2 | H268Q and V309L and A330S and P331S |
| IgG1 | C220S and C226S and C229S and P238S |
| IgG1 | C226S and C229S and E233P and L234V, and L235A |
| IgG1 | E233P and L234V and L235A and G236-deleted |
| | P238A |
| | D265A |
| | N297A |
| | A327Q or A327G |
| | P329A |
| IgG1 | K322A and L234A and L235A |
| IgG1 | L234F and L235E and P331S |
| IgG1 or IgG4 | T394D |
| IgG2 | C232S or C233S |
| | N297A or N297Q |
| IgG2 | V234A and G237A and P238S and H268A and V309L and A330S and P331S |
| IgG1, IgG2, or IgG4 | delta a, b, c, ab, ac, g modifications |
| IgG1 | Any of the above listed mutations together with A330L or L234F and/or L235E and/or P331S |
| IgG1, IgG2, or IgG4 | Any of the above listed mutations together with M252Y and/or S254T and/or T256E |

In certain embodiments, the anti-CD33 antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the Fc region contains one or more modifications. For example, in some embodiments, the Fc region contains one or more amino acid substitutions (e.g., relative to a wild-type Fc region of the same isotype).

In some embodiments, the one or more amino acid substitutions are selected from N297A, N297Q (Bolt S et al. (1993) *Eur J Immunol* 23:403-411), D265A, D270A, L234A, L235A (McEarchern et al., (2007) *Blood,* 109:1185-1192), C226S, C229S (McEarchern et al., (2007) *Blood,* 109:1185-1192), P238S (Davis et al., (2007) *J Rheumatol,* 34:2204-2210), E233P, L234V (McEarchern et al., (2007) *Blood,* 109:1185-1192), P238A, A327Q, A327G, P329A (Shields R L, et al., (2001)*J Biol Chem.* 276(9):6591-604), K322A, L234F, L235E (Hezareh, et al., (2001) J Virol 75, 12161-12168; Oganesyan et al., (2008). *Acta Crystallographica* 64, 700-704), P331S (Oganesyan et al., (2008) *Acta Crystallographica* 64, 700-704), T394D (Wilkinson et al. (2013) *MAbs* 5(3): 406-417), A330L, M252Y, S254T, and/or T256E, where the amino acid position is according to the EU numbering convention. In certain embodiments, the Fc region further includes an amino acid deletion at a position corresponding to glycine 236 according to the EU numbering convention.

In some embodiments, the anti-CD33 antibody has an IgG1 isotype with a heavy chain constant region that contains a C220S amino acid substitution according to the EU numbering convention. In some embodiments, the Fc region further contains one or more additional amino acid substitutions selected from A330L, L234F; L235E, and/or P331S according to EU numbering convention. In certain embodiments, the anti-CD33 antibody has an IgG2 isotype. In some embodiments, the anti-CD33 antibody contains a human IgG2 constant region. In some embodiments, the human IgG2 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from P238S, V234A, G237A, H268A, H268Q, H268E, V309L, N297A, N297Q, V309L, A330S, P331S, C232S, C233S, M252Y, S254T, and/or T256E, where the amino acid position is according to the EU numbering convention (Vafa O. et al., (2014) Methods 65:114-126).

In certain embodiments, the anti-CD33 antibody has an IgG4 isotype. In some embodiments, the anti-CD33 antibody contains a human IgG4 constant region. In some embodiments, the human IgG4 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from E233P, F234V, L235A, G237A, E318A (Hutchins et al. (1995) *Proc Natl Acad Sci USA,*

92:11980-11984), S228P, L234A/F234A, L236E, S241P, L248E (Reddy et al., (2000) *J Immunol,* 164:1925-1933; Angal et al., (1993) *Mol Immunol.* 30(1):105-8; U.S. Pat. No. 8,614,299 B2; Vafa O. et al., (2014) Methods 65:114-126), T394D, M252Y, S254T, T256E, N297A, and/or N297Q, where the amino acid position is according to the EU numbering convention. In some embodiments the antibody has an IgG4 isotype, and comprises an S228P amino acid substitution at residue position 228, an F234A amino acid substitution at residue position 234, and an L235A amino acid substitution at residue position 235 (residue position according to EU numbering).

In some embodiments, the Fc region further contains one or more additional amino acid substitutions selected from a M252Y, S254T, and/or T256E, where the amino acid position is according to the EU numbering convention.

Further IgG Mutations

In some embodiments, one or more of the IgG1 variants described herein may be combined with an A330L mutation (Lazar et al., (2006) Proc Natl Acad Sci USA, 103:4005-4010), or one or more of L234F, L235E, and/or P331S mutations (Sazinsky et al., (2008) Proc Natl Acad Sci USA, 105:20167-20172), where the amino acid position is according to the EU numbering convention, to eliminate complement activation. In some embodiments, the IgG variants described herein may be combined with one or more mutations to enhance the anti-CD33 antibody half-life in human serum (e.g. M252Y, S254T, T256E mutations according to the EU numbering convention) (Dall' Acqua et al., (2006) J Biol Chem, 281:23514-23524; and Strohl e al., (2009) Current Opinion in Biotechnology, 20:685-691).

In some embodiments, an IgG4 variant of the present disclosure may be combined with an S228P mutation according to the EU numbering convention (Angal et al., (1993) Mol Immunol, 30:105-108) and/or with one or more mutations described in Peters et al., (2012) J Biol Chem. 13; 287(29):24525-33) to enhance antibody stabilization.

Bispecific Antibodies

Certain aspects of the present disclosure relate to bispecific antibodies that bind to one or more domains on a CD33 protein of the present disclosure and a second antigen. Methods of generating bispecific antibodies are well known in the art and described herein. In some embodiments, bispecific antibodies of the present disclosure bind to one or more amino acid residues of a CD33 protein of the present disclosure, such as one or more amino acid residues of human CD33 (SEQ ID NO: 1), or amino acid residues on a CD33 protein corresponding to amino acid residues of SEQ ID NO: 1. In some embodiments, bispecific antibodies of the present disclosure recognize a first antigen and a second antigen. In some embodiments, the first antigen is a CD33 protein or a naturally occurring variant thereof. In some embodiments, the second antigen is also a CD33 protein, or a naturally occurring variant thereof. In some embodiments, the second antigen is an antigen facilitating transport across the blood-brain-barrier (see, e.g., Gabathuler R., *Neurobiol. Dis.* 37 (2010) 48-57). Such second antigens include, without limitation, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, Angiopep peptides such as ANG1005 (see, e.g., Gabathuler, 2010), and other cell surface proteins that are enriched on blood-brain barrier endothelial cells (see, e.g., Daneman et al., PLoS One. 2010 Oct. 29; 5(10):e13741). In some embodiments, the second antigen is a disease-causing protein including, without limitation, amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides. In some embodiments, the second antigen is one or more ligands and/or proteins expressed on immune cells, including without limitation, CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR, LAG3, DR5, CD39, CD70, CD73, TREM1, TREM2, Siglec-5, Siglec-7, Siglec-9, Siglec-11, SirpA, CD47, CSF1-receptor, CD3, and phosphatidylserine. In some embodiments, the second antigen is a protein, lipid, polysaccharide, or glycolipid expressed on one or more tumor cells.

Antibody Fragments

Certain aspects of the present disclosure relate to antibody fragments that bind to one or more of a CD33 protein of the present disclosure, a naturally occurring variant of a CD33 protein, and a disease variant of a CD33 protein. In some embodiments, the antibody fragment is an Fab, Fab', Fab'-SH, F(ab')2, Fv or scFv fragment.

In some embodiments, the antibody fragment is used in combination with a second CD33 antibody and/or with one or more antibodies that specifically bind a disease-causing protein selected from: amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and any combination thereof; or with one or more antibodies that bind an immunomodulatory protein selected from the group consisting of: CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR, LAG3, DR5, CD39, CD70, CD73, TREM1, TREM2, CD47, CSF-1 receptor, Siglec-5, Siglec-7, Siglec-9, Siglec-11, phosphatidylserine, and any combination thereof.

In some embodiments, antibody fragments of the present disclosure may be functional fragments that bind the same epitope as any of the anti-CD33 antibodies of the present disclosure. In some embodiments, the antibody fragments are miniaturized versions of the anti-CD33 antibodies or antibody fragments of the present disclosure that have the same epitope of the corresponding full-length antibody, but have much smaller molecule weight. Such miniaturized anti-CD33 antibody fragments may have better brain penetration ability and a shorter half-life, which is advantageous for imaging and diagnostic utilities (see e.g., Litje S et al., *Bioconjug Chem.* 2014 Feb. 19; 25(2):335-41; Tavaré R et al., *Proc Natl Acad Sci USA.* 2014 Jan. 21; 111(3):1108-13; and Wiehr S et al., *Prostate.* 2014 May; 74(7):743-55). Accordingly, in some embodiments, anti-CD33 antibody fragments of the present disclosure have better brain penetration as compared to their corresponding full-length antibodies and/or have a shorter half-life as compared to their corresponding full-length antibodies.

Antibody Frameworks

Any of the antibodies described herein further include a framework. In some embodiments, the framework is a human immunoglobulin framework. For example, in some embodiments, an antibody (e.g., an anti-CD33 antibody) comprises HVRs as in any of the above embodiments and further comprises an acceptor human framework, e.g., a human immunoglobulin framework or a human consensus framework. Human immunoglobulin frameworks may be part of the human antibody, or a non-human antibody may be humanized by replacing one or more endogenous frameworks with human framework region(s). Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

Full Length Antibodies

In some embodiments, the anti-CD33 antibodies of the present disclosure comprise full-length heavy chains comprising the variable heavy chain sequences described above and full-length light chains comprising the variable light chain sequences described above. In certain embodiments, an anti-CD33 antibody comprises a full-length heavy chain sequence of SEQ ID NO: 120 or 121, and a full-length light chain sequence of SEQ ID NO: 122.

CD33 Activities

Modulated Expression of Immune-Related Proteins

In some embodiments, anti-CD33 antibodies of the present disclosure may modulate expression of PD-L1, PD-L2, B7-H2, B7-H3, CD200R, CD163 and/or CD206 after binding to a CD33 protein expressed in a cell. Modulated (e.g., increased or decreased) expression may include, without limitation, modulation in gene expression, modulation in transcriptional expression, or modulation in protein expression. Any method known in the art for determining gene, transcript (e.g., mRNA), and/or protein expression may be used. For example, Northern blot analysis may be used to determine anti-inflammatory mediator gene expression levels, RT-PCR may be used to determine the level of anti-inflammatory mediator transcription, and Western blot analysis may be used to determine anti-inflammatory mediator protein levels.

As used herein, PD-L1, PD-L2, B7-H2, B7-H3, CD200R, CD163 and/or CD206 may have modulated expression if its expression in one or more cells of a subject treated with anti-CD33 antibodies of the present disclosure is modulated (e.g., increased or decreased) as compared to the expression of PD-L1, PD-L2, B7-H2, B7-H3, CD200R, CD163 and/or CD206 expressed in one or more cells of a corresponding subject that is not treated with the antibody. In some embodiments, an anti-CD33 antibody of the present disclosure may modulate PD-L1, PD-L2, B7-H2, B7-H3, CD200R, CD163 and/or CD206 expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to PD-L1, PD-L2, B7-H3, CD200R, CD163 and/or CD206 expression in one or more cells of a corresponding subject that is not treated with the antibody. In other embodiments, an anti-CD33 antibody of the present disclosure modulates PD-L 1, PD-L2, B7-H2, B7-H3, CD200R, CD163 and/or CD206 expression in one or more cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to PD-L1, PD-L2, B7-H2, B7-H3, CD200R, CD163 and/or CD206 expression in one or more cells of a corresponding subject that is not treated with the antibody.

In some embodiments, anti-CD33 antibodies of the present disclosure are useful for preventing, lowering the risk of, or treating conditions and/or diseases associated with abnormal levels of PD-L1, PD-L2, B7-H2, B7-H3, CD200R, CD163 and/or CD206, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

In some embodiments, an anti-CD33 antibody of the present disclosure may modulate (e.g., increase) expression of one or more Stage 2 microglia type associated with neurodegenerative diseases (disease-associated microglia (DAM) markers). Disease-associated microglia refer to microglia that exhibit increased expression of ApoE3, Tyrobp, B2m, Trem2, Cst7, Cts1, Lp1, Cd9, Ax1, Csf1, Ccl6, Itgax, Clec7a, Lilrb4, Timp2, and decreased expression of microglial homeostatic molecules Cx3crl and P2ry12 or P2ry13 as compared to resting or non-activated microglia.

Accordingly, in some embodiments, and anti-CD33 antibody of the present disclosure may increase expression of one or more DAM markers ApoE3, Tyrobp, B2m, Trem2, Cst7, Cts1, Lp1, Cd9, Ax1, Csf1, Ccl6, Itgax, Clec7a, Lilrb4, Timp2, or any combination thereof in one or more cells of an individual by at least 10/0, at least 15%, at least 20/6, at least 25%, at least 30/6, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to expression of one or more DAM markers, such as ApoE3, Tyrobp, B2m, Trem2, Cst7, Cts1, Lp1, Cd9, Ax1, Csf1, Ccl6, Itgax, Clec7a, Lilrb4, Timp2, and any combination thereof in one or more cells of a corresponding individual that is not treated with the anti-CD33 antibody. See Keren-Shaul et al. Cell 169:1276-1290 (2017), which is incorporated by reference in its entirety. In other embodiments, an anti-CD33 antibody of the present disclosure modulate (e.g. increase) expression of one or more DAM markers, such as ApoE3, Tyrobp, B2m, Trem2, Cst7, Cts1, Lp1, Cd9, Ax1, Csf1, Ccl6, Itgax, Clec7a, Lilrb4, Timp2, Trem2, and any combination thereof in one or more cells of an individual by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to expression of one or more DAM markers, such as ApoE3, Tyrobp, B2m, Trem2, Cst7, Cts1, Lp1, Cd9, Ax1, Csf1, Ccl6, Itgax, Clec7a, Lilrb4, Timp2, and any combination thereof in one or more cells of a corresponding individual that is not treated with the anti-CD33 antibody. In some embodiments, the DAM marker is Cst7. In some embodiments, the DAM marker is Ccl6. In some embodiments, the DAM marker is Itgax. In some embodiments, the modulation is increased expression. In some embodiments, the increase in the number of DAM or the expression thereof is associated with an increase in microglia phagocytic activity, including an increase in microglia phagocytic activity without inflammatory activity. In some embodiments, an anti-CD33 antibody of the present disclosure causes an increase in the number or expression of DAM by releasing or circumventing a restraint imposed on microglia immune activity by at least one microglia checkpoint molecule.

Further provided herein are methods of determining whether an individual is a responder or is a non-responder to an anti-CD33 antibody treatment which comprises the steps of: (a) measuring the levels of one or more Stage 2 microglia type associated with neurodegenerative diseases (DAM) markers, such as ApoE3, Tyrobp, B2m, Trem2, Cst7, Cts1, Lp1, Cd9, Ax1, Csf1, Ccl6, Itgax, Clec7a, Lilrb4, Timp2, and any combination thereof in a sample from an individual obtained from said individual before the treatment, (b) measuring the level of one or more Stage 2 microglia type associated with neurodegenerative diseases (DAM) markers, such as ApoE3, Tyrobp, B2m, Trem2, Cst7, Cts1, Lp1, Cd9, Ax1, Csf1, Ccl6, Itgax, Clec7a, Lilrb4, Timp2, and any combination thereof in a sample from an individual obtained from said at a time point after first treatment, and (c) comparing the levels measured at step ii) with the levels measured at step i) wherein a difference between said levels is indicative that said individual is a responder or non-responder. In some embodiments, the difference between said levels is an increase and is indicative that said individual is a responder. In some embodiments, the difference between said levels is a decrease or no change and is indicative that said individual is a non-responder. In some embodiments, the DAM marker is Cst7. In some embodiments, the DAM marker is Ccl6. In some embodiments, the DAM marker is Itgax.

Enhancement or Normalization of the Ability of Bone Marrow-Derived Dendritic Cells to Induce Antigen-Specific T Cell Proliferation In some embodiments, anti-CD33 antibodies of the present disclosure may enhance and/or normalize the ability of bone marrow-derived dendritic cells to induce antigen-specific T cell proliferation after binding to a CD33 protein expressed in a cell.

In some embodiments, antagonist anti-CD33 antibodies of the present disclosure may enhance and/or normalize the ability of bone marrow-derived dendritic cells to induce antigen-specific T cell proliferation in one or more bone marrow-derived dendritic cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the ability of bone marrow-derived dendritic cells to induce antigen-specific T cell proliferation in one or more bone marrow-derived dendritic cells of a corresponding subject that is not treated with the antibody. In other embodiments, an antagonist anti-CD33 antibody may enhance and/or normalize the ability of bone marrow-derived dendritic cells to induce antigen-specific T cell proliferation in one or more bone marrow-derived dendritic cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the ability of bone marrow-derived dendritic cells to induce antigen-specific T cell proliferation in one or more bone marrow-derived dendritic cells of a corresponding subject that is not treated with the antibody.

In some embodiments, anti-CD33 antibodies of the present disclosure are beneficial for preventing, lowering the risk of, or treating conditions and/or diseases associated with decreased or dysregulated ability of bone marrow-derived dendritic cells to induce antigen-specific T cell proliferation, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Proliferation and Survival of CD33-Expressing Cells

In some embodiments, anti-CD33 antibodies of the present disclosure may increase the proliferation, survival, and/or function of dendritic cells, macrophages, monocytes, neutrophils, osteoclasts, Langerhans cells of skin, Kupffer cells, T cells, T helper cells, cytotoxic T cells, and microglial cells after binding to CD33 protein expressed on a cell.

Microglial cells are a type of glial cell that are the resident macrophages of the brain and spinal cord, and thus act as the first and main form of active immune defense in the central nervous system (CNS). Microglial cells constitute 20% of the total glial cell population within the brain. Microglial cells are constantly scavenging the CNS for plaques, damaged neurons and infectious agents. The brain and spinal cord are considered "immune privileged" organs in that they are separated from the rest of the body by a series of endothelial cells known as the blood-brain barrier, which prevents most pathogens from reaching the vulnerable nervous tissue. In the case where infectious agents are directly introduced to the brain or cross the blood-brain barrier, microglial cells must react quickly to limit inflammation and destroy the infectious agents before they damage the sensitive neural tissue. Due to the unavailability of antibodies from the rest of the body (few antibodies are small enough to cross the blood brain barrier), microglia must be able to recognize foreign bodies, swallow them, and act as antigen-presenting cells activating T cells. Since this process must be done quickly to prevent potentially fatal damage, microglial cells are extremely sensitive to even small pathological changes in the CNS. They achieve this sensitivity in part by having unique potassium channels that respond to even small changes in extracellular potassium.

As used herein, macrophages of the present disclosure include, without limitation, M1 macrophages, activated M1 macrophages, and M2 macrophages. As used herein, microglial cells of the present disclosure include, without limitation, M1 microglial cells, activated M1 microglial cells, and M2 microglial cells.

In some embodiments, anti-CD33 antibodies of the present disclosure may increase the expression of CD80, CD83 and/or CD86 on dendritic cells, monocytes, and/or macrophages.

As used herein, the rate of proliferation, survival, and/or function of macrophages, dendritic cells, monocytes, T cells, neutrophils, and/or microglia may include increased expression if the rate of proliferation, survival, and/or function of dendritic cells, macrophages, monocytes, neutrophils, osteoclasts, Langerhans cells of skin, Kupffer cells, and/or microglia in a subject treated with an anti-CD33 antibody of the present disclosure is greater than the rate of proliferation, survival, and/or function of dendritic cells, macrophages, monocytes, osteoclasts, Langerhans cells of skin, Kupffer cells, T cells, neutrophils, and/or microglia in a corresponding subject that is not treated with the antibody. In some embodiments, an anti-CD33 antibody of the present disclosure may increase the rate of proliferation, survival, and/or function of dendritic cells, macrophages, monocytes, osteoclasts, Langerhans cells of skin, Kupffer cells, T cells, and/or microglia in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the rate of proliferation, survival, and/or function of dendritic cells, macrophages, monocytes, osteoclasts, Langerhans cells of skin, Kupffer cells, T cells, and/or microglia in a corresponding subject that is not treated with the antibody. In other embodiments, an anti-CD33 antibody of the present disclosure may increase the rate of proliferation, survival, and/or function of dendritic cells, macrophages, monocytes, osteoclasts, Langerhans cells of skin, Kupffer cells, T cells, and/or microglia in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the rate of proliferation, survival, and/or function of dendritic cells, macrophages, monocytes, osteoclasts, Langerhans cells of skin, Kupffer cells, T cells, and/or microglia in a corresponding subject that is not treated with the antibody.

In some embodiments, anti-CD33 antibodies of the present disclosure are beneficial for preventing, lowering the risk of, or treating conditions and/or diseases associated with a reduction in proliferation, survival, increased apoptosis and/or function of dendritic cells, neutrophils, macrophages, monocytes, osteoclasts, Langerhans cells of skin, Kupffer cells, T cells, and/or microglia including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

CD33-Dependent Activation of Immune Cells

In some embodiments, antagonist anti-CD33 antibodies of the present disclosure may increase the activity of cytotoxic T cells helper T cells or both. In some embodiments, antagonist anti-CD33 antibodies of the present disclosure are beneficial for preventing, lowering the risk of, or treating conditions and/or diseases associated with decreased activity of cytotoxic T cells helper T cells or both, including without limitation, tumors, including solid tumors such as bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

In some embodiments, antagonist anti-CD33 antibodies of the present disclosure may induce an increase in proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells. In some embodiments, antagonist anti-CD33 antibodies of the present disclosure induce an increase in proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in the presence of myeloid-derived suppressor cells (MDSC).

As used herein, the rate of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells may include an increased rate if the rate of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a subject treated with an anti-CD33 antibody of the present disclosure is greater than the rate of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a corresponding subject that is not treated with the antibody. In some embodiments, an anti-CD33 antibody of the present disclosure may increase proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a corresponding subject that is not treated with the antibody. In other embodiments, an anti-CD33 antibody of the present disclosure may increase proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a corresponding subject that is not treated with the antibody.

CD33-Dependent Inhibition of Tumor-Associated Immune Cells

In some embodiments, agonist anti-CD33 antibodies of the present disclosure may decrease the activity, decrease the proliferation, decrease the survival, decrease the functionality, decrease infiltration to tumors or lymphoid organs (e.g., the spleen and lymph nodes), the number of CD14$^+$ myeloid cells, decrease tumor growth rate, reduce tumor volume, reduce or inhibit differentiation, survival, and/or one or more functions of myeloid-derived suppressor cells (MDSC), and/or promote apoptosis of T-regulatory cells or inhibitory tumor-imbedded immunosuppressor dendritic cells or, tumor-associated macrophages or, myeloid-derived suppressor cells. In some embodiments, agonist anti-CD33 antibodies of the present disclosure are beneficial for preventing, lowering the risk of, or treating conditions and/or diseases associated with the activity of one or more type of immune suppressor cells, including without limitation, tumors, including solid tumors that do not express CD33 such as bladder cancer, brain cancer, breast cancer, colon cancer, rectal cancer, endometrial cancer, kidney cancer, renal cell cancer, renal pelvis cancer, lung cancer, melanoma, non-Hodgkin's lymphoma, pancreatic cancer, prostate cancer, ovarian cancer, fibrosarcoma, thyroid cancer, and blood tumors that express CD33, such as leukemia cells.

In some embodiments, antagonist anti-CD33 antibodies of the present disclosure may decrease the number of CD14$^+$ myeloid cells, decrease tumor growth rate, reduce tumor volume, or reduce or inhibit differentiation, survival, and/or one or more functions of myeloid-derived suppressor cells (MDSC).

In some embodiments, an anti-CD33 antibody of the present disclosure may decrease the number of CD14$^+$ myeloid cells, decrease tumor growth rate, reduce tumor volume, or reduce or inhibit differentiation, survival, and/or one or more functions of myeloid-derived suppressor cells (MDSC) in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the number of CD14$^+$ myeloid cells, tumor growth rate, tumor volume, or level of differentiation, survival, and/or one or more functions of myeloid-derived suppressor cells (MDSC) in a corresponding subject that is not treated with the antibody. In other embodiments, an anti-CD33 antibody of the present disclosure, may decrease the number of CD14$^+$ myeloid cells, decrease tumor growth rate, reduce tumor volume, or reduce or inhibit differentiation, survival, and/or one or more functions of myeloid-derived suppressor cells (MDSC) in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the number of CD14$^+$ myeloid cells, tumor growth rate, tumor volume, or level of differentiation, survival, and/or one or more functions of myeloid-derived suppressor cells (MDSC) in a corresponding subject that is not treated with the antibody.

Increased Efficacy of Checkpoint Inhibitor Therapies

In some embodiments, antagonist anti-CD33 antibodies of the present disclosure may increase the efficacy of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3.

In some embodiments, an anti-CD33 antibody of the present disclosure may increase the efficacy of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a subject receiving such one or more therapies by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of effectiveness of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a corresponding subject receiving such one or more therapies that is not treated with the antibody. In other embodiments, an anti-CD33 antibody of the present disclosure may increase the efficacy of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a subject receiving such one or more therapies by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of effectiveness of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a corresponding subject receiving such one or more therapies that is not treated with the antibody.

Increased Efficacy of Chemotherapeutic Agents

In some embodiments, antagonist anti-CD33 antibodies of the present disclosure may increase the efficacy of one or more chemotherapy agents, such as gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), oxaliplatin (Elotaxin®), leucovorin, and/or temozolomide (Temodar®).

In some embodiments, an anti-CD33 antibody of the present disclosure may increase the efficacy of one or more chemotherapy agents in a subject receiving such one or more therapies by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of effectiveness of one or more chemotherapy agents in a corresponding subject receiving such one or more therapies that is not treated with the antibody. In other embodiments, an anti-CD33 antibody of the present disclosure may increase the efficacy of one or more chemotherapy agents in a subject receiving such one or more therapies by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of effectiveness of one or more chemotherapy agents in a corresponding subject receiving such one or more therapies that is not treated with the antibody.

Antibody Preparation

Anti-CD33 antibodies of the present disclosure can encompass polyclonal antibodies, monoclonal antibodies, humanized and chimeric antibodies, human antibodies, antibody fragments (e.g., Fab, Fab'-SH, Fv, scFv, and F(ab')$_2$), bispecific and polyspecific antibodies, multivalent antibodies, heteroconjugate antibodies, conjugated antibodies, library derived antibodies, antibodies having modified effector functions, fusion proteins containing an antibody portion, and any other modified configuration of the immunoglobulin molecule that includes an antigen recognition site, such as an epitope having amino acid residues of a CD33 protein of the present disclosure, including glycosylation variants of antibodies, amino acid sequence variants of antibodies, and covalently modified antibodies. The anti-CD33 antibodies may be human, murine, rat, or of any other origin (including chimeric or humanized antibodies).

(1) Polyclonal Antibodies

Polyclonal antibodies, such as polyclonal anti-CD33 antibodies, are generally raised in animals by multiple subcutaneous (sc) or intraperitoneal (ip) injections of the relevant antigen and an adjuvant. It may be useful to conjugate the relevant antigen (e.g., a purified or recombinant CD33 protein of the present disclosure) to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the desired antigen, immunogenic conjugates, or derivatives by combining, e.g., 100 pg (for rabbits) or 5 pg (for mice) of the protein or conjugate with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response.

(2) Monoclonal Antibodies

Monoclonal antibodies, such as monoclonal anti-CD33 antibodies, are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal anti-CD33 antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization (e.g., a purified or recombinant CD33 protein of the present disclosure). Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The immunizing agent will typically include the antigenic protein (e.g., a purified or recombinant CD33 protein of the present disclosure) or a fusion variant thereof. Generally peripheral blood lymphocytes ("PBLs") are used if cells of human origin are desired, while spleen or lymph node cells are used if non-human mammalian sources are desired. The lymphoctyes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine or human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors (available from the Salk Institute Cell Distribution Center, San Diego, Calif. USA), as well as SP-2 cells and derivatives thereof (e.g., X63-Ag8-653) (available from the American Type Culture Collection, Manassas, Va. USA). Human myeloma and mouse-human heteromyeloma cell lines have also been described for the production of human monoclonal antibodies (Kozbor, *J.*

*Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen (e.g., a CD33 protein of the present disclosure). Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen (e.g., a CD33 protein of the present disclosure). Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose chromatography, hydroxylapatite chromatography, gel electrophoresis, dialysis, affinity chromatography, and other methods as described above.

Anti-CD33 monoclonal antibodies may also be made by recombinant DNA methods, such as those disclosed in U.S. Pat. No. 4,816,567, and as described above. DNA encoding the monoclonal antibodies is readily isolated and sequenced using conventional procedures (e.g., by using oligonucleotide probes that specifically bind to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opin. Immunol.*, 5:256-262 (1993) and Plückthun, *Immunol. Rev.* 130:151-188 (1992).

In certain embodiments, anti-CD33 antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) described the isolation of murine and human antibodies, respectively, from phage libraries. Subsequent publications describe the production of high affinity (nanomolar ("nM") range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nucl. Acids Res.*, 21:2265-2266 (1993)). Thus, these techniques are viable alternatives to traditional monoclonal antibody hybridoma techniques for isolation of monoclonal antibodies of desired specificity (e.g., those that bind a CD33 protein of the present disclosure).

The DNA encoding antibodies or fragments thereof may also be modified, for example, by substituting the coding sequence for human heavy- and light-chain constant domains in place of the homologous murine sequences (U.S. Pat. No. 4,816,567; Morrison, et al., *Proc. Nal Acad. Sci. USA*, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein (e.g., anti-CD33 antibodies of the present disclosure or fragments thereof) may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid anti-CD33 antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(3) Humanized Antibodies

Anti-CD33 antibodies of the present disclosure or antibody fragments thereof may further include humanized or human antibodies. Humanized forms of non-human (e.g., murine) antibodies are chimeric immunoglobulins, immunoglobulin chains or fragments thereof (such as Fab, Fab'-SH, Fv, scFv, F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally will also comprise at least a portion of an immunoglobulin constant region (Fc), typically that of a human immunoglobulin. Jones et al., *Nature* 321: 522-525 (1986); Riechmann et al., *Nature* 332: 323-329 (1988) and Presta, *Curr. Opin. Struct. Biol.* 2: 593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., *Nature* 321:522-525 (1986); Riechmann et al., *Nature* 332:323-327 (1988); Verhoeyen et al., *Science* 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., *J. Immunol.*, 151:2296 (1993); Chothia et al., *J. Mol. Biol.*, 196:901 (1987). Another method uses a particular framework derived from the consensus sequence of all human antibodies of a particular subgroup of light or heavy chains. The same framework may be used for several different humanized antibodies. Carter et al., *Proc. Nat'l Acad Sci. USA* 89:4285 (1992); Presta et al., *J. Immunol.* 151:2623 (1993).

Furthermore, it is important that antibodies be humanized with retention of high affinity for the antigen and other favorable biological properties. To achieve this goal, according to a preferred method, humanized antibodies are prepared by a process of analyzing the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen or antigens (e.g., CD33 proteins of the present disclosure), is achieved. In general, the CDR residues are directly and most substantially involved in influencing antigen binding.

Various forms of the humanized anti-CD33 antibody are contemplated. For example, the humanized anti-CD33 antibody may be an antibody fragment, such as an Fab, which is optionally conjugated with one or more cytotoxic agent(s) in order to generate an immunoconjugate. Alternatively, the humanized anti-CD33 antibody may be an intact antibody, such as an intact IgG1 antibody.

(4) Antibody Fragments

In certain embodiments there are advantages to using anti-CD33 antibody fragments, rather than whole anti-CD33 antibodies. Smaller fragment sizes allow for rapid clearance and better brain penetration.

Various techniques have been developed for the production of antibody fragments. Traditionally, these fragments were derived via proteolytic digestion of intact antibodies (see, e.g., Morimoto et al., *J. Biochem. Biophys. Method* 24:107-117 (1992); and Brennan et al., *Science* 229:81 (1985)). However, these fragments can now be produced directly by recombinant host cells, for example, using nucleic acids encoding anti-CD33 antibodies of the present disclosure. Fab, Fv and scFv antibody fragments can all be expressed in and secreted from *E. coli*, thus allowing the straightforward production of large amounts of these fragments. A anti-CD33 antibody fragments can also be isolated from the antibody phage libraries as discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Production of Fab and $F(ab')_2$ antibody fragments with increased in vivo half-lives are described in U.S. Pat. No. 5,869,046. In other embodiments, the antibody of choice is a single chain Fv fragment (scFv). See WO 93/16185; U.S. Pat. Nos. 5,571,894 and 5,587,458. The anti-CD33 antibody fragment may also be a "linear antibody," e.g., as described in U.S. Pat. No. 5,641,870. Such linear antibody fragments may be monospecific or bispecific.

(5) Bispecific and Polyspecific Antibodies

Bispecific antibodies (BsAbs) are antibodies that have binding specificities for at least two different epitopes, including those on the same or another protein (e.g., one or more CD33 proteins of the present disclosure). Alternatively, one part of a BsAb can be armed to bind to the target CD33 antigen, and another can be combined with an arm that binds to a second protein. Such antibodies can be derived from full length antibodies or antibody fragments (e.g., $F(ab')_2$ bispecific antibodies).

Methods for making bispecific antibodies are known in the art. Traditional production of full length bispecific antibodies is based on the coexpression of two immunoglobulin heavy-chain/light chain pairs, where the two chains have different specificities. Millstein et al., *Nature*, 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only half of the bispecific molecules provides for an easy way of separation. This approach is disclosed in WO 94/04690. For further details of generating bispecific antibodies, see, for example, Suresh et al., *Methods in Enzymology* 121: 210 (1986).

According to another approach described in WO 96/27011 or U.S. Pat. No. 5,731,168, the interface between a pair of antibody molecules can be engineered to maximize the percentage of heterodimers which are recovered from recombinant cell culture. The preferred interface comprises at least a part of the $C_H3$ region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Nat'l Acad. Sci. USA*, 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.*, 152:5368 (1994).

Antibodies with more than two valencies are also contemplated. For example, trispecific antibodies can be prepared. Tutt et al., *J. Immunol.* 147:60 (1991).

Exemplary bispecific antibodies may bind to two different epitopes on a given molecule (e.g., a CD33 protein of the present disclosure). Alternatively, an arm targeting a CD33 signaling component may be combined with an arm which binds to a triggering molecule on a leukocyte such as a T cell receptor molecule (e.g., CD2, CD3, CD28 or B7), or Fc receptors for IgG (FcγR), such as FcγRI (CD64), FcγRII (CD32) and FcγRIII (CD16) so as to focus cellular defense mechanisms to the cell expressing the particular protein. Bispecific antibodies may also be used to localize cytotoxic agents to cells which express a particular protein. Such antibodies possess a protein-binding arm and an arm which binds a cytotoxic agent or a radionuclide chelator, such as EOTUBE, DPTA, DOTA or TETA. Another bispecific antibody of interest binds the protein of interest and further binds tissue factor (TF).

(6) Multivalent Antibodies

A multivalent antibody may be internalized (and/or catabolized) faster than a bivalent antibody by a cell expressing an antigen to which the antibodies bind. The anti-CD33 antibodies of the present disclosure or antibody fragments thereof can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises an Fc region or a hinge region. In this scenario, the antibody will comprise an Fc region and three or more antigen binding sites amino-terminal to the Fc region. The preferred multivalent antibody herein contains three to about eight, but preferably four, antigen binding sites. The multivalent antibody contains at least one polypeptide chain (and preferably two polypeptide chains), wherein the polypeptide chain or chains comprise two or more variable domains. For instance, the polypeptide chain or chains may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$—$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain. The multivalent antibodies may recognize the CD33 antigen as well as, without limitation, additional antigens A beta peptide, antigen or an alpha synuclain protein antigen or, Tau protein antigen or, TDP-43 protein antigen or, prion protein antigen or, huntingtin protein antigen, or RAN, translation Products antigen, including the DiPeptide Repeats, (DPRs peptides) composed of glycine-alanine (GA), glycine-proline (GP), glycine-arginine (GR), proline-alanine (PA), or proline-arginine (PR), insulin receptor, insulin like growth factor receptor, transferrin receptor, or any other antigen that facilitates antibody transfer across the blood brain barrier.

(7) Heteroconjugate Antibodies

Heteroconjugate antibodies are also within the scope of the present disclosure. Heteroconjugate antibodies are composed of two covalently joined antibodies (e.g., anti-CD33 antibodies of the present disclosure or antibody fragments thereof). For example, one of the antibodies in the heteroconjugate can be coupled to avidin, the other to biotin. Such antibodies have, for example, been proposed to target immune system cells to unwanted cells, U.S. Pat. No. 4,676,980, and have been used to treat HIV infection. International Publication Nos. WO 91/00360, WO 92/200373 and EP 0308936. It is contemplated that the antibodies may be prepared in vitro using known methods in synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

(8) Effector Function Engineering

It may also be desirable to modify an anti-CD33 antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII. In some embodiments, the effector function is impaired by removing N-glycosylation of the Fc region (e.g., in the CH 2 domain of IgG) of the antibody. In some embodiments, the effector function is impaired by modifying regions such as 233-236, 297, and/or 327-331 of human IgG as described in PCT WO 99/58572 and Armour et al., *Molecular Immunology* 40: 585-593 (2003); Reddy et al., *J. Immunology* 164:1925-1933 (2000).

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(9) Other Amino Acid Sequence Modifications

Amino acid sequence modifications of anti-CD33 antibodies of the present disclosure, or antibody fragments thereof, are also contemplated. For example, it may be desirable to improve the binding affinity and/or other biological properties of the antibodies or antibody fragments. Amino acid sequence variants of the antibodies or antibody fragments are prepared by introducing appropriate nucleotide changes into the nucleic acid encoding the antibodies or antibody fragments, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics (i.e., the ability to bind or physically interact with a CD33 protein of the present disclosure). The amino acid changes also may alter post-translational processes of the antibody, such as changing the number or position of glycosylation sites.

A useful method for identification of certain residues or regions of the anti-CD33 antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the target antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino- ("N") and/or carboxy- ("C") terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table D below under the heading of "preferred substitutions". If such substitutions result in a change in biological activity, then more substantial changes, denominated "exemplary substitutions" in Table D, or as further described below in reference to amino acid classes, may be introduced and the products screened.

TABLE D

Amino acid substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr,
(3) acidic: asp, glu;
(4) basic: asn, gin, his, lys, arg;
(5) residues that influence chain orientation: gly, pro; and
(6) aromatic: trp, tyr, phe.

Non-conservative substitutions entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

A particularly preferred type of substitutional variant involves substituting one or more hypervariable region residues of a parent antibody (e.g. a humanized or human anti-CD33 antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen (e.g., a CD33 protein of the present disclosure). Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IgE antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibodies (e.g., anti-CD33 antibodies of the present disclosure) or antibody fragments.

(10) Antibody Conjugates

Anti-CD33 antibodies of the present disclosure, or antibody fragments thereof, can be conjugated to a detectable marker, a toxin, or a therapeutic agent. Any suitable method known in the art for conjugating molecules, such as a detectable marker, a toxin, or a therapeutic agent to antibodies may be used.

For example, drug conjugation involves coupling of a biological active cytotoxic (anticancer) payload or drug to an antibody that specifically targets a certain tumor marker (e.g. a protein that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue, OncLive Jul. 5, 2012; ADC Review on antibody-drug conjugates; and Ducry et al., (2010). *Bioconjugate Chemistry* 21 (1): 5-13).

In some embodiments, an anti-CD33 antibody of the present disclosure may be conjugated to a toxin selected from ricin, ricin A-chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, and a cisplatin.

(11) Other Antibody Modifications

Anti-CD33 antibodies of the present disclosure, or antibody fragments thereof, can be further modified to contain additional non-proteinaceous moieties that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: The Science and Practice of Pharmacy*, 20th Ed., Alfonso Gennaro, Ed., Philadelphia College of Pharmacy and Science (2000).

Binding Assays and Other Assays

Anti-CD33 antibodies of the present disclosure may be tested for antigen binding activity, e.g., by known methods such as ELISA, surface plasmon resonance (SPR), Western blot, etc.

In some embodiments, competition assays may be used to identify an antibody that competes with any of the antibodies described herein. In some embodiments, competition assays may be used to identify an antibody that competes with any of the antibodies listed in Tables 7, 8, 9, 10, 11, and 12, or selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54 for binding to CD33. In certain embodiments, such a competing antibody binds to the same epitope (e.g., a linear or a conformational epitope) that is bound by any of the antibodies listed in Tables 7, 8, 9, 10, 11, and 12, or selected from 6C7H1, 6C7H2, 6C7H3, 6C7H4, 6C7H5, 6C7H6, 6C7H7, 6C7H8, 6C7H9, 6C7H10, 6C7H11, 6C7H12, 6C7H13, 6C7H14, 6C7H15, 6C7H16, 6C7H17, 6C7H18, 6C7H19, 6C7H20, 6C7H21, 6C7H22, 6C7H23, 6C7H24, 6C7H25, 6C7H26, 6C7H27, 6C7H28, 6C7H29, 6C7H30, 6C7H31, 6C7H32, 6C7H33, 6C7H34, 6C7H35, 6C7H36, 6C7H37, 6C7H38, 6C7H39, 6C7H40, 6C7H41, 6C7H42, 6C7H43, 6C7H44, 6C7H45, 6C7H46, 6C7H47, 6C7H48, 6C7H49, 6C7H50, 6C7H51, 6C7H52, 6C7H53, and 6C7H54. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized CD33 or cells expressing CD33 on a cell surface are incubated in a solution comprising a first labeled antibody that binds to CD33 (e.g., human or non-human primate) and a second unlabeled antibody that is being tested for its ability to compete with the first antibody for binding to CD33. The second antibody may be present in a hybridoma supernatant. As a control, immobilized CD33 or cells expressing CD33 is incubated in a solution comprising the first labeled antibody but not the second unlabeled antibody. After incubation under conditions permissive for binding of the first antibody to CD33, excess unbound antibody is removed, and the amount of label associated with immobilized CD33 or cells expressing CD33 is measured. If the amount of label associated with immobilized CD33 or cells expressing CD33 is substantially reduced in the test sample relative to the control sample, then that indicates that the second antibody is competing with the first antibody for binding to CD33. See, Harlow and Lane (1988) *Antibodies: A Laboratory Manual* ch. 14 (Cold Spring Harbor Laboratory, Cold Spring Harbor, N.Y.).

Nucleic Acids, Vectors, and Host Cells

Anti-CD33 antibodies of the present disclosure may be produced using recombinant methods and compositions, e.g., as described in U.S. Pat. No. 4,816,567. In some embodiments, isolated nucleic acids having a nucleotide sequence encoding any of the anti-CD33 antibodies of the present disclosure are provided. Such nucleic acids may encode an amino acid sequence comprising the $V_L$ and/or an amino acid sequence comprising the $V_H$ of the anti-CD33 antibody (e.g., the light and/or heavy chains of the antibody). In some embodiments, one or more vectors (e.g., expression vectors) comprising such nucleic acids are provided. In some embodiments, a host cell comprising such nucleic acid is also provided. In some embodiments, the host cell comprises (e.g., has been transduced with): (1) a vector comprising a nucleic acid that encodes an amino acid sequence comprising the $V_L$ of the antibody and an amino acid sequence comprising the $V_H$ of the antibody, or (2) a first vector comprising a nucleic acid that encodes an amino acid sequence comprising the $V_L$ of the antibody and a second vector comprising a nucleic acid that encodes an amino acid sequence comprising the $V_H$ of the antibody. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells.

Methods of making an anti-CD33 antibody of the present disclosure are provided. In some embodiments, the method includes culturing a host cell of the present disclosure comprising a nucleic acid encoding the anti-CD33 antibody, under conditions suitable for expression of the antibody. In some embodiments, the antibody is subsequently recovered from the host cell (or host cell culture medium).

For recombinant production of an anti-CD33 antibody of the present disclosure, a nucleic acid encoding the anti-CD33 antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors comprising a nucleic acid sequence encoding any of the anti-CD33 antibodies of the present disclosure, or fragments thereof, polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones comprising the vector. Suitable examples include plasmids and bacterial viruses, e.g., pUC18, pUC19, Bluescript (e.g., pBS SK+) and its derivatives, mpl8, mpl9, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Suitable host cells for cloning or expression of antibody-encoding vectors include prokaryotic or eukaryotic cells. For example, anti-CD33 antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523). After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross Nat. Biotech. 22:1409-1414 (2004); and Li et al. Nat. Biotech. 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al. *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al. *Proc. Nal. Acad Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

Pharmaceutical Compostions/Formulations

Provided herein are pharmaceutical compositions and/or pharmaceutical formulations comprising the anti-CD33 antibodies of the present disclosure and a pharmaceutically acceptable carrier.

In some embodiments, pharmaceutically acceptable carriers preferably are nontoxic to recipients at the dosages and concentrations employed. The antibodies described herein may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutically acceptable carriers can include, depending on the formulation desired, pharmaceutically-acceptable, non-toxic carriers of diluents, which are vehicles commonly used to formulate pharmaceutical compositions for animal or human administration. In certain embodiments, the pharmaceutical composition can comprise formulation materials for modifying, maintaining or preserving, for example, the pH, osmolarity, viscosity, clarity, color, isotonicity, odor, sterility, stability, rate of dissolution or release, adsorption or penetration of the composition.

In certain embodiments, pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Further examples of formulations that are suitable for various types of administration can be found in *Remington: The Science and Practice of Pharmacy*, Pharmaceutical Press 22nd ed. (2013). For a brief review of methods for drug delivery, see, Langer, *Science* 249:1527-1533 (1990).

Formulations suitable for parenteral administration include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-CD33 antibody of the present disclosure, in a biodegradable or bioerodible implant. The rate of release of the therapeutically active agent is controlled by the rate of transport through the polymeric matrix, and the biodegradation of the implant. Implants may be particles, sheets, patches, plaques, fibers, microcapsules and the like and may be of any size or shape compatible with the selected site of insertion. Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an anti-CD33 antibody of the present disclosure may be administered to an individual in need of treatment with the antibody, preferably a human, in accord with known methods, such as intravenous administration as a bolus or by continuous infusion over a period of time, by intramuscular, intraperitoneal, intracerobrospinal, intracranial, intraspinal, subcutaneous, intra-articular, intrasynovial, intrathecal, oral, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vivo administration of any of the anti-CD33 antibodies of the present disclosure, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease, disorder, or condition to be treated, the treatment is sustained until a desired suppression of symptoms is achieved.

An exemplary dosing regimen may include administering an initial dose of an anti-CD33 antibody of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, and about 21 mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays.

The dosing regimen, including the anti-CD33 antibody administered, can vary over time independently of the dose used.

Dosages for a particular anti-CD33 antibody may be determined empirically in individuals who have been given one or more administrations of the anti-CD33 antibody. Individuals are given incremental doses of an anti-CD33 antibody. To assess efficacy of an anti-CD33 antibody, a clinical symptom of any of the diseases, disorders, or conditions of the present disclosure (e.g., frontotemporal dementia, Alzheimer's disease, vascular dementia, seizures, retinal dystrophy, a traumatic brain injury, a spinal cord injury, long-term depression, atherosclerotic vascular diseases, and undesirable symptoms of normal aging) can be monitored.

Administration of an anti-CD33 antibody of the present disclosure can be continuous or intermittent, depending, for example, on the recipient's physiological condition, whether the purpose of the administration is therapeutic or prophylactic, and other factors known to skilled practitioners. The administration of an anti-CD33 antibody, may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the present disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Therapeutic Uses

As disclosed herein, anti-CD33 antibodies of the present disclosure may be used for preventing, reducing risk, or treating various diseases and disorders.

Anti-CD33 antibodies of the present disclosure may be used for preventing, reducing risk, or treating dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and/or *Haemophilus* influenza. In some embodiments, the CD33 antibodies are agonist antibodies. In some embodiments, the antibodies are inert antibodies. In some embodiments, the antibodies are antagonist antibodies.

In some embodiments, the present disclosure provides methods of preventing, reducing risk, or treating dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and/or *Haemophilus* influenza, by administering to an individual in need thereof a therapeutically effective amount of an antibody of the present disclosure that decreases cellular levels of CD33, inhibits interaction between CD33 and one or more CD33 ligands, or both.

In some embodiments, the present disclosure provides methods of preventing, reducing risk, or treating cancer, by administering to an individual in need thereof, a therapeutically effective amount of an antibody of the present disclosure that decreases cellular levels of CD33, inhibits interaction between CD33 and one or more CD33 ligands, or both. In some embodiments, the antibody inhibits one or more CD33 activities selected from: (a) promoting proliferation, maturation, migration, differentiation, and/or functionality of one or more of immunosuppressor dendritic cells, immunosuppressor macrophages, immunosuppressor neutrophils, non-tumorigenic myeloid derived suppressor cells, tumor-associated macrophages, non-tumorigenic $CD14^+$ myeloid cells, and regulatory T cells; (b) enhancing infiltration of one or more of immunosuppressor dendritic cells, immunosuppressor macrophages, immunosuppressor neutrophils, non-tumorigenic myeloid derived suppressor cells, tumor-associated macrophages, and regulatory T cells into tumors; (c) increasing number of tumor-promoting myeloid/granulocytic immune-suppressive cells and/or non-tumorigenic $CD14^+$ myeloid cells in a tumor, in peripheral blood, or other lymphoid organ; (d) decreasing activation of tumor-specific T lymphocytes with tumor killing potential; (e) decreasing infiltration of tumor-specific T lymphocytes with tumor killing potential; (f) increasing tumor volume; (g) increasing tumor growth rate; (h) increasing metastasis; (i) increasing rate of tumor recurrence; (j) increasing expression of one or more PD-1 ligands; (k) decreasing efficacy of one or more immune-therapies that modulate anti-tumor T cell responses, optionally wherein the one or more immune-therapies are immune-therapies that target one or more proteins selected from the group consisting of CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR, LAG3, DR5, CD39, CD70, CD73, TREM1, TREM2, Siglec-5, Siglec-7, Siglec-9, Siglec-11, SirpA, CD47, CSF-1 receptor, and any combination thereof, or of one or more cancer vaccines; and (1) decreasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), oxaliplatin (Elotaxin®), leucovorin, temozolmide (Temodar®), and any combination thereof. In some embodiments, the antibody exhibits one or more activities selected from: (a) increasing the number of tumor infiltrating $CD3^+$ T cells; (b) decreasing cellular levels of CD33 in non-tumorigenic $CD14^+$myeloid cells, optionally wherein the non-tumorigenic $CD14^+$ myeloid cells are tumor infiltrating cells or optionally wherein the non-tumorigenic $CD14^+$ myeloid cells are present in blood; (c) reducing the number of non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (d) reducing PD-L1 levels in one or more cells, optionally wherein the one or more cells are non-tumorigenic myeloid-derived suppressor cells (MDSC); (e) decreasing tumor growth rate of solid tumors; (f) reducing tumor volume; (g) increasing efficacy of one or more PD-1 inhibitors; (h) increasing efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, OX40, TIM3, LAG3, or any combination thereof; (i) increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), oxaliplatin (Elotaxin®), leucovorin, temozolmide (Temodar®), and any combination thereof; and (j) killing CD33-expressing immunosuppressor myeloid cells and/or CD14-expressing cells in solid tumors and associated blood vessels when conjugated to a chemical or radioactive toxin.

As disclosed herein, anti-CD33 antibodies of the present disclosure may also be used for inducing and/or promoting the survival maturation, functionality, migration, or proliferation of one or more immune cells (e.g., innate immune cells or adaptive immune cells). In some embodiments, the present disclosure provides methods of inducing or promoting the survival, maturation, functionality, migration, or proliferation of one or more immune cells in an individual in need thereof, by administering to the individual a therapeutically effective amount of an antibody of the present disclosure that decreases cellular levels of CD33, inhibits interaction between CD33 and one or more CD33 ligands, or both. In some embodiments, the one or more immune cells are selected from dendritic cells, macrophages, microglia, neutrophils, T cells, T helper cells, cytotoxic T cells, and any combination thereof.

In some embodiments, the antibody is an agonist anti-CD33 antibody. In some embodiments, the antibody is a transient agonist anti-CD33 antibody of the present disclosure that initially acts as an agonist and then acts as a long-term antagonist antibody. In some embodiments, the antibody is an inert anti-CD33 antibody. In some embodiments, the antibody is an antagonist anti-CD33 antibody. In some embodiments, the anti-CD33 antibody reduces cellular (e.g., cell surface, intracellular, or total) levels of CD33. In some embodiments, the anti-CD33 antibody induces degradation of CD33. In some embodiments, the anti-CD33 antibody induces cleavage of CD33. In some embodiments, the anti-CD33 antibody induces internalization of CD33. In some embodiments, the anti-CD33 antibody induces shedding of CD33. In some embodiments, the anti-CD33 antibody induces downregulation of CD33 expression. In some embodiments, the anti-CD33 antibody inhibits interaction (e.g., binding) between CD33 and one or more CD33 ligands. In some embodiments, the anti-CD33 antibody transiently activates and then induces degradation of CD33. In some embodiments, the anti-CD33 antibody transiently activates and then induces cleavage of CD33. In some embodiments, the anti-CD33 antibody transiently activates and then induces internalization of CD33. In some embodiments, the anti-CD33 antibody transiently activates and then induces shedding of CD33. In some embodiments, the anti-CD33 antibody transiently activates and then induces downregulation of CD33 expression. In some embodiments, the anti-CD33 antibody transiently activates and then induces decreased expression of CD33. In certain embodiments, the individual has a CD33 variant allele having single nucleotide polymorphisms (SNPs) rs3865444 CC or AC. In certain embodiments, the individual has a CD33 variant allele having single nucleotide polymorphisms (SNPs) 2459419 CC or CT.

As disclosed herein, anti-CD33 antibodies of the present disclosure may further be used for decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, and/or chronic myeloid leukemia (CML) cells. In some embodiments, the present disclosure provides methods of decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, or chronic myeloid leukemia (CML) cells in an individual in need thereof, by administering to the individual a therapeutically effective amount of an antibody that binds or interacts with CD33. In some embodiments, the antibody is selected from an antagonist antibody, an inert antibody, or an agonist antibody. In some embodiments, the antibody is an isolated anti-CD33 antibody or anti-CD33 antibody conjugate of the present disclosure. In some embodiments, the anti-CD33 antibody conjugate comprises an anti-CD33 antibody conjugated to a detectable marker, a toxin, or a therapeutic agent.

As disclosed herein, anti-CD33 antibodies of the present disclosure may be used for decreasing cellular levels of CD33, inhibiting interaction between CD33 and one or more CD33 ligands, or both on one or more cells in vitro or in vivo. In some embodiments, the present disclosure provides methods of decreasing cellular levels of CD33, inhibiting interaction between CD33 and one or more CD33 ligands, or both on one or more cells in an individual in need thereof, by administering to the individual a therapeutically effective amount of an isolated anti-CD33 antibody of the present disclosure. In some embodiments, the anti-CD33 antibody decreases cellular levels of CD33 in vivo.

As disclosed herein, anti-CD33 antibodies of the present disclosure may be used for decreasing cellular levels of CD33 on one or more cells, including without limitation, dendritic cells, bone marrow-derived dendritic cells, monocytes, microglia, T cells, and macrophages, and/or cell lines. In some embodiments, the present disclosure provides methods of decreasing cellular levels of CD33 on one or more cells in an individual in need thereof, by administering to the individual a therapeutically effective amount of an anti-CD33 antibody of the present disclosure. In some embodiments, the one or more cells are selected from dendritic cells, bone marrow-derived dendritic cells, monocytes, microglia, T cells, and macrophages, and any combination thereof. In some embodiments, the anti-CD33 antibody decreases cellular levels of CD33 in vivo. Cellular levels of CD33 may refer to, without limitation, cell surface levels of CD33, intracellular levels of CD33, and total levels of CD33. In some embodiments, a decrease in cellular levels of CD33 comprises decrease in cell surface levels of CD33. As used herein, cell surface levels of CD33 may be measured by any in vitro cell-based assays or suitable in vivo model described herein or known in the art. In some embodiments, a decrease in cellular levels of CD33 comprises a decrease in intracellular levels of CD33. As used herein, intracellular levels of CD33 may be measured by any in vitro cell-based assays or suitable in vivo model described herein or known in the art. In some embodiments, a decrease in cellular levels of CD33 comprises a decrease in total levels of CD33. As used herein, total levels of CD33 may be measured by any in vitro cell-based assays or suitable in vivo model described herein or known in the art. In some embodiments, the anti-CD33 antibodies induce CD33 degradation, CD33 cleavage, CD33 internalization, CD33 shedding, and/or downregulation of CD33 expression. In some embodiments, cellular levels of CD33 are measured on primary cells (e.g., dendritic cells, bone marrow-derived dendritic cells, monocytes, microglia, T cells, and macrophages) or on cell lines utilizing an in vitro cell assay.

Other aspects of the present disclosure relate to a method of selecting a subject in need thereof for treatment with an anti-CD33 antibody, the method comprising: a. obtaining a sample (e.g., blood sample) from the subject; b. detecting the CD33 alleles present in the subject; and c. selecting the subject for treatment with the antibody that binds or interacts with CD33 is the subject has one or more CD33 alleles, wherein the one or more CD33 alleles are selected from the group consisting of rs3865444$^{AC}$, and rs3865444$^{CC}$. Other aspects of the present disclosure relate to a method of assessing responsiveness of a subject in need thereof to an antibody that binds or interacts with CD33, the method comprising: a. measuring the expression levels of CD45$^+$ and CD14$^+$ on non-tumorigenic myeloid cells in a blood sample obtained from the subject prior to administering to the subject an anti-CD33 antibody; b. administering to the subject a therapeutically effective amount of the antibody; and c. measuring the expression levels of CD45$^+$ and CD14$^+$ on non-tumorigenic myeloid cells in a blood sample obtained from the subject after administration of the anti-CD33 antibody, wherein a reduction in the levels of CD45$^+$ CD14$^+$ on non-tumorigenic myeloid cells after administration of the anti-CD33 antibody indicates the subject is responsive to the agent. Any suitable methods for obtaining a sample, such as a blood sample, may be used. Further, it will be appreciated that any known method of detecting CD33 variants and/or alleles, such as SNP analysis, may be used. In some embodiments, the method of assessing responsiveness further comprises administering one or more additional therapeutically effective amounts of the antibody. In some embodiments, the subject is human.

In some embodiments the individual has a variant of CD33. In some embodiments, the variant includes, without limitation, one or more polymorphisms selected from: (a) SNP rs3865444$^{AC}$. (b) SNP rs3865444$^{CC}$; (c) SNP rs35112940$^{GG,\ AA,\ AG}$; and (d) SNP rs12459419$^{CC,\ CT\ or\ TT}$; and any combinations thereof.

In some embodiments, the methods of the present disclosure may further involve the coadministration of anti-CD33 antibodies or bispecific anti-CD33 antibodies, with antibodies that bind to pattern recognition receptors, antibodies that bind to Toll-like receptors, antibodies that bind to damage-associated molecular pattern (DAMP) receptors, and/or antibodies that bind to cytokine or antibodies to interleukins).

In some embodiments, the methods of the present disclosure may further include administering to the individual at least one antibody that specifically binds to an inhibitory checkpoint molecule, and/or one or more standard or investigational anti-cancer therapies. In some embodiments, the at least one antibody that specifically binds to an inhibitory checkpoint molecule is administered in combination with the anti-CD33 antibody. In some embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, an anti-TNFa antibody, an anti-Siglec-5 antibody, an anti-Siglec-7 antibody, an anti-Siglec-9 antibody, an anti-Siglec-11 antibody, an antagonistic anti-TREM1 antibody, an antagonistic anti-TREM2 antibody, and any combination thereof. In some embodiments, the one or more standard or investigational anti-cancer therapies are selected from radiotherapy, cytotoxic chemotherapy, targeted therapy, imatinib therapy, trastuzumab therapy, etanercept therapy, adoptive cell transfer (ACT) therapy, chimeric antigen receptor T cell transfer (CAR-T) therapy, vaccine therapy, and cytokine therapy.

In some embodiments, the methods of the present disclosure may further include administering to the individual at least one antibody that specifically binds to an inhibitory cytokine. In some embodiments, the at least one antibody that specifically binds to an inhibitory cytokine is administered in combination with the anti-CD33 antibody. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the methods of the present disclosure may further include administering to the individual at least one agonistic antibody that specifically binds to a stimulatory checkpoint protein. In some embodiments, the at least one agonistic antibody that specifically binds to a stimulatory checkpoint protein is administered in combination with the anti-CD33 antibody. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, and any combination thereof.

In some embodiments, the methods of the present disclosure may further include administering to the individual at least one stimulatory cytokine. In some embodiments, the at least one stimulatory cytokine is administered in combination with the anti-CD33 antibody. In some embodiments, the at least one stimulatory cytokine is selected from IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, MIP-1-beta, and any combination thereof.

In some embodiments, a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

In some embodiments, administering an anti-CD33 antibody of the present disclosure can prevent, reduce the risk, and/or treat dementia. In some embodiments, an anti-CD33 antibody may modulate one or more CD33 activities in an individual having dementia.

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Cruts, M. & Van Broeckhoven, C., Trends Genet. 24:186-194 (2008); Neary, D., et al., Neurology 51:1546-1554 (1998); Ratnavalli, E., Brayne, C., Dawson, K. & Hodges, J. R., Neurology 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., Nature 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., Arch. Neurol. 64:1388-1394 (2007)). A majority of those FTD cases with Ub inclusions (FTD-U) were shown to carry mutations in the Progranulin gene.

In some embodiments, administering an anti-CD33 antibody of the present disclosure, can prevent, reduce the risk, and/or treat FTD. In some embodiments, administering an anti-CD33 antibody, may modulate one or more CD33 activities in an individual having FTD.

Alzheimer's Disease

Alzheimer's disease (AD) is the most common form of dementia. There is no cure for the disease, which worsens as it progresses, and eventually leads to death. Most often, AD is diagnosed in people over 65 years of age. However, the less-prevalent early-onset Alzheimer's can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

In some embodiments, administering an anti-CD33 antibody of the present disclosure can prevent, reduce the risk, and/or treat Alzheimer's disease. In some embodiments, administering an anti-CD33 antibody, may modulate one or more CD33 activities in an individual having Alzheimer's disease.

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

In some embodiments, administering an anti-CD33 antibody of the present disclosure can prevent, reduce the risk, and/or treat Parkinson's disease. In some embodiments, administering an anti-CD33 antibody, may modulate one or more CD33 activities in an individual having Parkinson's disease.

Amyotrophic Lateral Sclerosis (ALS)

As used herein, amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

It has been shown that Progranulin plays a role in ALS (Schymick, J C et al., (2007) J Neurol Neurosurg Psychiatry; 78:754-6) and protects again the damage caused by ALS causing proteins such as TDP-43 (Laird, A S et al., (2010). PLoS ONE 5: e13368). It was also demonstrated that pro-NGF induces p75 mediated death of oligodendrocytes and corticospinal neurons following spinal cord injury (Beatty et al., Neuron (2002), 36, pp. 375-386; Giehl et al, Proc. Natl. Acad. Sci USA (2004), 101, pp 6226-30).

In some embodiments, administering an anti-CD33 antibody of the present disclosure can prevent, reduce the risk, and/or treat ALS. In some embodiments, administering an anti-CD33 antibody, may modulate one or more CD33 activities in an individual having amyotrophic lateral sclerosis.

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

In some embodiments, administering as an anti-CD33 antibody of the present disclosure can prevent, reduce the risk, and/or treat Huntington's disease (HD). In some embodiments, administering an anti-CD33 antibody, may modulate one or more CD33 activities in an individual having Huntington's disease.

Taupathy Disease

Taupathy diseases, or Tauopathies, are a class of neurodegenerative disease caused by aggregation of the microtubule-associated protein tau within the brain. Alzheimer's disease (AD) is the most well-known taupathy disease, and involves an accumulation of tau protein within neurons in the form of insoluble neurofibrillary tangles (NFTs). Other taupathy diseases and disorders include progressive supranuclear palsy, dementia pugilistica (chromic traumatic encephalopathy), frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, and frontotemporal lobar degeneration.

In some embodiments, administering an anti-CD33 antibody of the present disclosure, can prevent, reduce the risk, and/or treat taupathy disease. In some embodiments, administering an anti-CD33 antibody, may modulate one or more CD33 activities in an individual having a taupathy disease.

Multiple Sclerosis

Multiple sclerosis (MS) can also be referred to as disseminated sclerosis or encephalomyelitis disseminata. MS is an inflammatory disease in which the fatty myelin sheaths around the axons of the brain and spinal cord are damaged, leading to demyelination and scarring as well as a broad spectrum of signs and symptoms. MS affects the ability of nerve cells in the brain and spinal cord to communicate with each other effectively. Nerve cells communicate by sending electrical signals called action potentials down long fibers called axons, which are contained within an insulating substance called myelin. In MS, the body's own immune system attacks and damages the myelin. When myelin is lost, the axons can no longer effectively conduct signals. MS onset usually occurs in young adults, and is more common in women. http://en.wikipedia.org/wiki/Multiple_sclerosis-cite_note-pmid18970977-1

Symptoms of MS include, without limitation, changes in sensation, such as loss of sensitivity or tingling; pricking or numbness, such as hypoesthesia and paresthesia; muscle weakness; clonus; muscle spasms; difficulty in moving; difficulties with coordination and balance, such as ataxia; problems in speech, such as dysarthria, or in swallowing, such as dysphagia; visual problems, such as nystagmus, optic neuritis including phosphenes, and diplopia; fatigue; acute or chronic pain; and bladder and bowel difficulties; cognitive impairment of varying degrees; emotional symptoms of depression or unstable mood; Uhthoffs phenomenon, which is an exacerbation of extant symptoms due to an exposure to higher than usual ambient temperatures; and Lhermitte's sign, which is an electrical sensation that runs down the back when bending the neck.

In some embodiments, administering an anti-CD33 antibody of the present disclosure can prevent, reduce the risk, and/or treat multiple sclerosis. In some embodiments, administering an anti-CD33 antibody may modulate one or more CD33 activities in an individual having multiple sclerosis.

Cancer

Further aspects of the present disclosure provide methods for preventing, reducing risk, or treating cancer, by administering to an individual in need thereof a therapeutically effective amount of an isolated anti-CD33 antibody of the present disclosure. Any of the isolated antibodies of the present disclosure may be used in these methods. In some embodiments, the isolated antibody is an agonist antibody of the present disclosure. In other embodiments, the isolated antibody is an antagonist antibody of the present disclosure.

In other embodiments, the isolated antibody is an inert antibody of the present disclosure. In other embodiments, the isolated antibody is an antibody conjugate of the present disclosure.

As disclosed herein, the tumor microenvironment is known to contain a heterogeneous immune infiltrate, which includes T lymphocytes, macrophages and cells of myeloid/granulocytic lineage. The presence and activity of T-regulatory cells, tumor-imbedded immunosuppressor myeloid cells, and/or M2-macrophages in tumors is associated with poor prognosis. In contrast, the presence and activity of cytotoxic T cells is beneficial for cancer therapy. Therapies that directly or indirectly enhance the activity of cytotoxic T cells and reduce the number and activity of the various immunosuppressor cells, are expected to provide significant therapeutic benefit. A seminal preclinical study has shown synergies between drugs that target immunosuppressor cells (e.g., CSF1/CSF1R blocking antibodies) and immune checkpoint blocking antibodies that activate cytotoxic T cells, indicating that manipulating both cell types shows efficacy in tumor models where individual therapies are poorly effective (Zhu Y; *Cancer Res.* 2014 Sep. 15; 74(18): 5057-69). Therefore, in some embodiments, blocking CD33, which is expressed on myeloid cells, subset of T cells, and tumor-associated immune cells, may stimulate beneficial anti-tumor immune response, resulting in a therapeutic anti-tumor immune response.

In some embodiments, the methods for preventing, reducing risk, or treating an individual having cancer further include administering to the individual at least one antibody that specifically binds to an inhibitory checkpoint molecule. Examples of antibodies that specifically bind to an inhibitory checkpoint molecule include, without limitation, an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-BTLA antibody, an anti-GAL9 antibody, an anti-TIM3 antibody, an anti-A2AR antibody, an anti-LAG-3 antibody, an anti-phosphatidylserine antibody, and any combination thereof. In some embodiments, the at least one antibody that specifically binds to an inhibitory checkpoint molecule is administered in combination with an antagonist anti-CD33 antibody of the present disclosure.

In some embodiments, a cancer to be prevented or treated by the methods of the present disclosure includes, without limitation, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases.

In some embodiments, the cancer is colorectal cancer. In some embodiments, the cancer is selected from non-small cell lung cancer, glioblastoma, neuroblastoma, renal cell carcinoma, bladder cancer, ovarian cancer, melanoma, breast carcinoma, gastric cancer, and hepatocellular carcinoma. In some embodiments, the cancer is triple-negative breast carcinoma. In some embodiments, the cancer may be an early stage cancer or a late stage cancer. In some embodiments, the cancer may be a primary tumor. In some embodiments, the cancer may be a metastatic tumor at a second site derived from any of the above types of cancer.

In some embodiments, anti-CD33 antibodies of the present disclosure may be used for preventing, reducing risk, or treating cancer, including, without limitation, bladder cancer breast cancer, colon and rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

In some embodiments, the present disclosure provides methods of preventing, reducing risk, or treating an individual having cancer, by administering to the individual a therapeutically effective amount of an anti-CD33 antibody of the present disclosure.

In some embodiments, the method further includes administering to the individual at least one antibody that specifically binds to an inhibitory immune checkpoint molecule, and/or another standard or investigational anti-cancer therapy. In some embodiments, the at least one antibody that specifically binds to an inhibitory checkpoint molecule is administered in combination with the anti-CD33 antibody of the present disclosure. In some embodiments, the at least one antibody that specifically binds to an inhibitory checkpoint molecule is selected from an anti-PD-L 1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, and any combination thereof. In some embodiments, the standard or investigational anti-cancer therapy is one or more therapies selected from radiotherapy, cytotoxic chemotherapy, targeted therapy, imatinib (Gleevec®), trastuzumab (Herceptin®), adoptive cell transfer (ACT), chimeric antigen receptor T cell transfer (CAR-T), vaccine therapy, and cytokine therapy.

In some embodiments, the method further includes administering to the individual at least one antibody that specifically binds to an inhibitory cytokine. In some embodiments, the at least one antibody that specifically binds to an inhibitory cytokine is administered in combination with the anti-CD33 antibody of the present disclosure. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the method further includes administering to the individual at least one agonistic antibody that specifically binds to a stimulatory immune checkpoint protein. In some embodiments, the at least one agonistic antibody that specifically binds to a stimulatory checkpoint protein is administered in combination with the anti-CD33 antibody of the present disclosure. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof.

In some embodiments, the method further includes administering to the individual at least one stimulatory cytokine. In some embodiments, the at least one stimulatory cytokine is administered in combination with the anti-CD33 antibody of the present disclosure. In some embodiments, the at least one stimulatory cytokine is selected from TNF-α, IL-6, IL-8, CRP, IL-20 family member, LIF, OSM, CNTF, IL-11, IL-12, IL-17, IL-8, CRP, IFN-α, IFN-β, IL-2, IL-18, GM-CSF, G-CSF, and any combination thereof.

In some embodiments, a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

An antibody provided herein (and any additional therapeutic agent) can be administered by any suitable means, including parenteral, intrapulmonary, intranasal, intralesional administration, intracerobrospinal, intracranial, intraspinal, intrasynovial, intrathecal, oral, topical, or inhalation routes. Parenteral infusions include intramuscular, intravenous administration as a bolus or by continuous infusion over a period of time, intraarterial, intra-articular, intraperitoneal, or subcutaneous administration. In some embodiments, the administration is intravenous administration. In some embodiments, the administration is subcutaneous. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies provided herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99/6 of the dosages described herein, or in any dosage and by any route that is empirically/clinically determined to be appropriate.

For the prevention or treatment of disease, the appropriate dosage of an antibody of the present disclosure (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 Ag/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the antibody). In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. An initial higher loading dose, followed by one or more lower doses may be administered. However, other dosage regimens may be useful. The progress of this therapy is easily monitored by conventional techniques and assays.

Diagnostic Uses

In some embodiments of any of the antibodies, any of the anti-CD33 antibodies provided herein is useful for detecting the presence of CD33 in a sample or an individual. The term "detecting" as used herein encompasses quantitative or qualitative detection. Provided herein are methods of using the antibodies of this disclosure for diagnostic purposes, such as the detection of CD33 in an individual or in tissue samples derived from an individual. In some embodiments, the individual is a human.

The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}$F and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

Kits/Articles of Manufacture

Provided herein are articles of manufacture (e.g., kit) comprising an anti-CD33 antibody described herein. Article of manufacture may include one or more containers comprising an antibody described herein. Containers may be any suitable packaging including, but is not limited to, vials, bottles, jars, flexible packaging (e.g., sealed Mylar or plastic bags), and the like. The containers may be unit doses, bulk packages (e.g., multi-dose packages) or sub-unit doses.

In some embodiments, the kits may further include a second agent. In some embodiments, the second agent is a pharmaceutically-acceptable buffer or diluting agent including, but not limited to, such as bacteriostatic water for injection (BWFI), phosphate-buffered saline, Ringer's solution and dextrose solution. In some embodiments, the second agent is a pharmaceutically active agent.

In some embodiments of any of the articles of manufacture, the article of manufactures further include instructions for use in accordance with the methods of this disclosure. The instructions generally include information as to dosage, dosing schedule, and route of administration for the intended treatment. In some embodiments, these instructions comprise a description of administration of the isolated antibody of the present disclosure (e.g., an anti-CD33 antibody described herein) to prevent, reduce risk, or treat an individual having a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza, according to any methods of this disclosure. In some embodiments, the instructions include instructions for use of the anti-CD33 antibody and the second agent (e.g., second pharmaceutically active agent).

In some embodiments, the instructions comprise a description of how to detect a CD33 protein, for example in an individual, in a tissue sample, or in a cell. The kit and/or article of manufacture may further comprise a description of selecting an individual suitable for treatment based on identifying whether that individual has the disease and the stage of the disease.

In some embodiments, the kits and/or articles of manufacture may further include another antibody of the present disclosure (e.g., at least one antibody that specifically binds to an inhibitory checkpoint molecule, at least one antibody that specifically binds to an inhibitory cytokine, and/or at least one agonistic antibody that specifically binds to a stimulatory checkpoint protein) and/or at least one stimulatory cytokine. In some embodiments, the kits and/or articles of manufacture may further include instructions for using the antibody and/or stimulatory cytokine in combination with an anti-CD33 antibody described herein, instructions for using an anti-CD33 antibody described herein in combination with an antibody and/or stimulatory cytokine, or instructions for using an anti-CD33 antibody described herein and an antibody and/or stimulatory cytokine, according to any methods of this disclosure.

The instructions generally include information as to dosage, dosing schedule, and route of administration for the intended treatment. The containers may be unit doses, bulk packages (e.g., multi-dose packages) or sub-unit doses. Instructions supplied in the kits and/or articles of manufacture of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a disease of the present disclosure. Instructions may be provided for practicing any of the methods described herein.

The kits and/or articles of manufacture of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit and/or article of manufacture may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is an anti-CD33 antibody described herein. The container may further comprise a second pharmaceutically active agent.

Kits and/or articles of manufacture may optionally provide additional components such as buffers and interpretive information. Normally, the kit comprises a container and a label or package insert(s) on or associated with the container.

The present disclosure will be more fully understood by reference to the following Examples. They should not, however, be construed as limiting the scope of the present disclosure. All citations throughout the disclosure are hereby expressly incorporated by reference.

EXAMPLES

Example 1: Humanization of a Murine Anti-CD33 Antibody, and Binding Parameters of Such Humanized Variants The purpose of the following Example was to generate humanized variants of a mouse anti-human CD33 antibody, 6C7, and to characterize the binding of the humanized antibodies to CD33. The mouse 6C7 antibody contained a heavy chain variable region comprising the sequence EVKLEESGG-GLVQPGGSMKLSCVGSGFTFSNYCMNWVRQS-PEKGLEWVAEIRLKSNNYVTN YVESVKGRFTISRDD-SKSRVYLQMNNLRGEDTGFYYCTRDGYYVPFAYWG QGTLVTVSA (SEQ ID NO:3), and a light chain variable region comprising the sequence of QLVLTQSSSASFSL-GASAKLTCTLSSQH-STYTIEWYQQQPLKPPKYVMELKKDGSHSTGD GIPDRFSGSSSGADRYLSISNIQPEDEAIYICGVGD-TIKEQFVYVFGGGTKVTVL (SEQ ID NO:4). Anti-CD33 antibody 6C7 was previously disclosed in WO2016/201388, wherein the heavy chain variable region was encoded by SEQ ID NO:65 and the light chain variable region was encoded by SEQ ID NO:242.

Anti-CD33 antibody 6C7 was humanized by grafting the CDRs of the parental mouse antibody onto human germline frameworks closest in sequence to the mouse antibody. Antibodies with one or more framework back-mutations were also generated. In total, 7 humanized antibodies of anti-CD33 antibody 6C7 were produced: 6C7H1 through 6C7H7. The heavy chain variable region sequences of anti-CD33 antibodies are depicted in Table 11 below. The light chain variable region sequences of the anti-CD33 antibodies are depicted in Table 12 below.

The 7 humanized anti-CD33 antibodies of 6C7 were evaluated for binding to primary dendritic cells by flow cytometry, and binding was compared to that of an anti-CD33 6C7 chimeric antibody that contained the variable heavy chain sequence and the variable light chain sequence of anti-CD33 antibody 6C7. Monocytes were isolated from blood from healthy human donors using the RosetteSep™ monocyte isolation antibody cocktail (StemCell Technologies). The isolated monocytes were differentiated into dendritic cells with 100 ng/mL GM-CSF and 100 ng/mL IL-4 (Peprotech). Dendritic cells were incubated with dilutions of the anti-CD33 antibodies for 30 minutes on ice in the dark, followed by a 30-minute incubation with a fluorescently-conjugated anti-human IgG secondary antibody. Cells were washed twice in FACS buffer (PBS+2% FBS, 2 mM EDTA), and flow cytometry was performed on a BD FACS Canto. Data were analyzed using FlowJo software (Ashland, Oreg.). The results are shown in FIG. 1.

Of the 7 humanized antibodies tested for binding to dendritic cells, only 5 of the antibodies bound to cells: 6C7H3, 6C7H4, 6C7H5, 6C7H6, and 6C7H7. Anti-CD33 antibodies 6C7H1 and 6C7H2 did not bind to dendritic cells in these experiments.

Example 2: CD33 Cell Surface Downregulation by Humanized Anti-CD33 Antibodies

The purpose of the following Example was to test whether humanized anti-CD33 6C7 antibodies (as described in Example 1 above) were able to reduce the cell surface level of CD33 on primary human dendritic cells.

Figure 2:
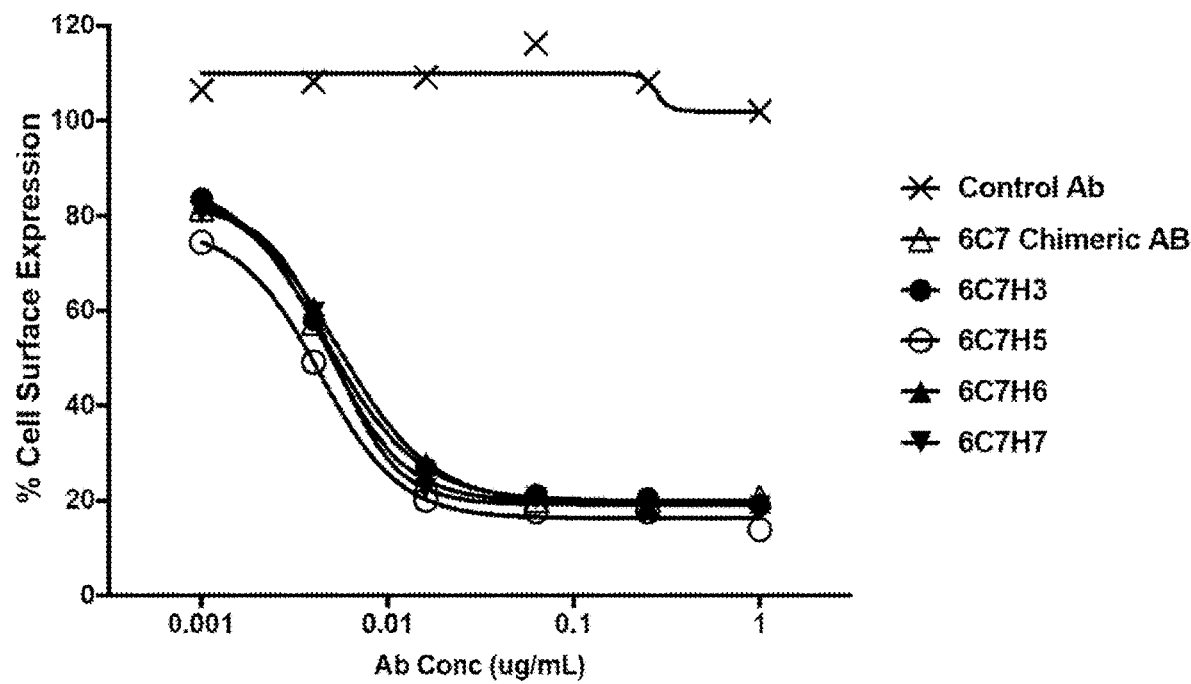
FIG. 2 sets forth data showing anti-CD33 antibodies of the present disclosure down-regulate CD33 cell surface levels in human dendritic cells.

Monocytes were isolated from blood from healthy human donors using the RosetteSep™ monocyte isolation antibody cocktail (StemCell Technologies). The isolated monocytes were differentiated into dendritic cells with 100 ng/mL GM-CSF and 100 ng/mL IL-4 (Peprotech). Dendritic cells were plated in 96-well plates at 100,000 cells per well, in 24-well plates at 200,000 cells per mL, or in 6-well dishes at 500,000 cells in 2 mL RPMI supplemented with 10% Hyclone FBS, 2 mM glutamine, pen/strep, and non-essential amino acids. Anti-CD33 antibodies, or isotype control antibodies, were added to the wells and were incubated for 24 hours at 37° C. with 5% $CO_2$. Cell surface receptor expression was detected by FACS analysis according to standard techniques. Briefly, cells were incubated with anti-CD33-FITC clone HIM3-4 (BD Biosciences) for 30 minutes on ice in the dark. Cells were washed twice in FACS buffer (PBS+2% FBS, 2 mM EDTA), and flow cytometry was performed on a BD FACS Canto. Data were analyzed using FlowJo software (Ashland, Oreg.), and CD33 surface expression was calculated as a percent of receptor expression relative to the expression in the absence of antibody. The results are shown in FIG. 2.

All four humanized anti-CD33 antibodies tested (6C7H3, 6C7H5, 6C7H6, 6C7H7), as well as anti-CD33 chimeric antibody 6C7 were able to reduce the cell surface levels of CD33 on the surface of dendritic cells, with anti-CD33 antibody 6C7H5 being the most potent of the humanized antibodies.

Example 3: Engineering of Anti-CD33 Antibody 6C7H5 and Characterization of Such Modified Antibodies The purpose of the following example was to generate and characterize variants of anti-CD33 antibody 6C7H5 that removed sequences that may result in antibody instability, while maintaining binding and other desirable functional properties of anti-CD33 antibody 6C7H5.

Engineering of anti-CD33 antibody 6C7H5 was performed by targeted mutagenesis in the heavy and/or light chains of the humanized antibody, after which the antibody variants were expressed in mammalian cells and purified for further analysis. 24 variant antibodies of 6C7H5 were generated that contained modifications in HVR H3 and HVR L2. These 24 antibodies were tested for binding to recombinant CD33 by ELISA, and only 1 of the 24 antibodies displayed binding above background levels (data not shown). The heavy chain variable region HVR sequences of this antibody, antibody 6C7H8, is depicted in Table 7 below. The light chain variable region HVR sequences of this antibody are depicted in Table 8 below. The heavy chain framework regions of this antibody are depicted in Table 9 below. The light chain framework regions of this antibody are depicted in Table 10 below. The heavy chain variable region sequence of this antibody is depicted in Table 11 below. The light chain variable region sequence of this antibody is depicted in Table 12 below.

Binding to Dendritic Cells and Cynomolgus CD33

Figure 3:
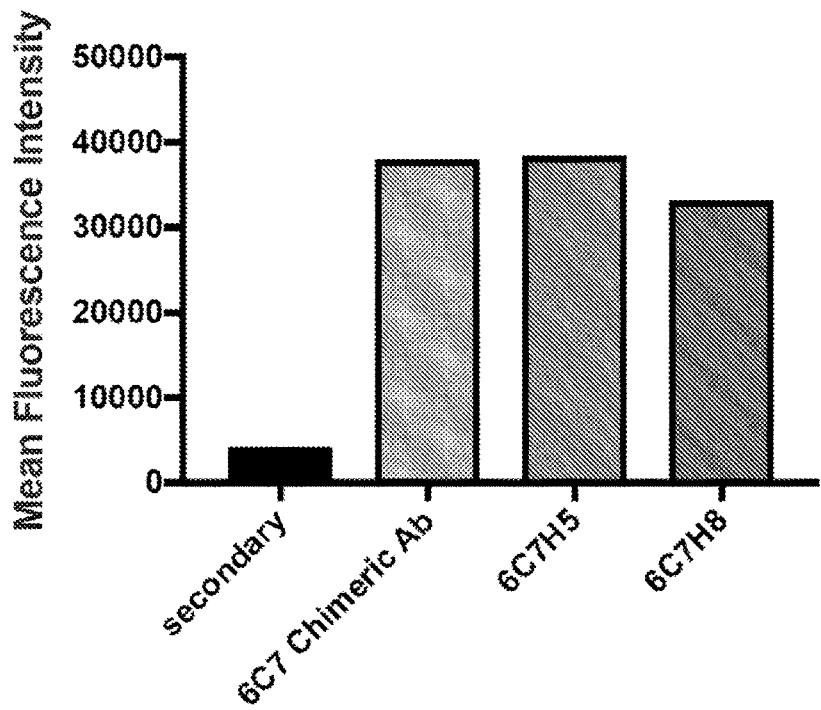
FIG. 3 sets forth data showing anti-CD33 antibodies of the present disclosure bind to primary human dendritic cells.

Anti-CD33 antibody 6C7H8 was tested for binding to mammalian cells by flow cytometry using the method described in Example 1 above, at an antibody concentration of 2 µg/mL. The results are shown in FIG. 3.

Anti-CD33 antibody 6C7H8 was found to bind to dendritic cells at levels similar to the parental humanized antibody, anti-CD33 antibody 6C7H5, and the anti-CD33 antibody 6C7 Chimeric antibody.

Figure 4:
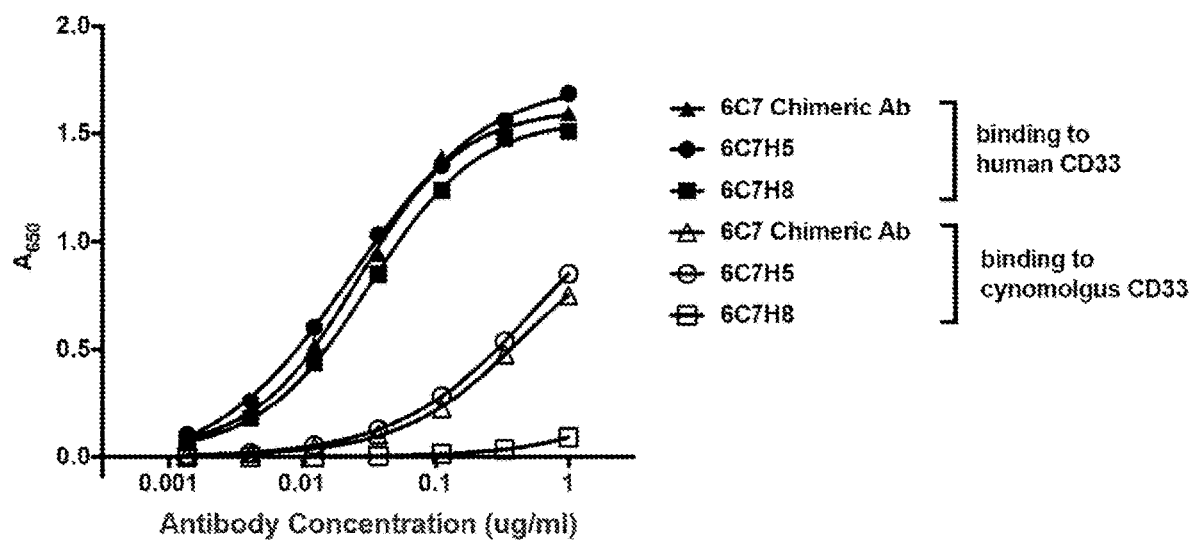
FIG. 4 sets forth data showing anti-CD33 antibodies of the present disclosure bind to human CD33 and cyno CD33 protein.

Anti-CD33 antibody 6C7H8 was also evaluated for binding to cynomolgus CD33 by ELISA. Briefly, ELISA plates were coated with recombinant human CD33 protein (Sino Biologicals) or recombinant cynomolgus CD33 protein (NovoProtein) overnight, after which antibodies were added and incubated for 2 hours. The bound antibodies were detected with horseradish peroxidase-conjugated anti-human IgG antibodies (Jackson Immunoresearch) and developed with TMB. The results are shown in FIG. 4 and are summarized in Table 4 below.

Antibody 6C7H8, its parental antibody, 6C7H5, and the 6C7 Chimeric antibody, all bound to human CD33 similarly. In contrast, while antibody 6C7H5 and the 6C7 Chimeric antibody showed modest binding to cynomolgus CD33, anti-CD33 antibody 6C7H8 exhibited little or no binding to cynomolgus CD33.

Downregulation of Surface CD33

Figure 5:
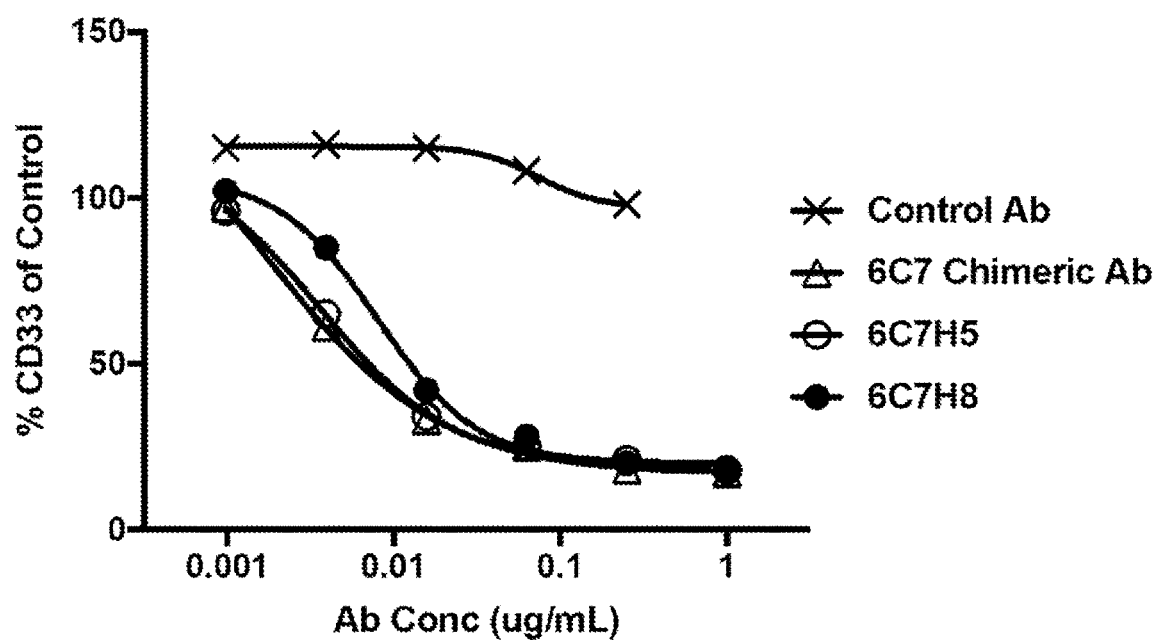
FIG. 5 sets forth data showing anti-CD33 antibodies of the present disclosure down-regulate cell surface levels of CD33 in human dendritic cells.

Anti-CD33 antibody 6C7H8 was evaluated for its ability to reduce the level of CD33 on the surface of dendritic cells, using the method described in Example 2 above. The results are shown in FIG. 5 and are summarized in Table 1 below.

TABLE 1

CD33 cell surface downregulation by 6C7 Chimeric Ab, parental humanized 6C7H5, and 6C7H8

| Antibody | Receptor downregulation, ($EC_{50}$) (pM): |
|---|---|
| 6C7 Chimeric Ab | 43.0 |
| 6C7H5 | 42.4 |
| 6C7H8 | 77.9 |

Anti-CD33 antibody 6C7H8 reduced the levels of CD33 on the surface of dendritic cells, but exhibited somewhat reduced potency compared to the parental humanized antibody (antibody 6C7H5) and the 6C7 Chimeric antibody.

Variants of Humanized 6C7H8

Figure 6A:
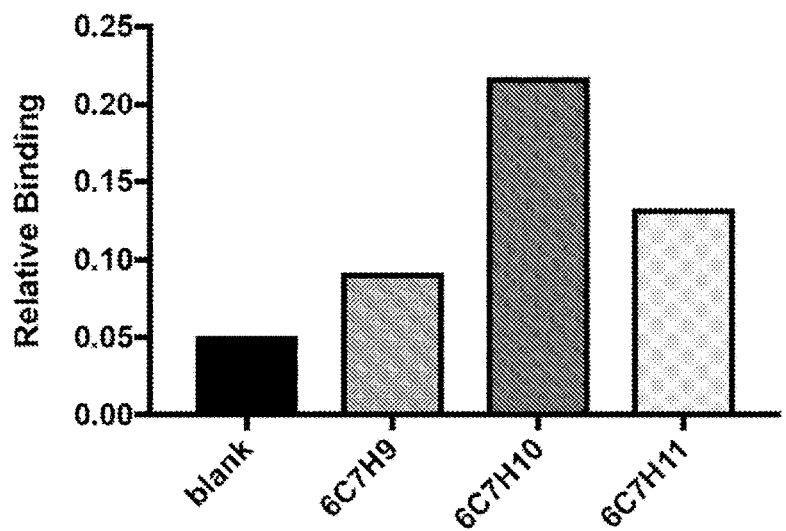
FIG. 6A and FIG. 6B set forth data showing anti-CD33 antibodies of the present disclosure bind recombinant human CD33.
Figure 6B:
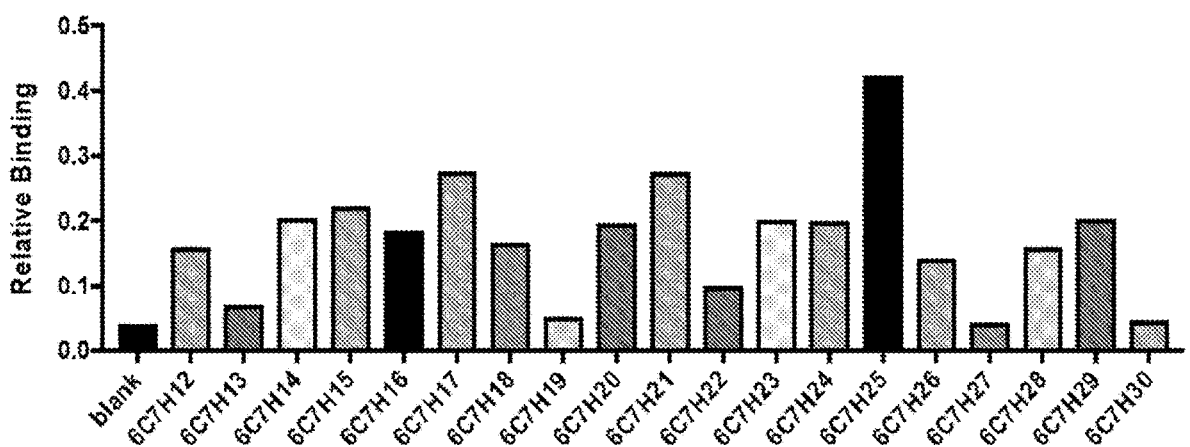

Additional protein engineering was performed on anti-CD33 antibody 6C7H8 to restore binding and other functional properties that were contained in antibody 6C7H5 but were reduced in antibody 6C7H8. Targeted mutagenesis of HVR H1, HVR L2, and framework 1 and framework 2 in the heavy chain of antibody 6C7H8 was performed, from which 35 additional anti-CD33 antibodies were generated. In a separate engineering approach, targeted mutagenesis of HVR H1 in antibody 6C7H8 by targeted mutagenesis yielded 19 additional variant anti-CD33 antibodies. The anti-CD33 antibodies were tested for binding to recombinant CD33 by ELISA. The results are shown in FIG. 6A and FIG. 6B.

Of the 35 anti-CD33 antibodies containing modifications in HVR H1 and HVR L2, just 3 antibodies exhibited binding to CD33 above background levels. The binding of these 3 anti-CD33 antibodies (6C7H9, 6C7H10, and 6C7H11) to CD33 is shown in FIG. 6A. The 19 anti-CD33 antibodies containing modifications in HVR H1, antibody variants 6C7H12 through 6C7H30, exhibited a range of binding to CD33, with antibody 6C7H25 showing the strongest binding and some antibodies, including 6C7H13, 6C7H19, 6C7H27, and 6C7H30, showing only modest binding above background levels, as shown in FIG. 6B. The heavy chain variable region HVR sequences of antibody variants 6C7H9 through 6C7H30 are depicted in Table 7 below. The light chain variable region HVR sequences of the antibodies are depicted in Table 8 below. The heavy chain framework regions of the antibodies are depicted in Table 9 below. The light chain framework regions of the antibodies are depicted in Table 10 below. The heavy chain variable region sequences of the antibodies are depicted in Table 11 below. The light chain variable region sequences of the antibodies are depicted in Table 12 below.

Variants of Humanized 6C7H8: Affinity Parameters

Affinity parameters of the antibody variants for human CD33 were measured by BioLayer Interferometry in a ForteBio assay according to standard techniques (Estep et al. (2013) MAbs 5(2): 270-8) and were compared to those of the parental antibody (antibody 6C7H8) and the parental humanized antibody (antibody 6C7H5). Briefly, the antibodies were captured on anti-human Fc Biosensors (Pall ForteBio). Recombinant human CD33 (10 nM, Sino Biologicals) was then bound to the captured anti-CD33 surface (200 s association time, 1200 s dissociation time). Local fitting was used to extract association and dissociation rate constants ($k_a$ and $k_d$, respectively) for each antibody. Apparent affinity constants ($K_D$) were calculated from the ratio $k_d/k_a$. The results are shown in Table 2 below.

TABLE 2

Affinity parameters of antibody variants

| Antibody | Apparent $k_a$ $(Ms)^{-1}$ | Apparent $k_d$ $(s^{-1})$ | Apparent $K_D$ (nM) |
|---|---|---|---|
| 6C7H5 | 2.75E+05 | 1.20E−04 | 0.436 |
| 6C7H8 | 5.72E+05 | 4.13E−04 | 0.722 |
| 6C7H10 | 1.47E+06 | 8.23E−04 | 0.561 |
| 6C7H12 | 7.49E+05 | 6.94E−04 | 0.926 |
| 6C7H13 | 8.01E+05 | 3.10E−03 | 3.88 |
| 6C7H14 | 9.91E+05 | 7.98E−04 | 0.805 |
| 6C7H15 | 8.01E+05 | 8.25E−04 | 1.03 |
| 6C7H16 | 1.30E+06 | 1.02E−03 | 0.782 |
| 6C7H17 | 6.13E+05 | 5.23E−04 | 0.853 |
| 6C7H18 | 1.05E+06 | 6.40E−04 | 0.609 |
| 6C7H19 | 4.79E+06 | 1.14E−03 | 0.238 |
| 6C7H20 | 7.39E+05 | 4.57E−04 | 0.619 |
| 6C7H21 | 4.98E+05 | 2.63E−04 | 0.528 |
| 6C7H22 | 2.41E+06 | 1.13E−03 | 0.467 |
| 6C7H23 | 1.24E+06 | 6.91E−04 | 0.558 |
| 6C7H24 | 1.37E+06 | 7.57E−04 | 0.552 |
| 6C7H25 | 5.29E+05 | 1.30E−04 | 0.246 |
| 6C7H26 | 1.32E+06 | 9.44E−04 | 0.718 |
| 6C7H27 | 1.34E+06 | 3.65E−03 | 2.73 |
| 6C7H28 | 1.13E+06 | 8.59E−04 | 0.76 |
| 6C7H29 | 8.75E+05 | 8.68E−04 | 0.991 |
| 6C7H30 | 4.65E+06 | 5.90E−03 | 1.27 |

Variants of Humanized 6C7H8: Dendritic Cell Binding

Figure 7:
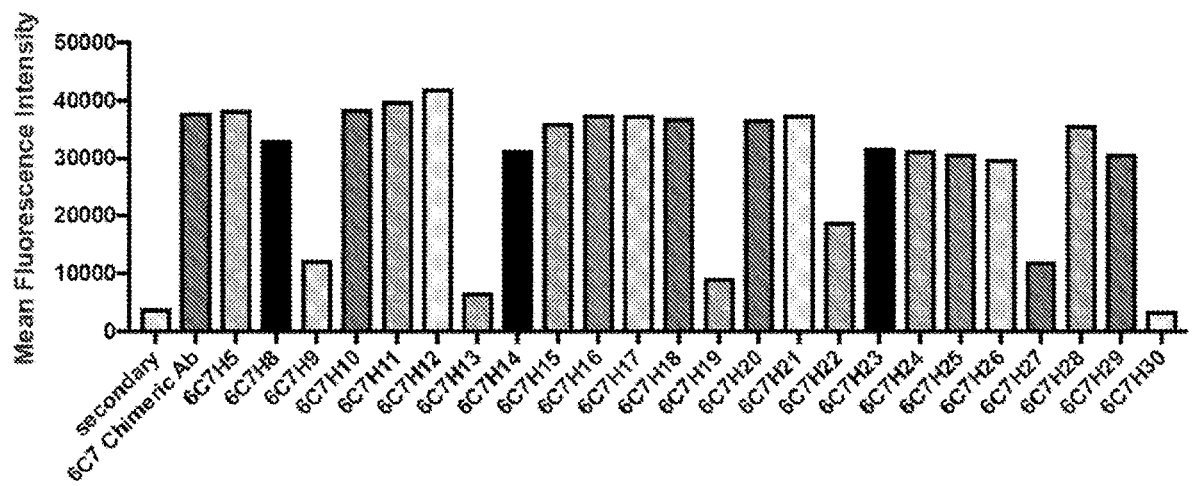
FIG. 7 sets forth data showing anti-CD33 antibodies of the present disclosure bind primary human dendritic cells.

The antibody variants were evaluated for binding to primary human dendritic cells, according to the method described in Example 1, at an antibody concentration of 2 μg/mL. The results are shown in FIG. 7.

Of the three antibody variants with modifications in HVR H1 and HVR L2, only two antibodies, 6C7H10 and 6C7H11, bound to dendritic cells at levels similarly to that of the parental antibody (6C7H8), the parental humanized antibody (6C7H5), or the 6C7 Chimeric antibody. The 6C7H9 antibody variant exhibited substantially reduced binding to dendritic cells. Of the 19 anti-CD33 antibody variants with modifications in HVR1, 14 of the antibodies bound to dendritic cells at levels similar to that of the parental antibody (6C7H8), the parental humanized antibody (6C7H5), or the 6C7 Chimeric antibody. Five anti-CD33 antibodies (6C7H13, 6C7H19, 6C7H22, 6C7H27, and 6C7H30) exhibited binding that was less than 60% of that of any of the parental antibodies. While the apparent affinity constants ($K_D$) of these five anti-CD33 antibodies were within 10-fold of the parental antibodies, all five anti-CD33 antibodies that exhibited reduced binding to cells had the fastest dissociation rate constants.

Variants of Humanized 6C7H8: Downregulation of Surface CD33

Figure 8A:
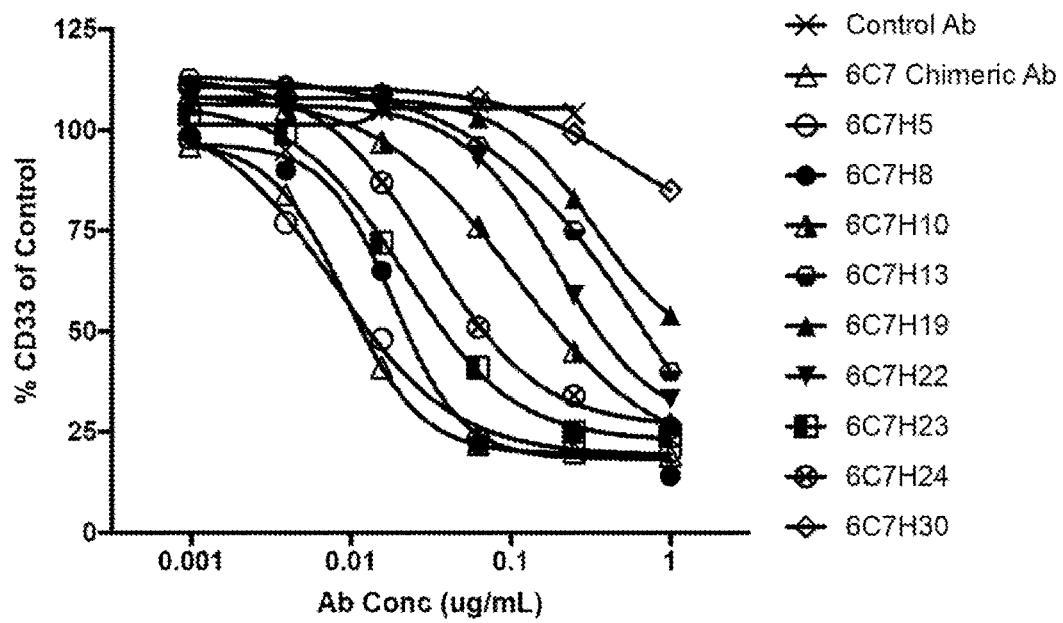
FIG. 8A and FIG. 8B set forth data comparing the reduction of cell surface levels of CD33 in dendritic cells by various anti-CD33 antibodies of the present disclosure.
Figure 8B:
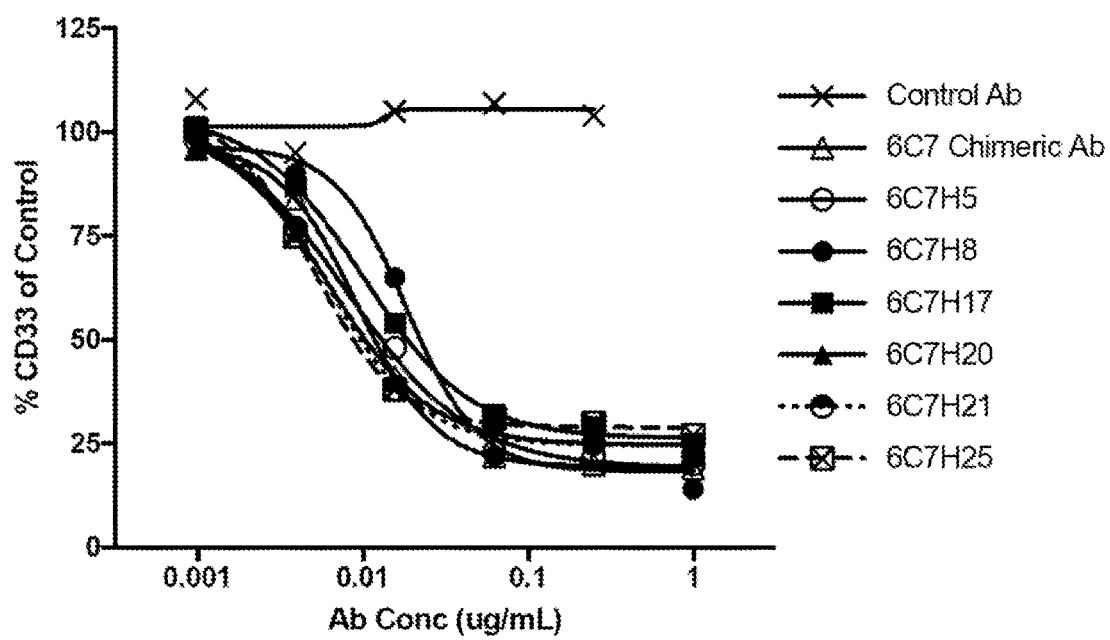

Anti-CD33 antibody variants 6C7H9 through 6C7H30 were evaluated for their ability to reduce the level of CD33 on the surface of dendritic cells, according to the method described in Example 2. The anti-CD33 antibody variants were compared with the parental antibody (6C7H8), the parental humanized antibody (6C7H5), and the 6C7 Chimeric antibody. The half-maximal effective concentrations ($EC_{50}$) and the maximal reduction in CD33 are summarized in Table 3 below. The results of these studies for 11 of the anti CD33 antibody variants (6C7H10, 6C7H13, 6C7H17, 6C7H19, 6C7H20, 6C7H21, 6C7H22, 6C7H23, 6C7H24, 6C7H25, and 6C7H30) are shown in FIG. 8A and FIG. 8B;

here, they are compared to the parental 6C7H8 antibody, the parental 6C7H5 humanized antibody, and the 6C7 Chimeric antibody.

TABLE 3

CD33 cell surface downregulation by 6C7 Chimeric Ab, parental humanized 6C7H5, 6C7H8, and antibody variants of 6C7H8

| Antibody | Receptor downregulation, ($EC_{50}$) (pM): | Fold increase in potency compared to 6C7H5 | Maximal reduction in CD33 (% remaining) |
|---|---|---|---|
| 6C7 Chimeric Ab | 43.0 | — | 20.6 |
| 6C7H5 | 42.4 | — | 21.0 |
| 6C7H8 | 77.9 | 0.5 | 21.5 |
| 6C7H10 | 777.6 | 0.1 | 21.2 |
| 6C7H12 | 159.8 | 0.3 | 27.5 |
| 6C7H13 | 3642.9 | 0.01 | nd |
| 6C7H14 | 164.4 | 0.3 | 28.4 |
| 6C7H15 | 251.6 | 0.2 | 27.7 |
| 6C7H16 | 305.3 | 0.1 | 28.0 |
| 6C7H17 | 51.9 | 0.8 | 32.1 |
| 6C7H18 | 148.3 | 0.3 | 29.2 |
| 6C7H19 | nd | nd | nd |
| 6C7H20 | 40.8 | 1.0 | 29.0 |
| 6C7H21 | 34.7 | 1.2 | 28.3 |
| 6C7H22 | 1228.0 | 0.03 | nd |
| 6C7H23 | 120.1 | 0.4 | 26.2 |
| 6C7H24 | 319.4 | 0.1 | 22.5 |
| 6C7H25 | 27.6 | 1.6 | 30.3 |
| 6C7H26 | 174.6 | 0.2 | 28.3 |
| 6C7H27 | 1515.1 | 0.03 | nd |
| 6C7H28 | 146.9 | 0.3 | 27.6 |
| 6C7H29 | 134.3 | 0.3 | 27.3 |
| 6C7H30 | nd | nd | nd | nd: values could not be assigned due to weak potencies

The antibodies exhibited a range of potencies for reducing CD33 levels on the surface of dendritic cells. As expected, anti-CD33 antibodies that showed substantially reduced binding to cells, exemplified by 6C7H13, 6C7H19, 6C7H22, 6C7H27, and 6C7H30, had substantially reduced potencies in downregulating CD33. Ten additional anti-CD33 antibodies also exhibited reduced potencies in reducing cell surface CD33 levels (e.g., between 0.1- and 0.3-fold improvement in potency in reducing cell surface CD33 levels compared to that observed with the parental humanized antibody 6C7H5). Four anti-CD33 antibodies (6C7H17, 6C7H20, 6C7H21, and 6C7H25) showed similar or slightly improved potencies in reducing cell surface CD33 levels, with 0.8- to 1.6-fold improvement compared to that observed with the parental humanized anti-CD33 antibody 6C7H5. Surprisingly, the affinities of several of the similar or improved potency anti-CD33 antibodies were similar to the affinities of antibodies that showed reduced potencies in downregulating CD33, as exemplified by antibodies 6C7H10, 6C7H14, 6C7H16, 6C7H18, 6C7H24, 6C7H26, and 6C7H28. Thus, the affinity of an anti-CD33 antibody to its target was not predictive for the ability of the anti-CD33 antibody to downregulate CD33 on the surface of cells.

While anti-CD33 antibodies 6C7H17, 6C7H20, 6C7H21, and 6C7H25 had similar or slightly improved potencies in downregulating CD33, compared to that observed with the parental humanized antibody (6C7H5) and the 6C7 Chimeric antibody, the anti-CD33 antibody variants with similar or improved potencies did not show as extensive maximal reduction in CD33 levels.

Additional Antibody Variants

To obtain antibodies with improved binding and functional activities, further engineering of anti-CD33 antibodies of the present disclosure was performed by targeted mutagenesis in HVR H1, HVR H3, HVR L2, HVR L3, heavy chain framework 1, heavy chain framework 2, heavy chain framework 3, light chain framework 1, and light chain framework 2, yielding 24 additional anti-CD33 antibody variants (6C7H31 through 6C7H54). The heavy chain variable region HVR sequences of anti-CD33 antibody variants 6C7H31 through 6C7H54 are depicted in Table 7 below. The light chain variable region HVR sequences of the antibodies are depicted in Table 8 below. The heavy chain framework regions of the antibodies are depicted in Table 9 below. The light chain framework regions of the antibodies are depicted in Table 10 below. The heavy chain variable region sequences of the antibodies are depicted in Table 11 below. The light chain variable region sequences of the antibodies are depicted in Table 12 below.

Additional Antibody Variants: Binding to Dendritic Cells and Cynomolgus CD33

Figure 9:
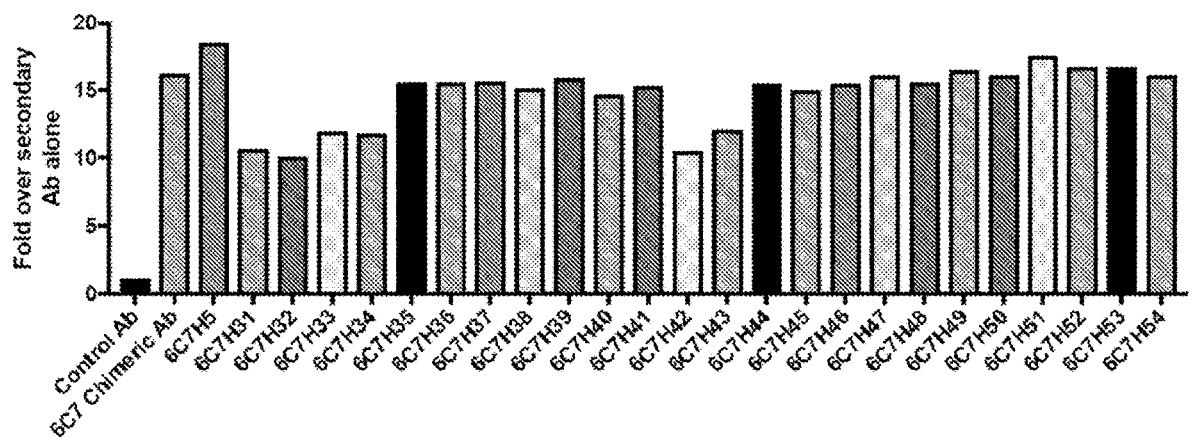
FIG. 9 sets forth data showing anti-CD33 antibody variants of the present disclosure binding to primary human dendritic cells.

The anti-CD33 antibody variants 6C7H31 through 6C7H54 were evaluated for binding to primary human dendritic cells by flow cytometry, according to the method described in Example 1, at an antibody concentration of 1 µg/mL. The anti-CD33 antibody variants were compared to the parental humanized antibody (6C7H5) and the 6C7 Chimeric antibody. The results of these studies are shown in FIG. 9.

Of the 24 anti-CD33 antibody variants tested for binding to dendritic cells, 18 anti-CD33 antibody variants exhibited similar binding to primary human dendritic cells as that observed with the parental humanized antibody (6C7H5) and the 6C7 Chimeric antibody. Six anti-CD33 antibodies (6C7H31, 6C7H32, 6C7H33, 6C7H34, 6C7H42, and 6C7H43) showed somewhat reduced binding to these cells.

Figure 10A:
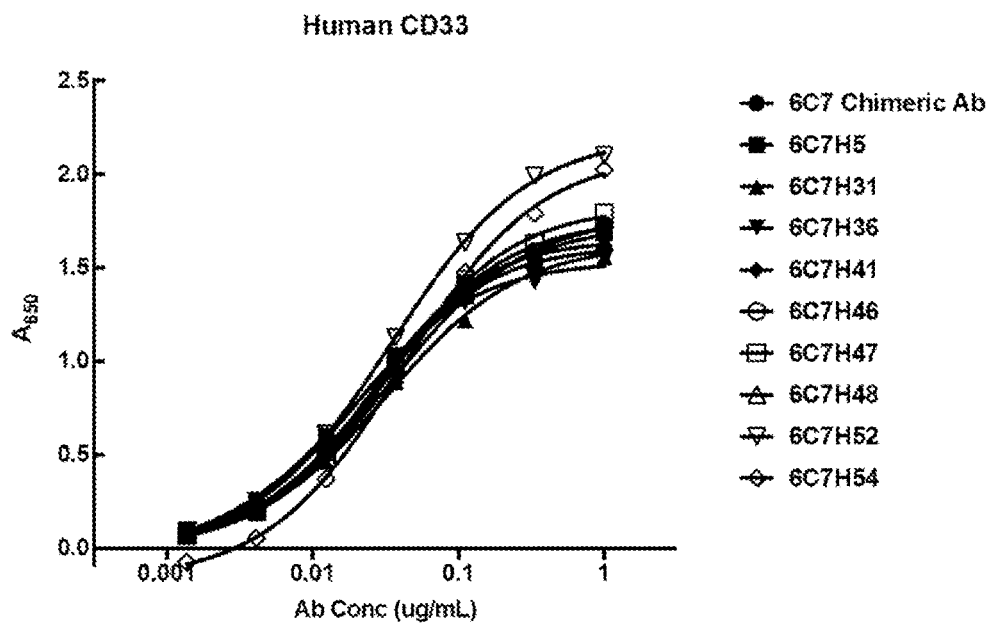
FIG. 10A and FIG. 10B set forth data showing anti-CD33 antibody variants of the present disclosure bind to human CD33 and cyno CD33 protein, respectively.
Figure 10B:
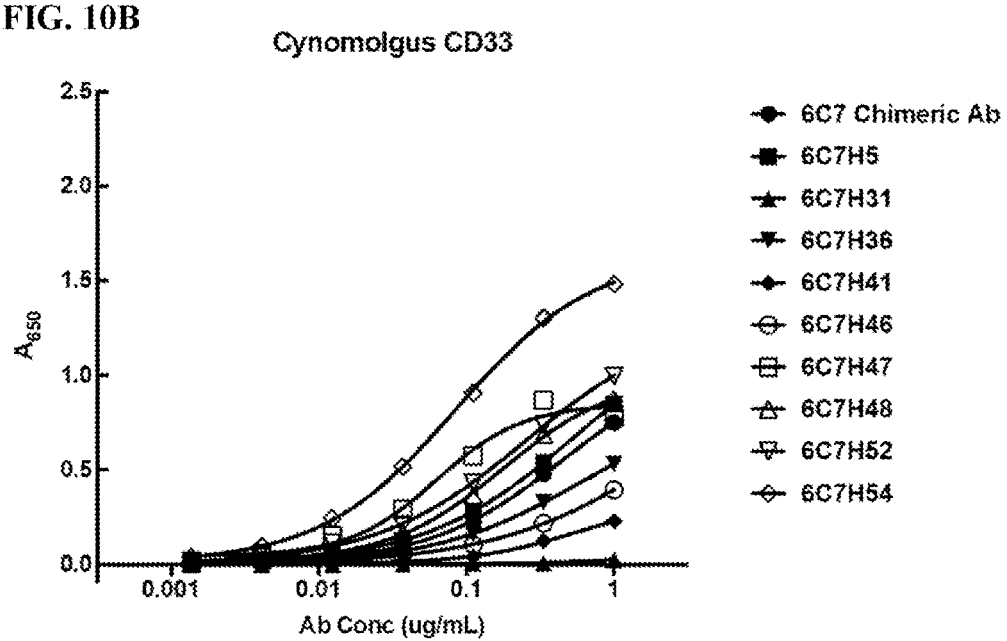

The anti-CD33 antibody variants were further evaluated for their ability to bind to cynomolgus CD33 in an ELISA assay, according to the method described above. The anti-CD33 antibody variants were compared to the parental humanized antibody (6C7H5) and the 6C7 Chimeric antibody. The results are summarized in Table 4 below, and the binding data for 8 of the anti-CD33 antibody variants are shown in FIGS. 10A and 10B.

TABLE 4

Binding of anti-CD33 antibody variants to human CD33 and cynomolgus CD33

| Antibody | Binding to human CD33, ($EC_{50}$) (nM): | Binding to cynomolgus CD33 ($EC_{50}$) (nM): | Relative potency (human/cyno) | Relative maximal binding (cyno/human) |
|---|---|---|---|---|
| 6C7 Chimeric Ab | 0.17 | 2.96 | 0.06 | 0.47 |
| 6C7H5 | 0.16 | 3.84 | 0.04 | 0.50 |
| 6C7H8 | 0.21 | nd | nd | 0.06 |
| 6C7H21 | 0.16 | nd | nd | nd |
| 6C7H31 | 0.21 | nd | nd | 0.02 |
| 6C7H32 | 0.20 | nd | nd | 0.01 |

TABLE 4-continued

Binding of anti-CD33 antibody variants to human CD33 and cynomolgus CD33

| Antibody | Binding to human CD33, ($EC_{50}$) (nM): | Binding to cynomolgus CD33 ($EC_{50}$) (nM): | Relative potency (human/cyno) | Relative maximal binding (cyno/human) |
|---|---|---|---|---|
| 6C7H33 | 0.17 | nd | nd | 0.01 |
| 6C7H34 | 0.17 | nd | nd | 0.01 |
| 6C7H35 | 0.21 | nd | nd | 0.04 |
| 6C7H36 | 0.13 | 4.00 | 0.03 | 0.34 |
| 6C7H37 | 0.26 | 5.62 | 0.05 | 0.45 |
| 6C7H38 | 0.21 | 4.87 | 0.04 | 0.36 |
| 6C7H39 | 0.23 | nd | nd | 0.02 |
| 6C7H40 | 0.19 | nd | nd | 0.03 |
| 6C7H41 | 0.23 | nd | nd | 0.13 |
| 6C7H42 | 0.20 | nd | nd | 0.08 |
| 6C7H43 | 0.17 | nd | nd | 0.11 |
| 6C7H44 | 0.18 | nd | nd | 0.09 |
| 6C7H45 | 0.15 | nd | nd | 0.31 |
| 6C7H46 | 0.19 | 16.75 | 0.01 | 0.23 |
| 6C7H47 | 0.22 | 0.42 | 0.52 | 0.43 |
| 6C7H48 | 0.17 | 1.19 | 0.14 | 0.53 |
| 6C7H49 | 0.30 | nd | nd | nd |
| 6C7H50 | 0.22 | nd | nd | 0.21 |
| 6C7H51 | 0.19 | nd | nd | 0.08 |
| 6C7H52 | 0.23 | 1.70 | 0.14 | 0.47 |
| 6C7H53 | 0.18 | 25.59 | 0.01 | 0.39 |
| 6C7H54 | 0.28 | 0.57 | 0.49 | 0.73 | nd: values could not be calculated due to poor binding to cynomolgus CD33

Of the 26 anti-CD33 antibody variants tested, 19 showed either no binding to cynomolgus CD33 or substantially reduced binding, as compared to that observed with the parental humanized antibody (6C7H5) or the 6C7 Chimeric antibody. Three anti-CD33 antibodies (6C7H36, 6C7H37, and 6C7H38) bound similarly to cynomolgus CD33 as observed with the parental humanized antibody (6C7H5) and the 6C7 Chimeric antibody. Four anti-CD33 antibodies (6C7H47, 6C7H48, 6C7H52, and 6C7H54) showed substantially improved binding to cynomolgus CD33. One anti-CD33 antibody, 6C7H54, surprisingly showed both improved potency and the strongest maximal binding to cynomolgus CD33.

Additional Antibody Variants: Affinity Parameters

The affinity parameters of anti-CD33 antibody 6C7H54 for human CD33 and cynomolgus CD33 were measured by BioLayer Interferometry in a ForteBio assay, according to the method described above. The results are summarized in Table 5 below.

TABLE 5

Binding affinity of 6C7H54 on human CD33 and cynomolgus CD33

| Antigen | Apparent $k_a$ $(Ms)^{-1}$ | Apparent $k_d$ $(s^{-1})$ | Apparent $K_D$ (nM) |
|---|---|---|---|
| human CD33 | 5.45E+05 | 3.32E−05 | 0.061 |
| cynomolgus CD33 | 5.89E+05 | 1.05E−04 | 0.178 |

The anti-CD33 antibody 6C7H54 was found to have unexpectedly improved affinity to human CD33, compared to that observed with the parental humanized antibody (6C7H5) or the 6C7 Chimeric antibody (see Table 2). Moreover, the binding affinity of antibody 6C7H54 to cynomolgus CD33 was found to be within 3-fold of the binding affinity of this antibody to human CD33.

Additional Antibody Variants: Downregulation of Surface CD33

Figure 11:
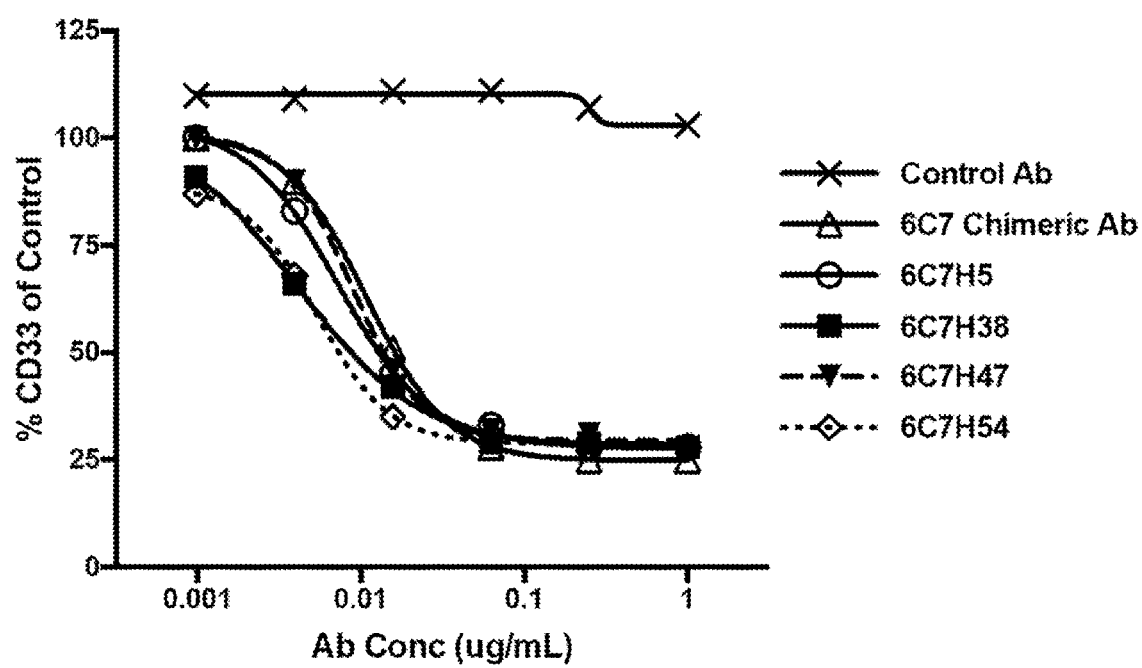
FIG. 11 sets forth data showing anti-CD33 antibody variants of the present disclosure reduce cell surface levels of CD33 in primary human dendritic cells.

The 24 anti-CD33 antibody variants (6C7H31 through 6C7H54) were further evaluated for their ability to reduce the levels of CD33 on the surface of dendritic cells, according to the method described in Example 2 above. The anti-CD33 antibody variants were compared to the parental humanized antibody, 6C7H5, and the 6C7 Chimeric antibody for their ability to reduce CD33 cell surface levels on human dendritic cells. The half-maximal effective concentrations ($EC_{50}$) are summarized in Table 6 below and the results for 3 of the anti-CD33 variants (6C7H38, 6C7H47, and 6C7H54) are shown in FIG. 11, where they are compared to the parental 6C7H5 humanized antibody and the 6C7 Chimeric antibody.

TABLE 6

Downregulation of cell surface CD33 by antibody variants 6C7H31 through 6C7H54

| Antibody | Receptor downregulation, (EC$_{50}$) (pM): | Fold increase in potency compared to 6C7H5 |
|---|---|---|
| 6C7 Chimeric Ab | 43.0 | — |
| 6C7H5 | 42.4 | — |
| 6C7H31 | 67.7 | 0.6 |
| 6C7H32 | 47.2 | 0.9 |
| 6C7H33 | 50.0 | 0.8 |
| 6C7H34 | 60.3 | 0.7 |
| 6C7H35 | 51.0 | 0.8 |
| 6C7H36 | 49.1 | 0.9 |
| 6C7H37 | 59.3 | 0.7 |
| 6C7H38 | 27.0 | 1.6 |
| 6C7H39 | 38.7 | 1.1 |
| 6C7H40 | 37.2 | 1.1 |
| 6C7H41 | 34.2 | 1.2 |
| 6C7H42 | 39.4 | 1.1 |
| 6C7H43 | 49.8 | 0.9 |
| 6C7H44 | 45.7 | 0.9 |
| 6C7H45 | 44.5 | 1.0 |
| 6C7H46 | 61.7 | 0.7 |
| 6C7H47 | 59.0 | 0.7 |
| 6C7H48 | 56.3 | 0.8 |
| 6C7H49 | 69.7 | 0.6 |
| 6C7H50 | 57.8 | 0.7 |
| 6C7H51 | 42.4 | 1.0 |
| 6C7H52 | 47.7 | 0.9 |
| 6C7H53 | 35.4 | 1.2 |
| 6C7H54 | 30.2 | 1.2 |

All of the anti-CD33 antibodies reduced CD33 on the surface of dendritic cells and exhibited potencies that were within 2-fold of that observed with the parental humanized antibody (6C7H5) and the 6C7 Chimeric antibody. Of the two anti-CD33 antibodies that showed the strongest binding to cynomolgus CD33 (6C7H473 and 6C7H54), antibody 6C7H54 was more potent in downregulating CD33 and was more potent than both the parental humanized antibody (6C7H5) and the 6C7 Chimeric antibody at decreasing or reducing cell surface levels of CD33 on these cells. All of the antibodies exhibited similar maximal reduction in CD33 (FIG. 11 and data not shown). Of the 24 anti-CD33 antibody variants generated using the engineering methodology as described above, and out of a total of 102 anti-CD33 antibody variants generated through the four engineering campaigns, anti-CD33 antibody 6C77H54 exhibited both potent downregulation of CD33 and maximal reduction of cell surface CD33 levels; additionally, this anti-CD33 antibody displayed unexpectedly improved affinity to both human CD33 and cynomolgus CD33, compared to that observed with the parental humanized antibody (6C7H5) and the 6C7 Chimeric antibody.

TABLE 7

Heavy chain HVR-H1, HVR-H2, and HVR-H3 sequences of anti-CD33 antibodies

| Antibody | HVR-H1 | SEQ ID NO: | HVR-H2 | SEQ ID NO: | HVR-H3 | SEQ ID NO: |
|---|---|---|---|---|---|---|
| 6C7H1; 6C7H2; 6C7H3; 6C7H4; 6C7H5; 6C7H6; 6C7H7 | NYCMN | 8 | EIRLKSNNYVTNYAASVKG | 33 | DGYYVPFAY | 38 |
| 6C7H8 | NYCMN | 8 | EIRLKSNNYVTNYAASVKG | 33 | AGYYVPFAY | 39 |
| 6C7H9; 6C7H10; 6C7H11 | EYAMN | 9 | EIRLKSNNYVTNYAASVKG | 33 | AGYYVPFAY | 39 |
| 6C7H12 | NYGMN | 10 | EIRLKSNNYVTNYAASVKG | 33 | AGYYVPFAY | 39 |
| 6C7H13 | NYFMN | 11 | EIRLKSNNYVTNYAASVKG | 33 | AGYYVPFAY | 39 |
| 6C7H14 | NYAMN | 12 | EIRLKSNNYVTNYAASVKG | 33 | AGYYVPFAY | 39 |
| 6C7H15 | NYSMN | 13 | EIRLKSNNYVTNYAASVKG | 33 | AGYYVPFAY | 39 |
| 6C7H16 | NYLMN | 14 | EIRLKSNNYVTNYAASVKG | 33 | AGYYVPFAY | 39 |
| 6C7H17 | NYYMN | 15 | EIRLKSNNYVTNYAASVKG | 33 | AGYYVPFAY | 39 |
| 6C7H18 | NYHMN | 16 | EIRLKSNNYVTNYAASVKG | 33 | AGYYVPFAY | 39 |

TABLE 7-continued

Heavy chain HVR-H1, HVR-H2, and HVR-H3 sequences of anti-CD33 antibodies

| Antibody | HVR-H1 | SEQ ID NO: | HVR-H2 | SEQ ID NO: | HVR-H3 | SEQ ID NO: |
|---|---|---|---|---|---|---|
| 6C7H19 | NYRMN | 17 | EIRLKSNNYVTNYAASVKG | 33 | AGYYVPFAY | 39 |
| 6C7H20 | NYPMN | 18 | EIRLKSNNYVTNYAASVKG | 33 | AGYYVPFAY | 39 |
| 6C7H21 | NYQMN | 19 | EIRLKSNNYVTNYAASVKG | 33 | AGYYVPFAY | 39 |
| 6C7H22 | NYTMN | 20 | EIRLKSNNYVTNYAASVKG | 33 | AGYYVPFAY | 39 |
| 6C7H23 | NYVMN | 21 | EIRLKSNNYVTNYAASVKG | 33 | AGYYVPFAY | 39 |
| 6C7H24 | NYNMN | 22 | EIRLKSNNYVTNYAASVKG | 33 | AGYYVPFAY | 39 |
| 6C7H25; 6C7H47; 6C7H48; 6C7H53; 6C7H54 | NYEMN | 23 | EIRLKSNNYVTNYAASVKG | 33 | AGYYVPFAY | 39 |
| 6C7H26 | NYIMN | 24 | EIRLKSNNYVTNYAASVKG | 33 | AGYYVPFAY | 39 |
| 6C7H27 | DYTMN | 25 | EIRLKSNNYVTNYAASVKG | 33 | AGYYVPFAY | 39 |
| 6C7H28 | DYSMN | 26 | EIRLKSNNYVTNYAASVKG | 33 | AGYYVPFAY | 39 |
| 6C7H29 | AYSMN | 27 | EIRLKSNNYVTNYAASVKG | 33 | AGYYVPFAY | 39 |
| 6C7H30 | NYWMN | 28 | EIRLKSNNYVTNYAASVKG | 33 | AGYYVPFAY | 39 |
| 6C7H31; 6C7H32; 6C7H33; 6C7H34 | EYDML | 29 | EIRLKSNNYVTNYAASVKG | 33 | AGYYVPFAY | 39 |
| 6C7H35; 6C7H36; 6C7H37; 6C7H38 | EYAML | 30 | EIRLKSNNYVTNYAASVKG | 33 | AGYYVPFTY | 40 |
| 6C7H39; 6C7H40; 6C7H41; 6C7H42 | EYDML | 29 | EIRLKSNNYVTNYAASVKG | 33 | AGYYVPFAY | 39 |
| 6C7H43; 6C7H44; 6C7H49; 6C7H50 | EYDML | 29 | EIRLKSNNYVTNYAASVKG | 33 | AGYYVPFAY | 39 |
| 6C7H45; 6C7H46; 6C7H51; 6C7H52 | EYAML | 30 | EIRLKSNNYVTNYAASVKG | 33 | AGYYVPFAY | 39 |

TABLE 8

Light chain HVR-L1, HVR-L2, and HVR-L3 sequences of anti-CD33 antibodies

| Antibody | HVR-L1 | SEQ ID NO: | HVR-L2 | SEQ ID NO: | HVR-L3 | SEQ ID NO: |
|---|---|---|---|---|---|---|
| 6C7H1; 6C7H2; 6C7H3; 6C7H4; 6C7H5; 6C7H6; 6C7H7 | TLSSQHSTYTIE | 47 | LKKDGSHSTGD | 52 | GVGDTIKEQFVYV | 58 |
| 6C7H8; 6C7H10; 6C7H12; 6C7H13; | TLSSQHSTYTIE | 47 | LKKEGSHSTGD | 53 | GVGDTIKEQFVYV | 58 |

TABLE 8-continued

Light chain HVR-L1, HVR-L2, and HVR-L3 sequences of anti-CD33 antibodies

| Antibody | HVR-L1 | SEQ ID NO: | HVR-L2 | SEQ ID NO: | HVR-L3 | SEQ ID NO: |
|---|---|---|---|---|---|---|
| 6C7H14; 6C7H15; 6C7H16; 6C7H17; 6C7H18; 6C7H19; 6C7H20; 6C7H21; 6C7H22; 6C7H23; 6C7H24; 6C7H25; 6C7H26; 6C7H27; 6C7H28; 6C7H29; 6C7H30 | | | | | | |
| 6C7H9 | TLSSQHSTYTIE | 47 | LKKKGSHSTGD | 54 | GVGDTIKEQFVYV | 58 |
| 6C7H11 | TLSSQHSTYTIE | 47 | LKKGGSHSTGD | 55 | GVGDTIKEQFVYV | 58 |
| 6C7H31; 6C7H35; 6C7H39; 6C7H49; 6C7H51; 6C7H53 | TLSSQHSTYTIE | 47 | LKKEGSHSTGD | 53 | GVGVTIKEQFVYV | 59 |
| 6C7H32; 6C7H36; 6C7H40; 6C7H43; 6C7H45; 6C7H47 | TLSSQHSTYTIE | 47 | LKKEGSHSTGD | 53 | GVGHTIKEQFVYE | 60 |
| 6C7H33; 6C7H37; 6C7H41; 6C7H50; 6C7H52; 6C7H54 | TLSSQHSTYTIE | 47 | LKKEGSHSTGD | 53 | GVGHTIKEQFVYV | 61 |
| 6C7H34; 6C7H38; 6C7H42; 6C7H44; 6C7H46; 6C7H48 | TLSSQHSTYTIE | 47 | LKKEGSHSTGD | 53 | GVGLTIKEQFVYV | 62 |

TABLE 9

Heavy chain framework sequences of anti-CD33 antibodies

| Antibody | VH FR1 | SEQ ID NO: | VH FR2 | SEQ ID NO: | VH FR3 | SEQ ID NO: | VH FR4 | SEQ ID NO: |
|---|---|---|---|---|---|---|---|---|
| 6C7H1; 6C7H3; 6C7H6 | EVQLVESGGGLVQPGGSLRLSCAASGFTFS | 5 | WVRQAPGKGLEWVG | 31 | RFTISRDDSKNSLYLQMNSLKTEDTAVYYCAR | 34 | WGQGTLVTVSS | 41 |
| 6C7H2; 6C7H5; 6C7H8 GSLRLSCAGSGFTFS | EVQLVESGGGLVQPG | 6 | WVRQAPGKGLEWVA | 32 | RFTISRDDSKNSVYLQMNSLKTEDTGVYYCTR | 35 | WGQGTLVTVSS | 41 |
| 6C7H4; 6C7H7 | EVQLVESGGGLVQPGGSLRLSCAGSGFTFS | 6 | WVRQAPGKGLEWVA | 32 | RFTISRDDSKNSLYLQMNSLKTEDTAVYYCTR | 36 | WGQGTLVTVSS | 41 |
| 6C7H9; 6C7H10; 6C7H11 | EVQLVESGGGLVQPGGSLRLSCAASGFTFS | 5 | WVRQAPGKGLEWVG | 31 | RFTISRDDSKNSVYLQMNSLKTEDTGVYYCTR | 35 | WGQGTLVTVSS | 41 |

TABLE 9-continued

Heavy chain framework sequences of anti-CD33 antibodies

| Antibody | VH FR1 | SEQ ID NO: | VH FR2 | SEQ ID NO: | VH FR3 | SEQ ID NO: | VH FR4 | SEQ ID NO: |
|---|---|---|---|---|---|---|---|---|
| 6C7H12; 6C7H13; 6C7H14; 6C7H15; 6C7H16; 6C7H17; 6C7H18; 6C7H19; 6C7H20; 6C7H21; 6C7H22; 6C7H23; 6C7H24; 6C7H25; 6C7H26; 6C7H27; 6C7H28; 6C7H29; 6C7H30; 6C7H47; 6C7H48; 6C7H53; 6C7H54 | EVQLV ESGGG LVQPG GSLRL SCAGS GFTFS | 6 | WVRQAP GKGLEW VA | 32 | RFTISR DDSKNS VYLQMN SLKTED TGVYYC TR | 35 | WGQGT LVTVS S | 41 |
| 6C7H31; 6C7H32; 6C7H33; 6C7H34 | EVQLV ESGGG LVQPG GSLRL SCAAS GSTFS | 7 | WVRQAP GKGLEW VG | 31 | RFTISR DDSKNS VYLQMN SLKTED TGVYYC TR | 35 | WGQGT LVTVS S | 41 |
| 6C7H35; 6C7H36; 6C7H37; 6C7H38; 6C7H43; 6C7H44; 6C7H45; 6C7H46; 6C7H49; 6C7H50; 6C7H51; 6C7H52 | EVQLV ESGGG LVQPG GSLRL SCAAS GFTFS | 5 | WVRQAP GKGLEW VG | 31 | RFTISR DDSKNS VYLQMN SLKTED TGVYYC TR | 35 | WGQGT LVTVS S | 41 |
| 6C7H39; 6C7H40; 6C7H41; 6C7H42 | EVQLV ESGGG LVQPG GSLRL SCAAS GFTFS | 5 | WVRQAP GKGLEW VG | 31 | RFTISR DDTKNS VYLQMN SLKTED TGVYYC TR | 37 | WGQGT LVTVS S | 41 |

TABLE 10

Light chain framework sequences of anti-CD33 antibodies

| Antibody | VL FR1 | SEQ ID NO: | VL FR2 | SEQ ID NO: | VL FR3 | SEQ ID NO: | VL FR4 | SEQ ID NO: |
|---|---|---|---|---|---|---|---|---|
| 6C7H1; 6C7H2 | QLVLT QSPSA SASLG ASVKL TC | 42 | WHQQQ PEKGP RYLMK | 48 | GIPDR FSGSS SGAER YLTIS SLQSE DEADY YC | 56 | FGGGTKL TVL | 63 |

TABLE 10-continued

Light chain framework sequences of anti-CD33 antibodies

| Antibody | VL FR1 | SEQ ID NO: | VL FR2 | SEQ ID NO: | VL FR3 | SEQ ID NO: | VL FR4 | SEQ ID NO: |
|---|---|---|---|---|---|---|---|---|
| 6C7H3; 6C7H4; 6C7H5; 6C7H8; 6C7H10; 6C7H12; 6C7H13; 6C7H14; 6C7H15; 6C7H16; 6C7H17; 6C7H18; 6C7H19; 6C7H20; 6C7H21; 6C7H22; 6C7H23; 6C7H24; 6C7H25; 6C7H26; 6C7H27; 6C7H28; 6C7H29; 6C7H30 | QLVLT QSPSA SASLG ASVKL TC | 42 | WYQQQ PEKGP RYLME | 49 | GIPDR FSGSS SGAER YLTIS SLQSE DEADY YC | 56 | FGGGTKL TVL | 63 |
| 6C7H6; 6C7H7 | QLVLT QSPSA SASLG ASAKL TC | 43 | WYQQQ PEKGP RYVME | 50 | GIPDR FSGSS SGAER YLTIS SIQSE DEADY IC | 57 | FGGGTKV TVL | 64 |
| 6C7H9; 6C7H11 | QLVLT QSPSA SASLG ASVKL TC | 42 | WYQQQ PEKGP RYLME | 49 | GIPDR FSGSS SGAER YLTIS SLQSE DEADY YC | 56 | FGGGTKL TVL | 63 |
| 6C7H31; 6C7H35; 6C7H39; 6C7H49; 6C7H51; 6C7H53 | QPVLT QSPSA SASLG ASVKL TC | 44 | WYQQQ PEKGP RYLME | 49 | GIPDR FSGSS SGAER YLTIS SLQSE DEADY YC | 56 | FGGGTKL TVL | 63 |
| 6C7H32; 6C7H36; 6C7H40; 6C7H43; 6C7H45; 6C7H47; 6C7H33; 6C7H37; 6C7H41; 6C7H50; 6C7H52; 6C7H54 | QLMLT QSPSA SASLG ASVKL TC | 45 | WYQQQ PGKGP RYLME | 51 | GIPDR FSGSS SGAER YLTIS SLQSE DEADY YC | 56 | FGGGTKL TVL | 63 |
| 6C7H34; 6C7H38; 6C7H42; 6C7H44; 6C7H46; 6C7H48 | QPMLT QSPSA SASLG ASVKL TC | 46 | WYQQQ PGKGP RYLME | 51 | GIPDR FSGSS SGAER YLTIS SLQSE DEADY YC | 56 | FGGGTKL TVL | 63 |

TABLE 11

Heavy chain variable region sequences of anti-CD33 antibodies

| Antibody | HCVR | SEQ ID NO: |
|---|---|---|
| 6C7H1; 6C7H3; and 6C7H6 | EVQLVESGGGLVQPGGSLRLSCAASGFTFSNYCMNWVRQAPGKGLEWVGEIRLKSNNYVTNYAASVKGRFTISRDDSKNSLYLQMNSLKTEDTAVYYCARDGYYVPFAYWGQGTLVTVSS | 65 |
| 6C7H2 and 6C7H5 | EVQLVESGGGLVQPGGSLRLSCAGSGFTFSNYCMNWVRQAPGKGLEWVAEIRLKSNNYVTNYAASVKGRFTISRDDSKNSVYLQMNSLKTEDTGVYYCTRDGYYVPFAYWGQGTLVTVSS | 66 |
| 6C7H4 and 6C7H7 | EVQLVESGGGLVQPGGSLRLSCAGSGFTFSNYCMNWVRQAPGKGLEWVAEIRLKSNNYVTNYAASVKGRFTISRDDSKNSLYLQMNSLKTEDTAVYYCTRDGYYVPFAYWGQGTLVTVSS | 67 |
| 6C7H8 | EVQLVESGGGLVQPGGSLRLSCAGSGFTFSNYCMNWVRQAPGKGLEWVAEIRLKSNNYVTNYAASVKGRFTISRDDSKNSVYLQMNSLKTEDTGVYYCTRAGYYVPFAYWGQGTLVTVSS | 68 |
| 6C7H9; 6C7H10; and 6C7H11 | EVQLVESGGGLVQPGGSLRLSCAASGFTFSEYAMNWVRQAPGKGLEWVGEIRLKSNNYVTNYAASVKGRFTISRDDSKNSVYLQMNSLKTEDTGVYYCTRAGYYVPFAYWGQGTLVTVSS | 69 |
| 6C7H12 | EVQLVESGGGLVQPGGSLRLSCAGSGFTFSNYGMNWVRQAPGKGLEWVAEIRLKSNNYVTNYAASVKGRFTISRDDSKNSVYLQMNSLKTEDTGVYYCTRAGYYVPFAYWGQGTLVTVSS | 70 |
| 6C7H13 | EVQLVESGGGLVQPGGSLRLSCAGSGFTFSNYFMNWVRQAPGKGLEWVAEIRLKSNNYVTNYAASVKGRFTISRDDSKNSVYLQMNSLKTEDTGVYYCTRAGYYVPFAYWGQGTLVTVSS | 71 |
| 6C7H14 | EVQLVESGGGLVQPGGSLRLSCAGSGFTFSNYAMNWVRQAPGKGLEWVAEIRLKSNNYVTNYAASVKGRFTISRDDSKNSVYLQMNSLKTEDTGVYYCTRAGYYVPFAYWGQGTLVTVSS | 72 |
| 6C7H15 | EVQLVESGGGLVQPGGSLRLSCAGSGFTFSNYSMNWVRQAPGKGLEWVAEIRLKSNNYVTNYAASVKGRFTISRDDSKNSVYLQMNSLKTEDTGVYYCTRAGYYVPFAYWGQGTLVTVSS | 73 |
| 6C7H16 | EVQLVESGGGLVQPGGSLRLSCAGSGFTFSNYLMNWVRQAPGKGLEWVAEIRLKSNNYVTNYAASVKGRFTISRDDSKNSVYLQMNSLKTEDTGVYYCTRAGYYVPFAYWGQGTLVTVSS | 74 |
| 6C7H17 | EVQLVESGGGLVQPGGSLRLSCAGSGFTFSNYYMNWVRQAPGKGLEWVAEIRLKSNNYVTNYAASVKGRFTISRDDSKNSVYLQMNSLKTEDTGVYYCTRAGYYVPFAYWGQGTLVTVSS | 75 |
| 6C7H18 | EVQLVESGGGLVQPGGSLRLSCAGSGFTFSNYHMNWVRQAPGKGLEWVAEIRLKSNNYVTNYAASVKGRFTISRDDSKNSVYLQMNSLKTEDTGVYYCTRAGYYVPFAYWGQGTLVTVSS | 76 |
| 6C7H19 | EVQLVESGGGLVQPGGSLRLSCAGSGFTFSNYRMNWVRQAPGKGLEWVAEIRLKSNNYVTNYAASVKGRFTISRDDSKNSVYLQMNSLKTEDTGVYYCTRAGYYVPFAYWGQGTLVTVSS | 77 |
| 6C7H20 | EVQLVESGGGLVQPGGSLRLSCAGSGFTFSNYPMNWVRQAPGKGLEWVAEIRLKSNNYVTNYAASVKGRFTISRDDSKNSVYLQMNSLKTEDTGVYYCTRAGYYVPFAYWGQGTLVTVSS | 78 |
| 6C7H21 | EVQLVESGGGLVQPGGSLRLSCAGSGFTFSNYQMNWVRQAPGKGLEWVAEIRLKSNNYVTNYAASVKGRFTISRDDSKNSVYLQMNSLKTEDTGVYYCTRAGYYVPFAYWGQGTLVTVSS | 79 |
| 6C7H22 | EVQLVESGGGLVQPGGSLRLSCAGSGFTFSNYTMNWVRQAPGKGLEWVAEIRLKSNNYVTNYAASVKGRFTISRDDSKNSVYLQMNSLKTEDTGVYYCTRAGYYVPFAYWGQGTLVTVSS | 80 |
| 6C7H23 | EVQLVESGGGLVQPGGSLRLSCAGSGFTFSNYVMNWVRQAPGKGLEWVAEIRLKSNNYVTNYAASVKGRFTISRDDSKNSVYLQMNSLKTEDTGVYYCTRAGYYVPFAYWGQGTLVTVSS | 81 |
| 6C7H24 | EVQLVESGGGLVQPGGSLRLSCAGSGFTFSNYNMNWVRQAPGKGLEWVAEIRLKSNNYVTNYAASVKGRFTISRDDSKNSVYLQMNSLKTEDTGVYYCTRAGYYVPFAYWGQGTLVTVSS | 82 |
| 6C7H25; 6C7H47; 6C7H48; 6C7H53; and 6C7H54 | EVQLVESGGGLVQPGGSLRLSCAGSGFTFSNYEMNWVRQAPGKGLEWVAEIRLKSNNYVTNYAASVKGRFTISRDDSKNSVYLQMNSLKTEDTGVYYCTRAGYYVPFAYWGQGTLVTVSS | 83 |

TABLE 11-continued

Heavy chain variable region sequences of anti-CD33 antibodies

| Antibody | HCVR | SEQ ID NO: |
|---|---|---|
| 6C7H26 | EVQLVESGGGLVQPGGSLRLSCAGSGFTESNYIMNWVRQA PGKGLEWVAEIRLKSNNYVTNYAASVKGRFTISRDDSKNS VYLQMNSLKTEDTGVYYCTRAGYYVPFAYWGQGTLVTVSS | 84 |
| 6C7H27 | EVQLVESGGGLVQPGGSLRLSCAGSGFTFSDYTMNWVRQA PGKGLEWVAEIRLKSNNYVTNYAASVKGRFTISRDDSKNS VYLQMNSLKTEDTGVYYCTRAGYYVPFAYWGQGTLVTVSS | 85 |
| 6C7H28 | EVQLVESGGGLVQPGGSLRLSCAGSGFTFSDYSMNWVRQA PGKGLEWVAEIRLKSNNYVTNYAASVKGRFTISRDDSKNS VYLQMNSLKTEDTGVYYCTRAGYYVPFAYWGQGTLVTVSS | 86 |
| 6C7H29 | EVQLVESGGGLVQPGGSLRLSCAGSGFTFSAYSMNWVRQA PGKGLEWVAEIRLKSNNYVTNYAASVKGRFTISRDDSKNS VYLQMNSLKTEDTGVYYCTRAGYYVPFAYWGQGTLVTVSS | 87 |
| 6C7H30 | EVQLVESGGGLVQPGGSLRLSCAGSGFTFSNYWMNWVRQA PGKGLEWVAEIRLKSNNYVTNYAASVKGRFTISRDDSKNS VYLQMNSLKTEDTGVYYCTRAGYYVPFAYWGQGTLVTVSS | 88 |
| 6C7H31; 6C7H32; 6C7H33; and 6C7H34 | EVQLVESGGGLVQPGGSLRLSCAASGSTFSEYDMLWVRQA PGKGLEWVGEIRLKSNNYVTNYAASVKGRFTISRDDSKNS VYLQMNSLKTEDTGVYYCTRAGYYVPFAYWGQGTLVTVSS | 89 |
| 6C7H35; 6C7H36; 6C7H37; and 6C7H38 | EVQLVESGGGLVQPGGSLRLSCAASGFTFSEYAMLWVRQA PGKGLEWVGEIRLKSNNYVTNYAASVKGRFTISRDDSKNS VYLQMNSLKTEDTGVYYCTRAGYYVPFTYWGQGTLVTVSS | 90 |
| 6C7H39; 6C7H40; 6C7H41; and 6C7H42 | EVQLVESGGGLVQPGGSLRLSCAASGFTFSEYDMLWVRQA PGKGLEWVGEIRLKSNNYVTNYAASVKGRFTISRDDTKNS VYLQMNSLKTEDTGVYYCTRAGYYVPFAYWGQGTLVTVSS | 91 |
| 6C7H43; 6C7H44; 6C7H49; and 6C7H50 | EVQLVESGGGLVQPGGSLRLSCAASGFTFSEYDMLWVRQA PGKGLEWVGEIRLKSNNYVTNYAASVKGRFTISRDDSKNS VYLQMNSLKTEDTGVYYCTRAGYYVPFAYWGQGTLVTVSS | 92 |
| 6C7H45; 6C7H46; 6C7H51; and 6C7H52 | EVQLVESGGGLVQPGGSLRLSCAASGFTFSEYAMLWVRQA PGKGLEWVGEIRLKSNNYVTNYAASVKGRFTISRDDSKNS VYLQMNSLKTEDTGVYYCTRAGYYVPFAYWGQGTLVTVSS | 93 |

TABLE 12

Light chain variable region sequences of anti-CD33 antibodies

| Antibody | LCVR | SEQ ID NO: |
|---|---|---|
| 6C7H1 and 6C7H2 | QLVLTQSPSASASLGASVKLTCTLSSQHSTYTIEW HQQQPEKGPRYLMKLKKDGSHSTGDGIPDRFSGSS SGAERYLTISSLQSEDEADYYCGVGDTIKEQFVYV FGGGTKLTVL | 94 |
| 6C7H3; 6C7H4; and 6C7H5 | QLVLTQSPSASASLGASVKLTCTLSSQHSTYTIEW YQQQPEKGPRYLMELKKDGSHSTGDGIPDRFSGSS SGAERYLTISSLQSEDEADYYCGVGDTIKEQFVYV FGGGTKLTVL | 95 |
| 6C7H6 and 6C7H7 | QLVLTQSPSASASLGASAKLTCTLSSQHSTYTIEW YQQQPEKGPRYVMELKKDGSHSTGDGIPDRFSGSS SGAERYLTISSIQSEDEADYICGVGDTIKEQFVYV FGGGTKVTVL | 96 |
| 6C7H8; 6C7H10; 6C7H12; 6C7H13; 6C7H14; 6C7H15; 6C7H16; 6C7H17; 6C7H18; 6C7H19; 6C7H20; 6C7H21; 6C7H22; 6C7H23; 6C7H24; 6C7H25; 6C7H26; 6C7H27; 6C7H28; 6C7H29; and 6C7H30 | QLVLTQSPSASASLGASVKLTCTLSSQHSTYTIEW YQQQPEKGPRYLMELKKEGSHSTGDGIPDRFSGSS SGAERYLTISSLQSEDEADYYCGVGDTIKEQFVYV FGGGTKLTVL | 97 |

TABLE 12-continued

Light chain variable region sequences of anti-CD33 antibodies

| Antibody | LCVR | SEQ ID NO: |
|---|---|---|
| 6C7H9 | QLVLTQSPSASASLGASVKLTCTLSSQHSTYTIEWYQQQPEKGPRYLMELKKKGSHSTGDGIPDRFSGSSSGAERYLTISSLQSEDEADYYCGVGDTIKEQFVYVFGGGTKLTVL | 98 |
| 6C7H11 | QLVLTQSPSASASLGASVKLTCTLSSQHSTYTIEWYQQQPEKGPRYLMELKKGGSHSTGDGIPDRFSGSSSGAERYLTISSLQSEDEADYYCGVGDTIKEQFVYVFGGGTKLTVL | 99 |
| 6C7H31; 6C7H35; 6C7H39; 6C7H49; 6C7H51; and 6C7H53 | QPVLTQSPSASASLGASVKLTCTLSSQHSTYTIEWYQQQPEKGPRYLMELKKEGSHSTGDGIPDRFSGSSSGAERYLTISSLQSEDEADYYCGVGVTIKEQFVYVFGGGTKLTVL | 100 |
| 6C7H32; 6C7H36; 6C7H40; 6C7H43; 6C7H45; and 6C7H47 | QLMLTQSPSASASLGASVKLTCTLSSQHSTYTIEWYQQQPGKGPRYLMELKKEGSHSTGDGIPDRFSGSSSGAERYLTISSLQSEDEADYYCGVGHTIKEQFVYEFGGGTKLTVL | 101 |
| 6C7H33; 6C7H37; 6C7H41; 6C7H50; 6C7H52; and 6C7H54 | QLMLTQSPSASASLGASVKLTCTLSSQHSTYTIEWYQQQPGKGPRYLMELKKEGSHSTGDGIPDRFSGSSSGAERYLTISSLQSEDEADYYCGVGHTIKEQFVYVFGGGTKLTVL | 102 |
| 6C7H34; 6C7H38; 6C7H42; 6C7H44; 6C7H46; and 6C7H48 | QPMLTQSPSASASLGASVKLTCTLSSQHSTYTIEWYQQQPGKGPRYLMELKKEGSHSTGDGIPDRFSGSSSGAERYLTISSLQSEDEADYYCGVGLTIKEQFVYVFGGGTKLTVL | 103 |

Example 4: Characterization of the Impact of the Fc Region on an Internalizing Anti-CD33 Antibody The purpose of this example was to evaluate the impact of the Fc on the ability of an anti-CD33 antibody to decrease the cell surface level of CD33 on primary myeloid cells in vitro and in vivo.

The Fc region of an antibody can interact with Fcγ receptors expressed on the surface of cells, and myeloid and other immune cells that endogenously express CD33 also express multiple Fcγ receptors. Thus, the impact of different human IgG isotypes' interaction between the antibody's Fc and cell-surface Fcγ receptors and the clustering ability of the antibodies on the ability of the antibody to internalize the receptor was tested.

Figure 12A:
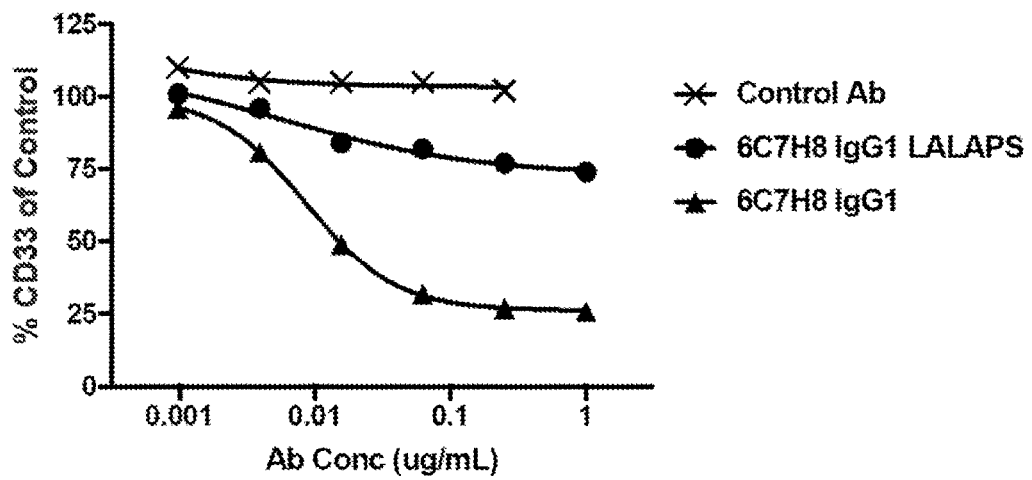
FIG. 12A, FIG. 12B, and FIG. 12C set forth data showing anti-CD33 antibody variants with Fc variants reduce cell surface levels of CD33 in primary human dendritic cells.
Figure 12B:
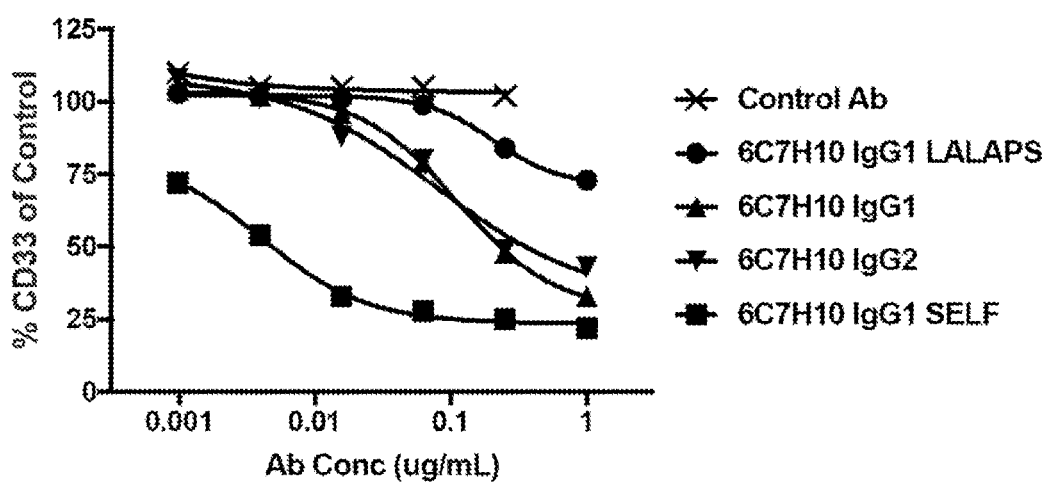
Figure 12C:
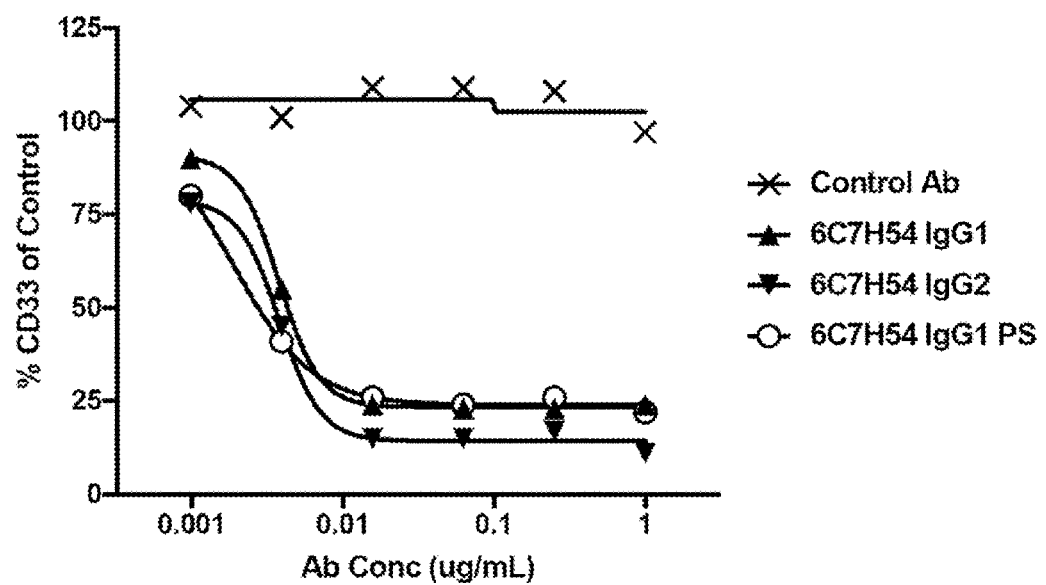

Anti-CD33 antibodies containing the 6C7H8, the 6C7H10, or the 6C7H54 variable regions and different human IgG variants were generated. The Fc's tested included IgG1, which binds all Fcγ receptors; IgG1 P331S, which contains the P331S mutation and shows decreased binding to C1q but binds all Fcγ receptors; IgG1 IgG1 SELF, which contains the S267E and L328F mutations and exhibits enhanced binding to CD32B and the R131 variant of CD32A; IgG2, which shows substantial binding only to CD32A; and IgG1 LALAPS, which contains the L234A, L235A, and P331S mutations, and exhibits little or no binding to any of the Fcγ receptors. The antibodies were evaluated for their ability to reduce the level of cell-surface CD33 on primary human dendritic cells, according to the method described in Example 2. The data are shown in FIGS. 12A, 12B, and 12C; Table 13 summarizes the half-maximal effective concentration ($EC_{50}$) and the maximal CD33 downregulation by the antibodies.

TABLE 13

CD33 cell surface downregulation with Fc variant anti-CD33 antibodies

| Antibody | Receptor downregulation, (pM, $EC_{50}$) | Fold change in potency from IgG1 | Maximal downregulation (% CD33 remaining) |
|---|---|---|---|
| 6C7H8 IgG1 | 77.9 | — | 21.5 |
| 6C7H8 IgG1 LALAPS | 83.7 | 0.93 | 67.4 |
| 6C7H10 IgG1 | 777.6 | — | 21.2 |
| 6C7H10 IgG2 | 772.5 | 1.01 | 24.2 |
| 6C7H10 IgG1 SELF | 30.1 | 25.8 | 19.6 |
| 6C7H10 IgG1 LALAPS | 1352.2 | 0.58 | 62.3 |
| 6C7H54 IgG1 | 30.2 | — | 26.1 |
| 6C7H54 IgG2 | 25.3 | 1.20 | 14.3 |
| 6C7H54 IgG1 PS | 12.6 | 2.40 | 23.9 |

The anti-CD33 antibodies constructed using different Fc variants exhibited a range of abilities to reduce the levels of CD33 on the surface of dendritic cells. The IgG1 SELF isotype conveyed the strongest potency, as antibody 6C7H10 on IgG1 SELF was 25.8-fold more potent than antibody 6C7H10 IgG1 antibody in downregulating CD33, and the two antibodies showed similar maximal levels of CD33 reduction. Surprisingly, antibody 6C7H8 IgG1 LAL-APS and antibody 6C7H10 IgG1 LALAPS antibodies were substantially less effective in downregulating CD33 than their cognate wild-type IgG1 antibodies, with both IgG1 LALAPS antibodies reducing CD33 levels by less than 40%. Antibody 6C7H10 IgG2 and antibody 6C7H54 IgG2 antibodies were similar in potency to their wild-type IgG1 counterparts. While antibody 6C7H10 IgG2 antibody maximally reduced CD33 to a similar level as antibody 6C7H10 IgG1, antibody 6C7H54 IgG2 antibody showed more extensive maximal CD33 reduction than antibody 6C7H54 IgG1. In contrast, antibody 6C7H54 IgG1 PS showed slightly improved potency in downregulating CD33 compared to that observed with antibody 6C7H54 IgG1, but the two antibodies showed similar maximal CD33 reduction. These data showed that the Fc region strongly affected both potency and maximal receptor reduction by an anti-CD33 antibody, suggesting that receptor downregulation is enhanced by interaction of the antibody with one or more Fcγ receptors.

INFORMAL SEQUENCE LISTING
CD33 Sequences (SEQ ID NOs: 1-2)
Amino acid sequence of human CD33 (SEQ ID NO: 1):
MPLLLLLPLLWAGALAMDPNFWLQVQESVTVQEGLCVLVPCTFFHPIPY

YDKNSPVHGYWFREGAIISRDSPVATNKLDQEVQEETQGRFRLLGDPSR

NNCSLSIVDARRRDNGSYFFRMERGSTKYSYKSPQLSVHVTDLTHRPKI

LIPGTLEPGHSKNLTCSVSWACEQGTPPIFSWLSAAPTSLGPRTTHSSV

LIITPRPQDHGTNLTCQVKFAGAGVTTERTIQLNVTYVPQNPTTGIFPG

DGSGKQETRAGVVHGAIGGAGVTALLALCLCLIFFIVKTHRRKAARTAV

GRNDTHPTTGSASPKHQKKSKLHGPTETSSCSGAAPTVEMDEELHYASL

NFHGMNPSKDTSTEYSEVRTQ

Amino acid sequence of cyno CD33 (SEQ ID NO: 2)
MDGEHLKGRNQGAQETSASDMPLLLLPLLWAGALAMDPRVRLEVQESVT

VQEGLCVLVPCTFFHPVPYHTRNSPVHGYWFREGAIVSLDSPVATNKLD

QEVQEETQGRFRLLGDPSRNNCSLSIVDARRRDNGSYFFRMEKGSTKYS

YKSTQLSVHVTDLTHRPQILIPGALDPDHSKNLTCSVPWACEQGTPPIF

SWMSAAPTSLGLRTTHSSVLIITPRPQDHGTNLTCQVKFPGAGVTTERT

IQLNVSYASQNPRTDIFLGDGSGKQGVVQGAIGGAGVTVLLALCLCLIF

FTVKTHRRKAARTAVGRIDTHPATGPTSSKHQKKSKLHGATETSGCSGT

TLTVEMDEELHYASLNFHGMNPSEDTSTEYSEVRTQ

Reference anti-CD33 antibody sequences (SEQ ID NOs: 3-4)
Heavy chain variable region of mouse 6C7 antibody (SEQ ID NO: 3)
EVKLEESGGGLVQPGGSMKLSCVGSGFTFSNYCMNWVRQSPEKGLEWVA

EIRLKSNNYVTNYVESVKGRFTISRDDSKSRVYLQMNNLRGEDTGFYYC

TRDGYYVPFAYWGQGTLVTVSA

Light chain variable region of mouse 6C7 antibody (SEQ ID NO: 4)
QLVLTQSSSASFSLGASAKLTCTLSSQHSTYTIEWYQQQPLKPPKYVME

LKKDGSHSTGDGIPDRFSGSSSGADRYLSISNIQPEDEAIYICGVGDTI

KEQFVYVFGGGTKVTVL

| | Heavy Chain Hypervariable Region Sequences (SEQ ID NOs: 8-30, 33, 38-40) | | | | | |
|---|---|---|---|---|---|---|
| Antibody | HVR-H1 | SEQ ID NO: | HVR-H2 | SEQ ID NO: | HVR-H3 | SEQ ID NO: |
| 6C7H1; 6C7H2; 6C7H3; 6C7H4; 6C7H5; 6C7H6; 6C7H7 | NYCMN | 8 | EIRLKSNNYV TNYAASVKG | 33 | DGYYVPFAY | 38 |
| 6C7H8 | NYCMN | 8 | EIRLKSNNYV TNYAASVKG | 33 | AGYYVPFAY | 39 |
| 6C7H9; 6C7H10; 6C7H11 | EYAMN | 9 | EIRLKSNNYV TNYAASVKG | 33 | AGYYVPFAY | 39 |
| 6C7H12 | NYGMN | 10 | EIRLKSNNYV TNYAASVKG | 33 | AGYYVPFAY | 39 |
| 6C7H13 | NYFMN | 11 | EIRLKSNNYV TNYAASVKG | 33 | AGYYVPFAY | 39 |
| 6C7H14 | NYAMN | 12 | EIRLKSNNYV TNYAASVKG | 33 | AGYYVPFAY | 39 |
| 6C7H15 | NYSMN | 13 | EIRLKSNNYV TNYAASVKG | 33 | AGYYVPFAY | 39 |
| 6C7H16 | NYLMN | 14 | EIRLKSNNYV TNYAASVKG | 33 | AGYYVPFAY | 39 |

-continued

Heavy Chain Hypervariable Region Sequences
(SEQ ID NOs: 8-30, 33, 38-40)

| Antibody | HVR-H1 | SEQ ID NO: | HVR-H2 | SEQ ID NO: | HVR-H3 | SEQ ID NO: |
|---|---|---|---|---|---|---|
| 6C7H17 | NYYMN | 15 | EIRLKSNNYVTNYAASVKG | 33 | AGYYVPFAY | 39 |
| 6C7H18 | NYHMN | 16 | EIRLKSNNYVTNYAASVKG | 33 | AGYYVPFAY | 39 |
| 6C7H19 | NYRMN | 17 | EIRLKSNNYVTNYAASVKG | 33 | AGYYVPFAY | 39 |
| 6C7H20 | NYPMN | 18 | EIRLKSNNYVTNYAASVKG | 33 | AGYYVPFAY | 39 |
| 6C7H21 | NYQMN | 19 | EIRLKSNNYVTNYAASVKG | 33 | AGYYVPFAY | 39 |
| 6C7H22 | NYTMN | 20 | EIRLKSNNYVTNYAASVKG | 33 | AGYYVPFAY | 39 |
| 6C7H23 | NYVMN | 21 | EIRLKSNNYVTNYAASVKG | 33 | AGYYVPFAY | 39 |
| 6C7H24 | NYNMN | 22 | EIRLKSNNYVTNYAASVKG | 33 | AGYYVPFAY | 39 |
| 6C7H25; 6C7H47; 6C7H48; 6C7H53; 6C7H54 | NYEMN | 23 | EIRLKSNNYVTNYAASVKG | 33 | AGYYVPFAY | 39 |
| 6C7H26 | NYIMN | 24 | EIRLKSNNYVTNYAASVKG | 33 | AGYYVPFAY | 39 |
| 6C7H27 | DYTMN | 25 | EIRLKSNNYVTNYAASVKG | 33 | AGYYVPFAY | 39 |
| 6C7H28 | DYSMN | 26 | EIRLKSNNYVTNYAASVKG | 33 | AGYYVPFAY | 39 |
| 6C7H29 | AYSMN | 27 | EIRLKSNNYVTNYAASVKG | 33 | AGYYVPFAY | 39 |
| 6C7H30 | NYWMN | 28 | EIRLKSNNYVTNYAASVKG | 33 | AGYYVPFAY | 39 |
| 6C7H31; 6C7H32; 6C7H33; 6C7H34 | EYDML | 29 | EIRLKSNNYVTNYAASVKG | 33 | AGYYVPFAY | 39 |
| 6C7H35; 6C7H36; 6C7H37; 6C7H38 | EYAML | 30 | EIRLKSNNYVTNYAASVKG | 33 | AGYYVPFTY | 40 |
| 6C7H39; 6C7H40; 6C7H41; 6C7H42 | EYDML | 29 | EIRLKSNNYVTNYAASVKG | 33 | AGYYVPFAY | 39 |
| 6C7H43; 6C7H44; 6C7H49; 6C7H50 | EYDML | 29 | EIRLKSNNYVTNYAASVKG | 33 | AGYYVPFAY | 39 |
| 6C7H45; 6C7H46; 6C7H51; 6C7H52 | EYAML | 30 | EIRLKSNNYVTNYAASVKG | 33 | AGYYVPFAY | 39 |

Light Chain Hypervariable Region Sequences
(SEQ ID NOs: 47, 52-55, 58-62)

| Antibody | HVR-L1 | SEQ ID NO: | HVR-L2 | SEQ ID NO: | HVR-L3 | SEQ ID NO: |
|---|---|---|---|---|---|---|
| 6C7H1; 6C7H2; 6C7H3; 6C7H4; 6C7H5; 6C7H6; 6C7H7 | TLSSQHSTYTIE | 47 | LKKDGSHSTGD | 52 | GVGDTIKEQFVYV | 58 |
| 6C7H8; 6C7H10; 6C7H12; 6C7H13; 6C7H14; 6C7H15; 6C7H16; 6C7H17; 6C7H18; 6C7H19; 6C7H20; 6C7H21; 6C7H22; 6C7H23; 6C7H24; 6C7H25; 6C7H26; 6C7H27; 6C7H28; 6C7H29; 6C7H30 | TLSSQHSTYTIE | 47 | LKKEGSHSTGD | 53 | GVGDTIKEQFVYV | 58 |
| 6C7H9 | TLSSQHSTYTIE | 47 | LKKKGSHSTGD | 54 | GVGDTIKEQFVYV | 58 |
| 6C7H11 | TLSSQHSTYTIE | 47 | LKKGGSHSTGD | 55 | GVGDTIKEQFVYV | 58 |
| 6C7H31; 6C7H35; 6C7H39; 6C7H49; 6C7H51; 6C7H53 | TLSSQHSTYTIE | 47 | LKKEGSHSTGD | 53 | GVGVTIKEQFVYV | 59 |
| 6C7H32; 6C7H36; 6C7H40; 6C7H43; 6C7H45; 6C7H47 | TLSSQHSTYTIE | 47 | LKKEGSHSTGD | 53 | GVGHTIKEQFVYE | 60 |
| 6C7H33; 6C7H37; 6C7H41; 6C7H50; 6C7H52; 6C7H54 | TLSSQHSTYTIE | 47 | LKKEGSHSTGD | 53 | GVGHTIKEQFVYV | 61 |
| 6C7H34; 6C7H38; 6C7H42; 6C7H44; 6C7H46; 6C7H48 | TLSSQHSTYTIE | 47 | LKKEGSHSTGD | 53 | GVGLTIKEQFVYV | 62 |

Heavy Chain Framework Sequences
(SEQ ID NOs: 5-7, 31-32, 34-37, 41)

| Antibody | VH FR1 | SEQ ID NO: | VH FR2 | SEQ ID NO: | VH FR3 | SEQ ID NO: | VH FR4 | SEQ ID NO: |
|---|---|---|---|---|---|---|---|---|
| 6C7H1; 6C7H3; 6C7H6 | EVQLVESGGGLVQPGGSLRLSCAASGFTFS | 5 | WVRQAPGKGLEWVG | 31 | RFTISRDDSKNSLYLQMNSLKTEDTAVYYCAR | 34 | WGQGTLVTVSS | 41 |
| 6C7H2; 6C7H5; 6C7H8 | EVQLVESGGGLVQPGGSLRLSCAGSGFTFS | 6 | WVRQAPGKGLEWVA | 32 | RFTISRDDSKNSVYLQMNSLKTEDTGVYYCTR | 35 | WGQGTLVTVSS | 41 |
| 6C7H4; 6C7H7 | EVQLVESGGGLVQPGGSLRLSCAGSGFTFS | 6 | WVRQAPGKGLEWVA | 32 | RFTISRDDSKNSLYLQMNSLKTEDTAVYYCTR | 36 | WGQGTLVTVSS | 41 |
| 6C7H9; 6C7H10; 6C7H11 | EVQLVESGGGLVQPG | 5 | WVRQAPGKGLEWVG | 31 | RFTISRDDSKNSVYLQMN | 35 | WGQGTLVTVSS | 41 |

-continued

Heavy Chain Framework Sequences
(SEQ ID NOs: 5-7, 31-32, 34-37, 41)

| Antibody | VH FR1 | SEQ ID NO: | VH FR2 | SEQ ID NO: | VH FR3 | SEQ ID NO: | VH FR4 | SEQ ID NO: |
|---|---|---|---|---|---|---|---|---|
| | GSLRLSCAASGFTFS | | | | SLKTEDTGVYYCTR | | | |
| 6C7H12; 6C7H13; 6C7H14; 6C7H15; 6C7H16; 6C7H17; 6C7H18; 6C7H19; 6C7H20; 6C7H21; 6C7H22; 6C7H23; 6C7H24; 6C7H25; 6C7H26; 6C7H27; 6C7H28; 6C7H29; 6C7H30; 6C7H47; 6C7H48; 6C7H53; 6C7H54 | EVQLVESGGGLVQPGGSLRLSCAGSGFTFS | 6 | WVRQAPGKGLEWVA | 32 | RFTISRDDSKNSVYLQMNSLKTEDTGVYYCTR | 35 | WGQGTLVTVSS | 41 |
| 6C7H31; 6C7H32; 6C7H33; 6C7H34 | EVQLVESGGGLVQPGGSLRLSCAASGSTFS | 7 | WVRQAPGKGLEWVG | 31 | RFTISRDDSKNSVYLQMNSLKTEDTGVYYCTR | 35 | WGQGTLVTVSS | 41 |
| 6C7H35; 6C7H36; 6C7H37; 6C7H38; 6C7H43; 6C7H44; 6C7H45; 6C7H46; 6C7H49; 6C7H50; 6C7H51; 6C7H52 | EVQLVESGGGLVQPGGSLRLSCAASGFTFS | 5 | WVRQAPGKGLEWVG | 31 | RFTISRDDSKNSVYLQMNSLKTEDTGVYYCTR | 35 | WGQGTLVTVSS | 41 |
| 6C7H39; 6C7H40; 6C7H41; 6C7H42 | EVQLVESGGGLVQPGGSLRLSCAASGFTFS | 5 | WVRQAPGKGLEWVG | 31 | RFTISRDDTKNSVYLQMNSLKTEDTGVYYCTR | 37 | WGQGTLVTVSS | 41 |

Light Chain Framework Sequences
(SEQ ID NOs. 42-46, 48-51, 56-57, 63-64)

| Antibody | VL FR1 | SEQ ID NO: | VL FR2 | SEQ ID NO: | VL FR3 | SEQ ID NO: | VL FR4 | SEQ ID NO: |
|---|---|---|---|---|---|---|---|---|
| 6C7H1; 6C7H2 | QLVLTQSPSASASLGASVKLTC | 42 | WHQQQPEKGPRYLMK | 48 | GIPDRFSGSSGAERYLTISSLQSEDEADYYC | 56 | FGGGTKLTVL | 63 |

| Light Chain Framework Sequences (SEQ ID NOs. 42-46, 48-51, 56-57, 63-64) ||||||||
|---|---|---|---|---|---|---|---|
| Antibody | VL FR1 | SEQ ID NO: | VL FR2 | SEQ ID NO: | VL FR3 | SEQ ID NO: | VL FR4 | SEQ ID NO: |
| 6C7H3; 6C7H4; 6C7H5; 6C7H8; 6C7H10; 6C7H12; 6C7H13; 6C7H14; 6C7H15; 6C7H16; 6C7H17; 6C7H18; 6C7H19; 6C7H20; 6C7H21; 6C7H22; 6C7H23; 6C7H24; 6C7H25; 6C7H26; 6C7H27; 6C7H28; 6C7H29; 6C7H30 | QLVLT QSPSA SASLG ASVKL TC | 42 | WYQQQ PEKGP RYLME | 49 | GIPDR FSGSS SGAER YLTIS SLQSE DEADY YC | 56 | FGGGTKL TVL | 63 |
| 6C7H6; 6C7H7 | QLVLT QSPSA SASLG ASAKL TC | 43 | WYQQQ PEKGP RYVME | 50 | GIPDR FSGSS SGAER YLTIS SIQSE DEADY IC | 57 | FGGGTKV TVL | 64 |
| 6C7H9; 6C7H11 | QLVLT QSPSA SASLG ASVKL TC | 42 | WYQQQ PEKGP RYLME | 49 | GIPDR FSGSS SGAER YLTIS SLQSE DEADY YC | 56 | FGGGTKL TVL | 63 |
| 6C7H31; 6C7H35; 6C7H39; 6C7H49; 6C7H51; 6C7H53 | QPVLT QSPSA SASLG ASVKL TC | 44 | WYQQQ PEKGP RYLME | 49 | GIPDR FSGSS SGAER YLTIS SLQSE DEADY YC | 56 | FGGGTKL TVL | 63 |
| 6C7H32; 6C7H36; 6C7H40; 6C7H43; 6C7H45; 6C7H47; 6C7H33; 6C7H37; 6C7H41; 6C7H50; 6C7H52; 6C7H54 | QLMLT QSPSA SASLG ASVKL TC | 45 | WYQQQ PGKGP RYLME | 51 | GIPDR FSGSS SGAER YLTIS SLQSE DEADY YC | 56 | FGGGTKL TVL | 63 |
| 6C7H34; 6C7H38; 6C7H42; 6C7H44; 6C7H46; 6C7H48 | QPMLT QSPSA SASLG ASVKL TC | 46 | WYQQQ PGKGP RYLME | 51 | GIPDR FSGSS SGAER YLTIS SLQSE DEADY YC | 56 | FGGGTKL TVL | 63 |

| | Heavy Chain Variable Region Sequences (SEQ ID NOs: 65-93) | |
|---|---|---|
| Antibody | HCVR | SEQ ID NO: |
| 6C7H1; 6C7H3; and 6C7H6 | EVQLVESGGGLVQPGGSLRLSCAASGFTFSNYCMNWVRQA PGKGLEWVGEIRLKSNNYVTNYAASVKGRFTISRDDSKNS LYLQMNSLKTEDTAVYYCARDGYYVPFAYWGQGTLVTVSS | 65 |
| 6C7H2 and 6C7H5 | EVQLVESGGGLVQPGGSLRLSCAGSGFTFSNYCMNWVRQA PGKGLEWVAEIRLKSNNYVTNYAASVKGRFTISRDDSKNS VYLQMNSLKTEDTGVYYCTRDGYYVPFAYWGQGTLVTVSS | 66 |
| 6C7H4 and 6C7H7 | EVQLVESGGGLVQPGGSLRLSCAGSGFTFSNYCMNWVRQA PGKGLEWVAEIRLKSNNYVTNYAASVKGRFTISRDDSKNS LYLQMNSLKTEDTAVYYCTRDGYYVPFAYWGQGTLVTVSS | 67 |
| 6C7H8 | EVQLVESGGGLVQPGGSLRLSCAGSGFTFSNYCMNWVRQA PGKGLEWVAEIRLKSNNYVTNYAASVKGRFTISRDDSKNS VYLQMNSLKTEDTGVYYCTRAGYYVPFAYWGQGTLVTVSS | 68 |
| 6C7H9; 6C7H10; and 6C7H11 | EVQLVESGGGLVQPGGSLRLSCAASGFTFSEYAMNWVRQA PGKGLEWVGEIRLKSNNYVTNYAASVKGRFTISRDDSKNS VYLQMNSLKTEDTGVYYCTRAGYYVPFAYWGQGTLVTVSS | 69 |
| 6C7H12 | EVQLVESGGGLVQPGGSLRLSCAGSGFTFSNYGMNWVRQA PGKGLEWVAEIRLKSNNYVTNYAASVKGRFTISRDDSKNS VYLQMNSLKTEDTGVYYCTRAGYYVPFAYWGQGTLVTVSS | 70 |
| 6C7H13 | EVQLVESGGGLVQPGGSLRLSCAGSGFTFSNYFMNWVRQA PGKGLEWVAEIRLKSNNYVTNYAASVKGRFTISRDDSKNS VYLQMNSLKTEDTGVYYCTRAGYYVPFAYWGQGTLVTVSS | 71 |
| 6C7H14 | EVQLVESGGGLVQPGGSLRLSCAGSGFTFSNYAMNWVRQA PGKGLEWVAEIRLKSNNYVTNYAASVKGRFTISRDDSKNS VYLQMNSLKTEDTGVYYCTRAGYYVPFAYWGQGTLVTVSS | 72 |
| 6C7H15 | EVQLVESGGGLVQPGGSLRLSCAGSGFTFSNYSMNWVRQA PGKGLEWVAEIRLKSNNYVTNYAASVKGRFTISRDDSKNS VYLQMNSLKTEDTGVYYCTRAGYYVPFAYWGQGTLVTVSS | 73 |
| 6C7H16 | EVQLVESGGGLVQPGGSLRLSCAGSGFTFSNYLMNWVRQA PGKGLEWVAEIRLKSNNYVTNYAASVKGRFTISRDDSKNS VYLQMNSLKTEDTGVYYCTRAGYYVPFAYWGQGTLVTVSS | 74 |
| 6C7H17 | EVQLVESGGGLVQPGGSLRLSCAGSGFTFSNYYMNWVRQA PGKGLEWVAEIRLKSNNYVTNYAASVKGRFTISRDDSKNS VYLQMNSLKTEDTGVYYCTRAGYYVPFAYWGQGTLVTVSS | 75 |
| 6C7H18 | EVQLVESGGGLVQPGGSLRLSCAGSGFTFSNYHMNWVRQA PGKGLEWVAEIRLKSNNYVTNYAASVKGRFTISRDDSKNS VYLQMNSLKTEDTGVYYCTRAGYYVPFAYWGQGTLVTVSS | 76 |
| 6C7H19 | EVQLVESGGGLVQPGGSLRLSCAGSGFTFSNYRMNWVRQA PGKGLEWVAEIRLKSNNYVTNYAASVKGRFTISRDDSKNS VYLQMNSLKTEDTGVYYCTRAGYYVPFAYWGQGTLVTVSS | 77 |
| 6C7H20 | EVQLVESGGGLVQPGGSLRLSCAGSGFTFSNYPMNWVRQA PGKGLEWVAEIRLKSNNYVTNYAASVKGRFTISRDDSKNS VYLQMNSLKTEDTGVYYCTRAGYYVPFAYWGQGTLVTVSS | 78 |
| 6C7H21 | EVQLVESGGGLVQPGGSLRLSCAGSGFTFSNYQMNWVRQA PGKGLEWVAEIRLKSNNYVTNYAASVKGRFTISRDDSKNS VYLQMNSLKTEDTGVYYCTRAGYYVPFAYWGQGTLVTVSS | 79 |
| 6C7H22 | EVQLVESGGGLVQPGGSLRLSCAGSGFTFSNYTMNWVRQA PGKGLEWVAEIRLKSNNYVTNYAASVKGRFTISRDDSKNS VYLQMNSLKTEDTGVYYCTRAGYYVPFAYWGQGTLVTVSS | 80 |
| 6C7H23 | EVQLVESGGGLVQPGGSLRLSCAGSGFTFSNYVMNWVRQA PGKGLEWVAEIRLKSNNYVTNYAASVKGRFTISRDDSKNS VYLQMNSLKTEDTGVYYCTRAGYYVPFAYWGQGTLVTVSS | 81 |
| 6C7H24 | EVQLVESGGGLVQPGGSLRLSCAGSGFTFSNYNMNWVRQA PGKGLEWVAEIRLKSNNYVTNYAASVKGRFTISRDDSKNS VYLQMNSLKTEDTGVYYCTRAGYYVPFAYWGQGTLVTVSS | 82 |
| 6C7H25; 6C7H47; 6C7H48; 6C7H53; and 6C7H54 | EVQLVESGGGLVQPGGSLRLSCAGSGFTFSNYEMNWVRQA PGKGLEWVAEIRLKSNNYVTNYAASVKGRFTISRDDSKNS VYLQMNSLKTEDTGVYYCTRAGYYVPFAYWGQGTLVTVSS | 83 |

Heavy Chain Variable Region Sequences (SEQ ID NOs: 65-93)

| Antibody | HCVR | SEQ ID NO: |
|---|---|---|
| 6C7H26 | EVQLVESGGGLVQPGGSLRLSCAGSGFTFSNYIMNWVRQA PGKGLEWVAEIRLKSNNYVTNYAASVKGRFTISRDDSKNS VYLQMNSLKTEDTGVYYCTRAGYYVPFAYWGQGTLVTVSS | 84 |
| 6C7H27 | EVQLVESGGGLVQPGGSLRLSCAGSGFTFSDYTMNWVRQA PGKGLEWVAEIRLKSNNYVTNYAASVKGRFTISRDDSKNS VYLQMNSLKTEDTGVYYCTRAGYYVPFAYWGQGTLVTVSS | 85 |
| 6C7H28 | EVQLVESGGGLVQPGGSLRLSCAGSGFTFSDYSMNWVRQA PGKGLEWVAEIRLKSNNYVTNYAASVKGRFTISRDDSKNS VYLQMNSLKTEDTGVYYCTRAGYYVPFAYWGQGTLVTVSS | 86 |
| 6C7H29 | EVQLVESGGGLVQPGGSLRLSCAGSGFTFSAYSMNWVRQA PGKGLEWVAEIRLKSNNYVTNYAASVKGRFTISRDDSKNS VYLQMNSLKTEDTGVYYCTRAGYYVPFAYWGQGTLVTVSS | 87 |
| 6C7H30 | EVQLVESGGGLVQPGGSLRLSCAGSGFTFSNYWMNWVRQA PGKGLEWVAEIRLKSNNYVTNYAASVKGRFTISRDDSKNS VYLQMNSLKTEDTGVYYCTRAGYYVPFAYWGQGTLVTVSS | 88 |
| 6C7H31; 6C7H32; 6C7H33; and 6C7H34 | EVQLVESGGGLVQPGGSLRLSCAAGSTFSEYDMLWVRQA PGKGLEWVGEIRLKSNNYVTNYAASVKGRFTISRDDSKNS VYLQMNSLKTEDTGVYYCTRAGYYVPFAYWGQGTLVTVSS | 89 |
| 6C7H35; 6C7H36; 6C7H37; and 6C7H38 | EVQLVESGGGLVQPGGSLRLSCAASGFTFSEYAMLWVRQA PGKGLEWVGEIRLKSNNYVTNYAASVKGRFTISRDDSKNS VYLQMNSLKTEDTGVYYCTRAGYYVPFTYWGQGTLVTVSS | 90 |
| 6C7H39; 6C7H40; 6C7H41; and 6C7H42 | EVQLVESGGGLVQPGGSLRLSCAASGFTFSEYDMLWVRQA PGKGLEWVGEIRLKSNNYVTNYAASVKGRFTISRDDTKNS VYLQMNSLKTEDTGVYYCTRAGYYVPFAYWGQGTLVTVSS | 91 |
| 6C7H43; 6C7H44; 6C7H49; and 6C7H50 | EVQLVESGGGLVQPGGSLRLSCAASGFTFSEYDMLWVRQA PGKGLEWVGEIRLKSNNYVTNYAASVKGRFTISRDDSKNS VYLQMNSLKTEDTGVYYCTRAGYYVPFAYWGQGTLVTVSS | 92 |
| 6C7H45; 6C7H46; 6C7H51; and 6C7H52 | EVQLVESGGGLVQPGGSLRLSCAASGFTFSEYAMLWVRQA PGKGLEWVGEIRLKSNNYVTNYAASVKGRFTISRDDSKNS VYLQMNSLKTEDTGVYYCTRAGYYVPFAYWGQGTLVTVSS | 93 |

Light Chain Variable Region Sequences (SEQ ID NOs: 94-103)

| Antibody | LCVR | SEQ ID NO: |
|---|---|---|
| 6C7H1 and 6C7H2 | QLVLTQSPSASASLGASVKLTCTLSSQHSTYTIEW HQQQPEKGPRYLMKLKKDGSHSTGDGIPDRFSGSS SGAERYLTISSLQSEDEADYYCGVGDTIKEQFVYV FGGGTKLTVL | 94 |
| 6C7H3; 6C7H4; and 6C7H5 | QLVLTQSPSASASLGASVKLTCTLSSQHSTYTIEW YQQQPEKGPRYLMELKKDGSHSTGDGIPDRFSGSS SGAERYLTISSLQSEDEADYYCGVGDTIKEQFVYV FGGGTKLTVL | 95 |
| 6C7H6 and 6C7H7 | QLVLTQSPSASASLGASAKLTCTLSSQHSTYTIEW YQQQPEKGPRYVMELKKDGSHSTGDGIPDRFSGSS SGAERYLTISSIQSEDEADYICGVGDTIKEQFVYV FGGGTKVTVL | 96 |
| 6C7H8; 6C7H10; 6C7H12; 6C7H13; 6C7H14; 6C7H15; 6C7H16; 6C7H17; 6C7H18; 6C7H19; 6C7H20; 6C7H21; 6C7H22; 6C7H23; 6C7H24; 6C7H25; 6C7H26; 6C7H27; 6C7H28; 6C7H29; and 6C7H30 | QLVLTQSPSASASLGASVKLTCTLSSQHSTYTIEW YQQQPEKGPRYLMELKKEGSHSTGDGIPDRFSGSS SGAERYLTISSLQSEDEADYYCGVGDTIKEQFVYV FGGGTKLTVL | 97 |

-continued

Light Chain Variable Region Sequences (SEQ ID NOs: 94-103)

| Antibody | LCVR | SEQ ID NO: |
|---|---|---|
| 6C7H9 | QLVLTQSPSASASLGASVKLTCTLSSQHSTYTIEW YQQQPEKGPRYLMELKKKGSHSTGDGIPDRFSGSS SGAERYLTISSLQSEDEADYYCGVGDTIKEQFVYV FGGGTKLTVL | 98 |
| 6C7H11 | QLVLTQSPSASASLGASVKLTCTLSSQHSTYTIEW YQQQPEKGPRYLMELKKGGSHSTGDGIPDRFSGSS SGAERYLTISSLQSEDEADYYCGVGDTIKEQFVYV FGGGTKLTVL | 99 |
| 6C7H31; 6C7H35; 6C7H39; 6C7H49; 6C7H51; and 6C7H53 | QPVLTQSPSASASLGASVKLTCTLSSQHSTYTIEW YQQQPEKGPRYLMELKKEGSHSTGDGIPDRFSGSS SGAERYLTISSLQSEDEADYYCGVGVTIKEQFVYV FGGGTKLTVL | 100 |
| 6C7H32; 6C7H36; 6C7H40; 6C7H43; 6C7H45; and 6C7H47 | QLMLTQSPSASASLGASVKLTCTLSSQHSTYTIEW YQQQPGKGPRYLMELKKEGSHSTGDGIPDRFSGSS SGAERYLTISSLQSEDEADYYCGVGHTIKEQFVYE FGGGTKLTVL | 101 |
| 6C7H33; 6C7H37; 6C7H41; 6C7H50; 6C7H52; and 6C7H54 | QLMLTQSPSASASLGASVKLTCTLSSQHSTYTIEW YQQQPGKGPRYLMELKKEGSHSTGDGIPDRFSGSS SGAERYLTISSLQSEDEADYYCGVGHTIKEQFVYV FGGGTKLTVL | 102 |
| 6C7H34; 6C7H38; 6C7H42; 6C7H44; 6C7H46; and 6C7H48 | QPMLTQSPSASASLGASVKLTCTLSSQHSTYTIEW YQQQPGKGPRYLMELKKEGSHSTGDGIPDRFSGSS SGAERYLTISSLQSEDEADYYCGVGLTIKEQFVYV FGGGTKLTVL | 103 |

```
Miscellaneous Sequences
                                       (SEQ ID NO: 104)    35
motif D/Ex0-2YxxL/IX6-8YxxL/I (SEQ ID NO: 105)
ASTKGPSVFP LAPCSRSTSE STAALGCLVK DYFPEPVTVS

WNSGALTSGV HTFPAVLQSS GLYSLSSVVT VPSSNFGTQT    40

YTCNVDHKPS NTKVDKTVER KCCVECPPCP
```

Human Fc variant Sequences

| Human Fc variant | Amino acid sequence | SEQ ID NO: |
|---|---|---|
| IgG1-WT | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPELLGGPSVFLFPPKPKDTLMISRTPEVTCVVVDVS HEDPEVKFNWYVDGVEVHNAKTKPREEQYNSTYRV VSVLTVLHQDWLNGKEYKCKVSNKALPAPIEKTISK AKGQPREPQVYTLPPSRDELTKNQVSLTCLVKGFYPS DIAVEWESNGQPENNYKTTPPVLDSDGSFFLYSKLTV DKSRWQQGNVFSCSVMHEALHNHYTQKSLSLSPGK | 106 |
| IgG1-WT without terminal lysine | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPELLGGPSVFLFPPKPKDTLMISRTPEVTCVVVDVS HEDPEVKFNWYVDGVEVHNAKTKPREEQYNSTYRV VSVLTVLHQDWLNGKEYKCKVSNKALPAPIEKTISK AKGQPREPQVYTLPPSRDELTKNQVSLTCLVKGFYPS DIAVEWESNGQPENNYKTTPPVLDSDGSFFLYSKLTV DKSRWQQGNVFSCSVMHEALHNHYTQKSLSLSPG | 107 |
| IgG1-LALAPS (L234A, L235A, | ASTKGPSVFPLAPSSKSTSGGTAALGCLVKDYFPEPVT VSWNSGALTSGVHTFPAVLQSSGLYSLSSVVTVPSSS | 108 |

Human Fc variant Sequences

| Human Fc variant | Amino acid sequence | SEQ ID NO: |
|---|---|---|
| and P331S) | LGTQTYICNVNHKPSNTKVDKKVEPKSCDKTHTCPPC PAPEAAGGPSVFLFPPKPKDTLMISRTPEVTCVVVDVS HEDPEVKFNWYVDGVEVHNAKTKPREEQYNSTYRV VSVLTVLHQDWLNGKEYKCKVSNKALPASIEKTISK AKGQPREPQVYTLPPSRDELTKNQVSLTCLVKGFYPS DIAVEWESNGQPENNYKTTPPVLDSDGSFFLYSKLTV DKSRWQQGNVFSCSVMHEALHNHYTQKSLSLSPGK | |
| IgG1-LALAPS (L234A, L235A, and P331S) without terminal lysine | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPEAAGGPSVFLFPPKPKDTLMISRTPEVTCVVVDVS HEDPEVKFNWYVDGVEVHNAKTKPREEQYNSTYRV VSVLTVLHQDWLNGKEYKCKVSNKALPASIEKTISK AKGQPREPQVYTLPPSRDELTKNQVSLTCLVKGFYPS DIAVEWESNGQPENNYKTTPPVLDSDGSFFLYSKLTV DKSRWQQGNVFSCSVMHEALHNHYTQKSLSLSPG | 109 |
| IgG1-PS (P331S) | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPELLGGPSVFLFPPKPKDTLMISRTPEVTCVVVDVS HEDPEVKFNWYVDGVEVHNAKTKPREEQYNSTYRV VSVLTVLHQDWLNGKEYKCKVSNKALPASIEKTISK AKGQPREPQVYTLPPSRDELTKNQVSLTCLVKGFYPS DIAVEWESNGQPENNYKTTPPVLDSDGSFFLYSKLTV DKSRWQQGNVFSCSVMHEALHNHYTQKSLSLSPGK | 110 |
| IgG1-PS (P331S) without terminal lysine | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPELLGGPSVFLFPPKPKDTLMISRTPEVTCVVVDVS HEDPEVKFNWYVDGVEVHNAKTKPREEQYNSTYRV VSVLTVLHQDWLNGKEYKCKVSNKALPASIEKTISK AKGQPREPQVYTLPPSRDELTKNQVSLTCLVKGFYPS DIAVEWESNGQPENNYKTTPPVLDSDGSFFLYSKLTV DKSRWQQGNVFSCSVMHEALHNHYTQKSLSLSPG | 111 |
| IgG1-PSEG (P331S and E430G) | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPELLGGPSVFLFPPKPKDTLMISRTPEVTCVVVDVS HEDPEVKFNWYVDGVEVHNAKTKPREEQYNSTYRV VSVLTVLHQDWLNGKEYKCKVSNKALPASIEKTISK AKGQPREPQVYTLPPSRDELTKNQVSLTCLVKGFYPS DIAVEWESNGQPENNYKTTPPVLDSDGSFFLYSKLTV DKSRWQQGNVFSCSVMHGALHNHYTQKSLSLSPGK | 112 |
| IgG1-PSEG (P331S and E430G) without terminal lysine | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPELLGGPSVFLFPPKPKDTLMISRTPEVTCVVVDVS HEDPEVKFNWYVDGVEVHNAKTKPREEQYNSTYRV VSVLTVLHQDWLNGKEYKCKVSNKALPASIEKTISK AKGQPREPQVYTLPPSRDELTKNQVSLTCLVKGFYPS DIAVEWESNGQPENNYKTTPPVLDSDGSFFLYSKLTV DKSRWQQGNVFSCSVMHGALHNHYTQKSLSLSPG | 113 |
| IgG1-NSLF (N325S and L328F) | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPELLGGPSVFLFPPKPKDTLMISRTPEVTCVVVDVS HEDPEVKFNWYVDGVEVHNAKTKPREEQYNSTYRV VSVLTVLHQDWLNGKEYKCKVSSKAFPAPIEKTISKA KGQPREPQVYTLPPSRDELTKNQVSLTCLVKGFYPSD IAVEWESNGQPENNYKTTPPVLDSDGSFFLYSKLTVD KSRWQQGNVFSCSVMHEALHNHYTQKSLSLSPGK | 114 |
| IgG1-NSLF (N325S and L328F) without terminal lysine | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPELLGGPSVFLFPPKPKDTLMISRTPEVTCVVVDVS HEDPEVKFNWYVDGVEVHNAKTKPREEQYNSTYRV VSVLTVLHQDWLNGKEYKCKVSSKAFPAPIEKTISKA | 115 |

Human Fc variant Sequences

| Human Fc variant | Amino acid sequence | SEQ ID NO: |
|---|---|---|
| | KGQPREPQVYTLPPSRDELTKNQVSLTCLVKGFYPSD IAVEWESNGQPENNYKTTPPVLDSDGSFFLYSKLTVD KSRWQQGNVFSCSVMHEALHNHYTQKSLSLSPG | |
| IgG1-SELF (S267E and L328F) | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPELLGGPSVFLFPPKPKDTLMISRTPEVTCVVVDVE HEDPEVKFNWYVDGVEVHNAKTKPREEQYNSTYRV VSVLTVLHQDWLNGKEYKCKVSNKAFPAPIEKTISKA KGQPREPQVYTLPPSRDELTKNQVSLTCLVKGFYPSD IAVEWESNGQPENNYKTTPPVLDSDGSFFLYSKLTVD KSRWQQGNVFSCSVMHEALHNHYTQKSLSLSPGK | 116 |
| IgG1-SELF (S267E and L328F) without terminal lysine | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPELLGGPSVFLFPPKPKDTLMISRTPEVTCVVVDVE HEDPEVKFNWYVDGVEVHNAKTKPREEQYNSTYRV VSVLTVLHQDWLNGKEYKCKVSNKAFPAPIEKTISKA KGQPREPQVYTLPPSRDELTKNQVSLTCLVKGFYPSD IAVEWESNGQPENNYKTTPPVLDSDGSFFLYSKLTVD KSRWQQGNVFSCSVMHEALHNHYTQKSLSLSPG | 117 |
| IgG2 | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKCCVECPPCPA PPVAGPSVFLFPPKPKDTLMISRTPEVTCVVVDVSHED PEVQFNWYVDGVEVHNAKTKPREEQFNSTFRVVSVL TVVHQDWLNGKEYKCKVSNKGLPAPIEKTISKTKGQ PREPQVYTLPPSREEMTKNQVSLTCLVKGFYPSDIAV EWESNGQPENNYKTTPPMLDSDGSFFLYSKLTVDKS RWQQGNVFSCSVMHEALHNHYTQKSLSLSPGK | 118 |
| IgG2 without terminal lysine | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKCCVECPPCPA PPVAGPSVFLFPPKPKDTLMISRTPEVTCVVVDVSHED PEVQFNWYVDGVEVHNAKTKPREEQFNSTFRVVSVL TVVHQDWLNGKEYKCKVSNKGLPAPIEKTISKTKGQ PREPQVYTLPPSREEMTKNQVSLTCLVKGFYPSDIAV EWESNGQPENNYKTTPPMLDSDGSFFLYSKLTVDKS RWQQGNVFSCSVMHEALHNHYTQKSLSLSPG | 119 |

Full-length Antibody Sequences
(6C7H54 variable regions; IgG2)
Heavy Chain with Terminal Lysine
(SEQ ID NO: 120)

EVQLVESGGGLVQPGGSLRLSCAGSGFTFSNYEMNWVRQAPGKGLEW

VAEIRLKSNNYVTNYAASVKGRFTISRDDSKNSVYLQMNSLKTEDTG

VYYCTRAGYYVPFAYWGQGTLVTVSSASTKGPSVFPLAPCSRSTSES

TAALGCLVKDYFPEPVTVSWNSGALTSGVHTFPAVLQSSGLYSLSSV

VTVPSSNFGTQTYTCNVDHKPSNTKVDKTVERKCCVECPPCPAPPVA

GPSVFLFPPKPKDTLMISRTPEVTCVVVDVSHEDPEVQFNWYVDGVE

VHNAKTKPREEQFNSTFRVVSVLTVVHQDWLNGKEYKCKVSNKGLPA

PIEKTISKTKGQPREPQVYTLPPSREEMTKNQVSLTCLVKGFYPSDI

AVEWESNGQPENNYKTTPPMLDSDGSFFLYSKLTVDKSRWQQGNVFS

CSVMHEALHNHYTQKSLSLSPGK

Heavy Chain without Terminal Lysine
(SEQ ID NO: 121)

EVQLVESGGGLVQPGGSLRLSCAGSGFTFSNYEMNWVRQAPGKGLEW

VAEIRLKSNNYVTNYAASVKGRFTISRDDSKNSVYLQMNSLKTEDTG

VYYCTRAGYYVPFAYWGQGTLVTVSSASTKGPSVFPLAPCSRSTSES

TAALGCLVKDYFPEPVTVSWNSGALTSGVHTFPAVLQSSGLYSLSSV

VTVPSSNFGTQTYTCNVDHKPSNTKVDKTVERKCCVECPPCPAPPVA

GPSVFLFPPKPKDTLMISRTPEVTCVVVDVSHEDPEVQFNWYVDGVE

VHNAKTKPREEQFNSTFRVVSVLTVVHQDWLNGKEYKCKVSNKGLPA

PIEKTISKTKGQPREPQVYTLPPSREEMTKNQVSLTCLVKGFYPSDI

AVEWESNGQPENNYKTTPPMLDSDGSFFLYSKLTVDKSRWQQGNVFS

CSVMHEALHNHYTQKSLSLSPG

-continued

Light Chain
(SEQ ID NO: 122)
QLMLTQSPSASASLGASVKLTCTLSSQHSTYTIEWYQQQPGKGPRYL

MELKKEGSHSTGDGIPDRFSGSSSGAERYLTISSLQSEDEADYYCGV

GHTIKEQFVYVFGGGTKLTVLGQPKAAPSVTLFPPSSEELQANKATL

VCLISDFYPGAVTVAWKADSSPVKAGVETTTPSKQSNNKYAASSYLS

LTPEQWKSHRSYSCQVTHEGSTVEKTVAPTECS

---

What is claimed is:

1. An isolated antibody that binds to CD33, wherein the antibody comprises a heavy chain variable region comprising an HVR-H1, HVR-H2, and HVR-H3 and a light chain variable region comprising an HVR-L1, HVR-L2, and HVR-L3, wherein the HVR-H1 comprises the amino acid sequence of SEQ ID NO: 23, the HVR-H2 comprises the amino acid sequence of SEQ ID NO: 33, the HVR-H3 comprises the amino acid sequence of SEQ ID NO: 39, the HVR-L1 comprises the amino acid sequence of SEQ ID NO: 47, the HVR-L2 comprises the amino acid sequence of SEQ ID NO: 53, and the HVR-L3 comprises the amino acid sequence of SEQ ID NO: 60;

the HVR-H1 comprises the amino acid sequence of SEQ ID NO: 23, the HVR-H2 comprises the amino acid sequence of SEQ ID NO: 33, the HVR-H3 comprises the amino acid sequence of SEQ ID NO: 39, the HVR-L1 comprises the amino acid sequence of SEQ ID NO: 47, the HVR-L2 comprises the amino acid sequence of SEQ ID NO: 53, and the HVR-L3 comprises the amino acid sequence of SEQ ID NO: 62;

the HVR-H1 comprises the amino acid sequence of SEQ ID NO: 30, the HVR-H2 comprises the amino acid sequence of SEQ ID NO: 33, the HVR-H3 comprises the amino acid sequence of SEQ ID NO: 39, the HVR-L1 comprises the amino acid sequence of SEQ ID NO: 47, the HVR-L2 comprises the amino acid sequence of SEQ ID NO: 53, and the HVR-L3 comprises the amino acid sequence of SEQ ID NO: 61; or the HVR-H1 comprises the amino acid sequence of SEQ ID NO: 23, the HVR-H2 comprises the amino acid sequence of SEQ ID NO: 33, the HVR-H3 comprises the amino acid sequence of SEQ ID NO: 39, the HVR-L1 comprises the amino acid sequence of SEQ ID NO: 47, the HVR-L2 comprises the amino acid sequence of SEQ ID NO: 53, and the HVR-L3 comprises the amino acid sequence of SEQ ID NO: 61.

2. The antibody of claim 1, wherein the antibody comprises
- a heavy chain variable region comprising the amino acid sequence of SEQ ID NO: 83, and a light chain variable region comprising the amino acid sequence of SEQ ID NO: 101;
- a heavy chain variable region comprising the amino acid sequence of SEQ ID NO: 83, and a light chain variable region comprising the amino acid sequence of SEQ ID NO: 103;
- a heavy chain variable region comprising the amino acid sequence of SEQ ID NO: 93, and a light chain variable region comprising the amino acid sequence of SEQ ID NO: 102; or
- a heavy chain variable region comprising the amino acid sequence of SEQ ID NO: 83, and a light chain variable region comprising the amino acid sequence of SEQ ID NO: 102.

3. A monoclonal antibody that binds to human CD33, wherein the antibody comprises
- a heavy chain variable region comprising the amino acid sequence of SEQ ID NO: 83, and a light chain variable region comprising the amino acid sequence of SEQ ID NO: 101;
- a heavy chain variable region comprising the amino acid sequence of SEQ ID NO: 83, and a light chain variable region comprising the amino acid sequence of SEQ ID NO: 103;
- a heavy chain variable region comprising the amino acid sequence of SEQ ID NO: 93, and a light chain variable region comprising the amino acid sequence of SEQ ID NO: 102; or
- a heavy chain variable region comprising the amino acid sequence of SEQ ID NO: 83, and a light chain variable region comprising the amino acid sequence of SEQ ID NO: 102.

4. The antibody of claim 1, wherein the antibody is of the IgG class, the IgM class, or the IgA class.

5. The antibody of claim 4, wherein the antibody is of the IgG class and has an IgG1, IgG2, IgG3, or IgG4 isotype.

6. The antibody of claim 5, wherein the antibody comprises one or more amino acid substitutions in the Fc region at a residue position selected from the group consisting of: C127S, L234A, L234F, L235A, L235E, S267E, K322A, L328F, A330S, P331S, E345R, E430G, S440Y, and any combination thereof, wherein the numbering of the residues is according to EU numbering.

7. The antibody of claim 5, wherein the antibody has an IgG4 isotype, and wherein the antibody comprises an S228P amino acid substitution at residue position 228, an F234A amino acid substitution at residue position 234, and an L235A amino acid substitution at residue position 235, wherein the numbering of the residue position is according to EU numbering.

8. The antibody of claim 6, wherein:
(a) the Fc region comprises an amino acid substitution at position E430G, wherein the numbering of the residue position is according to EU numbering;
(b) the Fc region comprises an amino acid substitution at positions L234A, L235A, and P331S, wherein the numbering of the residue position is according to EU numbering;
(c) the Fc region comprises an amino acid substitution at positions L234A, L235A, P331S, and E430G, wherein the numbering of the residue position is according to EU numbering;
(d) the Fc region comprises an amino acid substitution at positions K322A and E430G, wherein the numbering of the residue position is according to EU numbering;
(e) the Fc region comprises an amino acid substitution at positions P331S and E430G, wherein the numbering of the residue position is according to EU numbering;
(f) the Fc region comprises an amino acid substitution at positions A330S, P331S, and E430G, wherein the numbering of the residue position is according to EU numbering;
(g) the Fc region comprises an amino acid substitution at positions K322A, A330S, and P331S, wherein the numbering of the residue position is according to EU numbering;
(h) the Fc region comprises an amino acid substitution at positions K322A, P331S, and E430G, wherein the numbering of the residue position is according to EU numbering;
(i) the Fc region comprises an amino acid substitution at position E430G, wherein the numbering of the residue position is according to EU numbering;
(j) the Fc region comprises an amino acid substitution at positions A330S, P331S, and E430G, wherein the numbering of the residue position is according to EU numbering;
(k) the Fc region comprises an amino acid substitution at positions S267E and L328F, wherein the numbering of the residue position is according to EU numbering;
(l) the Fc region comprises an amino acid substitution at position C127S, wherein the numbering of the residue position is according to EU numbering;
(m) the Fc region comprises an amino acid substitution at positions E345R, E430G and S440Y, wherein the numbering of the residue position is according to EU numbering;
(n) the Fc region comprises an amino acid substitution at position P331S, wherein the numbering of the residue position is according to EU numbering; or
(o) the Fc region comprises an amino acid substitution at positions L234A, L235A, P331S, wherein the numbering of the residue positions is according to EU numbering.

9. The antibody of claim 1, wherein the CD33 protein is a mammalian protein or a human protein.

10. The antibody of claim 1, wherein the CD33 protein is a wild-type protein.

11. The antibody of claim 1, wherein the CD33 protein is a naturally occurring variant.

12. The antibody of claim 1, wherein the CD33 protein is expressed on one or more cells selected from the group consisting of human dendritic cells, human macrophages, human monocytes, human osteoclasts, human neutrophils, human T cells, human T helper cell, human cytotoxic T cells, human granulocytes, and human microglia.

13. The antibody of claim 1, wherein the antibody binds specifically to a human CD33 protein.

14. The antibody of claim 1, wherein the antibody is an antibody fragment that binds to an epitope comprising amino acid residues on human CD33 or a mammalian CD33 protein.

15. The antibody of claim 14, wherein the fragment is an Fab, Fab', Fab'-SH, F(ab')$_2$, Fv, or scFv fragment.

16. The antibody of claim 1, wherein the antibody is an antibody fragment that binds to one or more human proteins selected from the group consisting of human CD33, a naturally occurring variant of human CD33, and a disease variant of human CD33.

17. The antibody of claim 14, wherein the antibody fragment is cross-linked to a second antibody fragment that binds to one or more human proteins selected from the group consisting of human CD33, a naturally occurring variant of human CD33, and a disease variant of human CD33.

18. The antibody of claim 1, wherein the antibody is a humanized antibody, a bispecific antibody, a monoclonal antibody, a multivalent antibody, a conjugated antibody, or a chimeric antibody.

19. The antibody of claim 18, wherein the antibody is a monoclonal antibody.

20. The antibody of claim 18, wherein the antibody is a bispecific antibody recognizing a first antigen and a second antigen.

21. The antibody of claim 20, wherein the first antigen is CD33 and the second antigen is:
  (a) an antigen facilitating transport across the blood-brain-barrier;
  (b) an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30 (A), a protein transduction domain, TAT, Syn-B, penetratin, a poly-arginine peptide, an angiopep peptide, and ANG1005;
  (c) a disease-causing agent selected from the group consisting of disease-causing peptides or proteins and disease-causing nucleic acids, wherein the disease-causing peptides or proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9or f72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the disease-causing nucleic acids are antisense GGCCCC (G2C4) repeat-expansion RNA;
  (d) ligands and/or proteins expressed on immune cells, wherein the ligands and/or proteins are selected from the group consisting of CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR, LAG3, DR5, CD39, CD70, CD73, TREM1, TREM2, Siglec-5, Siglec-7, Siglec-9, Siglec-11, SirpA, CD47, CSF1-receptor, and phosphatidylserine;
  (e) a protein, lipid, polysaccharide, or glycolipid expressed on one or more tumor cells;
  or
  (f) a Lewy body.

22. The antibody of claim 1, wherein the antibody has a dissociation constant (KD) for human CD33 that is at least 1.8-fold lower than an anti-CD33 antibody comprising a heavy chain variable region comprising the amino acid sequence of SEQ ID NO: 3 and a light chain variable region comprising the amino acid sequence of SEQ ID NO: 4, wherein the $K_D$ is determined by BioLayer Interferometry.

23. The antibody of claim 1, wherein the antibody has a dissociation constant ($K_D$) for human CD33 that ranges from about 2 nM to about 200 pM, or less than about 200 pM, and wherein the $K_D$ is determined by BioLayer Interferometry.

24. The antibody of claim 1, wherein the antibody reduces cell surface levels of CD33.

25. The antibody of claim 24, wherein the CD33 is expressed on the surface of human dendritic cells.

26. The antibody of claim 24, wherein the antibody reduces cell surface levels of CD33 in vitro.

27. The antibody of claim 24, wherein the antibody reduces cell surface levels of CD33 in vitro with a half maximal effective concentration ($EC_{50}$) that is less than 40 pM, as measured by flow cytometry.

28. The antibody of claim 1, wherein the antibody increases expression of one or more disease-associated microglia (DAM) markers.

29. The antibody of claim 28, wherein the one or more DAM markers is ApoE3, Tyrobp, B2m, Trem2, Cst7, Cts1, Lp1, Cd9, Ax1, Csf1, Ccl6, Itgax, Clec7a, Lilrb4, Timp2, or any combination thereof.

30. The antibody of claim 1, wherein the antibody comprises an Fc region comprising the amino acid sequence of SEQ ID NO: 118.

31. An isolated nucleic acid comprising a nucleic acid sequence encoding the antibody of claim 1.

32. A vector comprising the nucleic acid of claim 31.

33. An isolated host cell comprising the vector of claim 32.

34. A method of producing an antibody that binds to CD33, comprising culturing the cell of claim 33 so that the antibody is produced.

35. The method of claim 34, further comprising recovering the antibody produced by the cell.

36. An isolated antibody that binds to CD33 produced by the method of claim 34.

37. A pharmaceutical composition comprising the antibody of claim 1 and a pharmaceutically acceptable carrier.

38. A method of treating a disease selected from the group consisting of Alzheimer's disease, acute lymphoblastic leukemia (ALL), acute myeloid leukemia (AML), chronic lymphocytic leukemia (CLL), chronic myeloid leukemia (CML), and multiple myeloma, comprising administering to an individual in need thereof a therapeutically effective amount of the antibody of claim 1.

39. The method of claim 38, wherein the disease is Alzheimer's disease.

40. An isolated antibody that binds to CD33, wherein the antibody comprises a heavy chain variable region and a light chain variable region, wherein the heavy chain variable region comprises: an HVR-H1 comprising the amino acid sequence of SEQ ID NO: 23, an HVR-H2 comprising the amino acid sequence of SEQ ID NO:33, an HVR-H3 comprising the amino acid sequence of SEQ ID NO: 39; and wherein the light chain variable region comprises: an HVR-L1 comprising the amino acid sequence of SEQ ID NO:47, an HVR-L2 comprising the amino acid sequence of SEQ ID NO: 53, and an HVR-L3 comprising the amino acid sequence of SEQ ID NO: 61.

41. The antibody of claim 40, wherein the antibody binds specifically to a human CD33 protein.

42. The antibody of claim 40, wherein the antibody has a dissociation constant ($K_D$) for human CD33 that is at least 1.8-fold lower than an anti-CD33 antibody comprising a heavy chain variable region comprising the amino acid sequence of SEQ ID NO: 3 and a light chain variable region comprising the amino acid sequence of SEQ ID NO: 4, wherein the $K_D$ is determined by BioLayer Interferometry.

43. The antibody of claim 40, wherein the antibody has a dissociation constant (KD) for human CD33 that ranges from about 2 nM to about 200 pM, or less than about 200 pM, and wherein the Kp is determined by BioLayer Interferometry.

44. The antibody of claim 40, wherein the antibody reduces cell surface levels of CD33.

45. The antibody of claim 44, wherein the CD33 is expressed on the surface of human dendritic cells.

46. The antibody of claim 44, wherein the antibody reduces cell surface levels of CD33 in vitro.

47. The antibody of claim 44, wherein the antibody reduces cell surface levels of CD33 in vitro with a half maximal effective concentration ($EC_{50}$) that is less than 40 pM, as measured by flow cytometry.

48. The antibody of claim 40, wherein the antibody increases expression of one or more disease-associated microglia (DAM) markers.

49. The antibody of claim 48, wherein the one or more DAM markers is ApoE3, Tyrobp, B2m, Trem2, Cst7, Cts1, Lp1, Cd9, Ax1, Csf1, Ccl6, Itgax, Clec7a, Lilrb4, Timp2, or any combination thereof.

50. The antibody of claim 40, wherein the antibody is a monoclonal antibody.

51. The antibody of claim 40, wherein the antibody has an IgG2 isotype.

52. An isolated nucleic acid comprising a nucleic acid sequence encoding the antibody of claim 40.

53. A vector comprising the nucleic acid of claim 52.

54. An isolated host cell comprising the vector of claim 53.

55. A method of producing an antibody that binds to CD33, comprising culturing the cell of claim 54 so that the antibody is produced.

56. The method of claim 55, further comprising recovering the antibody produced by the cell.

57. An isolated antibody that binds to CD33 produced by the method of claim 56.

58. A pharmaceutical composition comprising the antibody of claim 40 and a pharmaceutically acceptable carrier.

59. A method of treating Alzheimer's disease, acute lymphoblastic leukemia (ALL), acute myeloid leukemia (AML), chronic lymphocytic leukemia (CLL), chronic myeloid leukemia (CML), and multiple myeloma, comprising administering to an individual in need thereof a therapeutically effective amount of the antibody of claim 40.

60. The method of claim 59, wherein the disease is Alzheimer's disease.

61. An isolated antibody that binds to CD33, wherein the antibody comprises a heavy chain variable region comprising the amino acid sequence of SEQ ID NO: 83 and a light chain variable region comprising the amino acid sequence of SEQ ID NO: 102.

62. The antibody of claim 61, wherein the antibody is a monoclonal antibody.

63. The antibody of claim 61, wherein the antibody has an IgG2 isotype.

64. An isolated nucleic acid comprising a nucleic acid sequence encoding the antibody of claim 61.

65. A vector comprising the nucleic acid of claim 64.

66. An isolated host cell comprising the vector of claim 65.

67. A method of producing an antibody that binds to CD33, comprising culturing the cell of claim 66 so that the antibody is produced.

68. The method of claim 67, further comprising recovering the antibody produced by the cell.

69. An isolated antibody that binds to CD33 produced by the method of claim 68.

70. A pharmaceutical composition comprising the antibody of claim 61 and a pharmaceutically acceptable carrier.

71. A method of treating Alzheimer's disease, acute lymphoblastic leukemia (ALL), acute myeloid leukemia (AML), chronic lymphocytic leukemia (CLL), chronic myeloid leukemia (CML), and multiple myeloma, comprising administering to an individual in need thereof a therapeutically effective amount of the antibody of claim 43.

72. The method of claim 71, wherein the disease is Alzheimer's disease.

73. An isolated antibody that binds to CD33, wherein the antibody comprises
  (a) a heavy chain comprising the amino acid sequence of SEQ ID. NO: 120 and a light chain comprising the amino acid sequence of SEQ ID NO: 122; or
  (b) a heavy chain comprising the amino acid sequence of SEQ ID. NO: 121 and a light chain comprising the amino acid sequence of SEQ ID NO: 122.

74. The antibody of claim 73, wherein the antibody is a monoclonal antibody.

75. The antibody of claim 73, wherein the antibody has an IgG2 isotype.

76. An isolated nucleic acid comprising a nucleic acid sequence encoding the antibody of claim 73.

77. A vector comprising the nucleic acid of claim 76.

78. An isolated host cell comprising the vector of claim 77.

79. A method of producing an antibody that binds to CD33, comprising culturing the cell of claim 78 so that the antibody is produced.

80. The method of claim 79, further comprising recovering the antibody produced by the cell.

81. An isolated antibody that binds to CD33 produced by the method of claim 80.

82. A pharmaceutical composition comprising the antibody of claim 73 and a pharmaceutically acceptable carrier.

83. A method of treating Alzheimer's disease, acute lymphoblastic leukemia (ALL), acute myeloid leukemia (AML), chronic lymphocytic leukemia (CLL), chronic myeloid leukemia (CML), and multiple myeloma, comprising administering to an individual in need thereof a therapeutically effective amount of the antibody of claim 44.

84. The method of claim 83, wherein the disease is Alzheimer's disease.

* * * * *